(12) United States Patent
Corvey et al.

(10) Patent No.: US 10,316,071 B2
(45) Date of Patent: Jun. 11, 2019

(54) FUSION MOLECULES

(71) Applicant: SANOFI, Paris (FR)

(72) Inventors: Carsten Corvey, Frankfurt am Main (DE); Heike Stump, Frankfurt am Main (DE); Jochen Kruip, Frankfurt am Main (DE); Christian Lange, Frankfurt am Main (DE); Ingo Focken, Frankfurt am Main (DE); Dorothea Rat, Frankfurt am Main (DE); Thomas Stuedemann, Frankfurt am Main (DE); Hans-Falk Rasser, Frankfurt am Main (DE); Juergen Schaefer, Frankfurt am Main (DE); Bernard Calandra, Paris (FR); Astrid Rey, Paris (FR); Michael Mourez, Paris (FR); Laurent Fraisse, Paris (FR); Christine Rothe, Freising (DE); Andrea Allersdorfer, Freising (DE); Alexander Wiedenmann, Herbrechtingen (DE); Marlon Hinner, Freising (DE); Bradley Lunde, Lebanon, NH (US); Kristian Jensen, Landshut (DE); Martin Hülsmeyer, Römerberg (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/203,613

(22) Filed: Jul. 6, 2016

(65) Prior Publication Data
US 2017/0029477 A1     Feb. 2, 2017

(30) Foreign Application Priority Data

Jul. 7, 2015  (EP) .................................... 15306106

(51) Int. Cl.
*C07K 14/00* (2006.01)
*A61K 38/00* (2006.01)
*C07K 14/47* (2006.01)

(52) U.S. Cl.
CPC .............. *C07K 14/47* (2013.01); *A61K 38/00* (2013.01); *C07K 2319/00* (2013.01); *C07K 2319/21* (2013.01); *C07K 2319/22* (2013.01); *C07K 2319/30* (2013.01); *C07K 2319/50* (2013.01); *C07K 2319/70* (2013.01)

(58) Field of Classification Search
CPC .... A61K 38/00; A61K 38/005; A61K 38/012; C07K 14/47; C07K 14/4703; C07K 2319/00; C07K 2319/21; C07K 2319/22; C07K 2319/30; C07K 2319/50; C07K 2319/70

See application file for complete search history.

(56) References Cited

U.S. PATENT DOCUMENTS

| | | |
|---|---|---|
| 5,728,553 A | 3/1998 | Goodey et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | DeSauvage et al. |
| 6,696,245 B2 | 2/2004 | Winter et al. |
| 2003/0069395 A1 | 4/2003 | Sato et al. |
| 2017/0267734 A1* | 9/2017 | Corvey .............. C07K 14/4703 |

FOREIGN PATENT DOCUMENTS

| | | |
|---|---|---|
| EP | 0 330 451 A2 | 8/1989 |
| EP | 0 361 991 A1 | 4/1990 |
| WO | 1999/064016 A1 | 12/1999 |
| WO | 2004/060918 A1 | 7/2004 |
| WO | 2006/056464 A2 | 6/2006 |
| WO | 2007/038619 A2 | 4/2007 |
| WO | 2009/156456 A1 | 12/2009 |
| WO | 2011/149962 A1 | 12/2011 |
| WO | 2014/076321 A1 | 5/2014 |

OTHER PUBLICATIONS

Houghten et al. (Vaccines, 1986, Edited by Fred Brown: Cold Spring Harbor Laboratory).*
Brandel et al. (Sep. 22, 2011) "Pyochelin, a siderophore of Pseudomonas aeruginosa: Physicochemical characterization of the iron(III), copper(II) and zinc(II) complexes," Dalton Trans. 41(9):2820-2834.
Dennis et al. (2002) "Albumin Binding as a General Strategy for Improving the Pharmacokinetics of Proteins," J. Biol. Chem. 277:35035-35043.
Flower (1996) "The lipocalin protein family: structure and function," Biochem J. 318 (Pt 1):1-14.
Fuertges et al. (1990) "The clinical efficacy of poly(ethylene glycol)-modified proteins," J. Control. Release 11:139-148.
Heinrichs et al. (1996) "PchR, a regulator of ferripyochelin receptor gene (fptA) expression in Pseudomonas aeruginosa, functions both as an activator and as a repressor," J. Bacteriol. 178(9):2586-2592.
Konig et al. (1998) "Use of an albumin-binding domain for the selective immobilisation of recombinant capture antibody fragments on ELISA plates," J. Immunol. Methods. 218:73-83.
Lamont et al. (2000) "Siderophore-mediated signaling regulates virulence factor production in Pseudomonas aeruginosa," Proc. Natl. Acad. Sci. USA. 99(10):7072-7077.
Meyer et al. (1996) "Pyoverdin is essential for virulence of Pseudomonas aeruginosa," Infection and Immunity. 64:518-523.

(Continued)

*Primary Examiner* — Padmavathi Baskar
(74) *Attorney, Agent, or Firm* — Lathrop Gage LLP; James H. Velema, Esq.

(57) ABSTRACT

The present invention relates to fusion molecules that have binding specificity for pyoverdine type I, II and III and pyochelin and can be used in various applications, including diagnostic and/or therapeutic applications, for example, to inhibit or reduce growth of *P. aeruginosa* and/or to prevent or treat *P. aeruginosa* biofilm infection as well as diseases or disorders associated with *P. aeruginosa* biofilm infection. The present invention also concerns methods of producing the fusion molecules described herein as well as compositions and kits comprising such fusion molecules. The present invention further relates to nucleic acid molecules encoding the fusion molecules described herein.

15 Claims, 30 Drawing Sheets

Figure 1A:
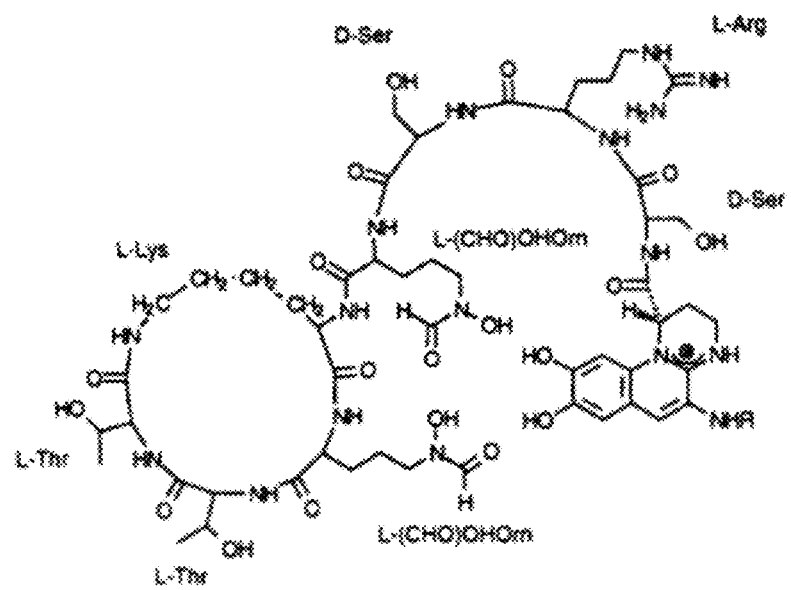

Specification includes a Sequence Listing.

(56) References Cited

OTHER PUBLICATIONS

Osborn et al. (2002) "Albutropin: A growth hormone-albumin fusion with improved pharmacokinetics and pharmacodynamics," J. Pharmacol. Exp. Ther. 303:540-548.
Schmidt et al. (1996) "Molecular interaction between the Strep-tag affinity peptide and its cognate target, streptavidin," J Mol Biol. 255(5):753-66.
Uniprot Database [online] "UniProtKB—P80188 (NGAL_HUMAN)," Accessible on the Internet at URL: http://www.uniprot.org/uniprot/P80188. [Last Accessed Sep. 20, 2016].
Vajo et al. (2000) "Genetically engineered insulin analogs: diabetes in the new millenium," Pharmacol. Rev. 52:1-9.
Banin et al. (2005) "Iron and Pseudomonas aeruginosa biofilm formation," Proc. Natl. Acad. Sci. USA. 102(31):11076-11081.
Breustedt et al. (2005) "The 1.8-A crystal structure of human tear lipocalin reveals an extended branched cavity with capacity for multiple ligands," J. Biol. Chem. 280:484-493.
Briskot et al. (1989) "Bacterial Constituents, XXXVII. Pyoverdin-Type Siderophores from Pseudomonas aeruginosa," Liebigs Ann. Chem. 1989(4):375-384.
Bruckdorfer et al. (2004) "From production of peptides in milligram amounts for research to multi-tons quantities for drugs of the future," Curr. Pharm. Biotechnol. 5:29-43.
Cornelis et al. (1989) "Evidence for different pyoverdine-mediated iron uptake systems among Pseudomonas aeruginosa strains," Infect. Immun. 57:3491-3497.
Costerton et al. (1999) "Bacterial biofilms: a common cause of persistent infections," Science. 284 (5418)1318-1322.
Flower et al. (2000) "The lipocalin protein family: structural and sequence overview," Biochim. Biophys. Acta. 1482(1-2):9-24.
Fluckinger et al. (2004) "Human tear lipocalin exhibits antimicrobial activity by scavenging microbial siderophores," Antimicrob. Agents Chemother. 48(9):3367-3372.

Gipp et al. (1991) "Zwei Pyoverdine aus Pseudomonas aeruginosa R.," Z. Naturforsch. C. 46c:534-541.—Chemical Structures Only.
Holmes et al. (2005) "Siderocalin (Lcn 2) also binds carboxymycobactins, potentially defending against mycobacterial infections through iron sequestration," Structure. 13(1):29-41.
Lowman (1997) "Bacteriophage display and discovery of peptide leads for drug development," Annu. Rev. Biophys. Biomol. Struct. 26:401-424.
Meyer et al. (1997) "Use of siderophores to type pseudomonads: the three Pseudomonas aeruginosa pyoverdine systems," Microbiology. 143(Pt 1):35-43.
Peek et al. (2012) "Pyoverdine, the Major Siderophore in Pseudomonas aeruginosa, Evades NGAL Recognition," Interdiscip. Perspect. Infect. Dis. 2012:843509. pp. 1-10.
Rodi et al. (1999) "Phage-display technology—finding a needle in a vast molecular haystack," Curr. Opin. Biotechnol. 10(1):87-93.
Singh et al. (2000) "Quorum-sensing signals indicate that cystic fibrosis lungs are infected with bacterial biofilms," Nature. 407:762-764.
Takase et al. (2000) "Impact of Siderophore Production on Pseudomonas aeruginosa Infections in Immunosuppressed Mice," Infection and Immunity.68(4):1834-1839.
Tappe et al. (1993) "Structure elucidation of a Pyoverdin Produced by Pseudomonas aeruginosa ATCC 27 853," Journal fur Praktische Chemie. 335(1):83-87.
Venturi et al. (2002) "High level production of functional antibody Fab fragments in an oxidizing bacterial cytoplasm," J. Mol. Biol. 315:1-8.
Visca et al. (1992) "Isolation and characterization of Pseudomonas aeruginosa mutants blocked in the synthesis of pyoverdin," J. Bacteriol. 174(17):5727-5731.
International Search Report with Written Opinion corresponding to International Patent Application No. PCT/EP2016/053226, dated Mar. 16, 2016.
International Search Report with Written Opinion corresponding to International Patent Application No. PCT/EP2016/065899, dated Oct. 4, 2016.

* cited by examiner

PVD group I
*P. aeruginosa* ATCC 15692 (PAO1)

PVD group II
*P. aeruginosa* ATCC 27853

PVD group III
*P. aeruginosa* R and Pa6

Dose-effect of SEQ ID NO: 19 in *P. aeruginosa*-induced lung infections in mice

MKHHHHHHHDYDIPTTENLYFQGQDSTSDLIPAPPLSKVPLQQNFQDNQFHG
KWYVVGVAGNTILREDKDPGKMNATIYELKEDKSYNVTDVRFIRKKCHYYIDT
FVPGSQPGEFTLGNIKSYPGTTSQLVRVVSTNYNQHAMVFFKIVRQNREIFW
ITLYGRTKELTSELKENFIRFSKSLGLPENHIVFPVPIDQCIDG

LM 1  LM 2 LM 3  LM 4

LM 1

LM 2

LM 3

LM 4 hu IgG4-Fc hu IgG4-Fc

LM 1

LM 2

LM 3

LM 4

A — Gene expression while treatment in the early phase of colonization

B — Gene expression while treatment during the established colonization

SEQUENCE LISTING

<160> NUMBER OF SEQ ID NOS: 186

<210> SEQ ID NO 1
<211> LENGTH: 178
<212> TYPE: PRT
<213> ORGANISM: Artificial Sequence
<220> FEATURE:
<223> OTHER INFORMATION: NGAL wt

<400> SEQUENCE: 1

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 2
<211> LENGTH: 178
<212> TYPE: PRT
<213> ORGANISM: Artificial Sequence
<220> FEATURE:
<223> OTHER INFORMATION: S0466.12C05

<400> SEQUENCE: 2

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Asn Ala Gly Asn Gly Trp Leu Arg Glu Asp Lys Asp Pro
        35                  40                  45

Ile Lys Met Met Ala Thr Ile Tyr Glu Leu Lys Glu Asp Lys Ser Tyr
    50                  55                  60

Asn Val Thr Val Val Gln Phe Trp Asp Lys Lys Cys Leu Tyr Gln Ile
65                  70                  75                  80

Gln Thr Phe Val Pro Gly Ser Gln Pro Gly Glu Phe Thr Leu Gly His
                85                  90                  95

Ile Lys Ser Lys Pro Gly His Thr Ser His Leu Val Arg Val Val Ser
            100                 105                 110

Thr Asn Tyr Asn Gln His Ala Met Val Phe Phe Lys Arg Val Trp Gln
```

```
                115                 120                 125
Asn Arg Glu Trp Phe Asp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: S0466.02P05

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Thr Ala Gly Asn Gly Phe Leu Arg Glu Asp Lys Asp Pro
        35                  40                  45

Leu Lys Met Trp Ala Thr Ile Tyr Glu Leu Lys Glu Asp Lys Ser Tyr
    50                  55                  60

Asn Val Thr Ser Val Trp Phe Ala Leu Lys Lys Cys Tyr Tyr Asp Ile
65                  70                  75                  80

Gly Thr Phe Val Pro Gly Ser Gln Pro Gly Glu Phe Thr Leu Gly Ile
                85                  90                  95

Ile Lys Ser Glu Pro Gly His Thr Ser Gln Leu Val Arg Val Val Ser
            100                 105                 110

Thr Asn Tyr Asn Gln His Ala Met Val Phe Phe Lys Trp Val Asn Gln
        115                 120                 125

Asn Arg Glu Asn Phe Gln Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: S0466.09A08

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60
```

```
Asn Val Thr Asp Val Gln Phe Ser Glu Lys Lys Cys Ser Tyr Ser Ile
 65                  70                  75                  80

Ile Thr Phe Val Pro Gly Ser Gln Pro Gly Glu Phe Thr Leu Gly Gly
                 85                  90                  95

Ile Lys Ser Asn Pro Gly Lys Thr Ser His Leu Val Arg Val Val Ser
            100                 105                 110

Thr Asn Tyr Asn Gln His Ala Met Val Phe Phe Lys Tyr Val Ala Gln
        115                 120                 125

Asn Arg Glu Gly Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: S0466.09M05

<400> SEQUENCE: 5

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Phe Ala Gly Asn Asn Arg Leu Arg Glu Asp Lys Asp Pro
             35                 40                  45

Pro Lys Met Met Ala Thr Ile Tyr Glu Leu Lys Glu Asp Lys Ser Tyr
     50                  55                  60

Asn Val Thr Asp Val Thr Phe Glu Ala Lys Lys Cys Arg Tyr Arg Ile
 65                  70                  75                  80

Ile Thr Phe Val Pro Gly Ser Gln Pro Gly Glu Phe Thr Leu Gly Tyr
                 85                  90                  95

Ile Lys Ser Lys Pro Gly Pro Thr Ser Phe Leu Val Arg Val Val Ser
            100                 105                 110

Thr Asn Tyr Asn Gln His Ala Met Val Phe Phe Lys Ser Val Thr Gln
        115                 120                 125

Asn Arg Glu Trp Phe Gly Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
<223> OTHER INFORMATION: S0466.09E05

<400> SEQUENCE: 6
```

-continued

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Gly Trp Leu Arg Glu Asp Lys Asp Pro
        35                  40                  45

Val Lys Met Met Ala Thr Ile Tyr Glu Leu Lys Glu Asp Lys Ser Tyr
    50                  55                  60

Asn Val Thr Val Val Asp Phe Glu Leu Lys Lys Cys Arg Tyr Met Ile
65                  70                  75                  80

Glu Thr Phe Val Pro Gly Ser Gln Pro Gly Glu Phe Thr Leu Gly Asp
                85                  90                  95

Ile Lys Ser Phe Pro Gly Trp Thr Ser Gln Leu Val Arg Val Val Ser
            100                 105                 110

Thr Asn Tyr Asn Gln His Ala Met Val Phe Phe Lys Gly Val Tyr Gln
        115                 120                 125

Asn Arg Glu Trp Phe His Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 7
<211> LENGTH: 178
<212> TYPE: PRT
<213> ORGANISM: Artificial Sequence
<220> FEATURE:
<223> OTHER INFORMATION: S0466.09E13

<400> SEQUENCE: 7

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Phe Phe Leu Arg Glu Asp Lys Asp Pro
        35                  40                  45

Ala Lys Met Pro Ala Thr Ile Tyr Glu Leu Lys Glu Asp Lys Ser Tyr
    50                  55                  60

Asn Val Thr Glu Val Trp Phe Leu Asn Lys Lys Cys Gln Tyr Glu Ile
65                  70                  75                  80

His Thr Phe Val Pro Gly Ser Gln Pro Gly Glu Phe Thr Leu Gly Tyr
                85                  90                  95

Ile Lys Ser Tyr Pro Gly Tyr Thr Ser His Leu Val Arg Val Val Ser
            100                 105                 110

Thr Asn Tyr Asn Gln His Ala Met Val Phe Phe Lys Val Val His Gln
        115                 120                 125

Asn Arg Asp Lys Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 8
<211> LENGTH: 178
<212> TYPE: PRT
<213> ORGANISM: Artificial Sequence
<220> FEATURE:
<223> OTHER INFORMATION: S0512.17L07

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Glu Lys Lys Cys Ile Tyr Ser Thr
65                  70                  75                  80

Ile Thr Phe Val Pro Gly Ser Gln Pro Gly Glu Phe Thr Leu Gly Gly
                85                  90                  95

Ile Lys Ser Ser Pro Gly Gln Thr Ser His Leu Val Arg Val Val Ser
            100                 105                 110

Thr Asn Tyr Asn Gln His Ala Met Val Phe Phe Lys Tyr Val Ile Gln
        115                 120                 125

Asn Arg Glu Gly Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial Sequence
<220> FEATURE:
<223> OTHER INFORMATION: S0512.17O10

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Asp Lys Lys Cys Ile Tyr Ser Ile
65                  70                  75                  80

Ile Thr Phe Val Pro Gly Ser Gln Pro Gly Glu Phe Thr Leu Gly Gly
                85                  90                  95

Ile Lys Ser Asn Pro Gly Asp Thr Ser His Leu Val Arg Val Val Ser
            100                 105                 110

Thr Asn Tyr Asn Gln His Ala Met Val Phe Phe Lys Tyr Val Val Gln
        115                 120                 125

Asn Arg Glu Gly Phe Asn Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial Sequence
<220> FEATURE:
<223> OTHER INFORMATION: S0512.19M08

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Trp Ala Gly Asn Thr Thr Leu Arg Glu Asp Lys Asp Pro
            35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Glu Lys Lys Cys Thr Tyr Ser Ile
65                  70                  75                  80

Ile Thr Phe Val Pro Gly Ser Gln Pro Gly Phe Thr Leu Gly Asp
                85                  90                  95

Ile Lys Ser Asn Pro Gly Glu Thr Ser His Leu Val Arg Val Met Ser
                100                 105                 110

Thr Asn Tyr Asn Gln His Ala Met Val Phe Phe Lys Tyr Val Asp Gln
            115                 120                 125

Asn Arg Glu Gly Phe Asn Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: Artificial Sequence
<220> FEATURE:
<223> OTHER INFORMATION: S0512.17O03

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Trp Ala Gly Asn Thr Thr Leu Arg Glu Asp Lys Asp Pro
            35                  40                  45

Pro Lys Met Pro Ala Thr Ile Tyr Glu Leu Lys Glu Asp Lys Ser Tyr
    50                  55                  60

```
Asn Val Thr Asp Val Gln Phe Pro Asp Lys Lys Cys Val Tyr Ser Ile
 65                  70                  75                  80

Ile Thr Phe Val Pro Gly Ser Gln Pro Gly Glu Phe Thr Leu Gly Gly
                 85                  90                  95

Ile Lys Ser Asn Pro Gly Asn Thr Ser His Leu Val Arg Val Val Ser
            100                 105                 110

Thr Asn Tyr Asn Gln His Ala Met Val Phe Phe Lys Tyr Val Val Gln
            115                 120                 125

Asn Arg Glu Gly Phe Asn Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 12
<211> LENGTH: 178
<212> TYPE: PRT
<213> ORGANISM: Artificial Sequence
<220> FEATURE:
<223> OTHER INFORMATION: S0510.05H10

<400> SEQUENCE: 12

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Gly Trp Leu Arg Glu Asp Lys Asp Pro
             35                  40                  45

Leu Lys Met Met Ala Thr Ile Tyr Glu Leu Lys Glu Asp Lys Ser Tyr
 50                  55                  60

Asn Val Thr Val Val Asp Phe Glu Leu Lys Lys Cys Arg Tyr Met Ile
 65                  70                  75                  80

Glu Thr Phe Val Pro Gly Ser Gln Pro Gly Glu Phe Thr Leu Gly Asp
                 85                  90                  95

Ile Lys Ser Ser Pro Gly Trp Thr Ser Gln Leu Val Arg Val Val Ser
            100                 105                 110

Thr Asn Tyr Asn Gln His Ala Met Val Phe Phe Lys Gly Val Tyr Gln
            115                 120                 125

Asn Arg Glu Trp Phe His Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 13
<211> LENGTH: 178
<212> TYPE: PRT
<213> ORGANISM: Artificial Sequence
<220> FEATURE:
<223> OTHER INFORMATION: S0530.06H10

<400> SEQUENCE: 13

Gln Asp Ser Thr Ser Asp Leu Ile Pro Ala Pro Pro Leu Ser Lys Val

```
              1               5                  10                 15
            Pro Leu Gln Gln Asn Phe Gln Asp Asn Gln Phe His Gly Lys Trp Tyr
                            20                  25                 30

Val Val Gly Trp Ala Gly Asn Thr Thr Leu Arg Glu Asp Lys Asp Pro
                            35                  40                 45

Pro Lys Met Pro Ala Val Ile Tyr Glu Leu Lys Glu Asp Lys Ser Tyr
                        50                  55                  60

Asn Val Thr Asp Val Gln Phe Pro Glu Lys Glu Cys Ile Tyr Ser Thr
            65                  70                  75                  80

Ile Thr Phe Val Pro Gly Ser Gln Pro Gly Glu Phe Thr Leu Gly Gly
                            85                  90                 95

Ile Lys Ser Ser Pro Gly Gln Thr Ser His Leu Val Arg Val Val Ser
                            100                 105                110

Thr Asn Tyr Asn Gln His Ala Met Val Phe Phe Lys Tyr Val Thr Gln
                            115                 120                125

Asn Arg Glu Gly Phe Asn Ile Thr Leu Tyr Gly Arg Thr Lys Glu Leu
                        130                 135                 140

Thr Ser Glu Leu Lys Glu Asn Phe Ile Arg Phe Ser Lys Ser Leu Gly
            145                 150                 155                 160

Leu Pro Glu Asn His Ile Val Phe Pro Val Pro Ile Asp Gln Cys Ile
                            165                 170                175

Asp Gly

<210> SEQ ID NO 14
<211> LENGTH: 178
<212> TYPE: PRT
<213> ORGANISM: Artificial Sequence
<220> FEATURE:
<223> OTHER INFORMATION: S0530.04N16

<400> SEQUENCE: 14

Gln Asp Ser Thr Ser Asp Leu Ile Pro Ala Pro Pro Leu Ser Lys Val
            1               5                   10                  15

Pro Leu Gln Gln Asn Phe Gln Asp Asn Gln Phe His Gly Lys Trp Tyr
                            20                  25                 30

Val Val Gly Leu Ala Gly Asn Gly Trp Leu Arg Glu Asp Glu Asp Pro
                            35                  40                 45

Leu Lys Met Met Ala Ala Val Tyr Glu Leu Arg Glu Asp Lys Ser Tyr
                        50                  55                  60

Asn Val Thr Val Val Asp Phe Glu Leu Glu Glu Cys Arg Tyr Met Thr
            65                  70                  75                  80

Glu Thr Phe Val Pro Gly Asn Gln Pro Gly Glu Phe Thr Leu Gly Asp
                            85                  90                 95

Ile Lys Ser Ser Pro Gly Trp Thr Ser Gln Leu Val Arg Val Val Ser
                            100                 105                110

Thr Asn Tyr Asn Gln His Ala Met Val Phe Phe Lys Gly Val Tyr Gln
                            115                 120                125

Asn Arg Glu Trp Phe His Ile Thr Leu Tyr Gly Arg Thr Lys Glu Leu
                        130                 135                 140

Thr Ser Glu Leu Lys Glu Asn Phe Ile Arg Phe Ser Lys Ser Leu Gly
            145                 150                 155                 160

Leu Pro Glu Asn His Ile Val Phe Pro Val Pro Ile Asp Gln Cys Ile
                            165                 170                175

Asp Gly
```

```
<210> SEQ ID NO 15
<211> LENGTH: 178
<212> TYPE: PRT
<213> ORGANISM: Artificial Sequence
<220> FEATURE:
<223> OTHER INFORMATION: S0544.01B06_H28Q_N65D

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Trp Ala Gly Asp Thr Thr Leu Arg Glu Asp Lys Asp Pro
            35                  40                  45

Pro Lys Met Pro Ala Val Ile Tyr Glu Leu Lys Glu Asp Lys Ser Tyr
        50                  55                  60

Asp Val Thr Asp Val Gln Phe Pro Glu Lys Glu Cys Ile Tyr Ser Thr
65                  70                  75                  80

Ile Thr Phe Val Pro Gly Ser Gln Pro Gly Glu Phe Thr Leu Gly Gly
                85                  90                  95

Ile Lys Ser Ser Pro Gly Gln Thr Ser His Leu Val Arg Val Val Ser
            100                 105                 110

Thr Asn Tyr Asn Gln His Ala Met Val Phe Phe Lys Tyr Val Thr Gln
        115                 120                 125

Asn Arg Glu Gly Phe Asn Ile Ala Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 16
<211> LENGTH: 178
<212> TYPE: PRT
<213> ORGANISM: Artificial Sequence
<220> FEATURE:
<223> OTHER INFORMATION: S0544.04C04_H28Q_N65D

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Trp Ala Gly Asn Thr Ala Leu Arg Glu Asp Lys Asp Pro
            35                  40                  45

Pro Lys Met Pro Ala Val Ile Tyr Glu Leu Lys Glu Asp Lys Ser Tyr
        50                  55                  60

Asp Val Thr Asp Val Gln Phe Pro Glu Lys Glu Cys Ile Tyr Ser Thr
65                  70                  75                  80

Ile Thr Phe Val Pro Gly Ser Gln Pro Gly Glu Phe Thr Leu Gly Gly
                85                  90                  95

Ile Lys Ser Ser Pro Gly Gln Thr Ser His Leu Val Arg Val Val Ser
            100                 105                 110

Thr Asn Tyr Asn Gln His Ala Met Val Phe Phe Lys Tyr Val Thr Gln
        115                 120                 125
```

Asn Arg Glu Gly Phe Asn Ile Ala Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 17
<211> LENGTH: 178
<212> TYPE: PRT
<213> ORGANISM: Artificial Sequence
<220> FEATURE:
<223> OTHER INFORMATION: S0530.04N16_N65D

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Gly Trp Leu Arg Glu Asp Glu Asp Pro
        35                  40                  45

Leu Lys Met Met Ala Ala Val Tyr Glu Leu Arg Glu Asp Lys Ser Tyr
    50                  55                  60

Asp Val Thr Val Val Asp Phe Glu Leu Glu Glu Cys Arg Tyr Met Thr
65                  70                  75                  80

Glu Thr Phe Val Pro Gly Asn Gln Pro Gly Glu Phe Thr Leu Gly Asp
                85                  90                  95

Ile Lys Ser Ser Pro Gly Trp Thr Ser Gln Leu Val Arg Val Val Ser
            100                 105                 110

Thr Asn Tyr Asn Gln His Ala Met Val Phe Phe Lys Gly Val Tyr Gln
        115                 120                 125

Asn Arg Glu Trp Phe His Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 18
<211> LENGTH: 178
<212> TYPE: PRT
<213> ORGANISM: Artificial Sequence
<220> FEATURE:
<223> OTHER INFORMATION: S0530.04N16_N65Q

<400> SEQUENCE: 18

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Gly Trp Leu Arg Glu Asp Glu Asp Pro
        35                  40                  45

Leu Lys Met Met Ala Ala Val Tyr Glu Leu Arg Glu Asp Lys Ser Tyr
    50                  55                  60

Gln Val Thr Val Val Asp Phe Glu Leu Glu Glu Cys Arg Tyr Met Thr

```
            65                  70                  75                  80
Glu Thr Phe Val Pro Gly Asn Gln Pro Gly Glu Phe Thr Leu Gly Asp
                    85                  90                  95

Ile Lys Ser Ser Pro Gly Trp Thr Ser Gln Leu Val Arg Val Val Ser
                100                 105                 110

Thr Asn Tyr Asn Gln His Ala Met Val Phe Lys Gly Val Tyr Gln
                115                 120                 125

Asn Arg Glu Trp Phe His Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 19
<211> LENGTH: 178
<212> TYPE: PRT
<213> ORGANISM: Artificial Sequence
<220> FEATURE:
<223> OTHER INFORMATION: S447.3 M1.1_N4

<400> SEQUENCE: 19

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Glu Val Leu Arg Glu Asp Lys Asp Pro
            35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Ser Ile
65                  70                  75                  80

Glu Thr Phe Val Pro Gly Ser Gln Pro Gly Glu Phe Thr Leu Gly Asn
                85                  90                  95

Ile Lys Ser Asn Pro Gly Gln Thr Ser Met Leu Val Arg Val Val Ser
                100                 105                 110

Thr Asn Tyr Asn Gln His Ala Met Val Phe Phe Lys Lys Val Lys Gln
                115                 120                 125

Asn Arg Glu Gly Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 20
<211> LENGTH: 178
<212> TYPE: PRT
<213> ORGANISM: Artificial Sequence
<220> FEATURE:
<223> OTHER INFORMATION: S449.1 M1.1_M5

<400> SEQUENCE: 20

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30

Val Val Gly Leu Ala Gly Asn Thr Ile Leu Arg Glu Asp Lys Asp Pro
        35                  40                  45

Gly Lys Met Asn Ala Thr Ile Tyr Glu Leu Lys Glu Asp Lys Ser Tyr
    50                  55                  60

Asn Val Thr Asp Val Arg Phe Ile Met Lys Lys Cys His Tyr Tyr Ile
 65                  70                  75                  80

Glu Thr Phe Val Pro Gly Ser Gln Pro Gly Glu Phe Thr Leu Gly Ile
                85                  90                  95

Ile Lys Ser Asn Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Met Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 21
<211> LENGTH: 178
<212> TYPE: PRT
<213> ORGANISM: Artificial Sequence
<220> FEATURE:
<223> OTHER INFORMATION: S449.5 M1.1_L10

<400> SEQUENCE: 21

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Ile Ala Gly Asn Thr Val Leu Arg Glu Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe Ala Pro Lys Lys Cys Ile Tyr Ser Ile
 65                  70                  75                  80

Ser Thr Phe Val Pro Gly Ser Gln Pro Gly Glu Phe Thr Leu Gly Met
                85                  90                  95

Ile Lys Ser Ser Pro Gly Gly Thr Ser Ala Leu Val Arg Val Val Ser
                100                 105                 110

Thr Asn Tyr Asn Gln His Ala Met Val Phe Phe Lys Lys Val Ser Gln
            115                 120                 125

Asn Arg Glu Val Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 22
<211> LENGTH: 178
<212> TYPE: PRT
<213> ORGANISM: Artificial Sequence
<220> FEATURE:
<223> OTHER INFORMATION: S449.8 M1.1_F3

<400> SEQUENCE: 22

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Asn Ile Leu Arg Glu Asp Lys Asp Pro
        35                  40                  45

Ala Lys Met Pro Ala Thr Ile Tyr Glu Leu Lys Glu Asp Lys Ser Tyr
    50                  55                  60

Asn Val Thr Glu Val Arg Phe Ser Gln Lys Lys Cys Met Tyr Ala Ile
65                  70                  75                  80

Tyr Thr Phe Val Pro Gly Ser Gln Pro Gly Glu Phe Thr Leu Gly Arg
                85                  90                  95

Ile Lys Ser Pro Pro Gly Thr Thr Ser Ile Leu Val Arg Val Val Ser
            100                 105                 110

Thr Asn Tyr Asn Gln His Ala Met Val Phe Phe Lys Lys Val Met Gln
        115                 120                 125

Asn Arg Glu Phe Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 23
<211> LENGTH: 178
<212> TYPE: PRT
<213> ORGANISM: Artificial Sequence
<220> FEATURE:
<223> OTHER INFORMATION: S449.5 M1.1_E8

<400> SEQUENCE: 23

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn His Ile Leu Arg Glu Asp Lys Asp Pro
        35                  40                  45

Ala Lys Met Pro Ala Thr Ile Tyr Glu Leu Lys Glu Asp Lys Ser Tyr
    50                  55                  60

Asn Val Thr Glu Val Arg Phe Gly Arg Lys Lys Cys His Tyr Trp Ile
65                  70                  75                  80

Glu Thr Phe Val Pro Gly Ser Gln Pro Gly Glu Phe Thr Leu Gly Arg
                85                  90                  95

Ile Lys Ser Asp Pro Gly Met Thr Ser Phe Leu Val Arg Val Val Ser
            100                 105                 110

Thr Asn Tyr Asn Gln His Ala Met Val Phe Phe Lys Ala Val Asp Gln
        115                 120                 125

Asn Arg Glu Asn Phe Trp Ile Thr Leu Tyr Gly Arg Thr Lys Glu Leu
```

```
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 24
<211> LENGTH: 178
<212> TYPE: PRT
<213> ORGANISM: Artificial Sequence
<220> FEATURE:
<223> OTHER INFORMATION: S437.1 M1.1_P2

<400> SEQUENCE: 24

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Asn Ala Gly Asn Gly Arg Leu Arg Glu Asp Lys Asp Pro
            35                  40                  45

Pro Lys Met Trp Ala Thr Ile Tyr Glu Leu Lys Glu Asp Lys Ser Tyr
50                  55                  60

Asn Val Thr Arg Val Trp Phe Asn Gln Lys Lys Cys Lys Tyr Asp Ile
65                  70                  75                  80

Glu Thr Phe Val Pro Gly Ser Gln Pro Gly Glu Phe Thr Leu Gly Asp
                85                  90                  95

Ile Lys Ser Thr Pro Gly Trp Thr Ser Asn Leu Val Arg Val Val Ser
            100                 105                 110

Thr Asn Tyr Asn Gln His Ala Met Val Phe Phe Lys Asn Val Met Gln
        115                 120                 125

Asn Arg Glu Ile Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 25
<211> LENGTH: 178
<212> TYPE: PRT
<213> ORGANISM: Artificial Sequence
<220> FEATURE:
<223> OTHER INFORMATION: S449.1 M1.1_I7

<400> SEQUENCE: 25

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Thr Leu Arg Glu Asp Lys Asp Pro
            35                  40                  45

Gly Lys Met Gly Ala Thr Ile Tyr Glu Leu Lys Glu Asp Lys Ser Tyr
50                  55                  60

Asn Val Thr Glu Val Arg Phe Gly Arg Lys Lys Cys Gly Tyr Trp Ile
65                  70                  75                  80
```

Glu Thr Phe Val Pro Gly Ser Gln Pro Gly Glu Phe Thr Leu Gly Ala
                85                  90                  95

Ile Lys Ser Trp Pro Gly Ile Thr Ser Gly Leu Val Arg Val Val Ser
            100                 105                 110

Thr Asn Tyr Asn Gln His Ala Met Val Phe Phe Lys Lys Val Asn Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 26
<211> LENGTH: 178
<212> TYPE: PRT
<213> ORGANISM: Artificial Sequence
<220> FEATURE:
<223> OTHER INFORMATION: S0475.06L06

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Ser Ile
65                  70                  75                  80

Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110

Thr Asn Tyr Asn Gln His Ala Met Val Phe Phe Lys Asn Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 27
<211> LENGTH: 178
<212> TYPE: PRT
<213> ORGANISM: Artificial Sequence
<220> FEATURE:
<223> OTHER INFORMATION: S0475.08G23

<400> SEQUENCE: 27

Gln Asp Ser Thr Ser Asp Leu Ile Pro Ala Pro Pro Leu Ser Lys Val
1               5                   10                  15

```
Pro Leu Gln Gln Asn Phe Gln Asp Asn Gln Phe His Gly Lys Trp Tyr
            20                  25                  30

Val Val Gly Val Ala Gly Asn Thr Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Ser Ile
65                  70                  75                  80

Glu Thr Phe Val Pro Gly Ser Gln Pro Gly Glu Phe Thr Leu Gly Asn
                85                  90                  95

Ile Lys Ser Tyr Pro Gly Gln Thr Ser Met Leu Val Arg Val Val Ser
            100                 105                 110

Thr Asn Tyr Asn Gln His Ala Met Val Phe Phe Lys Lys Val Lys Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 28
<211> LENGTH: 178
<212> TYPE: PRT
<213> ORGANISM: Artificial Sequence
<220> FEATURE:
<223> OTHER INFORMATION: S0475.06G17

<400> SEQUENCE: 28

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe His Lys Lys Lys Cys Asn Tyr Phe Ile
65                  70                  75                  80

Glu Thr Phe Val Pro Gly Ser Gln Pro Gly Glu Phe Thr Leu Gly Lys
                85                  90                  95

Ile Lys Ser His Pro Gly Gln Thr Ser Met Leu Val Arg Val Val Ser
            100                 105                 110

Thr Asn Tyr Asn Gln His Ala Met Val Phe Phe Lys Lys Val Lys Gln
        115                 120                 125

Asn Arg Glu Ala Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 29
```

```
<211> LENGTH: 178
<212> TYPE: PRT
<213> ORGANISM: Artificial Sequence
<220> FEATURE:
<223> OTHER INFORMATION: S0475.03N20

<400> SEQUENCE: 29

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Gln Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Trp Ile
65                  70                  75                  80

Glu Thr Phe Val Pro Gly Ser Gln Pro Gly Glu Phe Thr Leu Gly Asn
                85                  90                  95

Ile Lys Ser Asn Pro Gly His Thr Ser Met Leu Val Arg Val Val Ser
            100                 105                 110

Thr Asn Tyr Asn Gln His Ala Met Val Phe Phe Lys Lys Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 30
<211> LENGTH: 178
<212> TYPE: PRT
<213> ORGANISM: Artificial Sequence
<220> FEATURE:
<223> OTHER INFORMATION: S0474.05F20

<400> SEQUENCE: 30

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Thr Ile Tyr Glu Leu Lys Glu Asp Lys Ser Tyr
    50                  55                  60

Asn Val Thr Asp Val Arg Phe Ile Phe Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Met Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140
```

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 31
<211> LENGTH: 178
<212> TYPE: PRT
<213> ORGANISM: Artificial Sequence
<220> FEATURE:
<223> OTHER INFORMATION: S0474.01H22

<400> SEQUENCE: 31

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Thr Ile Tyr Glu Leu Lys Glu Asp Lys Ser Tyr
        50                  55                  60

Asn Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 32
<211> LENGTH: 178
<212> TYPE: PRT
<213> ORGANISM: Artificial Sequence
<220> FEATURE:
<223> OTHER INFORMATION: S0475.06L06_N65D_S79F

<400> SEQUENCE: 32

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Glu Val Leu Arg Asp Asp Lys Asp Pro
            35                  40                  45

Gly Lys Met Pro Ala Thr Ile Tyr Glu Leu Lys Glu Asp Lys Ser Tyr
        50                  55                  60

Asp Val Thr Glu Val Arg Phe His Asn Lys Lys Cys Asn Tyr Phe Ile
65                  70                  75                  80

```
Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110

Thr Asn Tyr Asn Gln His Ala Met Val Phe Phe Lys Asn Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 33
<211> LENGTH: 178
<212> TYPE: PRT
<213> ORGANISM: Artificial Sequence
<220> FEATURE:
<223> OTHER INFORMATION: S0475.06L06_N65Q_S79F

<400> SEQUENCE: 33

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Gln Val Thr Glu Val Arg Phe His Asn Lys Lys Cys Asn Tyr Phe Ile
65                  70                  75                  80

Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110

Thr Asn Tyr Asn Gln His Ala Met Val Phe Phe Lys Asn Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 34
<211> LENGTH: 178
<212> TYPE: PRT
<213> ORGANISM: Artificial Sequence
<220> FEATURE:
<223> OTHER INFORMATION: S0474.01H22_T54A_N65D

<400> SEQUENCE: 34

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
```

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
 50                  55                  60

Asp Val Thr Asp Val Arg Phe Ile Arg Lys Lys Cys His Tyr Tyr Ile
 65                  70                  75                  80

Asp Thr Phe Val Pro Gly Ser Gln Pro Gly Glu Phe Thr Leu Gly Asn
                 85                  90                  95

Ile Lys Ser Tyr Pro Gly Thr Thr Ser Gln Leu Val Arg Val Val Ser
             100                 105                 110

Thr Asn Tyr Asn Gln His Ala Met Val Phe Phe Lys Ile Val Arg Gln
             115                 120                 125

Asn Arg Glu Ile Phe Trp Ile Thr Leu Tyr Gly Arg Thr Lys Glu Leu
         130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                 165                 170                 175

Asp Gly

<210> SEQ ID NO 35
<211> LENGTH: 178
<212> TYPE: PRT
<213> ORGANISM: Artificial Sequence
<220> FEATURE:
<223> OTHER INFORMATION: S0474.01H22_T54A_N65Q

<400> SEQUENCE: 35

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Val Ala Gly Asn Thr Ile Leu Arg Glu Asp Lys Asp Pro
         35                  40                  45

Gly Lys Met Asn Ala Ala Ile Tyr Glu Leu Lys Glu Asp Lys Ser Tyr
 50                  55                  60

Gln Val Thr Asp Val Arg Phe Ile Arg Lys Lys Cys His Tyr Tyr Ile
 65                  70                  75                  80

Asp Thr Phe Val Pro Gly Ser Gln Pro Gly Glu Phe Thr Leu Gly Asn
                 85                  90                  95

Ile Lys Ser Tyr Pro Gly Thr Thr Ser Gln Leu Val Arg Val Val Ser
             100                 105                 110

Thr Asn Tyr Asn Gln His Ala Met Val Phe Phe Lys Ile Val Arg Gln
             115                 120                 125

Asn Arg Glu Ile Phe Trp Ile Thr Leu Tyr Gly Arg Thr Lys Glu Leu
         130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                 165                 170                 175

Asp Gly

<210> SEQ ID NO 36
<211> LENGTH: 178

<212> TYPE: PRT
<213> ORGANISM: Artificial Sequence
<220> FEATURE:
<223> OTHER INFORMATION: S0474.01H22_H28Q_T54A_N65D

<400> SEQUENCE: 36

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 37
<211> LENGTH: 178
<212> TYPE: PRT
<213> ORGANISM: Artificial Sequence
<220> FEATURE:
<223> OTHER INFORMATION: S0474.01H22_N65Q

<400> SEQUENCE: 37

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Thr Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 38
<211> LENGTH: 178
<212> TYPE: PRT
<213> ORGANISM: Artificial Sequence
<220> FEATURE:
<223> OTHER INFORMATION: S0466.14D07

<400> SEQUENCE: 38

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Phe Ala Gly Asn Trp Met Leu Arg Glu Asp Lys Asp Pro
            35                  40                  45

His Lys Met Asn Ala Thr Ile Tyr Glu Leu Lys Glu Asp Lys Ser Tyr
50                  55                  60

Asn Val Thr Glu Val Lys Phe Gln Ala Lys Lys Cys Ile Tyr Ser Ile
65                  70                  75                  80

His Thr Phe Val Pro Gly Ser Gln Pro Gly Glu Phe Thr Leu Gly Ile
                85                  90                  95

Ile Lys Ser Asn Pro Gly Gly Thr Ser Glu Leu Val Arg Val Val Ser
                100                 105                 110

Thr Asn Tyr Asn Gln His Ala Met Val Phe Phe Lys Trp Val His Gln
                115                 120                 125

Asn Arg Glu Phe Phe Gln Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 39
<211> LENGTH: 178
<212> TYPE: PRT
<213> ORGANISM: Artificial Sequence
<220> FEATURE:
<223> OTHER INFORMATION: S0466.05N20

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Phe Ala Gly Asn Arg Trp Leu Arg Glu Asp Lys Asp Pro
            35                  40                  45

Ile Lys Met Tyr Ala Thr Ile Tyr Glu Leu Lys Glu Asp Lys Ser Tyr
50                  55                  60

Asn Val Thr Gln Val Asn Phe Trp Leu Lys Lys Cys Ala Tyr Ser Ile
65                  70                  75                  80

Ser Thr Phe Val Pro Gly Ser Gln Pro Gly Glu Phe Thr Leu Gly Arg
```

```
                        85                  90                  95

Ile Lys Ser Ile Pro Gly Pro Thr Ser Glu Leu Val Arg Val Val Ser
                100                 105                 110

Thr Asn Tyr Asn Gln His Ala Met Val Phe Phe Lys Thr Val Ile Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 40
<211> LENGTH: 178
<212> TYPE: PRT
<213> ORGANISM: Artificial Sequence
<220> FEATURE:
<223> OTHER INFORMATION: S0466.16B14

<400> SEQUENCE: 40

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Leu Leu Leu Arg Glu Asp Lys Asp Pro
        35                  40                  45

Arg Lys Met Arg Ala Thr Ile Tyr Glu Leu Lys Glu Asp Lys Ser Tyr
    50                  55                  60

Asn Val Thr Asp Val Arg Phe Leu Tyr Lys Lys Cys Ile Tyr Ser Ile
65                  70                  75                  80

Ala Thr Phe Val Pro Gly Ser Gln Pro Gly Glu Phe Thr Leu Gly Gly
                85                  90                  95

Ile Lys Ser Ala Pro Gly Phe Thr Ser Glu Leu Val Arg Val Val Ser
                100                 105                 110

Thr Asn Tyr Asn Gln His Ala Met Val Phe Phe Lys Trp Val Ala Gln
            115                 120                 125

Asn Arg Glu Tyr Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 41
<211> LENGTH: 178
<212> TYPE: PRT
<213> ORGANISM: Artificial Sequence
<220> FEATURE:
<223> OTHER INFORMATION: S0466.15E20

<400> SEQUENCE: 41

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

```
Val Val Gly Phe Ala Gly Asn Trp Arg Leu Arg Glu Asp Lys Asp Pro
            35                  40                  45

Pro Lys Met Ser Ala Thr Ile Tyr Glu Leu Lys Glu Asp Lys Ser Tyr
 50                  55                  60

Asn Val Thr Asn Val Arg Phe Trp Pro Lys Lys Cys Arg Tyr Ser Ile
 65                  70                  75                  80

Ser Thr Phe Val Pro Gly Ser Gln Pro Gly Glu Phe Thr Leu Gly Met
                85                  90                  95

Ile Lys Ser Pro Pro Gly Gly Thr Ser Glu Leu Val Arg Val Val Ser
                100                 105                 110

Thr Asn Tyr Asn Gln His Ala Met Val Phe Phe Lys Trp Val Phe Gln
            115                 120                 125

Asn Arg Glu Phe Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 42
<211> LENGTH: 178
<212> TYPE: PRT
<213> ORGANISM: Artificial Sequence
<220> FEATURE:
<223> OTHER INFORMATION: S0466.13C10

<400> SEQUENCE: 42

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Glu Ala Gly Asn Leu Ala Leu Arg Glu Asp Lys Asp Pro
            35                  40                  45

Lys Lys Met Met Ala Thr Ile Tyr Glu Leu Lys Glu Asp Lys Ser Tyr
 50                  55                  60

Asn Val Thr Glu Val Arg Phe Arg His Lys Lys Cys Gln Tyr Asp Ile
 65                  70                  75                  80

Ala Thr Phe Val Pro Gly Ser Gln Pro Gly Glu Phe Thr Leu Gly Leu
                85                  90                  95

Ile Lys Ser Asp Pro Gly Gln Thr Ser Glu Leu Val Arg Val Val Ser
                100                 105                 110

Thr Asn Tyr Asn Gln His Ala Met Val Phe Phe Lys Lys Val Val Gln
            115                 120                 125

Asn Arg Glu Phe Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 43
<211> LENGTH: 178
<212> TYPE: PRT
```

<213> ORGANISM: Artificial Sequence
<220> FEATURE:
<223> OTHER INFORMATION: S0510.11H24

<400> SEQUENCE: 43

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asp Pro
        35                  40                  45

Met Lys Met Met Ala Thr Ile Tyr Glu Leu Lys Glu Asp Lys Ser Tyr
    50                  55                  60

Asn Val Thr Glu Val Arg Phe Arg Gln Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Ser Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 44
<211> LENGTH: 178
<212> TYPE: PRT
<213> ORGANISM: Artificial Sequence
<220> FEATURE:
<223> OTHER INFORMATION: S0512.01M12_x103Q

<400> SEQUENCE: 44

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Thr Leu Arg Glu Asp Lys Asp Pro
        35                  40                  45

Met Lys Met Met Ala Thr Ile Tyr Glu Leu Lys Glu Asp Lys Ser Tyr
    50                  55                  60

Asn Val Thr Glu Val Arg Phe Arg Arg Lys Lys Cys Lys Tyr Asp Ile
65                  70                  75                  80

Val Thr Phe Val Pro Gly Ser Gln Pro Gly Glu Phe Thr Leu Gly Val
                85                  90                  95

Ile Lys Ser Asp Pro Gly Gln Thr Ser Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
```

```
145                 150                 155                 160
Leu Pro Glu Asn His Ile Val Phe Pro Val Pro Ile Asp Gln Cys Ile
                165                 170                 175
Asp Gly

<210> SEQ ID NO 45
<211> LENGTH: 178
<212> TYPE: PRT
<213> ORGANISM: Artificial Sequence
<220> FEATURE:
<223> OTHER INFORMATION: S0512.01F10_x103Q

<400> SEQUENCE: 45

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Glu Ala Gly Asn Leu Ala Leu Arg Glu Asp Lys Asp Pro
            35                  40                  45

Met Lys Met Met Ala Thr Ile Tyr Glu Leu Lys Glu Asp Lys Ser Tyr
        50                  55                  60

Asn Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Ser Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 46
<211> LENGTH: 174
<212> TYPE: PRT
<213> ORGANISM: Artificial Sequence
<220> FEATURE:
<223> OTHER INFORMATION: S0510.10A04_x103Q

<400> SEQUENCE: 46

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Glu Ala Gly Asn Leu Ala Leu Arg Glu Asp Lys Asp Pro
            35                  40                  45

Lys Lys Met Met Ala Thr Ile Tyr Glu Leu Lys Glu Asp Lys Ser Tyr
        50                  55                  60

Asn Val Thr Glu Val Arg Phe Arg Tyr Lys Lys Cys Gln Tyr Asp Ile
65                  70                  75                  80

Val Thr Phe Val Pro Gly Ser Gln Pro Gly Glu Phe Thr Leu Ser Glu
                85                  90                  95
```

Pro Gly Gln Thr Ser Glu Leu Val Arg Val Ser Thr Asn Tyr Asn
            100                 105                 110

Gln His Ala Met Val Phe Phe Lys Val Val Gln Asn Arg Glu Phe
            115                 120                 125

Phe Trp Ile Thr Leu Tyr Gly Arg Thr Lys Glu Leu Thr Ser Glu Leu
            130                 135                 140

Lys Glu Asn Phe Ile Arg Phe Ser Lys Ser Leu Gly Leu Pro Glu Asn
145                 150                 155                 160

His Ile Val Phe Pro Val Pro Ile Asp Gln Cys Ile Asp Gly
                165                 170

<210> SEQ ID NO 47
<211> LENGTH: 178
<212> TYPE: PRT
<213> ORGANISM: Artificial Sequence
<220> FEATURE:
<223> OTHER INFORMATION: S0530.07G09

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Arg Arg Glu Asp Lys Asp Pro
        35                  40                  45

Met Lys Met Met Ala Thr Ile Tyr Glu Leu Lys Glu Asp Lys Ser Tyr
    50                  55                  60

Asn Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
            100                 105                 110

Thr Asn Tyr Asn Gln His Ala Met Val Phe Phe Lys Lys Val Val Gln
            115                 120                 125

Asn Arg Glu Tyr Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 48
<211> LENGTH: 178
<212> TYPE: PRT
<213> ORGANISM: Artificial Sequence
<220> FEATURE:
<223> OTHER INFORMATION: S0530.07K20

<400> SEQUENCE: 48

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asn Pro
        35                  40                  45

Met Lys Met Met Ala Thr Ile Tyr Glu Leu Lys Glu Asp Lys Ser Tyr
            50                  55                  60

Asn Val Thr Glu Val Arg Phe Arg His Lys Lys Cys Lys Tyr Asp Ile
 65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
            130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 49
<211> LENGTH: 178
<212> TYPE: PRT
<213> ORGANISM: Artificial Sequence
<220> FEATURE:
<223> OTHER INFORMATION: S0530.07K21

<400> SEQUENCE: 49

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Glu Ala Gly Asn Leu Ala Leu Arg Glu Gly Arg Asp Pro
            35                  40                  45

Met Lys Met Met Ala Thr Ile Tyr Glu Leu Lys Glu Asp Lys Ser Tyr
            50                  55                  60

Asn Val Thr Glu Val Arg Phe Arg His Lys Lys Cys Lys Tyr Asp Ile
 65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 50
<211> LENGTH: 178
<212> TYPE: PRT
<213> ORGANISM: Artificial Sequence
<220> FEATURE:
<223> OTHER INFORMATION: S0530.07G09_N65D

<400> SEQUENCE: 50

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Arg Arg Glu Asp Lys Asp Pro
        35                  40                  45

Met Lys Met Met Ala Thr Ile Tyr Glu Leu Lys Glu Asp Lys Ser Tyr
    50                  55                  60

Asp Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 51
<211> LENGTH: 178
<212> TYPE: PRT
<213> ORGANISM: Artificial Sequence
<220> FEATURE:
<223> OTHER INFORMATION: S0530.07K20_N65D

<400> SEQUENCE: 51

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asn Pro
        35                  40                  45

Met Lys Met Met Ala Thr Ile Tyr Glu Leu Lys Glu Asp Lys Ser Tyr
    50                  55                  60

Asp Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

Asp Gly

<210> SEQ ID NO 52
<211> LENGTH: 178
<212> TYPE: PRT
<213> ORGANISM: Artificial Sequence
<220> FEATURE:
<223> OTHER INFORMATION: S0530.07K21_N65D

<400> SEQUENCE: 52

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Glu Ala Gly Asn Leu Ala Leu Arg Glu Gly Arg Asp Pro
        35                  40                  45
Met Lys Met Met Ala Thr Ile Tyr Glu Leu Lys Glu Asp Lys Ser Tyr
    50                  55                  60
Asp Val Thr Glu Val Arg Phe Arg His Lys Lys Cys Lys Tyr Asp Ile
65                  70                  75                  80
Val Thr Phe Val Pro Gly Ser Gln Pro Gly Glu Phe Thr Leu Gly Leu
                85                  90                  95
Ile Lys Ser Asp Pro Gly Gln Thr Pro Glu Leu Val Arg Val Val Ser
            100                 105                 110
Thr Asn Tyr Asn Gln His Ala Met Val Phe Phe Lys Lys Val Val Gln
        115                 120                 125
Asn Arg Glu Tyr Phe Trp Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 53
<211> LENGTH: 178
<212> TYPE: PRT
<213> ORGANISM: Artificial Sequence
<220> FEATURE:
<223> OTHER INFORMATION: S0530.07G09_H28Q_N65D

<400> SEQUENCE: 53

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Glu Ala Gly Asn Leu Ala Arg Arg Glu Asp Lys Asp Pro
        35                  40                  45
Met Lys Met Met Ala Thr Ile Tyr Glu Leu Lys Glu Asp Lys Ser Tyr
    50                  55                  60
Asp Val Thr Glu Val Arg Phe Arg His Lys Lys Cys Lys Tyr Asp Ile
65                  70                  75                  80
Val Thr Phe Val Pro Gly Ser Gln Pro Gly Glu Phe Thr Leu Gly Leu
                85                  90                  95
Ile Lys Ser Asp Pro Gly Gln Thr Pro Glu Leu Val Arg Val Val Ser
            100                 105                 110
```

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 54
<211> LENGTH: 178
<212> TYPE: PRT
<213> ORGANISM: Artificial Sequence
<220> FEATURE:
<223> OTHER INFORMATION: S0455.04F12

<400> SEQUENCE: 54

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ile Leu Leu Arg Glu Asp Lys Asp Pro
        35                  40                  45

His Lys Met Leu Ala Thr Ile Tyr Glu Leu Lys Glu Asp Lys Ser Tyr
    50                  55                  60

Asn Val Thr His Val Thr Phe Lys Trp Lys Lys Cys Tyr Tyr Ala Ile
65                  70                  75                  80

Arg Thr Phe Val Pro Gly Ser Gln Pro Gly Glu Phe Thr Leu Gly Met
                85                  90                  95

Ile Lys Ser Glu Pro Gly His Thr Ser Met Leu Val Arg Val Val Ser
            100                 105                 110

Thr Asn Tyr Asn Gln His Ala Met Val Phe Phe Lys Trp Val Asp Gln
        115                 120                 125

Asn Arg Glu Glu Phe Leu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 55
<211> LENGTH: 178
<212> TYPE: PRT
<213> ORGANISM: Artificial Sequence
<220> FEATURE:
<223> OTHER INFORMATION: S0455.04F23

<400> SEQUENCE: 55

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Gln Trp Leu Arg Glu Asp Lys Asp Pro
        35                  40                  45

-continued

```
Arg Lys Met Trp Ala Thr Ile Tyr Glu Leu Lys Glu Asp Lys Ser Tyr
 50                  55                  60

Asn Val Thr Asp Val Asp Phe Ala Ile Lys Lys Cys His Tyr Arg Ile
 65                  70                  75                  80

Thr Thr Phe Val Pro Gly Ser Gln Pro Gly Glu Phe Thr Leu Gly Asn
                 85                  90                  95

Ile Lys Ser His Pro Gly Gly Thr Ser Gly Leu Val Arg Val Val Ser
                100                 105                 110

Thr Asn Tyr Asn Gln His Ala Met Val Phe Phe Lys Phe Val Ile Gln
                115                 120                 125

Asn Arg Glu Ala Phe Phe Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 56
<211> LENGTH: 178
<212> TYPE: PRT
<213> ORGANISM: Artificial Sequence
<220> FEATURE:
<223> OTHER INFORMATION: S0455.04F09

<400> SEQUENCE: 56

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Met Ala Gly Asn Phe His Leu Arg Glu Asp Lys Asp Pro
                 35                  40                  45

Ser Lys Met Pro Ala Thr Ile Tyr Glu Leu Lys Glu Asp Lys Ser Tyr
 50                  55                  60

Asn Val Thr His Val Pro Phe Trp Ala Lys Lys Cys Ala Tyr Lys Ile
 65                  70                  75                  80

Ile Thr Phe Val Pro Gly Ser Gln Pro Gly Glu Phe Thr Leu Gly Ala
                 85                  90                  95

Ile Lys Ser Gly Pro Gly Met Thr Ser Trp Leu Val Arg Val Val Ser
                100                 105                 110

Thr Asn Tyr Asn Gln His Ala Met Val Phe Phe Lys Gly Val Trp Gln
                115                 120                 125

Asn Arg Glu Thr Phe Val Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 57
<211> LENGTH: 178
<212> TYPE: PRT
<213> ORGANISM: Artificial Sequence
<220> FEATURE:
<223> OTHER INFORMATION: S0455.04M08

<400> SEQUENCE: 57

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Tyr Trp Leu Arg Glu Lys Asp Pro
        35                  40                  45

Ala Lys Met Tyr Ala Thr Ile Tyr Glu Leu Lys Glu Asp Lys Ser Tyr
    50                  55                  60

Asn Val Thr Asp Val Arg Phe Trp Arg Lys Lys Cys Arg Tyr Asp Ile
65                  70                  75                  80

Trp Thr Phe Val Pro Gly Ser Gln Pro Gly Glu Phe Thr Leu Gly Pro
                85                  90                  95

Ile Lys Ser Glu Pro Gly Gln Thr Ser Arg Leu Val Arg Val Val Ser
            100                 105                 110

Thr Asn Tyr Asn Gln His Ala Met Val Phe Phe Lys Leu Val Arg Gln
            115                 120                 125

Asn Arg Glu Ala Phe Asn Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 58
<211> LENGTH: 178
<212> TYPE: PRT
<213> ORGANISM: Artificial Sequence
<220> FEATURE:
<223> OTHER INFORMATION: S0522.15K24

<400> SEQUENCE: 58

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Leu Gly Met Ala Gly Asn Phe His Leu Arg Glu Asp Lys Asp Pro
        35                  40                  45

Ser Lys Met Pro Ala Thr Ile Tyr Glu Leu Lys Glu Asp Lys Ser Tyr
    50                  55                  60

Asn Val Thr His Val Pro Phe Trp Ala Lys Lys Cys Ala Tyr Lys Thr
65                  70                  75                  80

Ile Thr Phe Val Pro Gly Ser Gln Pro Gly Glu Phe Thr Leu Gly Ala
                85                  90                  95

Ile Lys Ser Gly Pro Gly Met Thr Ser Trp Leu Val Arg Val Val Ser
            100                 105                 110

Thr Asn Tyr Asn Gln His Ala Met Val Phe Ser Lys Gly Val Trp Gln
            115                 120                 125

Asn Arg Glu Thr Phe Val Ile Thr Leu Tyr Gly Arg Ala Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

Asp Gly

```
<210> SEQ ID NO 59
<211> LENGTH: 178
<212> TYPE: PRT
<213> ORGANISM: Artificial Sequence
<220> FEATURE:
<223> OTHER INFORMATION: S0527.05N11

<400> SEQUENCE: 59
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Phe His Leu Arg Glu Asp Lys Asp Pro
        35                  40                  45

Ser Lys Met Pro Ala Thr Ile Tyr Glu Leu Lys Glu Asp Lys Ser Tyr
    50                  55                  60

Asn Val Thr His Val Pro Phe Trp Ala Lys Lys Cys Ala Tyr Lys Thr
65                  70                  75                  80

Ile Thr Phe Val Pro Gly Ser Gln Pro Gly Glu Phe Thr Leu Gly Ala
                85                  90                  95

Ile Lys Ser Gly Pro Gly Met Thr Ser Trp Leu Val Arg Val Val Ser
            100                 105                 110

Thr Asn Tyr Asn Gln His Ala Met Val Phe Ser Lys Gly Val Trp Gln
        115                 120                 125

Asn Arg Glu Thr Phe Val Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 60
<211> LENGTH: 178
<212> TYPE: PRT
<213> ORGANISM: Artificial Sequence
<220> FEATURE:
<223> OTHER INFORMATION: S0522.05A05

<400> SEQUENCE: 60
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Gln Trp Leu Arg Glu Gly Arg Asp Pro
        35                  40                  45

Arg Lys Met Trp Ala Thr Ile Tyr Glu Leu Lys Glu Asp Lys Ser Tyr
    50                  55                  60

Asn Val Thr Asp Val Asp Phe Ala Ile Lys Lys Cys Leu Tyr Arg Ile
65                  70                  75                  80

Thr Thr Phe Val Pro Gly Ser Gln Pro Gly Glu Phe Thr Leu Gly Asn
                85                  90                  95

Ile Lys Ser His Pro Gly Gly Thr Ser Gly Leu Val Arg Val Val Ser
            100                 105                 110

-continued

```
Thr Asn Tyr Asn Gln His Ala Met Val Phe Phe Lys Phe Val Ile Gln
            115                 120                 125
Asn Arg Glu Ala Phe Phe Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 61
<211> LENGTH: 178
<212> TYPE: PRT
<213> ORGANISM: Artificial Sequence
<220> FEATURE:
<223> OTHER INFORMATION: S0522.05M06

<400> SEQUENCE: 61

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly His Ala Gly Asn Gln Trp Leu Arg Gly Asp Tyr Asp Pro
        35                  40                  45
Arg Lys Met Trp Ala Thr Ile Tyr Glu Leu Lys Glu Asp Lys Ser Tyr
    50                  55                  60
Asn Val Thr Asp Val Asp Phe Ala Ile Glu Lys Cys His Tyr Arg Ile
65                  70                  75                  80
Thr Thr Phe Val Pro Gly Ser Gln Pro Gly Glu Phe Thr Phe Gly Asn
                85                  90                  95
Ile Lys Ser His Pro Gly Gly Thr Ser Gly Leu Ala Arg Val Val Ser
            100                 105                 110
Thr Asn Tyr Asn Gln His Ala Met Val Phe Phe Lys Phe Val Ile Gln
        115                 120                 125
Asn Arg Glu Ala Phe Phe Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 62
<211> LENGTH: 178
<212> TYPE: PRT
<213> ORGANISM: Artificial Sequence
<220> FEATURE:
<223> OTHER INFORMATION: S0522.05A05_H28Q_N65D

<400> SEQUENCE: 62

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly His Ala Gly Asn Gln Trp Leu Arg Glu Gly Arg Asp Pro
        35                  40                  45
Arg Lys Met Trp Ala Thr Ile Tyr Glu Leu Lys Glu Asp Lys Ser Tyr
```

```
            50                  55                  60
Asp Val Thr Asp Val Asp Phe Ala Ile Lys Lys Cys Leu Tyr Arg Ile
 65                  70                  75                  80

Thr Thr Phe Val Pro Gly Ser Gln Pro Gly Glu Phe Thr Leu Gly Asn
                 85                  90                  95

Ile Lys Ser His Pro Gly Gly Thr Ser Gly Leu Val Arg Val Val Ser
                100                 105                 110

Thr Asn Tyr Asn Gln His Ala Met Val Phe Phe Lys Phe Val Ile Gln
            115                 120                 125

Asn Arg Glu Ala Phe Phe Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 63
<211> LENGTH: 178
<212> TYPE: PRT
<213> ORGANISM: Artificial Sequence
<220> FEATURE:
<223> OTHER INFORMATION: S0522.05M06_N65D

<400> SEQUENCE: 63

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly His Ala Gly Asn Gln Trp Leu Arg Gly Asp Tyr Asp Pro
             35                  40                  45

Arg Lys Met Trp Ala Thr Ile Tyr Glu Leu Lys Glu Asp Lys Ser Tyr
 50                  55                  60

Asp Val Thr Asp Val Asp Phe Ala Ile Glu Lys Cys His Tyr Arg Ile
 65                  70                  75                  80

Thr Thr Phe Val Pro Gly Ser Gln Pro Gly Glu Phe Thr Phe Gly Asn
                 85                  90                  95

Ile Lys Ser His Pro Gly Gly Thr Ser Gly Leu Ala Arg Val Val Ser
                100                 105                 110

Thr Asn Tyr Asn Gln His Ala Met Val Phe Phe Lys Phe Val Ile Gln
            115                 120                 125

Asn Arg Glu Ala Phe Phe Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 64
<211> LENGTH: 178
<212> TYPE: PRT
<213> ORGANISM: Artificial Sequence
<220> FEATURE:
<223> OTHER INFORMATION: 3004wt = NGAL98

<400> SEQUENCE: 64
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 65
<211> LENGTH: 534
<212> TYPE: DNA
<213> ORGANISM: Artificial Sequence
<220> FEATURE:
<223> OTHER INFORMATION: S0466.12C05

<400> SEQUENCE: 65
caggactcca cctcagacct gatcccagcc ccacctctga gcaaggtccc tctgcagcag    60
aacttccagg acaaccaatt ccatgggaaa tggtatgtcg tgggcaatgc cggaaatgga   120
tggctgcgtg aggataagga tccgatcaaa atgatggcga ccatttacga gttgaaagaa   180
gataaatcat ataacgtcac cgttgtgcaa ttttgggaca agaaatgcct gtaccaaatt   240
caaacctttg tgccggggag ccagccgggc gagtttactt taggccacat taaaagtaaa   300
ccgggccaca catcacactt ggtccgcgtc gtgagcacca actacaacca gcatgccatg   360
gtgttcttca gcgtgtgtg cagaaccgc gagtggtttg acatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534

<210> SEQ ID NO 66
<211> LENGTH: 534
<212> TYPE: DNA
<213> ORGANISM: Artificial Sequence
<220> FEATURE:
<223> OTHER INFORMATION: S0466.02P05

<400> SEQUENCE: 66
caggactcca cctcagacct gatcccagcc ccacctctga gcaaggtccc tctgcagcag    60
aacttccagg acaaccaatt ccatgggaaa tggtatgtcg tgggcaccgc cggaaatgga   120
ttcctgcgtg aggataagga tccgctgaaa atgtgggcga ccatttacga gttgaaagaa   180

```
gataaatcat ataacgtcac cagcgtgtgg tttgcactga agaaatgcta ctacgacatt    240
ggaacctttg tgccggggag ccagccgggc gagtttactt taggcatcat taaaagtgag    300
ccgggccaca catcacaatt ggtccgcgtc gtgagcacca actacaacca gcatgccatg    360
gtgttcttca agtgggtgaa tcagaaccgc gagaattttc aaatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 67
<211> LENGTH: 534
<212> TYPE: DNA
<213> ORGANISM: Artificial Sequence
<220> FEATURE:
<223> OTHER INFORMATION: S0466.09A08

<400> SEQUENCE: 67

```
caggactcca cctcagacct gatcccagcc ccacctctga gcaaggtccc tctgcagcag     60
aacttccagg acaaccaatt ccatgggaaa tggtatgtcg tgggctgggc cggaaatacc    120
accctgcgtg aggataagga tccgcctaaa atgcctgcga ccatttacga gttgaaagaa    180
gataaatcat ataacgtcac cgacgtgcaa tttagcgaga agaaatgcag ctacagcatt    240
atcacctttg tgccggggag ccagccgggc gagtttactt taggcggaat taaaagtaat    300
ccgggcaaaa catcacactt ggtccgcgtc gtgagcacca actacaacca gcatgccatg    360
gtgttcttca agtacgtggc acagaaccgc gagggattta atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 68
<211> LENGTH: 534
<212> TYPE: DNA
<213> ORGANISM: Artificial Sequence
<220> FEATURE:
<223> OTHER INFORMATION: S0466.09M05

<400> SEQUENCE: 68

```
caggactcca cctcagacct gatcccagcc ccacctctga gcaaggtccc tctgcagcag     60
aacttccagg acaaccaatt ccatgggaaa tggtatgtcg tgggcttcgc cggaaataat    120
cgtctgcgtg aggataagga tccgcctaaa atgatggcga ccatttacga gttgaaagaa    180
gataaatcat ataacgtcac cgacgtgacc tttgaggcaa agaaatgccg ttaccgtatt    240
atcacctttg tgccggggag ccagccgggc gagtttactt taggctacat taaaagtaaa    300
ccgggcccta catcattctt ggtccgcgtc gtgagcacca actacaacca gcatgccatg    360
gtgttcttca agagcgtgac ccagaaccgc gagtggtttg aatcacact gtacgggcgc    420 acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 69
<211> LENGTH: 534
<212> TYPE: DNA
<213> ORGANISM: Artificial Sequence
<220> FEATURE:
<223> OTHER INFORMATION: S0466.09E05

<400> SEQUENCE: 69

```
caggactcca cctcagacct gatcccagcc ccacctctga gcaaggtccc tctgcagcag    60
aacttccagg acaaccaatt ccatgggaaa tggtatgtcg tgggcctggc cggaaatgga   120
tggctgcgtg aggataagga tccggttaaa atgatggcga ccatttacga gttgaaagaa   180
gataaatcat ataacgtcac cgttgtggac tttgagctga agaaatgccg ttacatgatt   240
gagacctttg tgccggggag ccagccgggc gagtttactt taggcgacat aaaaagtttc   300
ccgggctgga catcacaatt ggtccgcgtc gtgagcacca actacaacca gcatgccatg   360
gtgttcttca agggagtgta ccagaaccgc gagtggtttc acatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

<210> SEQ ID NO 70
<211> LENGTH: 534
<212> TYPE: DNA
<213> ORGANISM: Artificial Sequence
<220> FEATURE:
<223> OTHER INFORMATION: S0466.09E13

<400> SEQUENCE: 70

```
caggactcca cctcagacct gatcccagcc ccacctctga gcaaggtccc tctgcagcag    60
aacttccagg acaaccaatt ccatgggaaa tggtatgtcg tgggcgttgc cggaaatttc   120
ttcctgcgtg aggataagga tccggcaaaa atgcctgcga ccatttacga gttgaaagaa   180
gataaatcat ataacgtcac cgaggtgtgg tttctgaata agaaatgcca atacgagatt   240
cacacctttg tgccggggag ccagccgggc gagtttactt taggctacat aaaaagttac   300
ccgggctaca catcacactt ggtccgcgtc gtgagcacca actacaacca gcatgccatg   360
gtgttcttca aggttgtgca ccagaaccgc gataaatttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

<210> SEQ ID NO 71
<211> LENGTH: 534
<212> TYPE: DNA
<213> ORGANISM: Artificial Sequence
<220> FEATURE:
<223> OTHER INFORMATION: S0512.17L07

<400> SEQUENCE: 71

```
caggactcca cctcagacct gatcccagcc ccacctctga gcaaggtccc tctgcagcag    60
aacttccagg acaaccaatt ccatgggaaa tggtatgtcg tgggctgggc cggaaatacg   120
acgctgcgtg aggataagga tccgcctaaa atgcctgcga ccatttacga gttgaaagaa   180
gataaatcat ataacgtcac cgatgtgcag tttcctgaga agaaatgcat ttactctact   240
attacctttg tgccggggag ccagccgggc gagtttactt taggcggtat aaaaagtagt   300
ccgggccaga catcacattt ggtccgcgtc gtgagcacca actacaacca gcatgccatg   360
gtgttcttca agtatgtgat tcagaaccgc gaggggttta atatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

<210> SEQ ID NO 72
<211> LENGTH: 534
<212> TYPE: DNA
<213> ORGANISM: Artificial Sequence

<220> FEATURE:
<223> OTHER INFORMATION: S0512.17O10

<400> SEQUENCE: 72

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggctgggc | cggaaatacg | 120 |
| acgctgcgtg | aggataagga | tccgcctaaa | atgcctgcga | ccatttacga | gttgaaagaa | 180 |
| gataaatcat | ataacgtcac | cgatgtgcag | tttccggata | agaaatgcat | ttactcgatt | 240 |
| attacctttg | tgccggggag | ccagccgggc | gagtttactt | taggcgggat | taaaagtaat | 300 |
| ccgggcgata | catcacattt | ggtccgcgtc | gtgagcacca | actacaacca | gcatgccatg | 360 |
| gtgttcttca | agtatgtggt | gcagaaccgc | gagggtttta | atatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 73
<211> LENGTH: 534
<212> TYPE: DNA
<213> ORGANISM: Artificial Sequence
<220> FEATURE:
<223> OTHER INFORMATION: S0512.19M08

<400> SEQUENCE: 73

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggctgggc | cggaaatacg | 120 |
| acgctgcgtg | aggataagga | tccgcctaaa | atgcctgcga | ccatttacga | gttgaaagaa | 180 |
| gataaatcat | ataacgtcac | cgatgtgcag | tttcctgaga | agaaatgcac | gtactcgatt | 240 |
| attacctttg | tgccggggag | ccagccgggc | gagtttactt | taggcgatat | taaaagtaat | 300 |
| ccgggcgaga | catcacattt | ggtccgcgtc | atgagcacca | actacaacca | gcatgccatg | 360 |
| gtgttcttca | agtatgtgga | tcagaaccgc | gagggggttta | atatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 74
<211> LENGTH: 534
<212> TYPE: DNA
<213> ORGANISM: Artificial Sequence
<220> FEATURE:
<223> OTHER INFORMATION: S0512.17O03

<400> SEQUENCE: 74

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggctgggc | cggaaatact | 120 |
| acgctgcgtg | aggataagga | tccgcctaaa | atgcctgcga | ccatttacga | gttgaaagaa | 180 |
| gataaatcat | ataacgtcac | cgatgtgcag | tttccggata | agaaatgcgt | gtactcgatt | 240 |
| attacctttg | tgccggggag | ccagccgggc | gagtttactt | taggcgggat | taaaagtaat | 300 |
| ccgggcaata | catcacattt | ggtccgcgtc | gtgagcacca | actacaacca | gcatgccatg | 360 |
| gtgttcttca | agtatgtggt | gcagaaccgc | gagggtttta | atatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

```
<210> SEQ ID NO 75
<211> LENGTH: 534
<212> TYPE: DNA
<213> ORGANISM: Artificial Sequence
<220> FEATURE:
<223> OTHER INFORMATION: S0510.05H10

<400> SEQUENCE: 75
caggactcca cctcagacct gatcccagcc ccacctctga gcaaggtccc tctgcagcag      60
aacttccagg acaaccaatt ccatgggaaa tggtatgtcg tgggccttgc cggaaatggt     120
tggctgcgtg aggataagga tccgcttaaa atgatggcga ccatttacga gttgaaagaa     180
gataaatcat ataacgtcac cgtggtggat tttgagctta agaaatgcag gtacatgatt     240
gagacctttg tgccggggag ccagccgggc gagtttactt taggcgatat taaaagttct     300
ccgggctgga catcacagtt ggtccgcgtc gtgagcacca actacaacca gcatgccatg     360
gtgttcttca aggggggtgta tcagaaccgc gagtggtttc atatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534

<210> SEQ ID NO 76
<211> LENGTH: 534
<212> TYPE: DNA
<213> ORGANISM: Artificial Sequence
<220> FEATURE:
<223> OTHER INFORMATION: S0530.06H10

<400> SEQUENCE: 76
caggactcca cctcagacct gatcccagcc ccacctctga gcaaggtccc tctgcagcag      60
aacttccagg acaaccaatt ccatgggaaa tggctgggc cggaaatacg                 120 acgctgcgtg aggataagga tccgcctaaa atgcctgcgg tcatttacga gttgaaagaa     180
gataaatcat ataacgtcac cgatgtgcag tttcccgaga aggaatgcat ttactctact     240
attacctttg tgccggggag ccagccgggc gagtttactt taggcggtat taaaagtagt     300
ccgggccaga catcacattt ggtccgcgtc gtgagcacca actacaacca gcatgccatg     360
gtgttcttca agtatgtgac tcagaaccgc gaggggttta atatcacgct gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534

<210> SEQ ID NO 77
<211> LENGTH: 534
<212> TYPE: DNA
<213> ORGANISM: Artificial Sequence
<220> FEATURE:
<223> OTHER INFORMATION: S0530.04N16

<400> SEQUENCE: 77
caggactcca cctcagacct gatcccagcc ccacctctga gcaaggtccc tctgcagcag      60
aacttccagg acaaccaatt ccatgggaaa tggtatgtcg tgggccttgc cggaaatggt     120
tggctgcgtg aggatgagga tccgcttaaa atgatggcgg ccgtttacga gttgagagaa     180
gataaatcat ataacgtcac cgtggtggat tttgagcttg aggaatgcag gtacatgact     240
gagacctttg tgccggggaa ccagccgggc gagtttactt taggcgatat taaaagttct     300
ccgggctgga catcacagct ggtccgcgtc gtgagcacca actacaacca gcatgccatg     360
gtgttcttca aggggggtgta tcagaaccgc gagtggtttc atatcacact gtacgggcgc     420
```

```
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 78
<211> LENGTH: 534
<212> TYPE: DNA
<213> ORGANISM: Artificial Sequence
<220> FEATURE:
<223> OTHER INFORMATION: S0544.01B06_H28Q_N65D

<400> SEQUENCE: 78

```
caggactcca cctcagacct gatcccagcc ccacctctga gcaaggtccc tctgcagcag     60
aacttccagg acaaccaatt ccaagggaaa tggtatgtcg tgggctgggc cggagatacg    120
acgctgcgtg aggataagga tccgcctaaa atgcctgcgg tcatttacga gttgaaagaa    180
gataaatcat atgatgtcac cgatgtgcag tttcccgaga aggaatgcat ttactctact    240
attacctttg tgccggggag ccagccgggc gagtttactt taggcggtat taaaagtagt    300
ccgggccaga catcacattt ggtccgcgtc gtgagcacca actacaacca gcatgccatg    360
gtgttcttca gtatgtgac  tcagaaccgc gaggggttta atatcgcgct gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 79
<211> LENGTH: 534
<212> TYPE: DNA
<213> ORGANISM: Artificial Sequence
<220> FEATURE:
<223> OTHER INFORMATION: S0544.04C04_H28Q_N65D

<400> SEQUENCE: 79

```
caggactcca cctcagacct gatcccagcc ccacctctga gcaaggtccc tctgcagcag     60
aacttccagg acaaccaatt ccaagggaaa tggtatgtcg tgggctgggc cggaaatacg    120
gctctgcgtg aggataagga tccgcctaaa atgcctgcgg tcatttacga gttgaaagaa    180
gataaatcat atgatgtcac cgatgtgcag tttcccgaga aggaatgcat ttactctact    240
attacctttg tgccggggag ccagccgggc gagtttactt taggcggtat taaaagtagt    300
ccgggccaga catcacattt ggtccgcgtc gtgagcacca actacaacca gcatgccatg    360
gtgttcttca gtatgtgac  tcagaaccgc gaggggttta atatcgctct gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 80
<211> LENGTH: 534
<212> TYPE: DNA
<213> ORGANISM: Artificial Sequence
<220> FEATURE:
<223> OTHER INFORMATION: S0530.04N16_N65D

<400> SEQUENCE: 80

```
caggactcca cctcagacct gatcccagcc ccacctctga gcaaggtccc tctgcagcag     60
aacttccagg acaaccaatt ccatgggaaa tggtatgtcg tgggccttgc cggaaatggt    120
tggctgcgtg aggatgagga tccgcttaaa atgatggcgg ccgtttacga gttgagagaa    180
gataaatcat atgacgtcac cgtggtggat tttgagcttg aggaatgcag gtacatgact    240
```

```
gagacctttg tgccggggaa ccagccgggc gagtttactt taggcgatat taaaagttct    300
ccgggctgga catcacagct ggtccgcgtc gtgagcacca actacaacca gcatgccatg    360
gtgttcttca agggggtgta tcagaaccgc gagtggtttc atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534

<210> SEQ ID NO 81
<211> LENGTH: 534
<212> TYPE: DNA
<213> ORGANISM: Artificial Sequence
<220> FEATURE:
<223> OTHER INFORMATION: S0530.04N16_N65Q

<400> SEQUENCE: 81
caggactcca cctcagacct gatcccagcc ccacctctga gcaaggtccc tctgcagcag    60
aacttccagg acaaccaatt ccatgggaaa tggtatgtcg tgggccttgc cggaaatggt    120
tggctgcgtg aggatgagga tccgcttaaa atgatggcgg ccgtttacga gttgagagaa    180
gataaatcat atcaggtcac cgtggtggat tttgagcttg aggaatgcag gtacatgact    240
gagacctttg tgccggggaa ccagccgggc gagtttactt taggcgatat taaaagttct    300
ccgggctgga catcacagct ggtccgcgtc gtgagcacca actacaacca gcatgccatg    360
gtgttcttca agggggtgta tcagaaccgc gagtggtttc atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534

<210> SEQ ID NO 82
<211> LENGTH: 534
<212> TYPE: DNA
<213> ORGANISM: Artificial Sequence
<220> FEATURE:
<223> OTHER INFORMATION: S447.3 M1.1_N4

<400> SEQUENCE: 82
caggactcca cctcagacct gatcccagcc ccacctctga gcaaggtccc tctgcagcag    60
aacttccagg acaaccaatt ccatgggaaa tggtatgtcg tgggcgttgc cggaaatgag    120
gttctgcgtg aggataagga tccgggaaaa atgcctgcga ccatttacga gttgaaagaa    180
gataaatcat ataacgtcac cgaggtgcgt tttcacaata agaaatgcaa ttacagcatt    240
gagacctttg tgccggggag ccagccgggc gagtttactt taggcaatat taaaagtaat    300
ccgggccaaa catcaatgtt ggtccgcgtc gtgagcacca actacaacca gcatgccatg    360
gtgttcttca agaaagtgaa acagaaccgc gagggatttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534

<210> SEQ ID NO 83
<211> LENGTH: 534
<212> TYPE: DNA
<213> ORGANISM: Artificial Sequence
<220> FEATURE:
<223> OTHER INFORMATION: S449.1 M1.1_M5

<400> SEQUENCE: 83
caggactcca cctcagacct gatcccagcc ccacctctga gcaaggtccc tctgcagcag    60
aacttccagg acaaccaatt ccatgggaaa tggtatgtcg tgggcctggc cggaaatacc    120
```

```
atcctgcgtg aggataagga tccgggaaaa atgaatgcga ccatttacga gttgaaagaa      180
gataaatcat ataacgtcac cgacgtgcgt tttatcatga agaaatgcca ctactacatt      240
gagacctttg tgccggggag ccagccgggc gagtttactt taggcatcat taaaagtaat      300
ccgggcacca catcacaatt ggtccgcgtc gtgagcacca actacaacca gcatgccatg      360
gtgttcttca agatcgtgcg tcagaaccgc gagatgtttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 84
<211> LENGTH: 534
<212> TYPE: DNA
<213> ORGANISM: Artificial Sequence
<220> FEATURE:
<223> OTHER INFORMATION: S449.5 M1.1_L10

<400> SEQUENCE: 84

```
caggactcca cctcagacct gatcccagcc ccacctctga gcaaggtccc tctgcagcag      60
aacttccagg acaaccaatt ccatgggaaa tggtatgtcg tgggcatcgc cggaaatacc     120
gttctgcgtg aggataagga tccgggaaaa atgcctgcga ccatttacga gttgaaagaa     180
gataaatcat ataacgtcac cgaggtgcgt tttgcaccta agaaatgcat ctacagcatt     240
agcacctttg tgccggggag ccagccgggc gagtttactt taggcatgat taaaagtagc     300
ccgggcggaa catcagcatt ggtccgcgtc gtgagcacca actacaacca gcatgccatg     360
gtgttcttca agaaagtgag ccagaaccgc gaggtttttt ggatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 85
<211> LENGTH: 534
<212> TYPE: DNA
<213> ORGANISM: Artificial Sequence
<220> FEATURE:
<223> OTHER INFORMATION: S449.8 M1.1_F3

<400> SEQUENCE: 85

```
caggactcca cctcagacct gatcccagcc ccacctctga gcaaggtccc tctgcagcag      60
aacttccagg acaaccaatt ccatgggaaa tggtatgtcg tgggcctggc cggaaataat     120
atcctgcgtg aggataagga tccggcaaaa atgcctgcga ccatttacga gttgaaagaa     180
gataaatcat ataacgtcac cgaggtgcgt tttagccaaa agaaatgcat gtacgcaatt     240
tacacctttg tgccggggag ccagccgggc gagtttactt taggccgtat taaaagtcct     300
ccgggcacca catcaatctt ggtccgcgtc gtgagcacca actacaacca gcatgccatg     360
gtgttcttca agaaagtgat gcagaaccgc gagttcttt ggatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 86
<211> LENGTH: 534
<212> TYPE: DNA
<213> ORGANISM: Artificial Sequence
<220> FEATURE:
<223> OTHER INFORMATION: S449.5 M1.1_E8

<400> SEQUENCE: 86

```
caggactcca cctcagacct gatcccagcc ccacctctga gcaaggtccc tctgcagcag    60
aacttccagg acaaccaatt ccatgggaaa tggtatgtcg tgggcctggc cggaaatcac   120
atcctgcgtg aggataagga tccggcaaaa atgcctgcga ccatttacga gttgaaagaa   180
gataaatcat ataacgtcac cgaggtgcgt tttggacgta agaaatgcca ctactggatt   240
gagacctttg tgccggggag ccagccgggc gagtttactt taggccgtat taaaagtgac   300
ccgggcatga catcattctt ggtccgcgtc gtgagcacca actacaacca gcatgccatg   360
gtgttcttca aggcagtgga ccagaaccgc gagaattttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 87
<211> LENGTH: 534
<212> TYPE: DNA
<213> ORGANISM: Artificial Sequence
<220> FEATURE:
<223> OTHER INFORMATION: S437.1 M1.1_P2

<400> SEQUENCE: 87

```
caggactcca cctcagacct gatcccagcc ccacctctga gcaaggtccc tctgcagcag    60
aacttccagg acaaccaatt ccatgggaaa tggtatgtcg tgggcaatgc cggaaatgga   120
cgtctgcgtg aggataagga tccgcctaaa atgtgggcga ccatttacga gttgaaagaa   180
gataaatcat ataacgtcac ccgtgtgtgg tttaatcaaa agaaatgcaa atacgacatt   240
gagacctttg tgccggggag ccagccgggc gagtttactt taggcgacat taaaagtacc   300
ccgggctgga catcaaattt ggtccgcgtc gtgagcacca actacaacca gcatgccatg   360
gtgttcttca agaatgtgat gcagaaccgc gagatctttt acatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 88
<211> LENGTH: 534
<212> TYPE: DNA
<213> ORGANISM: Artificial Sequence
<220> FEATURE:
<223> OTHER INFORMATION: S449.1 M1.1_I7

<400> SEQUENCE: 88

```
caggactcca cctcagacct gatcccagcc ccacctctga gcaaggtccc tctgcagcag    60
aacttccagg acaaccaatt ccatgggaaa tggtatgtcg tggcgttgc cggaaatacc   120
accctgcgtg aggataagga tccgggaaaa atgggagcga ccatttacga gttgaaagaa   180
gataaatcat ataacgtcac cgaggtgcgt tttggacgta agaaatgcgg atactggatt   240
gagacctttg tgccggggag ccagccgggc gagtttactt taggcgcaat taaaagttgg   300
ccgggcatca catcaggatt ggtccgcgtc gtgagcacca actacaacca gcatgccatg   360
gtgttcttca agaaagtgaa tcagaaccgc gaggttttttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 89
<211> LENGTH: 534

```
<212> TYPE: DNA
<213> ORGANISM: Artificial Sequence
<220> FEATURE:
<223> OTHER INFORMATION: S0475.06L06

<400> SEQUENCE: 89
caggactcca cctcagacct gatcccagcc ccacctctga gcaaggtccc tctgcagcag      60
aacttccagg acaaccaatt ccatgggaaa tggtatgtcg tgggcgtggc cggaaatgag     120
gtgctgcgtg atgataagga tccggggaaa atgcctgcga ccatttacga gttgaaagaa     180
gataaatcat ataacgtcac cgaggtgagg tttcataata agaaatgcaa ttactcgatt     240
gagacctttg tgccggggag ccagccgggc gagtttactt taggcaagat taaaagtaat     300
ccgggcgtga catcaatgtt ggtccgcgtc gtgagcacca actacaacca gcatgccatg     360
gtgttcttca agaatgtgaa gcagaaccgc gaggggtttt ggatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534

<210> SEQ ID NO 90
<211> LENGTH: 534
<212> TYPE: DNA
<213> ORGANISM: Artificial Sequence
<220> FEATURE:
<223> OTHER INFORMATION: S0475.08G23

<400> SEQUENCE: 90
caggactcca cctcagacct gatcccagcc ccacctctga gcaaggtccc tctgcagcag      60
aacttccagg acaaccaatt ccatgggaaa tggtatgtcg tgggcgtggc cggaaatact     120
gtgctgcgtg atgataagga tccggggaaa atgcctgcga ccatttacga gttgaaagaa     180
gataaatcat ataacgtcac cgaggtgagg tttcataata agaaatgcaa ttactctatt     240
gagacctttg tgccggggag ccagccgggc gagtttactt taggcaatat taaaagttat     300
ccgggccaga catcaatgtt ggtccgcgtc gtgagcacca actacaacca gcatgccatg     360
gtgttcttca agaaggtgaa gcagaaccgc gaggtgtttt ggatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534

<210> SEQ ID NO 91
<211> LENGTH: 534
<212> TYPE: DNA
<213> ORGANISM: Artificial Sequence
<220> FEATURE:
<223> OTHER INFORMATION: S0475.06G17

<400> SEQUENCE: 91
caggactcca cctcagacct gatcccagcc ccacctctga gcaaggtccc tctgcagcag      60
aacttccagg acaaccaatt ccatgggaaa tggtatgtcg tgggcgttgc cggaaatacg     120
gtgctgcgtg acgataagga tccgggtaaa atgcctgcga ccatttacga gttgaaagaa     180
gataaatcat ataacgtcac cgaggtgcgg tttcataaga agaaatgcaa ttactttatt     240
gagacctttg tgccggggag ccagccgggc gagtttactt taggcaagat taaaagtcat     300
ccgggccaga catcaatgtt ggtccgcgtc gtgagcacca actacaacca gcatgccatg     360
gtgttcttca agaaggtgaa gcagaaccgc gaggcgtttt ggatcacact gtacgggcgc     420
acgaaagaac tgacaagcga gctgaaggaa aattttatcc gcttttccaa atctctgggc     480
```

```
ctccctgaaa accacatcgt cttccctgtc ccaatcgacc agtgtatcga cggc        534
```

<210> SEQ ID NO 92
<211> LENGTH: 534
<212> TYPE: DNA
<213> ORGANISM: Artificial Sequence
<220> FEATURE:
<223> OTHER INFORMATION: S0475.03N20

<400> SEQUENCE: 92

```
caggactcca cctcagacct gatcccagcc ccacctctga gcaaggtccc tctgcagcag    60
aacttccagg acaaccaatt ccatgggaaa tggtatgtcg tgggcgttgc cggaaatcag   120
gtgctgcgtg atgataagga tccgggtaaa atgcctgcga ccatttacga gttgaaagaa   180
gataaatcat ataacgtcac cgaggtgagg tttcataata agaaatgcaa ttactggatt   240
gagacctttg tgccggggag ccagccgggc gagtttactt taggcaatat taaaagtaat   300
ccgggccata catcaatgtt ggtccgcgtc gtgagcacca actacaacca gcatgccatg   360
gtgttcttca agaaggtgaa gcagaaccgc gagggttttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 93
<211> LENGTH: 534
<212> TYPE: DNA
<213> ORGANISM: Artificial Sequence
<220> FEATURE:
<223> OTHER INFORMATION: S0474.05F20

<400> SEQUENCE: 93

```
caggactcca cctcagacct gatcccagcc ccacctctga gcaaggtccc tctgcagcag    60
aacttccagg acaaccaatt ccatgggaaa tggtatgtcg tgggcgttgc cggaaatacg   120
attctgcgtg aggataagga tccggggaaa atgaatgcga ccatttacga gttgaaagaa   180
gataaatcat ataacgtcac cgatgtgagg tttatttta agaaatgcca ttactatatt    240
gatacctttg tgccggggag ccagccgggc gagtttactt taggcaatat taaaagttat   300
ccgggcatga catcacagtt ggtccgcgtc gtgagcacca actacaacca gcatgccatg   360
gtgttcttca agattgtgag gcagaaccgc gagattttt ggatcacact gtacgggcgc    420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 94
<211> LENGTH: 534
<212> TYPE: DNA
<213> ORGANISM: Artificial Sequence
<220> FEATURE:
<223> OTHER INFORMATION: S0474.01H22

<400> SEQUENCE: 94

```
caggactcca cctcagacct gatcccagcc ccacctctga gcaaggtccc tctgcagcag    60
aacttccagg acaaccaatt ccatgggaaa tggtatgtcg tgggcgtggc cggaaatact   120
attctgcgtg aggataagga tccggggaaa atgaatgcaa ccatttacga gttgaaagaa   180
gataaatcat ataacgtcac cgatgtgagg tttattagga agaaatgcca ttactatatt   240
gatacctttg tgccggggag ccagccgggc gagtttactt taggcaatat taaaagttat   300
ccgggcacta catcacagtt ggtccgcgtc gtgagcacca actacaacca gcatgccatg   360
```

```
gtgttcttca agattgtgag gcagaaccgc gagatttttt ggatcacact gtacgggcgc    420
acgaaagaac tgacaagcga gctgaaggaa aattttatcc gctttccaa atctctgggc     480 ctccctgaaa accacatcgt cttccctgtc ccaatcgacc agtgtatcga cggc          534
```

<210> SEQ ID NO 95
<211> LENGTH: 534
<212> TYPE: DNA
<213> ORGANISM: Artificial Sequence
<220> FEATURE:
<223> OTHER INFORMATION: S0475.06L06_N65D_S79F

<400> SEQUENCE: 95

```
caggactcca cctcagacct gatcccagcc ccacctctga gcaaggtccc tctgcagcag    60
aacttccagg acaaccaatt ccatgggaaa tggtatgtcg tgggcgtggc cggaaatgag   120
gtgctgcgtg atgataagga tccggggaaa atgcctgcga ccatttacga gttgaaagaa   180
gataaatcat atgatgtcac cgaggtgagg tttcataata agaaatgcaa ttacttcatt   240
gagacctttg tgccggggag ccagccgggc gagtttactt taggcaagat taaaagtaat   300
ccgggcgtga catcaatgtt ggtccgcgtc gtgagcacca actacaacca gcatgccatg   360
gtgttcttca agaatgtgaa gcagaaccgc gagggggtttt ggatcacact gtacgggcgc   420
acgaaagaac tgacaagcga gctgaaggaa aattttatcc gctttccaa atctctgggc    480 ctccctgaaa accacatcgt cttccctgtc ccaatcgacc agtgtatcga cggc          534
```

<210> SEQ ID NO 96
<211> LENGTH: 534
<212> TYPE: DNA
<213> ORGANISM: Artificial Sequence
<220> FEATURE:
<223> OTHER INFORMATION: S0475.06L06_N65Q_S79F

<400> SEQUENCE: 96

```
caggactcca cctcagacct gatcccagcc ccacctctga gcaaggtccc tctgcagcag    60
aacttccagg acaaccaatt ccatgggaaa tggtatgtcg tgggcgtggc cggaaatgag   120
gtgctgcgtg atgataagga tccggggaaa atgcctgcga ccatttacga gttgaaagaa   180
gataaatcat atcaggtcac cgaggtgagg tttcataata agaaatgcaa ttacttcatt   240
gagacctttg tgccggggag ccagccgggc gagtttactt taggcaagat taaaagtaat   300
ccgggcgtga catcaatgtt ggtccgcgtc gtgagcacca actacaacca gcatgccatg   360
gtgttcttca agaatgtgaa gcagaaccgc gagggggtttt ggatcacact gtacgggcgc   420
acgaaagaac tgacaagcga gctgaaggaa aattttatcc gctttccaa atctctgggc    480 ctccctgaaa accacatcgt cttccctgtc ccaatcgacc agtgtatcga cggc          534
```

<210> SEQ ID NO 97
<211> LENGTH: 534
<212> TYPE: DNA
<213> ORGANISM: Artificial Sequence
<220> FEATURE:
<223> OTHER INFORMATION: S0474.01H22_T54A_N65D

<400> SEQUENCE: 97

```
caggactcca cctcagacct gatcccagcc ccacctctga gcaaggtccc tctgcagcag    60
aacttccagg acaaccaatt ccatgggaaa tggtatgtcg tgggcgtggc cggaaatact   120
attctgcgtg aggataagga tccggggaaa atgaatgcag ccatttacga gttgaaagaa   180
```

-continued

```
gataaatcat atgatgtcac cgatgtgagg tttattagga agaaatgcca ttactatatt      240
gatacctttg tgccggggag ccagccgggc gagtttactt taggcaatat taaaagttat      300
ccgggcacta catcacagtt ggtccgcgtc gtgagcacca actacaacca gcatgccatg      360
gtgttcttca agattgtgag gcagaaccgc gagattttt ggatcacact gtacgggcgc       420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 98
<211> LENGTH: 534
<212> TYPE: DNA
<213> ORGANISM: Artificial Sequence
<220> FEATURE:
<223> OTHER INFORMATION: S0474.01H22_T54A_N65Q

<400> SEQUENCE: 98

```
caggactcca cctcagacct gatcccagcc ccacctctga gcaaggtccc tctgcagcag      60
aacttccagg acaaccaatt ccatgggaaa tggtatgtcg tgggcgtggc cggaaatact      120
attctgcgtg aggataagga tccggggaaa atgaatgcag ccatttacga gttgaaagaa      180
gataaatcat atcaggtcac cgatgtgagg tttattagga agaaatgcca ttactatatt      240
gatacctttg tgccggggag ccagccgggc gagtttactt taggcaatat taaaagttat      300
ccgggcacta catcacagtt ggtccgcgtc gtgagcacca actacaacca gcatgccatg      360
gtgttcttca agattgtgag gcagaaccgc gagattttt ggatcacact gtacgggcgc       420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 99
<211> LENGTH: 534
<212> TYPE: DNA
<213> ORGANISM: Artificial Sequence
<220> FEATURE:
<223> OTHER INFORMATION: S0474.01H22_H28Q_T54A_N65D

<400> SEQUENCE: 99

```
caggactcca cctcagacct gatcccagcc ccacctctga gcaaggtccc tctgcagcag      60
aacttccagg acaaccaatt ccaagggaaa tggtatgtcg tgggcgtggc cggaaatact      120
attctgcgtg aggataagga tccggggaaa atgaatgcag ccatttacga gttgaaagaa      180
gataaatcat atgatgtcac cgatgtgagg tttattagga agaaatgcca ttactatatt      240
gatacctttg tgccggggag ccagccgggc gagtttactt taggcaatat taaaagttat      300
ccgggcacta catcacagtt ggtccgcgtc gtgagcacca actacaacca gcatgccatg      360
gtgttcttca agattgtgag gcagaaccgc gagattttt ggatcacact gtacgggcgc       420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 100
<211> LENGTH: 534
<212> TYPE: DNA
<213> ORGANISM: Artificial Sequence
<220> FEATURE:
<223> OTHER INFORMATION: S0474.01H22_N65Q

<400> SEQUENCE: 100

```
caggactcca cctcagacct gatcccagcc ccacctctga gcaaggtccc tctgcagcag      60
```

```
aacttccagg acaaccaatt ccatgggaaa tggtatgtcg tgggcgtggc cggaaatact    120
attctgcgtg aggataagga tccggggaaa atgaatgcaa ccatttacga gttgaaagaa    180
gataaatcat atcaggtcac cgatgtgagg tttattagga agaaatgcca ttactatatt    240
gatacctttg tgccggggag ccagccgggc gagtttactt taggcaatat taaaagttat    300
ccgggcacta catcacagtt ggtccgcgtc gtgagcacca actacaacca gcatgccatg    360
gtgttcttca agattgtgag gcagaaccgc gagatttttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 101
<211> LENGTH: 534
<212> TYPE: DNA
<213> ORGANISM: Artificial Sequence
<220> FEATURE:
<223> OTHER INFORMATION: S0466.14D07

<400> SEQUENCE: 101

```
caggactcca cctcagacct gatcccagcc ccacctctga gcaaggtccc tctgcagcag    60
aacttccagg acaaccaatt ccatgggaaa tggtatgtcg tgggcttcgc cggaaattgg    120
atgctgcgtg aggataagga tccgcacaaa atgaatgcga ccatttacga gttgaaagaa    180
gataaatcat ataacgtcac cgaggtgaaa tttcaagcaa agaaatgcat ctacagcatt    240
cacacctttg tgccggggag ccagccgggc gagtttactt taggcatcat taaaagtaat    300
ccgggcggaa catcagagtt ggtccgcgtc gtgagcacca actacaacca gcatgccatg    360
gtgttcttca gtgggtgca ccagaaccgc gagttctttc aaatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 102
<211> LENGTH: 534
<212> TYPE: DNA
<213> ORGANISM: Artificial Sequence
<220> FEATURE:
<223> OTHER INFORMATION: S0466.05N20

<400> SEQUENCE: 102

```
caggactcca cctcagacct gatcccagcc ccacctctga gcaaggtccc tctgcagcag    60
aacttccagg acaaccaatt ccatgggaaa tggtatgtcg tgggcttcgc cggaaatcgt    120
tggctgcgtg aggataagga tccgatcaaa atgtacgcga ccatttacga gttgaaagaa    180
gataaatcat ataacgtcac ccaagtgaat ttttggctga agaaatgcgc atacagcatt    240
agcacctttg tgccggggag ccagccgggc gagtttactt taggccgtat taaaagtatc    300
ccgggcccta catcagagtt ggtccgcgtc gtgagcacca actacaacca gcatgccatg    360
gtgttcttca agaccgtgat ccagaaccgc gagttctttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 103
<211> LENGTH: 534
<212> TYPE: DNA
<213> ORGANISM: Artificial Sequence
<220> FEATURE:

<223> OTHER INFORMATION: S0466.16B14

<400> SEQUENCE: 103

| | | | | | |
|---|---|---|---|---|---|
| caggactcca | cctcagacct | gatcccagcc | ccacctctga | gcaaggtccc | tctgcagcag | 60
| aacttccagg | acaaccaatt | ccatgggaaa | tggtatgtcg | tgggcttcgc | cggaaatctg | 120
| ctgctgcgtg | aggataagga | tccgcgtaaa | atgcgtgcga | ccatttacga | gttgaaagaa | 180
| gataaatcat | ataacgtcac | cgacgtgcgt | tttctgtaca | agaaatgcat | ctacagcatt | 240
| gcaacctttg | tgccggggag | ccagccgggc | gagtttactt | taggcggaat | taaaagtgca | 300
| ccgggcttca | catcagagtt | ggtccgcgtc | gtgagcacca | actacaacca | gcatgccatg | 360
| gtgttcttca | agtgggtggc | acagaaccgc | gagtactttg | agatcacact | gtacgggcgc | 420
| acgaaagaac | tgacaagcga | gctgaaggaa | aattttatcc | gcttttccaa | atctctgggc | 480
| ctccctgaaa | accacatcgt | cttccctgtc | ccaatcgacc | agtgtatcga | cggc | 534

<210> SEQ ID NO 104
<211> LENGTH: 534
<212> TYPE: DNA
<213> ORGANISM: Artificial Sequence
<220> FEATURE:
<223> OTHER INFORMATION: S0466.15E20

<400> SEQUENCE: 104

| | | | | | |
|---|---|---|---|---|---|
| caggactcca | cctcagacct | gatcccagcc | ccacctctga | gcaaggtccc | tctgcagcag | 60
| aacttccagg | acaaccaatt | ccatgggaaa | tggtatgtcg | tgggcttcgc | cggaaattgg | 120
| cgtctgcgtg | aggataagga | tccgcctaaa | atgagcgcga | ccatttacga | gttgaaagaa | 180
| gataaatcat | ataacgtcac | caatgtgcgt | ttttggccta | agaaatgccg | ttacagcatt | 240
| agcacctttg | tgccggggag | ccagccgggc | gagtttactt | taggcatgat | taaaagtcct | 300
| ccgggcggaa | catcagagtt | ggtccgcgtc | gtgagcacca | actacaacca | gcatgccatg | 360
| gtgttcttca | agtgggtgtt | ccagaaccgc | gagttctttg | agatcacact | gtacgggcgc | 420
| acgaaagaac | tgacaagcga | gctgaaggaa | aattttatcc | gcttttccaa | atctctgggc | 480
| ctccctgaaa | accacatcgt | cttccctgtc | ccaatcgacc | agtgtatcga | cggc | 534

<210> SEQ ID NO 105
<211> LENGTH: 534
<212> TYPE: DNA
<213> ORGANISM: Artificial Sequence
<220> FEATURE:
<223> OTHER INFORMATION: S0466.13C10

<400> SEQUENCE: 105

| | | | | | |
|---|---|---|---|---|---|
| caggactcca | cctcagacct | gatcccagcc | ccacctctga | gcaaggtccc | tctgcagcag | 60
| aacttccagg | acaaccaatt | ccatgggaaa | tggtatgtcg | tgggcgaggc | cggaaatctg | 120
| gcactgcgtg | aggataagga | tccgaaaaaa | atgatggcga | ccatttacga | gttgaaagaa | 180
| gataaatcat | ataacgtcac | cgaggtgcgt | tttcgtcaca | agaaatgcca | atacgacatt | 240
| gcaacctttg | tgccggggag | ccagccgggc | gagtttactt | taggcctgat | taaaagtgac | 300
| ccgggccaaa | catcagagtt | ggtccgcgtc | gtgagcacca | actacaacca | gcatgccatg | 360
| gtgttcttca | agaaagtggt | tcagaaccgc | gagttctttt | ggatcacact | gtacgggcgc | 420
| acgaaagaac | tgacaagcga | gctgaaggaa | aattttatcc | gcttttccaa | atctctgggc | 480
| ctccctgaaa | accacatcgt | cttccctgtc | ccaatcgacc | agtgtatcga | cggc | 534

<210> SEQ ID NO 106
<211> LENGTH: 534
<212> TYPE: DNA
<213> ORGANISM: Artificial Sequence
<220> FEATURE:
<223> OTHER INFORMATION: S0510.11H24

<400> SEQUENCE: 106

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggcgaggc | cggaaatctt | 120 |
| gctctgcgtg | aggataagga | tccgatgaaa | atgatggcga | ccatttacga | gttgaaagaa | 180 |
| gataaatcat | ataacgtcac | cgaggtgagg | tttaggcaga | agaaatgcaa | gtacgatatt | 240 |
| gttacctttg | tgccggggag | ccagccgggc | gagtttactt | taggccttat | taaaagtgat | 300 |
| ccgggccaga | catcagagtt | ggtccgcgtc | gtgagcacca | actacaacca | gcatgccatg | 360 |
| gtgttcttca | agaaggtggt | tcagaaccgc | gagtattttt | ggatcacact | gtacgggcgc | 420 |
| acgaaagaac | tgacaagcga | gctgaaggaa | aattttatcc | gctttccaa | atctctgggc | 480 |
| ctccctgaaa | accacatcgt | cttccctgtc | ccaatcgacc | agtgtatcga | cggc | 534 |

<210> SEQ ID NO 107
<211> LENGTH: 534
<212> TYPE: DNA
<213> ORGANISM: Artificial Sequence
<220> FEATURE:
<223> OTHER INFORMATION: S0512.01M12_X103Q

<400> SEQUENCE: 107

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggcgaggc | cggaaatctt | 120 |
| actctgcgtg | aggataagga | tccgatgaaa | atgatggcga | ccatttacga | gttgaaagaa | 180 |
| gataaatcat | ataacgtcac | cgaggtgagg | tttaggcgta | agaaatgcaa | gtacgatatt | 240 |
| gttacctttg | tgccggggag | ccagccgggc | gagtttactt | taggcgtgat | taaaagtgat | 300 |
| ccgggccaga | catcagagtt | ggtccgcgtc | gtgagcacca | actacaacca | gcatgccatg | 360 |
| gtgttcttca | agaaggtggt | tcagaaccgc | gagtattttt | ggatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 108
<211> LENGTH: 534
<212> TYPE: DNA
<213> ORGANISM: Artificial Sequence
<220> FEATURE:
<223> OTHER INFORMATION: S0512.01F10_X103Q

<400> SEQUENCE: 108

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggcgaggc | cggaaatctt | 120 |
| gctctgcgtg | aggataagga | tccgatgaaa | atgatggcga | ccatttacga | gttgaaagaa | 180 |
| gataaatcat | ataacgtcac | cgaggtgagg | tttaggcata | agaaatgcaa | gtacgatatt | 240 |
| gttacctttg | tgccggggag | ccagccgggc | gagtttactt | taggccttat | taaaagtgat | 300 |
| ccgggccaga | catcagagtt | ggtccgcgtc | gtgagcacca | actacaacca | gcatgccatg | 360 |
| gtgttcttca | agaaggtggt | tcagaaccgc | gagtattttt | ggatcacact | gtacgggcgc | 420 |

```
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 109
<211> LENGTH: 522
<212> TYPE: DNA
<213> ORGANISM: Artificial Sequence
<220> FEATURE:
<223> OTHER INFORMATION: S0510.10A04_X103Q
<400> SEQUENCE: 109

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
gctctgcgtg aggataagga tccgaagaaa atgatggcga ccatttacga gttgaaagaa    180
gataaatcat ataacgtcac cgaggtgagg tttcggtata agaaatgcca gtacgatatt    240
gttacctttg tgccggggag ccagccgggc gagtttactt taagtgagcc gggccagaca    300
tcagagttgg tccgcgtcgt gagcaccaac tacaaccagc atgccatggt gttcttcaag    360
aaggtggtgc agaaccgcga gtttttttgg atcacactgt acgggcgcac gaaagaactg    420
acaagcgagc tgaaggaaaa ttttatccgc ttttccaaat ctctgggcct ccctgaaaac    480
cacatcgtct ccctgtccc aatcgaccag tgtatcgacg gc                       522
```

<210> SEQ ID NO 110
<211> LENGTH: 534
<212> TYPE: DNA
<213> ORGANISM: Artificial Sequence
<220> FEATURE:
<223> OTHER INFORMATION: S0530.07G09

<400> SEQUENCE: 110

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
gctcggcgtg aggataagga tccgatgaaa atgatggcga ccatttacga gttgaaagaa    180
gataaatcat ataacgtcac cgaggtgagg tttaggcata agaaatgcaa gtacgatatt    240
gttacctttg tgccggggag ccagccgggc gagtttactt taggccttat taaaagtgat    300
ccgggccaga caccagagtt ggtccgcgtc gtgagcacca actacaacca gcatgccatg    360
gtgttcttca agaaggtggt ccagaaccgc gagtattttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 111
<211> LENGTH: 534
<212> TYPE: DNA
<213> ORGANISM: Artificial Sequence
<220> FEATURE:
<223> OTHER INFORMATION: S0530.07K20

<400> SEQUENCE: 111

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
gctctgcgtg aggataagaa tccgatgaaa atgatggcga ccatttacga gttgaaagaa    180
gataaatcat ataacgtcac cgaggtgagg tttaggcata agaaatgcaa gtacgatatt    240
gttaccttcg tgccggggag ccagccgggc gagtttactt taggccttat taaaagtgat    300
```

```
ccgggccaga cgccagagtt ggtccgcgtc gtgagcacca actacaacca gcatgccatg    360
gtgttcttca agaaggtggt tcagaaccgc gagtattttt ggatcacact gtacgggcgc    420
acgaaagaac tgccaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 112
<211> LENGTH: 534
<212> TYPE: DNA
<213> ORGANISM: Artificial Sequence
<220> FEATURE:
<223> OTHER INFORMATION: S0530.07K21

<400> SEQUENCE: 112

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
gctctgcgtg agggtaggga tccgatgaaa atgatggcga ccatttacga gttgaaagaa    180
gataaatcat ataacgtcac cgaggtgagg tttaggcata agaaatgcaa gtacgatatt    240
gttacctttg tgccggggag ccagccgggc gagtttactt taggccttat taaaagtgat    300
ccgggccaga caccagagtt ggtccgcgtc gtgagcacca actacaacca gcatgccatg    360
gtgttcttca agaaggtggt tcagaaccgc gagtattttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 113
<211> LENGTH: 534
<212> TYPE: DNA
<213> ORGANISM: Artificial Sequence
<220> FEATURE:
<223> OTHER INFORMATION: S0530.07G09_N65D

<400> SEQUENCE: 113

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
gctcggcgtg aggataagga tccgatgaaa atgatggcga ccatttacga gttgaaagaa    180
gataaatcat atgacgtcac cgaggtgagg tttaggcata agaaatgcaa gtacgatatt    240
gttacctttg tgccggggag ccagccgggc gagtttactt taggccttat taaaagtgat    300
ccgggccaga caccagagtt ggtccgcgtc gtgagcacca actacaacca gcatgccatg    360
gtgttcttca agaaggtggt ccagaaccgc gagtattttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 114
<211> LENGTH: 534
<212> TYPE: DNA
<213> ORGANISM: Artificial Sequence
<220> FEATURE:
<223> OTHER INFORMATION: S0530.07K20_N65D

<400> SEQUENCE: 114

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
```

```
gctctgcgtg aggataagaa tccgatgaaa atgatggcga ccatttacga gttgaaagaa      180
gataaatcat atgacgtcac cgaggtgagg tttaggcata agaaatgcaa gtacgatatt      240
gttaccttcg tgccggggag ccagccgggc gagtttactt taggccttat taaaagtgat     300
ccgggccaga cgccagagtt ggtccgcgtc gtgagcacca actacaacca gcatgccatg      360
gtgttcttca agaaggtggt tcagaaccgc gagtattttt ggatcacact gtacgggcgc      420
acgaaagaac tgccaagcga gctgaaggaa aattttatcc gcttttccaa atctctgggc      480
ctccctgaaa accacatcgt cttccctgtc ccaatcgacc agtgtatcga cggc            534

<210> SEQ ID NO 115
<211> LENGTH: 534
<212> TYPE: DNA
<213> ORGANISM: Artificial Sequence
<220> FEATURE:
<223> OTHER INFORMATION: S0530.07K21_N65D

<400> SEQUENCE: 115
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
gctctgcgtg agggtaggga tccgatgaaa atgatggcga ccatttacga gttgaaagaa    180
gataaatcat atgacgtcac cgaggtgagg tttaggcata agaaatgcaa gtacgatatt      240
gttacctttg tgccggggag ccagccgggc gagtttactt taggccttat taaaagtgat     300
ccgggccaga caccagagtt ggtccgcgtc gtgagcacca actacaacca gcatgccatg      360
gtgttcttca agaaggtggt tcagaaccgc gagtattttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 116
<211> LENGTH: 534
<212> TYPE: DNA
<213> ORGANISM: Artificial Sequence
<220> FEATURE:
<223> OTHER INFORMATION: S0530.07G09_H28Q_N65D

<400> SEQUENCE: 116
caggactcca cctcagacct gatcccagcc ccacctctga gcaaggtccc tctgcagcag      60
aacttccagg acaaccaatt ccaagggaaa tggtatgtcg tgggcgaggc cggaaatctt     120
gctcggcgtg aggataagga tccgatgaaa atgatggcga ccatttacga gttgaaagaa    180
gataaatcat atgacgtcac cgaggtgagg tttaggcata agaaatgcaa gtacgatatt      240
gttacctttg tgccggggag ccagccgggc gagtttactt taggccttat taaaagtgat     300
ccgggccaga caccagagtt ggtccgcgtc gtgagcacca actacaacca gcatgccatg      360
gtgttcttca agaaggtggt ccagaaccgc gagtattttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 117
<211> LENGTH: 534
<212> TYPE: DNA
<213> ORGANISM: Artificial Sequence
<220> FEATURE:
<223> OTHER INFORMATION: S0455.04F12

<400> SEQUENCE: 117
```

```
caggactcca cctcagacct gatcccagcc ccacctctga gcaaggtccc tctgcagcag    60
aacttccagg acaaccaatt ccatgggaaa tggtatgtcg tgggcctggc cggaaatatc   120
ctgctgcgtg aggataagga tccgcacaaa atgctggcga ccatttacga gttgaaagaa   180
gataaatcat ataacgtcac ccacgtgacc tttaaatgga gaaatgcta ctacgcaatt   240 cgtacctttg tgccggggag ccagccgggc gagtttactt taggcatgat taaaagtgag   300
ccgggccaca catcaatgtt ggtccgcgtc gtgagcacca actacaacca gcatgccatg   360
gtgttcttca agtgggtgga ccagaaccgc gaggagtttc tgatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 118
<211> LENGTH: 534
<212> TYPE: DNA
<213> ORGANISM: Artificial Sequence
<220> FEATURE:
<223> OTHER INFORMATION: S0455.04F23

<400> SEQUENCE: 118

```
caggactcca cctcagacct gatcccagcc ccacctctga gcaaggtccc tctgcagcag    60
aacttccagg acaaccaatt ccatgggaaa tggtatgtcg tgggccacgc cggaaatcaa   120
tggctgcgtg aggataagga tccgcgtaaa atgtgggcga ccatttacga gttgaaagaa   180
gataaatcat ataacgtcac cgacgtggac tttgcaatca agaaatgcca ctaccgtatt   240
accacctttg tgccggggag ccagccgggc gagtttactt taggcaatat taaaagtcac   300
ccgggcggaa catcaggatt ggtccgcgtc gtgagcacca actacaacca gcatgccatg   360
gtgttcttca agttcgtgat ccagaaccgc gaggcatttt tcatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 119
<211> LENGTH: 534
<212> TYPE: DNA
<213> ORGANISM: Artificial Sequence
<220> FEATURE:
<223> OTHER INFORMATION: S0455.04F09

<400> SEQUENCE: 119

```
caggactcca cctcagacct gatcccagcc ccacctctga gcaaggtccc tctgcagcag    60
aacttccagg acaaccaatt ccatgggaaa tggtatgtcg tgggcatggc cggaaatttc   120
cacctgcgtg aggataagga tccgagcaaa atgcctgcga ccatttacga gttgaaagaa   180
gataaatcat ataacgtcac ccacgtgcct ttttgggcaa agaaatgcgc atacaaaatt   240
atcacctttg tgccggggag ccagccgggc gagtttactt taggcgcaat taaaagtgga   300
ccgggcatga catcatggtt ggtccgcgtc gtgagcacca actacaacca gcatgccatg   360
gtgttcttca agggagtgtg gcagaaccgc gagacctttg ttatcacact gtacgggcgc   420
acgaaagaac tgcaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 120
<211> LENGTH: 534
<212> TYPE: DNA

<213> ORGANISM: Artificial Sequence
<220> FEATURE:
<223> OTHER INFORMATION: S0455.04M08

<400> SEQUENCE: 120

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggcgttgc | cggaaattac | 120 |
| tggctgcgtg | aggataagga | tccggcaaaa | atgtacgcga | ccatttacga | gttgaaagaa | 180 |
| gataaatcat | ataacgtcac | cgacgtgcgt | ttttggcgta | agaaatgccg | ttacgacatt | 240 |
| tggacctttg | tgccggggag | ccagccgggc | gagtttactt | taggccctat | taaaagtgag | 300 |
| ccgggccaaa | catcacggtt | ggtccgcgtc | gtgagcacca | actacaacca | gcatgccatg | 360 |
| gtgttcttca | agctggtgcg | tcagaaccgc | gaggcattta | atatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 121
<211> LENGTH: 534
<212> TYPE: DNA
<213> ORGANISM: Artificial Sequence
<220> FEATURE:
<223> OTHER INFORMATION: S0522.15K24

<400> SEQUENCE: 121

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcc | tgggcatggc | cggaaatttc | 120 |
| cacctgcgtg | aggataagga | tccgagcaag | atgcctgcga | ccatttacga | gttgaaagaa | 180 |
| gataaatcat | ataacgtcac | ccacgtgcct | ttttgggcaa | agaaatgcgc | atacaaaact | 240 |
| atcacctttg | tgccggggag | ccagccgggc | gagtttactt | taggcgcaat | taaaagtgga | 300 |
| ccgggcatga | catcatggtt | ggtccgcgtc | gtgagcacca | actacaacca | gcatgccatg | 360 |
| gtgttctcca | agggagtgtg | gcagaaccgc | gagacctttg | ttatcacact | gtacgggcgc | 420 |
| gcgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 122
<211> LENGTH: 534
<212> TYPE: DNA
<213> ORGANISM: Artificial Sequence
<220> FEATURE:
<223> OTHER INFORMATION: S0527.05N11

<400> SEQUENCE: 122

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggcatggc | cggaaatttc | 120 |
| cacctgcgtg | aggataagga | tccgagcaaa | atgcctgcga | ccatttacga | gttgaaagaa | 180 |
| gataaatcat | ataacgtcac | ccacgtgcct | ttttgggcaa | agaaatgcgc | atacaaaact | 240 |
| atcacctttg | tgccggggag | ccagccgggc | gagtttactt | taggcgcaat | taaaagtgga | 300 |
| ccgggcatga | catcatggtt | ggtccgcgtc | gtgagcacca | actacaacca | gcatgccatg | 360 |
| gtgttctcca | agggagtgtg | gcagaaccgt | gagacctttg | ttatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 123
<211> LENGTH: 534
<212> TYPE: DNA
<213> ORGANISM: Artificial Sequence
<220> FEATURE:
<223> OTHER INFORMATION: S0522.05A05

<400> SEQUENCE: 123

```
caggactcca cctcagacct gatcccagcc ccacctctga gcaaggtccc tctgcagcag      60
aacttccagg acaaccaatt ccatgggaaa tggtatgtcg tgggccacgc cggaaatcaa     120
tggctgcgtg agggtaggga tccgcgtaaa atgtgggcga ccatttacga gttgaaagaa     180
gataaatcat ataacgtcac cgacgtggac tttgcaatca agaaatgcct ctaccgtatt     240
accacctttg tgccagggag ccagccgggc gagtttactt taggcaatat taaaagtcac     300
ccgggcggaa catcaggatt ggtccgcgtc gtgagcacca actacaacca gcatgccatg     360
gtgttcttca agttcgtgat ccagaaccgc gaggcatttt tcatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 124
<211> LENGTH: 534
<212> TYPE: DNA
<213> ORGANISM: Artificial Sequence
<220> FEATURE:
<223> OTHER INFORMATION: S0522.05M06

<400> SEQUENCE: 124

```
caggactcca cctcagacct gatcccagcc ccacctctga gcaaggtccc tctgcagcag      60
aacttccagg acaaccaatt ccatgggaaa tggtatgtcg tgggccacgc cggaaatcaa     120
tggctgcgtg gggattacga tccgcgtaaa atgtgggcga ccatttacga gttgaaagaa     180
gataaatcat ataacgtcac cgacgtggac tttgcaatcg agaaatgcca ctaccgtatt     240
accacctttg tgccggggag ccagccgggc gagtttactt ttggcaatat aaaaagtcac     300
ccgggcggaa catcaggatt ggcccgcgtc gtgagcacca actacaacca gcatgccatg     360
gtgttcttca agttcgtgat ccagaaccgc gaggcatttt tcatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 125
<211> LENGTH: 534
<212> TYPE: DNA
<213> ORGANISM: Artificial Sequence
<220> FEATURE:
<223> OTHER INFORMATION: S0522.05A05_H28Q_N65D

<400> SEQUENCE: 125

```
caggactcca cctcagacct gatcccagcc ccacctctga gcaaggtccc tctgcagcag      60
aacttccagg acaaccaatt ccaagggaaa tggtatgtcg tgggccacgc cggaaatcaa     120
tggctgcgtg agggtaggga tccgcgtaaa atgtgggcga ccatttacga gttgaaagaa     180
gataaatcat atgacgtcac cgacgtggac tttgcaatca agaaatgcct ctaccgtatt     240
accacctttg tgccagggag ccagccgggc gagtttactt taggcaatat taaaagtcac     300
ccgggcggaa catcaggatt ggtccgcgtc gtgagcacca actacaacca gcatgccatg     360
```

```
gtgttcttca agttcgtgat ccagaaccgc gaggcatttt tcatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 126
<211> LENGTH: 534
<212> TYPE: DNA
<213> ORGANISM: Artificial Sequence
<220> FEATURE:
<223> OTHER INFORMATION: S0522.05M06_N65D

<400> SEQUENCE: 126

```
caggactcca cctcagacct gatcccagcc ccacctctga gcaaggtccc tctgcagcag    60
aacttccagg acaaccaatt ccatgggaaa tggtatgtcg tgggccacgc cggaaatcaa    120
tggctgcgtg gggattacga tccgcgtaaa atgtgggcga ccatttacga gttgaaagaa    180
gataaatcat atgacgtcac cgacgtggac tttgcaatcg agaaatgcca ctaccgtatt    240
accacctttg tgccggggag ccagccgggc gagtttactt ttggcaatat aaaaagtcac    300
ccgggcggaa catcaggatt ggcccgcgtc gtgagcacca actacaacca gcatgccatg    360
gtgttcttca agttcgtgat ccagaaccgc gaggcatttt tcatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 127
<211> LENGTH: 10
<212> TYPE: PRT
<213> ORGANISM: Artificial Sequence
<220> FEATURE:
<223> OTHER INFORMATION: C-terminal sequence of muteins

<400> SEQUENCE: 127

Ser Ala Trp Ser His Pro Gln Phe Glu Lys
1               5                   10

<210> SEQ ID NO 128
<211> LENGTH: 8
<212> TYPE: PRT
<213> ORGANISM: Artificial Sequence
<220> FEATURE:
<223> OTHER INFORMATION: SA linker and the Strep Tag II

<400> SEQUENCE: 128

Trp Ser His Pro Gln Phe Glu Lys
1               5

<210> SEQ ID NO 129
<211> LENGTH: 200
<212> TYPE: PRT
<213> ORGANISM: Artificial Sequence
<220> FEATURE:
<223> OTHER INFORMATION: Expressed protein amino acid sequence

<400> SEQUENCE: 129

Met Lys His His His His His His Asp Tyr Asp Ile Pro Thr Thr Glu
1               5                   10                  15

Asn Leu Tyr Phe Gln Gly Gln Asp Ser Thr Ser Asp Leu Ile Pro Ala
            20                  25                  30

Pro Pro Leu Ser Lys Val Pro Leu Gln Gln Asn Phe Gln Asp Asn Gln
        35                  40                  45

```
Phe His Gly Lys Trp Tyr Val Val Gly Val Ala Gly Asn Thr Ile Leu
 50                  55                  60

Arg Glu Asp Lys Asp Pro Gly Lys Met Asn Ala Thr Ile Tyr Glu Leu
 65                  70                  75                  80

Lys Glu Asp Lys Ser Tyr Asn Val Thr Asp Val Arg Phe Ile Arg Lys
                 85                  90                  95

Lys Cys His Tyr Tyr Ile Asp Thr Phe Val Pro Gly Ser Gln Pro Gly
            100                 105                 110

Glu Phe Thr Leu Gly Asn Ile Lys Ser Tyr Pro Gly Thr Thr Ser Gln
        115                 120                 125

Leu Val Arg Val Val Ser Thr Asn Tyr Asn Gln His Ala Met Val Phe
130                 135                 140

Phe Lys Ile Val Arg Gln Asn Arg Glu Ile Phe Trp Ile Thr Leu Tyr
145                 150                 155                 160

Gly Arg Thr Lys Glu Leu Thr Ser Glu Leu Lys Glu Asn Phe Ile Arg
                165                 170                 175

Phe Ser Lys Ser Leu Gly Leu Pro Glu Asn His Ile Val Phe Pro Val
            180                 185                 190

Pro Ile Asp Gln Cys Ile Asp Gly
        195                 200

<210> SEQ ID NO 130
<211> LENGTH: 4
<212> TYPE: PRT
<213> ORGANISM: Artificial Sequence
<220> FEATURE:
<223> OTHER INFORMATION: positions 95-98

<400> SEQUENCE: 130

Gly Asn Ile Lys
1

<210> SEQ ID NO 131
<211> LENGTH: 6
<212> TYPE: PRT
<213> ORGANISM: Artificial Sequence
<220> FEATURE:
<223> OTHER INFORMATION: examples of albumin binding peptides
<220> FEATURE:
<221> NAME/KEY: MISC_FEATURE
<222> LOCATION: (2)..(2)
<223> OTHER INFORMATION: Xaa can be any of Asp, Asn, Ser, Thr, or Trp
<220> FEATURE:
<221> NAME/KEY: MISC_FEATURE
<222> LOCATION: (3)..(3)
<223> OTHER INFORMATION: Xaa can be any of Asn, Gln, His, Ile, Leu, or
      Lys
<220> FEATURE:
<221> NAME/KEY: MISC_FEATURE
<222> LOCATION: (4)..(4)
<223> OTHER INFORMATION: Xaa can be any of Ala, Asp, Phe, Trp, or Tyr
<220> FEATURE:
<221> NAME/KEY: MISC_FEATURE
<222> LOCATION: (5)..(5)
<223> OTHER INFORMATION: Xaa can be any of Asp, Gly, Leu, Phe, Ser, or
      Thr

<400> SEQUENCE: 131

Cys Xaa Xaa Xaa Xaa Cys
1               5

<210> SEQ ID NO 132
<211> LENGTH: 7
<212> TYPE: PRT
<213> ORGANISM: Artificial Sequence
```

```
<220> FEATURE:
<223> OTHER INFORMATION: Linker

<400> SEQUENCE: 132

Asp Tyr Asp Ile Pro Thr Thr
1               5

<210> SEQ ID NO 133
<211> LENGTH: 7
<212> TYPE: PRT
<213> ORGANISM: Artificial Sequence
<220> FEATURE:
<223> OTHER INFORMATION: protease cleavage site

<400> SEQUENCE: 133

Glu Asn Leu Tyr Phe Gln Gly
1               5

<210> SEQ ID NO 134
<211> LENGTH: 742
<212> TYPE: PRT
<213> ORGANISM: Artificial Sequence
<220> FEATURE:
<223> OTHER INFORMATION: S0474.01H22_H28Q_T54A_N65D_(G4S)2S0544.04C04_
      H28Q_N65D_(G4S)2S0530.07G09_H28Q_N65D_(G4S)2 S0522.05A05_H28Q_N65D

<400> SEQUENCE: 134

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205

Asn Phe Gln Asp Asn Gln Phe Gln Gly Lys Trp Tyr Val Val Gly Trp
    210                 215                 220

Ala Gly Asn Thr Ala Leu Arg Glu Asp Lys Asp Pro Lys Met Pro
225                 230                 235                 240

Ala Val Ile Tyr Glu Leu Lys Glu Asp Lys Ser Tyr Asp Val Thr Asp
                245                 250                 255
```

```
Val Gln Phe Pro Glu Lys Glu Cys Ile Tyr Ser Thr Ile Thr Phe Val
            260                 265                 270

Pro Gly Ser Gln Pro Gly Phe Thr Leu Gly Gly Ile Lys Ser Ser
        275                 280                 285

Pro Gly Gln Thr Ser His Leu Val Arg Val Ser Thr Asn Tyr Asn
290                 295                 300

Gln His Ala Met Val Phe Phe Lys Tyr Val Thr Gln Asn Arg Glu Gly
305                 310                 315                 320

Phe Asn Ile Ala Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
                340                 345                 350

His Ile Val Phe Pro Val Pro Ile Asp Gln Cys Ile Asp Gly Gly Gly
                355                 360                 365

Gly Gly Ser Gly Gly Gly Ser Gln Asp Ser Thr Ser Asp Leu Ile
        370                 375                 380

Pro Ala Pro Pro Leu Ser Lys Val Pro Leu Gln Gln Asn Phe Gln Asp
385                 390                 395                 400

Asn Gln Phe Gln Gly Lys Trp Tyr Val Val Gly Glu Ala Gly Asn Leu
                405                 410                 415

Ala Arg Arg Glu Asp Lys Asp Pro Met Lys Met Met Ala Thr Ile Tyr
                420                 425                 430

Glu Leu Lys Glu Asp Lys Ser Tyr Asp Val Thr Glu Val Arg Phe Arg
                435                 440                 445

His Lys Lys Cys Lys Tyr Asp Ile Val Thr Phe Val Pro Gly Ser Gln
                450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
                500                 505                 510

Leu Tyr Gly Arg Thr Lys Glu Leu Thr Ser Glu Leu Lys Glu Asn Phe
                515                 520                 525

Ile Arg Phe Ser Lys Ser Leu Gly Leu Pro Glu Asn His Ile Val Phe
                530                 535                 540

Pro Val Pro Ile Asp Gln Cys Ile Asp Gly Gly Gly Gly Ser Gly
545                 550                 555                 560

Gly Gly Ser Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe Gln
                580                 585                 590

Gly Lys Trp Tyr Val Val Gly His Ala Gly Asn Gln Trp Leu Arg Glu
                595                 600                 605

Gly Arg Asp Pro Arg Lys Met Trp Ala Thr Ile Tyr Glu Leu Lys Glu
                610                 615                 620

Asp Lys Ser Tyr Asp Val Thr Asp Val Asp Phe Ala Ile Lys Lys Cys
625                 630                 635                 640

Leu Tyr Arg Ile Thr Thr Phe Val Pro Gly Ser Gln Pro Gly Glu Phe
                645                 650                 655

Thr Leu Gly Asn Ile Lys Ser His Pro Gly Thr Ser Gly Leu Val
                660                 665                 670
```

```
Arg Val Val Ser Thr Asn Tyr Asn Gln His Ala Met Val Phe Phe Lys
            675                 680                 685

Phe Val Ile Gln Asn Arg Glu Ala Phe Phe Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly
            740

<210> SEQ ID NO 135
<211> LENGTH: 742
<212> TYPE: PRT
<213> ORGANISM: Artificial Sequence
<220> FEATURE:
<223> OTHER INFORMATION: S0474.01H22_T54A_N65D_(G4S)2S0530.04N16_N65D_
      (G4S)2S0530.07G09_N65D_(G4S)2 S0522.05M06_N65D

<400> SEQUENCE: 135

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gln Asp Ser Thr
            180                 185                 190

Ser Asp Leu Ile Pro Ala Pro Pro Leu Ser Lys Val Pro Leu Gln Gln
            195                 200                 205

Asn Phe Gln Asp Asn Gln Phe His Gly Lys Trp Tyr Val Val Gly Leu
    210                 215                 220

Ala Gly Asn Gly Trp Leu Arg Glu Asp Glu Asp Pro Leu Lys Met Met
225                 230                 235                 240

Ala Ala Val Tyr Glu Leu Arg Glu Asp Lys Ser Tyr Asp Val Thr Val
                245                 250                 255

Val Asp Phe Glu Leu Glu Glu Cys Arg Tyr Met Thr Glu Thr Phe Val
            260                 265                 270

Pro Gly Asn Gln Pro Gly Glu Phe Thr Leu Gly Asp Ile Lys Ser Ser
        275                 280                 285
```

```
Pro Gly Trp Thr Ser Gln Leu Val Arg Val Ser Thr Asn Tyr Asn
    290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
                340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
        370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
                405                 410                 415

Ala Arg Arg Glu Asp Lys Asp Pro Met Lys Met Met Ala Thr Ile Tyr
                420                 425                 430

Glu Leu Lys Glu Asp Lys Ser Tyr Asp Val Thr Glu Val Arg Phe Arg
            435                 440                 445

His Lys Lys Cys Lys Tyr Asp Ile Val Thr Phe Val Pro Gly Ser Gln
        450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
                500                 505                 510

Leu Tyr Gly Arg Thr Lys Glu Leu Thr Ser Glu Leu Lys Glu Asn Phe
            515                 520                 525

Ile Arg Phe Ser Lys Ser Leu Gly Leu Pro Glu Asn His Ile Val Phe
        530                 535                 540

Pro Val Pro Ile Asp Gln Cys Ile Asp Gly Gly Gly Gly Gly Ser Gly
545                 550                 555                 560

Gly Gly Ser Gln Asp Ser Thr Ser Asp Leu Ile Pro Ala Pro Pro
            565                 570                 575

Leu Ser Lys Val Pro Leu Gln Gln Asn Phe Gln Asp Asn Gln Phe His
            580                 585                 590

Gly Lys Trp Tyr Val Val Gly His Ala Gly Asn Gln Trp Leu Arg Gly
        595                 600                 605

Asp Tyr Asp Pro Arg Lys Met Trp Ala Thr Ile Tyr Glu Leu Lys Glu
610                 615                 620

Asp Lys Ser Tyr Asp Val Thr Asp Val Asp Phe Ala Ile Glu Lys Cys
625                 630                 635                 640

His Tyr Arg Ile Thr Thr Phe Val Pro Gly Ser Gln Pro Gly Glu Phe
            645                 650                 655

Thr Phe Gly Asn Ile Lys Ser His Pro Gly Gly Thr Ser Gly Leu Ala
            660                 665                 670

Arg Val Val Ser Thr Asn Tyr Asn Gln His Ala Met Val Phe Phe Lys
        675                 680                 685

Phe Val Ile Gln Asn Arg Glu Ala Phe Phe Ile Thr Leu Tyr Gly Arg
        690                 695                 700
```

```
Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
            725                 730                 735

Asp Gln Cys Ile Asp Gly
            740
```

<210> SEQ ID NO 136
<211> LENGTH: 980
<212> TYPE: PRT
<213> ORGANISM: Artificial Sequence
<220> FEATURE:
<223> OTHER INFORMATION: S0474.01H22_H28Q_T54A_N65D(G4S)2S0544.04C04_
      H28Q_N65D(G4S)2S0530.07G09_H28Q_N65D_(G4S)2 S0522.05A05_H28Q_N65D_
      (G4S)2huIgG4Fc

<400> SEQUENCE: 136

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205

Asn Phe Gln Asp Asn Gln Phe Gln Gly Lys Trp Tyr Val Val Gly Trp
    210                 215                 220

Ala Gly Asn Thr Ala Leu Arg Glu Asp Lys Asp Pro Lys Met Pro
225                 230                 235                 240

Ala Val Ile Tyr Glu Leu Lys Glu Asp Lys Ser Tyr Asp Val Thr Asp
                245                 250                 255

Val Gln Phe Pro Glu Lys Glu Cys Ile Tyr Ser Thr Ile Thr Phe Val
            260                 265                 270

Pro Gly Ser Gln Pro Gly Glu Phe Thr Leu Gly Ile Lys Ser Ser
        275                 280                 285

Pro Gly Gln Thr Ser His Leu Val Arg Val Val Ser Thr Asn Tyr Asn
    290                 295                 300

Gln His Ala Met Val Phe Phe Lys Tyr Val Thr Gln Asn Arg Glu Gly
```

```
                305                 310                 315                 320
            Phe Asn Ile Ala Leu Tyr Gly Arg Thr Lys Glu Leu Thr Ser Glu Leu
                            325                 330                 335

Lys Glu Asn Phe Ile Arg Phe Ser Lys Ser Leu Gly Leu Pro Glu Asn
                            340                 345                 350

His Ile Val Phe Pro Val Pro Ile Asp Gln Cys Ile Asp Gly Gly Gly
                            355                 360                 365

Gly Gly Ser Gly Gly Gly Ser Gln Asp Ser Thr Ser Asp Leu Ile
                370                 375                 380

Pro Ala Pro Pro Leu Ser Lys Val Pro Leu Gln Gln Asn Phe Gln Asp
            385                 390                 395                 400

Asn Gln Phe Gln Gly Lys Trp Tyr Val Val Gly Ala Gly Asn Leu
                            405                 410                 415

Ala Arg Arg Glu Asp Lys Asp Pro Met Lys Met Met Ala Thr Ile Tyr
                            420                 425                 430

Glu Leu Lys Glu Asp Lys Ser Tyr Asp Val Thr Glu Val Arg Phe Arg
                            435                 440                 445

His Lys Lys Cys Lys Tyr Asp Ile Val Thr Phe Val Pro Gly Ser Gln
                            450                 455                 460

Pro Gly Glu Phe Thr Leu Gly Leu Ile Lys Ser Asp Pro Gly Gln Thr
            465                 470                 475                 480

Pro Glu Leu Val Arg Val Val Ser Thr Asn Tyr Asn Gln His Ala Met
                            485                 490                 495

Val Phe Phe Lys Lys Val Val Gln Asn Arg Glu Tyr Phe Trp Ile Thr
                            500                 505                 510

Leu Tyr Gly Arg Thr Lys Glu Leu Thr Ser Glu Leu Lys Glu Asn Phe
                            515                 520                 525

Ile Arg Phe Ser Lys Ser Leu Gly Leu Pro Glu Asn His Ile Val Phe
                            530                 535                 540

Pro Val Pro Ile Asp Gln Cys Ile Asp Gly Gly Gly Gly Ser Gly
            545                 550                 555                 560

Gly Gly Ser Gln Asp Ser Thr Ser Asp Leu Ile Pro Ala Pro Pro
                            565                 570                 575

Leu Ser Lys Val Pro Leu Gln Gln Asn Phe Gln Asp Asn Gln Phe Gln
                            580                 585                 590

Gly Lys Trp Tyr Val Val Gly His Ala Gly Asn Gln Trp Leu Arg Glu
                            595                 600                 605

Gly Arg Asp Pro Arg Lys Met Trp Ala Thr Ile Tyr Glu Leu Lys Glu
                            610                 615                 620

Asp Lys Ser Tyr Asp Val Thr Asp Val Asp Phe Ala Ile Lys Lys Cys
            625                 630                 635                 640

Leu Tyr Arg Ile Thr Thr Phe Val Pro Gly Ser Gln Pro Gly Glu Phe
                            645                 650                 655

Thr Leu Gly Asn Ile Lys Ser His Pro Gly Gly Thr Ser Gly Leu Val
                            660                 665                 670

Arg Val Val Ser Thr Asn Tyr Asn Gln His Ala Met Val Phe Phe Lys
                            675                 680                 685

Phe Val Ile Gln Asn Arg Glu Ala Phe Phe Ile Thr Leu Tyr Gly Arg
                            690                 695                 700

Thr Lys Glu Leu Thr Ser Glu Leu Lys Glu Asn Phe Ile Arg Phe Ser
            705                 710                 715                 720

Lys Ser Leu Gly Leu Pro Glu Asn His Ile Val Phe Pro Val Pro Ile
                            725                 730                 735
```

Asp Gln Cys Ile Asp Gly Gly Gly Gly Ser Gly Gly Gly Ser
                740                 745                 750

Glu Ser Lys Tyr Gly Pro Pro Cys Pro Pro Cys Pro Ala Pro Glu Phe
            755                 760                 765

Glu Gly Gly Pro Ser Val Phe Leu Phe Pro Pro Lys Pro Lys Asp Thr
770                 775                 780

Leu Met Ile Ser Arg Thr Pro Glu Val Thr Cys Val Val Val Asp Val
785                 790                 795                 800

Ser Gln Glu Asp Pro Glu Val Gln Phe Asn Trp Tyr Val Asp Gly Val
                805                 810                 815

Glu Val His Asn Ala Lys Thr Lys Pro Arg Glu Glu Gln Phe Asn Ser
            820                 825                 830

Thr Tyr Arg Val Val Ser Val Leu Thr Val Leu His Gln Asp Trp Leu
        835                 840                 845

Asn Gly Lys Glu Tyr Lys Cys Lys Val Ser Asn Lys Gly Leu Pro Ser
850                 855                 860

Ser Ile Glu Lys Thr Ile Ser Lys Ala Lys Gly Gln Pro Arg Glu Pro
865                 870                 875                 880

Gln Val Tyr Thr Leu Pro Pro Ser Gln Glu Glu Met Thr Lys Asn Gln
                885                 890                 895

Val Ser Leu Thr Cys Leu Val Lys Gly Phe Tyr Pro Ser Asp Ile Ala
            900                 905                 910

Val Glu Trp Glu Ser Asn Gly Gln Pro Glu Asn Asn Tyr Lys Thr Thr
        915                 920                 925

Pro Pro Val Leu Asp Ser Asp Gly Ser Phe Phe Leu Tyr Ser Arg Leu
930                 935                 940

Thr Val Asp Lys Ser Arg Trp Gln Glu Gly Asn Val Phe Ser Cys Ser
945                 950                 955                 960

Val Met His Glu Ala Leu His Asn His Tyr Thr Gln Lys Ser Leu Ser
                965                 970                 975

Leu Ser Leu Gly
            980

<210> SEQ ID NO 137
<211> LENGTH: 980
<212> TYPE: PRT
<213> ORGANISM: Artificial Sequence
<220> FEATURE:
<223> OTHER INFORMATION: S0474.01H22_T54A_N65D_(G4S)2 S0530.04N16_N65D_
      (G4S)2_S0530.07G09_N65D_(G4S)2_ S0522.05M06_N65D_(G4S)2_hIgG4Fc

<400> SEQUENCE: 137

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser

```
                100             105             110
Thr Asn Tyr Asn Gln His Ala Met Val Phe Lys Ile Val Arg Gln
            115             120             125
Asn Arg Glu Ile Phe Trp Ile Thr Leu Tyr Gly Arg Thr Lys Glu Leu
        130             135             140
Thr Ser Glu Leu Lys Glu Asn Phe Ile Arg Phe Ser Lys Ser Leu Gly
145             150             155             160
Leu Pro Glu Asn His Ile Val Phe Pro Val Pro Ile Asp Gln Cys Ile
            165             170             175
Asp Gly Gly Gly Gly Ser Gly Gly Gly Ser Gln Asp Ser Thr
        180             185             190
Ser Asp Leu Ile Pro Ala Pro Pro Leu Ser Lys Val Pro Leu Gln Gln
        195             200             205
Asn Phe Gln Asp Asn Gln Phe His Gly Lys Trp Tyr Val Val Gly Leu
        210             215             220
Ala Gly Asn Gly Trp Leu Arg Glu Asp Glu Asp Pro Leu Lys Met Met
225             230             235             240
Ala Ala Val Tyr Glu Leu Arg Glu Asp Lys Ser Tyr Asp Val Thr Val
            245             250             255
Val Asp Phe Glu Leu Glu Glu Cys Arg Tyr Met Thr Glu Thr Phe Val
            260             265             270
Pro Gly Asn Gln Pro Gly Glu Phe Thr Leu Gly Asp Ile Lys Ser Ser
        275             280             285
Pro Gly Trp Thr Ser Gln Leu Val Arg Val Val Ser Thr Asn Tyr Asn
        290             295             300
Gln His Ala Met Val Phe Lys Gly Val Tyr Gln Asn Arg Glu Trp
305             310             315             320
Phe His Ile Thr Leu Tyr Gly Arg Thr Lys Glu Leu Thr Ser Glu Leu
            325             330             335
Lys Glu Asn Phe Ile Arg Phe Ser Lys Ser Leu Gly Leu Pro Glu Asn
            340             345             350
His Ile Val Phe Pro Val Pro Ile Asp Gln Cys Ile Asp Gly Gly Gly
            355             360             365
Gly Gly Ser Gly Gly Gly Ser Gln Asp Ser Thr Ser Asp Leu Ile
        370             375             380
Pro Ala Pro Pro Leu Ser Lys Val Pro Leu Gln Gln Asn Phe Gln Asp
385             390             395             400
Asn Gln Phe His Gly Lys Trp Tyr Val Val Gly Glu Ala Gly Asn Leu
            405             410             415
Ala Arg Arg Glu Asp Lys Asp Pro Met Lys Met Met Ala Thr Ile Tyr
            420             425             430
Glu Leu Lys Glu Asp Lys Ser Tyr Asp Val Thr Glu Val Arg Phe Arg
            435             440             445
His Lys Lys Cys Lys Tyr Asp Ile Val Thr Phe Val Pro Gly Ser Gln
            450             455             460
Pro Gly Glu Phe Thr Leu Gly Leu Ile Lys Ser Asp Pro Gly Gln Thr
465             470             475             480
Pro Glu Leu Val Arg Val Val Ser Thr Asn Tyr Asn Gln His Ala Met
            485             490             495
Val Phe Phe Lys Lys Val Val Gln Asn Arg Glu Tyr Phe Trp Ile Thr
            500             505             510
Leu Tyr Gly Arg Thr Lys Glu Leu Thr Ser Glu Leu Lys Glu Asn Phe
        515             520             525
```

```
Ile Arg Phe Ser Lys Ser Leu Gly Leu Pro Glu Asn His Ile Val Phe
    530                 535                 540

Pro Val Pro Ile Asp Gln Cys Ile Asp Gly Gly Gly Gly Ser Gly
545                 550                 555                 560

Gly Gly Gly Ser Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe His
                580                 585                 590

Gly Lys Trp Tyr Val Val Gly His Ala Gly Asn Gln Trp Leu Arg Gly
                595                 600                 605

Asp Tyr Asp Pro Arg Lys Met Trp Ala Thr Ile Tyr Glu Leu Lys Glu
    610                 615                 620

Asp Lys Ser Tyr Asp Val Thr Asp Val Asp Phe Ala Ile Glu Lys Cys
625                 630                 635                 640

His Tyr Arg Ile Thr Thr Phe Val Pro Gly Ser Gln Pro Gly Glu Phe
                645                 650                 655

Thr Phe Gly Asn Ile Lys Ser His Pro Gly Gly Thr Ser Gly Leu Ala
                660                 665                 670

Arg Val Val Ser Thr Asn Tyr Asn Gln His Ala Met Val Phe Phe Lys
                675                 680                 685

Phe Val Ile Gln Asn Arg Glu Ala Phe Phe Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Gly Gly Gly Ser Gly Gly Gly Gly Ser
                740                 745                 750

Glu Ser Lys Tyr Gly Pro Pro Cys Pro Pro Cys Pro Ala Pro Glu Phe
                755                 760                 765

Glu Gly Gly Pro Ser Val Phe Leu Phe Pro Pro Lys Pro Lys Asp Thr
    770                 775                 780

Leu Met Ile Ser Arg Thr Pro Glu Val Thr Cys Val Val Val Asp Val
785                 790                 795                 800

Ser Gln Glu Asp Pro Glu Val Gln Phe Asn Trp Tyr Val Asp Gly Val
                805                 810                 815

Glu Val His Asn Ala Lys Thr Lys Pro Arg Glu Glu Gln Phe Asn Ser
                820                 825                 830

Thr Tyr Arg Val Val Ser Val Leu Thr Val Leu His Gln Asp Trp Leu
    835                 840                 845

Asn Gly Lys Glu Tyr Lys Cys Lys Val Ser Asn Lys Gly Leu Pro Ser
850                 855                 860

Ser Ile Glu Lys Thr Ile Ser Lys Ala Lys Gly Gln Pro Arg Glu Pro
865                 870                 875                 880

Gln Val Tyr Thr Leu Pro Pro Ser Gln Glu Glu Met Thr Lys Asn Gln
                885                 890                 895

Val Ser Leu Thr Cys Leu Val Lys Gly Phe Tyr Pro Ser Asp Ile Ala
                900                 905                 910

Val Glu Trp Glu Ser Asn Gly Gln Pro Glu Asn Asn Tyr Lys Thr Thr
                915                 920                 925

Pro Pro Val Leu Asp Ser Asp Gly Ser Phe Phe Leu Tyr Ser Arg Leu
930                 935                 940
```

```
Thr Val Asp Lys Ser Arg Trp Gln Glu Gly Asn Val Phe Ser Cys Ser
945                 950                 955                 960

Val Met His Glu Ala Leu His Asn His Tyr Thr Gln Lys Ser Leu Ser
            965                 970                 975

Leu Ser Leu Gly
        980
```

<210> SEQ ID NO 138
<211> LENGTH: 980
<212> TYPE: PRT
<213> ORGANISM: Artificial Sequence
<220> FEATURE:
<223> OTHER INFORMATION: hIgG4Fc_(G4S)2_S0474.01H22_T54A_N65D_
      (G4S)2S0530.04N16_N65D_(G4S)2_S0530.07G09_N65D_(G4S)2_
      S0522.05M06_N65D

<400> SEQUENCE: 138

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gln Asp
225                 230                 235                 240

Ser Thr Ser Asp Leu Ile Pro Ala Pro Pro Leu Ser Lys Val Pro Leu
                245                 250                 255

Gln Gln Asn Phe Gln Asp Asn Gln Phe His Gly Lys Trp Tyr Val Val
            260                 265                 270

Gly Val Ala Gly Asn Thr Ile Leu Arg Glu Asp Lys Asp Pro Gly Lys
        275                 280                 285

Met Asn Ala Ala Ile Tyr Glu Leu Lys Glu Asp Lys Ser Tyr Asp Val
    290                 295                 300

Thr Asp Val Arg Phe Ile Arg Lys Lys Cys His Tyr Tyr Ile Asp Thr
```

```
              305                 310                 315                 320
        Phe Val Pro Gly Ser Gln Pro Gly Glu Phe Thr Leu Gly Asn Ile Lys
                        325                 330                 335
        Ser Tyr Pro Gly Thr Thr Ser Gln Leu Val Arg Val Ser Thr Asn
                        340                 345                 350
        Tyr Asn Gln His Ala Met Val Phe Lys Ile Val Arg Gln Asn Arg
                        355                 360                 365
        Glu Ile Phe Trp Ile Thr Leu Tyr Gly Arg Thr Lys Glu Leu Thr Ser
        370                 375                 380
        Glu Leu Lys Glu Asn Phe Ile Arg Phe Ser Lys Ser Leu Gly Leu Pro
        385                 390                 395                 400
        Glu Asn His Ile Val Phe Pro Val Pro Ile Asp Gln Cys Ile Asp Gly
                        405                 410                 415
        Gly Gly Gly Gly Ser Gly Gly Gly Ser Gln Asp Ser Thr Ser Asp
                        420                 425                 430
        Leu Ile Pro Ala Pro Pro Leu Ser Lys Val Pro Leu Gln Gln Asn Phe
                        435                 440                 445
        Gln Asp Asn Gln Phe His Gly Lys Trp Tyr Val Val Gly Leu Ala Gly
                        450                 455                 460
        Asn Gly Trp Leu Arg Glu Asp Glu Asp Pro Leu Lys Met Met Ala Ala
        465                 470                 475                 480
        Val Tyr Glu Leu Arg Glu Asp Lys Ser Tyr Asp Val Thr Val Val Asp
                        485                 490                 495
        Phe Glu Leu Glu Glu Cys Arg Tyr Met Thr Glu Thr Phe Val Pro Gly
                        500                 505                 510
        Asn Gln Pro Gly Glu Phe Thr Leu Gly Asp Ile Lys Ser Ser Pro Gly
                        515                 520                 525
        Trp Thr Ser Gln Leu Val Arg Val Val Ser Thr Asn Tyr Asn Gln His
                        530                 535                 540
        Ala Met Val Phe Phe Lys Gly Val Tyr Gln Asn Arg Glu Trp Phe His
        545                 550                 555                 560
        Ile Thr Leu Tyr Gly Arg Thr Lys Glu Leu Thr Ser Glu Leu Lys Glu
                        565                 570                 575
        Asn Phe Ile Arg Phe Ser Lys Ser Leu Gly Leu Pro Glu Asn His Ile
                        580                 585                 590
        Val Phe Pro Val Pro Ile Asp Gln Cys Ile Asp Gly Gly Gly Gly Gly
                        595                 600                 605
        Ser Gly Gly Gly Gly Ser Gln Asp Ser Thr Ser Asp Leu Ile Pro Ala
        610                 615                 620
        Pro Pro Leu Ser Lys Val Pro Leu Gln Gln Asn Phe Gln Asp Asn Gln
        625                 630                 635                 640
        Phe His Gly Lys Trp Tyr Val Val Gly Glu Ala Gly Asn Leu Ala Arg
                        645                 650                 655
        Arg Glu Asp Lys Asp Pro Met Lys Met Met Ala Thr Ile Tyr Glu Leu
                        660                 665                 670
        Lys Glu Asp Lys Ser Tyr Asp Val Thr Glu Val Arg Phe Arg His Lys
                        675                 680                 685
        Lys Cys Lys Tyr Asp Ile Val Thr Phe Val Pro Gly Ser Gln Pro Gly
                        690                 695                 700
        Glu Phe Thr Leu Gly Leu Ile Lys Ser Asp Pro Gly Gln Thr Pro Glu
        705                 710                 715                 720
        Leu Val Arg Val Val Ser Thr Asn Tyr Asn Gln His Ala Met Val Phe
                        725                 730                 735
```

```
Phe Lys Lys Val Val Gln Asn Arg Glu Tyr Phe Trp Ile Thr Leu Tyr
             740                 745                 750

Gly Arg Thr Lys Glu Leu Thr Ser Glu Leu Lys Glu Asn Phe Ile Arg
         755                 760                 765

Phe Ser Lys Ser Leu Gly Leu Pro Glu Asn His Ile Val Phe Pro Val
     770                 775                 780

Pro Ile Asp Gln Cys Ile Asp Gly Gly Gly Gly Ser Gly Gly Gly Gly
785                 790                 795                 800

Gly Ser Gln Asp Ser Thr Ser Asp Leu Ile Pro Ala Pro Pro Leu Ser
             805                 810                 815

Lys Val Pro Leu Gln Gln Asn Phe Gln Asp Asn Gln Phe His Gly Lys
         820                 825                 830

Trp Tyr Val Val Gly His Ala Gly Asn Gln Trp Leu Arg Gly Asp Tyr
     835                 840                 845

Asp Pro Arg Lys Met Trp Ala Thr Ile Tyr Glu Leu Lys Glu Asp Lys
850                 855                 860

Ser Tyr Asp Val Thr Asp Val Asp Phe Ala Ile Glu Lys Cys His Tyr
865                 870                 875                 880

Arg Ile Thr Thr Phe Val Pro Gly Ser Gln Pro Gly Glu Phe Thr Phe
             885                 890                 895

Gly Asn Ile Lys Ser His Pro Gly Gly Thr Ser Gly Leu Ala Arg Val
         900                 905                 910

Val Ser Thr Asn Tyr Asn Gln His Ala Met Val Phe Phe Lys Phe Val
     915                 920                 925

Ile Gln Asn Arg Glu Ala Phe Phe Ile Thr Leu Tyr Gly Arg Thr Lys
930                 935                 940

Glu Leu Thr Ser Glu Leu Lys Glu Asn Phe Ile Arg Phe Ser Lys Ser
945                 950                 955                 960

Leu Gly Leu Pro Glu Asn His Ile Val Phe Pro Val Pro Ile Asp Gln
             965                 970                 975

Cys Ile Asp Gly
         980

<210> SEQ ID NO 139
<211> LENGTH: 980
<212> TYPE: PRT
<213> ORGANISM: Artificial Sequence
<220> FEATURE:
<223> OTHER INFORMATION: S0474.01H22_T54A_N65D_(G4S)2S0530.04N16_N65D_
      (G4S)2_hIgG4Fc_S0530.07G09_N65D_(G4S)2 S0522.05M06_N65D

<400> SEQUENCE: 139

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
             20                  25                  30

Val Val Gly Val Ala Gly Asn Thr Ile Leu Arg Glu Asp Lys Asp Pro
         35                  40                  45

Gly Lys Met Asn Ala Ala Ile Tyr Glu Leu Lys Glu Asp Lys Ser Tyr
     50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
             85                  90                  95

Ile Lys Ser Tyr Pro Gly Thr Thr Ser Gln Leu Val Arg Val Val Ser
```

-continued

```
              100                 105                 110
Thr Asn Tyr Asn Gln His Ala Met Val Phe Lys Ile Val Arg Gln
            115                 120                 125
Asn Arg Glu Ile Phe Trp Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Gly Ser Gly Gly Gly Ser Gln Asp Ser Thr
            180                 185                 190
Ser Asp Leu Ile Pro Ala Pro Pro Leu Ser Lys Val Pro Leu Gln Gln
            195                 200                 205
Asn Phe Gln Asp Asn Gln Phe His Gly Lys Trp Tyr Val Val Gly Leu
            210                 215                 220
Ala Gly Asn Gly Trp Leu Arg Glu Asp Glu Asp Pro Leu Lys Met Met
225                 230                 235                 240
Ala Ala Val Tyr Glu Leu Arg Glu Asp Lys Ser Tyr Asp Val Thr Val
                245                 250                 255
Val Asp Phe Glu Leu Glu Glu Cys Arg Tyr Met Thr Glu Thr Phe Val
            260                 265                 270
Pro Gly Asn Gln Pro Gly Glu Phe Thr Leu Gly Asp Ile Lys Ser Ser
            275                 280                 285
Pro Gly Trp Thr Ser Gln Leu Val Arg Val Val Ser Thr Asn Tyr Asn
            290                 295                 300
Gln His Ala Met Val Phe Phe Lys Gly Val Tyr Gln Asn Arg Glu Trp
305                 310                 315                 320
Phe His Ile Thr Leu Tyr Gly Arg Thr Lys Glu Leu Thr Ser Glu Leu
                325                 330                 335
Lys Glu Asn Phe Ile Arg Phe Ser Lys Ser Leu Gly Leu Pro Glu Asn
            340                 345                 350
His Ile Val Phe Pro Val Pro Ile Asp Gln Cys Ile Asp Gly Gly Gly
            355                 360                 365
Gly Gly Ser Gly Gly Gly Ser Glu Ser Lys Tyr Gly Pro Pro Cys
            370                 375                 380
Pro Pro Cys Pro Ala Pro Glu Phe Glu Gly Gly Pro Ser Val Phe Leu
385                 390                 395                 400
Phe Pro Pro Lys Pro Lys Asp Thr Leu Met Ile Ser Arg Thr Pro Glu
                405                 410                 415
Val Thr Cys Val Val Val Asp Val Ser Gln Glu Asp Pro Glu Val Gln
            420                 425                 430
Phe Asn Trp Tyr Val Asp Gly Val Glu Val His Asn Ala Lys Thr Lys
            435                 440                 445
Pro Arg Glu Glu Gln Phe Asn Ser Thr Tyr Arg Val Val Ser Val Leu
            450                 455                 460
Thr Val Leu His Gln Asp Trp Leu Asn Gly Lys Glu Tyr Lys Cys Lys
465                 470                 475                 480
Val Ser Asn Lys Gly Leu Pro Ser Ser Ile Glu Lys Thr Ile Ser Lys
                485                 490                 495
Ala Lys Gly Gln Pro Arg Glu Pro Gln Val Tyr Thr Leu Pro Pro Ser
            500                 505                 510
Gln Glu Glu Met Thr Lys Asn Gln Val Ser Leu Thr Cys Leu Val Lys
            515                 520                 525
```

```
Gly Phe Tyr Pro Ser Asp Ile Ala Val Glu Trp Glu Ser Asn Gly Gln
            530                 535                 540

Pro Glu Asn Asn Tyr Lys Thr Thr Pro Pro Val Leu Asp Ser Asp Gly
545                 550                 555                 560

Ser Phe Phe Leu Tyr Ser Arg Leu Thr Val Asp Lys Ser Arg Trp Gln
                565                 570                 575

Glu Gly Asn Val Phe Ser Cys Ser Val Met His Glu Ala Leu His Asn
            580                 585                 590

His Tyr Thr Gln Lys Ser Leu Ser Leu Ser Leu Gly Gly Gly Gly Gly
        595                 600                 605

Ser Gly Gly Gly Gly Ser Gln Asp Ser Thr Ser Asp Leu Ile Pro Ala
610                 615                 620

Pro Pro Leu Ser Lys Val Pro Leu Gln Gln Asn Phe Gln Asp Asn Gln
625                 630                 635                 640

Phe His Gly Lys Trp Tyr Val Val Gly Glu Ala Gly Asn Leu Ala Arg
                645                 650                 655

Arg Glu Asp Lys Asp Pro Met Lys Met Met Ala Thr Ile Tyr Glu Leu
            660                 665                 670

Lys Glu Asp Lys Ser Tyr Asp Val Thr Glu Val Arg Phe Arg His Lys
        675                 680                 685

Lys Cys Lys Tyr Asp Ile Val Thr Phe Val Pro Gly Ser Gln Pro Gly
690                 695                 700

Glu Phe Thr Leu Gly Leu Ile Lys Ser Asp Pro Gly Gln Thr Pro Glu
705                 710                 715                 720

Leu Val Arg Val Val Ser Thr Asn Tyr Asn Gln His Ala Met Val Phe
                725                 730                 735

Phe Lys Lys Val Val Gln Asn Arg Glu Tyr Phe Trp Ile Thr Leu Tyr
            740                 745                 750

Gly Arg Thr Lys Glu Leu Thr Ser Glu Leu Lys Glu Asn Phe Ile Arg
        755                 760                 765

Phe Ser Lys Ser Leu Gly Leu Pro Glu Asn His Ile Val Phe Pro Val
770                 775                 780

Pro Ile Asp Gln Cys Ile Asp Gly Gly Gly Gly Ser Gly Gly Gly Gly
785                 790                 795                 800

Gly Ser Gln Asp Ser Thr Ser Asp Leu Ile Pro Ala Pro Pro Leu Ser
                805                 810                 815

Lys Val Pro Leu Gln Gln Asn Phe Gln Asp Asn Gln Phe His Gly Lys
            820                 825                 830

Trp Tyr Val Val Gly His Ala Gly Asn Gln Trp Leu Arg Gly Asp Tyr
        835                 840                 845

Asp Pro Arg Lys Met Trp Ala Thr Ile Tyr Glu Leu Lys Glu Asp Lys
850                 855                 860

Ser Tyr Asp Val Thr Asp Val Asp Phe Ala Ile Glu Lys Cys His Tyr
865                 870                 875                 880

Arg Ile Thr Thr Phe Val Pro Gly Ser Gln Pro Gly Glu Phe Thr Phe
                885                 890                 895

Gly Asn Ile Lys Ser His Pro Gly Gly Thr Ser Gly Leu Ala Arg Val
            900                 905                 910

Val Ser Thr Asn Tyr Asn Gln His Ala Met Val Phe Phe Lys Phe Val
        915                 920                 925

Ile Gln Asn Arg Glu Ala Phe Phe Ile Thr Leu Tyr Gly Arg Thr Lys
930                 935                 940
```

```
Glu Leu Thr Ser Glu Leu Lys Glu Asn Phe Ile Arg Phe Ser Lys Ser
945                 950                 955                 960

Leu Gly Leu Pro Glu Asn His Ile Val Phe Pro Val Pro Ile Asp Gln
                965                 970                 975

Cys Ile Asp Gly
            980

<210> SEQ ID NO 140
<211> LENGTH: 228
<212> TYPE: PRT
<213> ORGANISM: Artificial Sequence
<220> FEATURE:
<223> OTHER INFORMATION: IgG4-Fc

<400> SEQUENCE: 140

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 141
<211> LENGTH: 10
<212> TYPE: PRT
<213> ORGANISM: Artificial Sequence
<220> FEATURE:
<223> OTHER INFORMATION: Linker

<400> SEQUENCE: 141

Gly Gly Gly Gly Ser Gly Gly Gly Gly Ser
1               5                   10

<210> SEQ ID NO 142
```

-continued

```
<211> LENGTH: 6
<212> TYPE: PRT
<213> ORGANISM: Artificial Sequence
<220> FEATURE:
<223> OTHER INFORMATION: Linker

<400> SEQUENCE: 142

Gly Ser Gly Gly Ser Gly
1               5

<210> SEQ ID NO 143
<211> LENGTH: 980
<212> TYPE: PRT
<213> ORGANISM: Artificial Sequence
<220> FEATURE:
<223> OTHER INFORMATION: S0474.01H22(H28Q;T54A;N65D) (G4S)2
      S0544.04C04(H28Q;N65D) (G4S)2 (FC;HuIgG4) (G4S)2 S0530.07G09(H28Q;
      N65D) (G4S)2 S0522.05A05(H28Q;N65D)

<400> SEQUENCE: 143

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gln Asp Ser Thr
            180                 185                 190

Ser Asp Leu Ile Pro Ala Pro Pro Leu Ser Lys Val Pro Leu Gln Gln
    195                 200                 205

Asn Phe Gln Asp Asn Gln Phe Gln Gly Lys Trp Tyr Val Val Gly Trp
        210                 215                 220

Ala Gly Asn Thr Ala Leu Arg Glu Asp Lys Asp Pro Lys Met Pro
225                 230                 235                 240

Ala Val Ile Tyr Glu Leu Lys Glu Asp Lys Ser Tyr Asp Val Thr Asp
                245                 250                 255

Val Gln Phe Pro Glu Lys Glu Cys Ile Tyr Ser Thr Ile Thr Phe Val
            260                 265                 270

Pro Gly Ser Gln Pro Gly Glu Phe Thr Leu Gly Gly Ile Lys Ser Ser
        275                 280                 285

Pro Gly Gln Thr Ser His Leu Val Arg Val Val Ser Thr Asn Tyr Asn
    290                 295                 300
```

```
Gln His Ala Met Val Phe Phe Lys Tyr Val Thr Gln Asn Arg Glu Gly
305                 310                 315                 320

Phe Asn Ile Ala Leu Tyr Gly Arg Thr Lys Glu Leu Thr Ser Glu Leu
            325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
            355                 360                 365

Gly Gly Ser Gly Gly Gly Ser Glu Ser Lys Tyr Gly Pro Pro Cys
    370                 375                 380

Pro Pro Cys Pro Ala Pro Glu Phe Glu Gly Gly Pro Ser Val Phe Leu
385                 390                 395                 400

Phe Pro Pro Lys Pro Lys Asp Thr Leu Met Ile Ser Arg Thr Pro Glu
            405                 410                 415

Val Thr Cys Val Val Val Asp Val Ser Gln Glu Asp Pro Glu Val Gln
            420                 425                 430

Phe Asn Trp Tyr Val Asp Gly Val Glu Val His Asn Ala Lys Thr Lys
            435                 440                 445

Pro Arg Glu Glu Gln Phe Asn Ser Thr Tyr Arg Val Val Ser Val Leu
    450                 455                 460

Thr Val Leu His Gln Asp Trp Leu Asn Gly Lys Glu Tyr Lys Cys Lys
465                 470                 475                 480

Val Ser Asn Lys Gly Leu Pro Ser Ser Ile Glu Lys Thr Ile Ser Lys
            485                 490                 495

Ala Lys Gly Gln Pro Arg Glu Pro Gln Val Tyr Thr Leu Pro Pro Ser
            500                 505                 510

Gln Glu Glu Met Thr Lys Asn Gln Val Ser Leu Thr Cys Leu Val Lys
            515                 520                 525

Gly Phe Tyr Pro Ser Asp Ile Ala Val Glu Trp Glu Ser Asn Gly Gln
    530                 535                 540

Pro Glu Asn Asn Tyr Lys Thr Thr Pro Pro Val Leu Asp Ser Asp Gly
545                 550                 555                 560

Ser Phe Phe Leu Tyr Ser Arg Leu Thr Val Asp Lys Ser Arg Trp Gln
            565                 570                 575

Glu Gly Asn Val Phe Ser Cys Ser Val Met His Glu Ala Leu His Asn
            580                 585                 590

His Tyr Thr Gln Lys Ser Leu Ser Leu Ser Leu Gly Gly Gly Gly Gly
    595                 600                 605

Ser Gly Gly Gly Gly Ser Gln Asp Ser Thr Ser Asp Leu Ile Pro Ala
    610                 615                 620

Pro Pro Leu Ser Lys Val Pro Leu Gln Gln Asn Phe Gln Asp Asn Gln
625                 630                 635                 640

Phe Gln Gly Lys Trp Tyr Val Val Gly Glu Ala Gly Asn Leu Ala Arg
            645                 650                 655

Arg Glu Asp Lys Asp Pro Met Lys Met Met Ala Thr Ile Tyr Glu Leu
            660                 665                 670

Lys Glu Asp Lys Ser Tyr Asp Val Thr Glu Val Arg Phe Arg His Lys
            675                 680                 685

Lys Cys Lys Tyr Asp Ile Val Thr Phe Val Pro Gly Ser Gln Pro Gly
            690                 695                 700

Glu Phe Thr Leu Gly Leu Ile Lys Ser Asp Pro Gly Gln Thr Pro Glu
705                 710                 715                 720
```

```
Leu Val Arg Val Val Ser Thr Asn Tyr Asn Gln His Ala Met Val Phe
                    725                 730                 735

Phe Lys Lys Val Val Gln Asn Arg Glu Tyr Phe Trp Ile Thr Leu Tyr
            740                 745                 750

Gly Arg Thr Lys Glu Leu Thr Ser Glu Leu Lys Glu Asn Phe Ile Arg
                755                 760                 765

Phe Ser Lys Ser Leu Gly Leu Pro Glu Asn His Ile Val Phe Pro Val
770                 775                 780

Pro Ile Asp Gln Cys Ile Asp Gly Gly Gly Gly Ser Gly Gly Gly
785                 790                 795                 800

Gly Ser Gln Asp Ser Thr Ser Asp Leu Ile Pro Ala Pro Pro Leu Ser
                805                 810                 815

Lys Val Pro Leu Gln Gln Asn Phe Gln Asp Asn Gln Phe Gln Gly Lys
                820                 825                 830

Trp Tyr Val Val Gly His Ala Gly Asn Gln Trp Leu Arg Glu Gly Arg
                835                 840                 845

Asp Pro Arg Lys Met Trp Ala Thr Ile Tyr Glu Leu Lys Glu Asp Lys
                850                 855                 860

Ser Tyr Asp Val Thr Asp Val Asp Phe Ala Ile Lys Lys Cys Leu Tyr
865                 870                 875                 880

Arg Ile Thr Thr Phe Val Pro Gly Ser Gln Pro Gly Glu Phe Thr Leu
                885                 890                 895

Gly Asn Ile Lys Ser His Pro Gly Gly Thr Ser Gly Leu Val Arg Val
                900                 905                 910

Val Ser Thr Asn Tyr Asn Gln His Ala Met Val Phe Lys Phe Val
                915                 920                 925

Ile Gln Asn Arg Glu Ala Phe Phe Ile Thr Leu Tyr Gly Arg Thr Lys
                930                 935                 940

Glu Leu Thr Ser Glu Leu Lys Glu Asn Phe Ile Arg Phe Ser Lys Ser
945                 950                 955                 960

Leu Gly Leu Pro Glu Asn His Ile Val Phe Pro Val Pro Ile Asp Gln
                965                 970                 975

Cys Ile Asp Gly
            980
```

<210> SEQ ID NO 144
<211> LENGTH: 752
<212> TYPE: PRT
<213> ORGANISM: Artificial Sequence
<220> FEATURE:
<223> OTHER INFORMATION: S0474.01H22(T54A;N65D) GQPKAAPS
S0530.04N16(N65D) GQPKAAPS S0530.07G09(N65Q) GQPKAAPS
S0522.05A05(N65D) Cterm StrepII 6His

<400> SEQUENCE: 144

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Ala Ile Tyr Glu Leu Lys Glu Asp Lys Ser Tyr
        50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
```

```
                85                  90                  95
Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gln Pro Lys Ala Ala Pro Ser Gln Asp Ser Thr Ser Asp
            180                 185                 190

Leu Ile Pro Ala Pro Pro Leu Ser Lys Val Pro Leu Gln Gln Asn Phe
            195                 200                 205

Gln Asp Asn Gln Phe His Gly Lys Trp Tyr Val Val Gly Leu Ala Gly
            210                 215                 220

Asn Gly Trp Leu Arg Glu Asp Glu Asp Pro Leu Lys Met Met Ala Ala
225                 230                 235                 240

Val Tyr Glu Leu Arg Glu Asp Lys Ser Tyr Asp Val Thr Val Val Asp
                245                 250                 255

Phe Glu Leu Glu Glu Cys Arg Tyr Met Thr Glu Thr Phe Val Pro Gly
            260                 265                 270

Asn Gln Pro Gly Glu Phe Thr Leu Gly Asp Ile Lys Ser Ser Pro Gly
            275                 280                 285

Trp Thr Ser Gln Leu Val Arg Val Val Ser Thr Asn Tyr Asn Gln His
            290                 295                 300

Ala Met Val Phe Phe Lys Gly Val Tyr Gln Asn Arg Glu Trp Phe His
305                 310                 315                 320

Ile Thr Leu Tyr Gly Arg Thr Lys Glu Leu Thr Ser Glu Leu Lys Glu
                325                 330                 335

Asn Phe Ile Arg Phe Ser Lys Ser Leu Gly Leu Pro Glu Asn His Ile
            340                 345                 350

Val Phe Pro Val Pro Ile Asp Gln Cys Ile Asp Gly Gly Gln Pro Lys
            355                 360                 365

Ala Ala Pro Ser Gln Asp Ser Thr Ser Asp Leu Ile Pro Ala Pro Pro
370                 375                 380

Leu Ser Lys Val Pro Leu Gln Gln Asn Phe Gln Asp Asn Gln Phe His
385                 390                 395                 400

Gly Lys Trp Tyr Val Val Gly Glu Ala Gly Asn Leu Ala Arg Arg Glu
                405                 410                 415

Asp Lys Asp Pro Met Lys Met Met Ala Thr Ile Tyr Glu Leu Lys Glu
            420                 425                 430

Asp Lys Ser Tyr Gln Val Thr Glu Val Arg Phe Arg His Lys Lys Cys
            435                 440                 445

Lys Tyr Asp Ile Val Thr Phe Val Pro Gly Ser Gln Pro Gly Glu Phe
            450                 455                 460

Thr Leu Gly Leu Ile Lys Ser Asp Pro Gly Gln Thr Pro Glu Leu Val
465                 470                 475                 480

Arg Val Val Ser Thr Asn Tyr Asn Gln His Ala Met Val Phe Phe Lys
                485                 490                 495

Lys Val Val Gln Asn Arg Glu Tyr Phe Trp Ile Thr Leu Tyr Gly Arg
            500                 505                 510
```

-continued

```
Thr Lys Glu Leu Thr Ser Glu Leu Lys Glu Asn Phe Ile Arg Phe Ser
            515                 520                 525
Lys Ser Leu Gly Leu Pro Glu Asn His Ile Val Phe Pro Val Pro Ile
        530                 535                 540
Asp Gln Cys Ile Asp Gly Gly Gln Pro Lys Ala Ala Pro Ser Gln Asp
545                 550                 555                 560
Ser Thr Ser Asp Leu Ile Pro Ala Pro Leu Ser Lys Val Pro Leu
                565                 570                 575
Gln Gln Asn Phe Gln Asp Asn Gln Phe His Gly Lys Trp Tyr Val Val
                580                 585                 590
Gly His Ala Gly Asn Gln Trp Leu Arg Glu Gly Arg Asp Pro Arg Lys
            595                 600                 605
Met Trp Ala Thr Ile Tyr Glu Leu Lys Glu Asp Lys Ser Tyr Asp Val
        610                 615                 620
Thr Asp Val Asp Phe Ala Ile Lys Lys Cys Leu Tyr Arg Ile Thr Thr
625                 630                 635                 640
Phe Val Pro Gly Ser Gln Pro Gly Glu Phe Thr Leu Gly Asn Ile Lys
                645                 650                 655
Ser His Pro Gly Gly Thr Ser Gly Leu Val Arg Val Val Ser Thr Asn
            660                 665                 670
Tyr Asn Gln His Ala Met Val Phe Phe Lys Phe Val Ile Gln Asn Arg
        675                 680                 685
Glu Ala Phe Phe Ile Thr Leu Tyr Gly Arg Thr Lys Glu Leu Thr Ser
690                 695                 700
Glu Leu Lys Glu Asn Phe Ile Arg Phe Ser Lys Ser Leu Gly Leu Pro
705                 710                 715                 720
Glu Asn His Ile Val Phe Pro Val Pro Ile Asp Gln Cys Ile Asp Gly
                725                 730                 735
Ser Ala Trp Ser His Pro Gln Phe Glu Lys His His His His His His
            740                 745                 750
```

<210> SEQ ID NO 145
<211> LENGTH: 746
<212> TYPE: PRT
<213> ORGANISM: Artificial Sequence
<220> FEATURE:
<223> OTHER INFORMATION: S0474.01H22(T54A;N65D) GSGGSG S0530.04N16(N65D)
    GSGGSG S0530.07G09(N65Q) GSGGSG S0522.05A05(N65D) Cterm StrepII
    6His

<400> SEQUENCE: 145

```
Gln Asp Ser Thr Ser Asp Leu Ile Pro Ala Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Val Ala Gly Asn Thr Ile Leu Arg Glu Asp Lys Asp Pro
        35                  40                  45
Gly Lys Met Asn Ala Ala Ile Tyr Glu Leu Lys Glu Asp Lys Ser Tyr
    50                  55                  60
Asp Val Thr Asp Val Arg Phe Ile Arg Lys Lys Cys His Tyr Tyr Ile
65                  70                  75                  80
Asp Thr Phe Val Pro Gly Ser Gln Pro Gly Glu Phe Thr Leu Gly Asn
                85                  90                  95
Ile Lys Ser Tyr Pro Gly Thr Thr Ser Gln Leu Val Arg Val Val Ser
                100                 105                 110
```

-continued

```
Thr Asn Tyr Asn Gln His Ala Met Val Phe Lys Ile Val Arg Gln
            115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Ser Gly Ser Gly Gln Asp Ser Thr Ser Asp Leu Ile
            180                 185                 190

Pro Ala Pro Pro Leu Ser Lys Val Pro Leu Gln Gln Asn Phe Gln Asp
            195                 200                 205

Asn Gln Phe His Gly Lys Trp Tyr Val Val Gly Leu Ala Gly Asn Gly
            210                 215                 220

Trp Leu Arg Glu Asp Glu Asp Pro Leu Lys Met Met Ala Ala Val Tyr
225                 230                 235                 240

Glu Leu Arg Glu Asp Lys Ser Tyr Asp Val Thr Val Val Asp Phe Glu
                245                 250                 255

Leu Glu Glu Cys Arg Tyr Met Thr Glu Thr Phe Val Pro Gly Asn Gln
            260                 265                 270

Pro Gly Glu Phe Thr Leu Gly Asp Ile Lys Ser Ser Pro Gly Trp Thr
            275                 280                 285

Ser Gln Leu Val Arg Val Val Ser Thr Asn Tyr Asn Gln His Ala Met
            290                 295                 300

Val Phe Phe Lys Gly Val Tyr Gln Asn Arg Glu Trp Phe His Ile Thr
305                 310                 315                 320

Leu Tyr Gly Arg Thr Lys Glu Leu Thr Ser Glu Leu Lys Glu Asn Phe
                325                 330                 335

Ile Arg Phe Ser Lys Ser Leu Gly Leu Pro Glu Asn His Ile Val Phe
            340                 345                 350

Pro Val Pro Ile Asp Gln Cys Ile Asp Gly Gly Ser Gly Ser Gly
            355                 360                 365

Gln Asp Ser Thr Ser Asp Leu Ile Pro Ala Pro Pro Leu Ser Lys Val
            370                 375                 380

Pro Leu Gln Gln Asn Phe Gln Asp Asn Gln Phe His Gly Lys Trp Tyr
385                 390                 395                 400

Val Val Gly Glu Ala Gly Asn Leu Ala Arg Arg Glu Asp Lys Asp Pro
                405                 410                 415

Met Lys Met Met Ala Thr Ile Tyr Glu Leu Lys Glu Asp Lys Ser Tyr
            420                 425                 430

Gln Val Thr Glu Val Arg Phe Arg His Lys Lys Cys Lys Tyr Asp Ile
            435                 440                 445

Val Thr Phe Val Pro Gly Ser Gln Pro Gly Glu Phe Thr Leu Gly Leu
450                 455                 460

Ile Lys Ser Asp Pro Gly Gln Thr Pro Glu Leu Val Arg Val Val Ser
465                 470                 475                 480

Thr Asn Tyr Asn Gln His Ala Met Val Phe Phe Lys Lys Val Val Gln
                485                 490                 495

Asn Arg Glu Tyr Phe Trp Ile Thr Leu Tyr Gly Arg Thr Lys Glu Leu
            500                 505                 510

Thr Ser Glu Leu Lys Glu Asn Phe Ile Arg Phe Ser Lys Ser Leu Gly
            515                 520                 525

Leu Pro Glu Asn His Ile Val Phe Pro Val Pro Ile Asp Gln Cys Ile
```

```
                    530                 535                 540
Asp Gly Gly Ser Gly Gly Ser Gly Gln Asp Ser Thr Ser Asp Leu Ile
545                 550                 555                 560

Pro Ala Pro Pro Leu Ser Lys Val Pro Leu Gln Gln Asn Phe Gln Asp
                    565                 570                 575

Asn Gln Phe His Gly Lys Trp Tyr Val Gly His Ala Gly Asn Gln
            580                 585                 590

Trp Leu Arg Glu Gly Arg Asp Pro Arg Lys Met Trp Ala Thr Ile Tyr
                595                 600                 605

Glu Leu Lys Glu Asp Lys Ser Tyr Asp Val Thr Asp Val Asp Phe Ala
            610                 615                 620

Ile Lys Lys Cys Leu Tyr Arg Ile Thr Thr Phe Val Pro Gly Ser Gln
625                 630                 635                 640

Pro Gly Glu Phe Thr Leu Gly Asn Ile Lys Ser His Pro Gly Gly Thr
                    645                 650                 655

Ser Gly Leu Val Arg Val Val Ser Thr Asn Tyr Asn Gln His Ala Met
                660                 665                 670

Val Phe Phe Lys Phe Val Ile Gln Asn Arg Glu Ala Phe Phe Ile Thr
            675                 680                 685

Leu Tyr Gly Arg Thr Lys Glu Leu Thr Ser Glu Leu Lys Glu Asn Phe
690                 695                 700

Ile Arg Phe Ser Lys Ser Leu Gly Leu Pro Glu Asn His Ile Val Phe
705                 710                 715                 720

Pro Val Pro Ile Asp Gln Cys Ile Asp Gly Ser Ala Trp Ser His Pro
                725                 730                 735

Gln Phe Glu Lys His His His His His His
            740                 745

<210> SEQ ID NO 146
<211> LENGTH: 758
<212> TYPE: PRT
<213> ORGANISM: Artificial Sequence
<220> FEATURE:
<223> OTHER INFORMATION: S0474.01H22(T54A;N65D) (G4S)2 S0530.04N16(N65D)
      (G4S)2 S0530.07G09(N65Q) (G4S)2 S0522.05A05(N65D) Cterm StrepII
      6His

<400> SEQUENCE: 146

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Ala Ile Tyr Glu Leu Lys Glu Asp Lys Ser Tyr
        50                  55                  60

Asp Val Thr Asp Val Arg Phe Ile Arg Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly Gly Gly Gly Ser Gly Gly Gly Ser Gln Asp Ser Thr
        180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Leu
        210                 215                 220

Ala Gly Asn Gly Trp Leu Arg Glu Asp Glu Pro Leu Lys Met Met
225                 230                 235                 240

Ala Ala Val Tyr Glu Leu Arg Glu Asp Lys Ser Tyr Asp Val Thr Val
            245                 250                 255

Val Asp Phe Glu Leu Glu Glu Cys Arg Tyr Met Thr Glu Thr Phe Val
            260                 265                 270

Pro Gly Asn Gln Pro Gly Glu Phe Thr Leu Gly Asp Ile Lys Ser Ser
            275                 280                 285

Pro Gly Trp Thr Ser Gln Leu Val Arg Val Val Ser Thr Asn Tyr Asn
290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
            325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
        370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
            405                 410                 415

Ala Arg Arg Glu Asp Lys Asp Pro Met Lys Met Met Ala Thr Ile Tyr
            420                 425                 430

Glu Leu Lys Glu Asp Lys Ser Tyr Gln Val Thr Glu Val Arg Phe Arg
            435                 440                 445

His Lys Lys Cys Lys Tyr Asp Ile Val Thr Phe Val Pro Gly Ser Gln
            450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
            485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Thr Ser Glu Leu Lys Glu Asn Phe
            515                 520                 525

Ile Arg Phe Ser Lys Ser Leu Gly Leu Pro Glu Asn His Ile Val Phe
            530                 535                 540

Pro Val Pro Ile Asp Gln Cys Ile Asp Gly Gly Gly Gly Ser Gly
545                 550                 555                 560
```

```
Gly Gly Gly Ser Gln Asp Ser Thr Ser Asp Leu Ile Pro Ala Pro Pro
                565                 570                 575
Leu Ser Lys Val Pro Leu Gln Gln Asn Phe Gln Asp Asn Gln Phe His
        580                 585                 590
Gly Lys Trp Tyr Val Val Gly His Ala Gly Asn Gln Trp Leu Arg Glu
            595                 600                 605
Gly Arg Asp Pro Arg Lys Met Trp Ala Thr Ile Tyr Glu Leu Lys Glu
610                 615                 620
Asp Lys Ser Tyr Asp Val Thr Asp Val Asp Phe Ala Ile Lys Lys Cys
625                 630                 635                 640
Leu Tyr Arg Ile Thr Thr Phe Val Pro Gly Ser Gln Pro Gly Glu Phe
                645                 650                 655
Thr Leu Gly Asn Ile Lys Ser His Pro Gly Gly Thr Ser Gly Leu Val
            660                 665                 670
Arg Val Val Ser Thr Asn Tyr Asn Gln His Ala Met Val Phe Phe Lys
        675                 680                 685
Phe Val Ile Gln Asn Arg Glu Ala Phe Ile Thr Leu Tyr Gly Arg
    690                 695                 700
Thr Lys Glu Leu Thr Ser Glu Leu Lys Glu Asn Phe Ile Arg Phe Ser
705                 710                 715                 720
Lys Ser Leu Gly Leu Pro Glu Asn His Ile Val Phe Pro Val Pro Ile
                725                 730                 735
Asp Gln Cys Ile Asp Gly Ser Ala Trp Ser His Pro Gln Phe Glu Lys
            740                 745                 750
His His His His His His
755

<210> SEQ ID NO 147
<211> LENGTH: 758
<212> TYPE: PRT
<213> ORGANISM: Artificial Sequence
<220> FEATURE:
<223> OTHER INFORMATION: S0474.01H22(N65Q;T54A) (G4S)2 S0530.04N16(N65Q)
      (G4S)2 S0530.07K20(N65Q) (G4S)2 S0522.15K24(N65Q) Cterm StrepII
      His

<400> SEQUENCE: 147

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Val Ala Gly Asn Thr Ile Leu Arg Glu Asp Lys Asp Pro
        35                  40                  45
Gly Lys Met Asn Ala Ala Ile Tyr Glu Leu Lys Glu Asp Lys Ser Tyr
    50                  55                  60
Gln Val Thr Asp Val Arg Phe Ile Arg Lys Lys Cys His Tyr Tyr Ile
65                  70                  75                  80
Asp Thr Phe Val Pro Gly Ser Gln Pro Gly Glu Phe Thr Leu Gly Asn
                85                  90                  95
Ile Lys Ser Tyr Pro Gly Thr Thr Ser Gln Leu Val Arg Val Val Ser
            100                 105                 110
Thr Asn Tyr Asn Gln His Ala Met Val Phe Phe Lys Ile Val Arg Gln
        115                 120                 125
Asn Arg Glu Ile Phe Trp Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
```

```
            145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Ser Gln Asp Ser Thr
                180                 185                 190
Ser Asp Leu Ile Pro Ala Pro Leu Ser Lys Val Pro Leu Gln Gln
                195                 200                 205
Asn Phe Gln Asp Asn Gln Phe His Gly Lys Trp Tyr Val Val Gly Leu
            210                 215                 220
Ala Gly Asn Gly Trp Leu Arg Glu Asp Glu Asp Pro Leu Lys Met Met
225                 230                 235                 240
Ala Ala Val Tyr Glu Leu Arg Glu Asp Lys Ser Tyr Gln Val Thr Val
                245                 250                 255
Val Asp Phe Glu Leu Glu Glu Cys Arg Tyr Met Thr Glu Thr Phe Val
                260                 265                 270
Pro Gly Asn Gln Pro Gly Glu Phe Thr Leu Gly Asp Ile Lys Ser Ser
                275                 280                 285
Pro Gly Trp Thr Ser Gln Leu Val Arg Val Val Ser Thr Asn Tyr Asn
            290                 295                 300
Gln His Ala Met Val Phe Lys Gly Val Tyr Gln Asn Arg Glu Trp
305                 310                 315                 320
Phe His Ile Thr Leu Tyr Gly Arg Thr Lys Glu Leu Thr Ser Glu Leu
                325                 330                 335
Lys Glu Asn Phe Ile Arg Phe Ser Lys Ser Leu Gly Leu Pro Glu Asn
                340                 345                 350
His Ile Val Phe Pro Val Pro Ile Asp Gln Cys Ile Asp Gly Gly Gly
                355                 360                 365
Gly Gly Ser Gly Gly Gly Ser Gln Asp Ser Thr Ser Asp Leu Ile
            370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                405                 410                 415
Ala Leu Arg Glu Asp Lys Asn Pro Met Lys Met Met Ala Thr Ile Tyr
                420                 425                 430
Glu Leu Lys Glu Asp Lys Ser Tyr Gln Val Thr Glu Val Arg Phe Arg
                435                 440                 445
His Lys Lys Cys Lys Tyr Asp Ile Val Thr Phe Val Pro Gly Ser Gln
            450                 455                 460
Pro Gly Glu Phe Thr Leu Gly Leu Ile Lys Ser Asp Pro Gly Gln Thr
465                 470                 475                 480
Pro Glu Leu Val Arg Val Val Ser Thr Asn Tyr Asn Gln His Ala Met
                485                 490                 495
Val Phe Phe Lys Lys Val Val Gln Asn Arg Glu Tyr Phe Trp Ile Thr
                500                 505                 510
Leu Tyr Gly Arg Thr Lys Glu Leu Pro Ser Glu Leu Lys Glu Asn Phe
                515                 520                 525
Ile Arg Phe Ser Lys Ser Leu Gly Leu Pro Glu Asn His Ile Val Phe
                530                 535                 540
Pro Val Pro Ile Asp Gln Cys Ile Asp Gly Gly Gly Gly Ser Gly
545                 550                 555                 560
Gly Gly Ser Gln Asp Ser Thr Ser Asp Leu Ile Pro Ala Pro Pro
                565                 570                 575
```

```
Leu Ser Lys Val Pro Leu Gln Gln Asn Phe Gln Asp Asn Gln Phe His
            580                 585                 590
Gly Lys Trp Tyr Val Leu Gly Met Ala Gly Asn Phe His Leu Arg Glu
            595                 600                 605
Asp Lys Asp Pro Ser Lys Met Pro Ala Thr Ile Tyr Glu Leu Lys Glu
            610                 615                 620
Asp Lys Ser Tyr Gln Val Thr His Val Pro Phe Trp Ala Lys Lys Cys
625                 630                 635                 640
Ala Tyr Lys Thr Ile Thr Phe Val Pro Gly Ser Gln Pro Gly Glu Phe
                    645                 650                 655
Thr Leu Gly Ala Ile Lys Ser Gly Pro Gly Met Thr Ser Trp Leu Val
                    660                 665                 670
Arg Val Val Ser Thr Asn Tyr Asn Gln His Ala Met Val Phe Ser Lys
                    675                 680                 685
Gly Val Trp Gln Asn Arg Glu Thr Phe Val Ile Thr Leu Tyr Gly Arg
            690                 695                 700
Ala Lys Glu Leu Thr Ser Glu Leu Lys Glu Asn Phe Ile Arg Phe Ser
705                 710                 715                 720
Lys Ser Leu Gly Leu Pro Glu Asn His Ile Val Phe Pro Val Pro Ile
                    725                 730                 735
Asp Gln Cys Ile Asp Gly Ser Ala Trp Ser His Pro Gln Phe Glu Lys
                    740                 745                 750
His His His His His His
            755
```

<210> SEQ ID NO 148
<211> LENGTH: 758
<212> TYPE: PRT
<213> ORGANISM: Artificial Sequence
<220> FEATURE:
<223> OTHER INFORMATION: S0474.01H22(N65Q;T54A) (G4S)2 S0530.04N16(N65Q)
    (G4S)2 S0530.07K20(N65Q) (G4S)2 S0522.05M06 (N65Q) Cterm StrepII
    His

<400> SEQUENCE: 148

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly Val Ala Gly Asn Thr Ile Leu Arg Glu Asp Lys Asp Pro
            35                  40                  45
Gly Lys Met Asn Ala Ala Ile Tyr Glu Leu Lys Glu Asp Lys Ser Tyr
        50                  55                  60
Gln Val Thr Asp Val Arg Phe Ile Arg Lys Lys Cys His Tyr Tyr Ile
65                  70                  75                  80
Asp Thr Phe Val Pro Gly Ser Gln Pro Gly Glu Phe Thr Leu Gly Asn
                    85                  90                  95
Ile Lys Ser Tyr Pro Gly Thr Thr Ser Gln Leu Val Arg Val Val Ser
                100                 105                 110
Thr Asn Tyr Asn Gln His Ala Met Val Phe Phe Lys Ile Val Arg Gln
            115                 120                 125
Asn Arg Glu Ile Phe Trp Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
145                 150                 155                 160
```

-continued

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190

Ser Asp Leu Ile Pro Ala Pro Pro Leu Ser Lys Val Pro Leu Gln Gln
            195                 200                 205

Asn Phe Gln Asp Asn Gln Phe His Gly Lys Trp Tyr Val Val Gly Leu
            210                 215                 220

Ala Gly Asn Gly Trp Leu Arg Glu Asp Glu Pro Leu Lys Met Met
225                 230                 235                 240

Ala Ala Val Tyr Glu Leu Arg Glu Asp Lys Ser Tyr Gln Val Thr Val
            245                 250                 255

Val Asp Phe Glu Leu Glu Glu Cys Arg Tyr Met Thr Glu Thr Phe Val
            260                 265                 270

Pro Gly Asn Gln Pro Gly Glu Phe Thr Leu Gly Asp Ile Lys Ser Ser
            275                 280                 285

Pro Gly Trp Thr Ser Gln Leu Val Arg Val Val Ser Thr Asn Tyr Asn
            290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
            325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
            370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
            405                 410                 415

Ala Leu Arg Glu Asp Lys Asn Pro Met Lys Met Met Ala Thr Ile Tyr
            420                 425                 430

Glu Leu Lys Glu Asp Lys Ser Tyr Gln Val Thr Glu Val Arg Phe Arg
            435                 440                 445

His Lys Lys Cys Lys Tyr Asp Ile Val Thr Phe Val Pro Gly Ser Gln
            450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
            485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Pro Ser Glu Leu Lys Glu Asn Phe
            515                 520                 525

Ile Arg Phe Ser Lys Ser Leu Gly Leu Pro Glu Asn His Ile Val Phe
            530                 535                 540

Pro Val Pro Ile Asp Gln Cys Ile Asp Gly Gly Gly Gly Ser Gly
545                 550                 555                 560

Gly Gly Ser Gln Asp Ser Thr Ser Asp Leu Ile Pro Ala Pro Pro
            565                 570                 575

Leu Ser Lys Val Pro Leu Gln Gln Asn Phe Gln Asp Asn Gln Phe His

```
                580             585              590
Gly Lys Trp Tyr Val Val Gly His Ala Gly Asn Gln Trp Leu Arg Gly
            595                 600                 605

Asp Tyr Asp Pro Arg Lys Met Trp Ala Thr Ile Tyr Glu Leu Lys Glu
            610                 615                 620

Asp Lys Ser Tyr Gln Val Thr Asp Val Asp Phe Ala Ile Glu Lys Cys
625                 630                 635                 640

His Tyr Arg Ile Thr Thr Phe Val Pro Gly Ser Gln Pro Gly Glu Phe
                645                 650                 655

Thr Phe Gly Asn Ile Lys Ser His Pro Gly Gly Thr Ser Gly Leu Ala
            660                 665                 670

Arg Val Val Ser Thr Asn Tyr Asn Gln His Ala Met Val Phe Phe Lys
            675                 680                 685

Phe Val Ile Gln Asn Arg Glu Ala Phe Phe Ile Thr Leu Tyr Gly Arg
            690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
            755

<210> SEQ ID NO 149
<211> LENGTH: 758
<212> TYPE: PRT
<213> ORGANISM: Artificial Sequence
<220> FEATURE:
<223> OTHER INFORMATION: S0474.01H22(N65Q;T54A) (G4S)2 S0530.04N16(N65Q)
      (G4S)2 S0530.07G09(N65Q) (G4S)2 S0522.15K24(N65Q) Cterm StrepII
      His

<400> SEQUENCE: 149

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Ala Ile Tyr Glu Leu Lys Glu Asp Lys Ser Tyr
        50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

```
Asp Gly Gly Gly Gly Ser Gly Gly Gly Ser Gln Asp Ser Thr
            180             185             190

Ser Asp Leu Ile Pro Ala Pro Pro Leu Ser Lys Val Pro Leu Gln Gln
        195             200             205

Asn Phe Gln Asp Asn Gln Phe His Gly Lys Trp Tyr Val Val Gly Leu
    210             215             220

Ala Gly Asn Gly Trp Leu Arg Glu Asp Glu Asp Pro Leu Lys Met Met
225             230             235             240

Ala Ala Val Tyr Glu Leu Arg Glu Asp Lys Ser Tyr Gln Val Thr Val
            245             250             255

Val Asp Phe Glu Leu Glu Glu Cys Arg Tyr Met Thr Glu Thr Phe Val
            260             265             270

Pro Gly Asn Gln Pro Gly Glu Phe Thr Leu Gly Asp Ile Lys Ser Ser
        275             280             285

Pro Gly Trp Thr Ser Gln Leu Val Arg Val Val Ser Thr Asn Tyr Asn
    290             295             300

Gln His Ala Met Val Phe Lys Gly Val Tyr Gln Asn Arg Glu Trp
305             310             315             320

Phe His Ile Thr Leu Tyr Gly Arg Thr Lys Glu Leu Thr Ser Glu Leu
            325             330             335

Lys Glu Asn Phe Ile Arg Phe Ser Lys Ser Leu Gly Leu Pro Glu Asn
        340             345             350

His Ile Val Phe Pro Val Pro Ile Asp Gln Cys Ile Asp Gly Gly Gly
    355             360             365

Gly Gly Ser Gly Gly Gly Ser Gln Asp Ser Thr Ser Asp Leu Ile
    370             375             380

Pro Ala Pro Pro Leu Ser Lys Val Pro Leu Gln Gln Asn Phe Gln Asp
385             390             395             400

Asn Gln Phe His Gly Lys Trp Tyr Val Val Gly Glu Ala Gly Asn Leu
        405             410             415

Ala Arg Arg Glu Asp Lys Asp Pro Met Lys Met Met Ala Thr Ile Tyr
            420             425             430

Glu Leu Lys Glu Asp Lys Ser Tyr Gln Val Thr Glu Val Arg Phe Arg
        435             440             445

His Lys Lys Cys Lys Tyr Asp Ile Val Thr Phe Val Pro Gly Ser Gln
    450             455             460

Pro Gly Glu Phe Thr Leu Gly Leu Ile Lys Ser Asp Pro Gly Gln Thr
465             470             475             480

Pro Glu Leu Val Arg Val Val Ser Thr Asn Tyr Asn Gln His Ala Met
            485             490             495

Val Phe Phe Lys Lys Val Gln Asn Arg Glu Tyr Phe Trp Ile Thr
        500             505             510

Leu Tyr Gly Arg Thr Lys Glu Leu Thr Ser Glu Leu Lys Glu Asn Phe
    515             520             525

Ile Arg Phe Ser Lys Ser Leu Gly Leu Pro Glu Asn His Ile Val Phe
    530             535             540

Pro Val Pro Ile Asp Gln Cys Ile Asp Gly Gly Gly Gly Ser Gly
545             550             555             560

Gly Gly Ser Gln Asp Ser Thr Ser Asp Leu Ile Pro Ala Pro Pro
            565             570             575

Leu Ser Lys Val Pro Leu Gln Gln Asn Phe Gln Asp Asn Gln Phe His
            580             585             590
```

-continued

```
Gly Lys Trp Tyr Val Leu Gly Met Ala Gly Asn Phe His Leu Arg Glu
            595                 600                 605

Asp Lys Asp Pro Ser Lys Met Pro Ala Thr Ile Tyr Glu Leu Lys Glu
610                 615                 620

Asp Lys Ser Tyr Gln Val Thr His Val Pro Phe Trp Ala Lys Lys Cys
625                 630                 635                 640

Ala Tyr Lys Thr Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
            660                 665                 670

Arg Val Val Ser Thr Asn Tyr Asn Gln His Ala Met Val Phe Ser Lys
        675                 680                 685

Gly Val Trp Gln Asn Arg Glu Thr Phe Val Ile Thr Leu Tyr Gly Arg
690                 695                 700

Ala Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755
```

```
<210> SEQ ID NO 150
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0530.04N16(N65D)
      (G4S)2 S0530.07K20(N65D) (G4S)2 S0522.15K24(N65D) Cterm StrepII
      His

<400> SEQUENCE: 150

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gly Ser Gly Gly Gly Gly Ser Gln Asp Ser Thr
```

```
                180                 185                 190
Ser Asp Leu Ile Pro Ala Pro Pro Leu Ser Lys Val Pro Leu Gln Gln
            195                 200                 205

Asn Phe Gln Asp Asn Gln Phe His Gly Lys Trp Tyr Val Val Gly Leu
        210                 215                 220

Ala Gly Asn Gly Trp Leu Arg Glu Asp Glu Asp Pro Leu Lys Met Met
225                 230                 235                 240

Ala Ala Val Tyr Glu Leu Arg Glu Asp Lys Ser Tyr Asp Val Thr Val
                245                 250                 255

Val Asp Phe Glu Leu Glu Glu Cys Arg Tyr Met Thr Glu Thr Phe Val
            260                 265                 270

Pro Gly Asn Gln Pro Gly Glu Phe Thr Leu Gly Asp Ile Lys Ser Ser
        275                 280                 285

Pro Gly Trp Thr Ser Gln Leu Val Arg Val Ser Thr Asn Tyr Asn
290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
        355                 360                 365

Gly Gly Ser Gly Gly Gly Ser Gln Asp Ser Thr Ser Asp Leu Ile
370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
                405                 410                 415

Ala Leu Arg Glu Asp Lys Asn Pro Met Lys Met Met Ala Thr Ile Tyr
            420                 425                 430

Glu Leu Lys Glu Asp Lys Ser Tyr Asp Val Thr Glu Val Arg Phe Arg
        435                 440                 445

His Lys Lys Cys Lys Tyr Asp Ile Val Thr Phe Val Pro Gly Ser Gln
450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Pro Ser Glu Leu Lys Glu Asn Phe
        515                 520                 525

Ile Arg Phe Ser Lys Ser Leu Gly Leu Pro Glu Asn His Ile Val Phe
530                 535                 540

Pro Val Pro Ile Asp Gln Cys Ile Asp Gly Gly Gly Gly Ser Gly
545                 550                 555                 560

Gly Gly Gly Ser Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe His
            580                 585                 590

Gly Lys Trp Tyr Val Leu Gly Met Ala Gly Asn Phe His Leu Arg Glu
        595                 600                 605
```

```
Asp Lys Asp Pro Ser Lys Met Pro Ala Thr Ile Tyr Glu Leu Lys Glu
        610                 615                 620

Asp Lys Ser Tyr Asp Val Thr His Val Pro Phe Trp Ala Lys Lys Cys
625                 630                 635                 640

Ala Tyr Lys Thr Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
        660                 665                 670

Arg Val Val Ser Thr Asn Tyr Asn Gln His Ala Met Val Phe Ser Lys
        675                 680                 685

Gly Val Trp Gln Asn Arg Glu Thr Phe Val Ile Thr Leu Tyr Gly Arg
    690                 695                 700

Ala Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755

<210> SEQ ID NO 151
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0530.04N16(N65D)
      (G4S)2 S0530.07K20(N65D) (G4S)2 S0522.05M06 (N65D) Cterm StrepII
      His

<400> SEQUENCE: 151

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190
```

```
Ser Asp Leu Ile Pro Ala Pro Pro Leu Ser Lys Val Pro Leu Gln Gln
            195                 200                 205

Asn Phe Gln Asp Asn Gln Phe His Gly Lys Trp Tyr Val Val Gly Leu
            210                 215                 220

Ala Gly Asn Gly Trp Leu Arg Glu Asp Glu Asp Pro Leu Lys Met Met
225                 230                 235                 240

Ala Ala Val Tyr Glu Leu Arg Glu Asp Lys Ser Tyr Asp Val Thr Val
            245                 250                 255

Val Asp Phe Glu Leu Glu Glu Cys Arg Tyr Met Thr Glu Thr Phe Val
            260                 265                 270

Pro Gly Asn Gln Pro Gly Glu Phe Thr Leu Gly Asp Ile Lys Ser Ser
            275                 280                 285

Pro Gly Trp Thr Ser Gln Leu Val Arg Val Val Ser Thr Asn Tyr Asn
            290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
            325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
            370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
            405                 410                 415

Ala Leu Arg Glu Asp Lys Asn Pro Met Lys Met Ala Thr Ile Tyr
            420                 425                 430

Glu Leu Lys Glu Asp Lys Ser Tyr Asp Val Thr Glu Val Arg Phe Arg
            435                 440                 445

His Lys Lys Cys Lys Tyr Asp Ile Val Thr Phe Val Pro Gly Ser Gln
450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
            485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Pro Ser Glu Leu Lys Glu Asn Phe
            515                 520                 525

Ile Arg Phe Ser Lys Ser Leu Gly Leu Pro Glu Asn His Ile Val Phe
            530                 535                 540

Pro Val Pro Ile Asp Gln Cys Ile Asp Gly Gly Gly Gly Ser Gly
545                 550                 555                 560

Gly Gly Ser Gln Asp Ser Thr Ser Asp Leu Ile Pro Ala Pro Pro
            565                 570                 575

Leu Ser Lys Val Pro Leu Gln Gln Asn Phe Gln Asp Asn Gln Phe His
            580                 585                 590

Gly Lys Trp Tyr Val Val Gly His Ala Gly Asn Gln Trp Leu Arg Gly
            595                 600                 605

Asp Tyr Asp Pro Arg Lys Met Trp Ala Thr Ile Tyr Glu Leu Lys Glu
```

```
            610                 615                 620
Asp Lys Ser Tyr Asp Val Thr Asp Val Asp Phe Ala Ile Glu Lys Cys
625                 630                 635                 640

His Tyr Arg Ile Thr Thr Phe Val Pro Gly Ser Gln Pro Gly Glu Phe
                    645                 650                 655

Thr Phe Gly Asn Ile Lys Ser His Pro Gly Gly Thr Ser Gly Leu Ala
                660                 665                 670

Arg Val Val Ser Thr Asn Tyr Asn Gln His Ala Met Val Phe Phe Lys
            675                 680                 685

Phe Val Ile Gln Asn Arg Glu Ala Phe Phe Ile Thr Leu Tyr Gly Arg
        690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                    725                 730                 735

Asp Gln Cys Ile Asp Gly Ser Ala Trp Ser His Pro Gln Phe Glu Lys
                740                 745                 750

His His His His His His
            755

<210> SEQ ID NO 152
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0530.04N16(N65D)
      (G4S)2 S0530.07G09(N65D) (G4S)2 S0522.15K24(N65D) Cterm StrepII
      His

<400> SEQUENCE: 152

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205
```

```
Asn Phe Gln Asp Asn Gln Phe His Gly Lys Trp Tyr Val Val Gly Leu
        210                 215                 220
Ala Gly Asn Gly Trp Leu Arg Glu Asp Glu Asp Pro Leu Lys Met Met
225                 230                 235                 240
Ala Ala Val Tyr Glu Leu Arg Glu Asp Lys Ser Tyr Asp Val Thr Val
                245                 250                 255
Val Asp Phe Glu Leu Glu Glu Cys Arg Tyr Met Thr Glu Thr Phe Val
            260                 265                 270
Pro Gly Asn Gln Pro Gly Glu Phe Thr Leu Gly Asp Ile Lys Ser Ser
        275                 280                 285
Pro Gly Trp Thr Ser Gln Leu Val Arg Val Val Ser Thr Asn Tyr Asn
        290                 295                 300
Gln His Ala Met Val Phe Phe Lys Gly Val Tyr Gln Asn Arg Glu Trp
305                 310                 315                 320
Phe His Ile Thr Leu Tyr Gly Arg Thr Lys Glu Leu Thr Ser Glu Leu
                325                 330                 335
Lys Glu Asn Phe Ile Arg Phe Ser Lys Ser Leu Gly Leu Pro Glu Asn
            340                 345                 350
His Ile Val Phe Pro Val Pro Ile Asp Gln Cys Ile Asp Gly Gly Gly
        355                 360                 365
Gly Gly Ser Gly Gly Gly Ser Gln Asp Ser Thr Ser Asp Leu Ile
        370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                405                 410                 415
Ala Arg Arg Glu Asp Lys Asp Pro Met Lys Met Met Ala Thr Ile Tyr
                420                 425                 430
Glu Leu Lys Glu Asp Lys Ser Tyr Asp Val Thr Glu Val Arg Phe Arg
            435                 440                 445
His Lys Lys Cys Lys Tyr Asp Ile Val Thr Phe Val Pro Gly Ser Gln
        450                 455                 460
Pro Gly Glu Phe Thr Leu Gly Leu Ile Lys Ser Asp Pro Gly Gln Thr
465                 470                 475                 480
Pro Glu Leu Val Arg Val Val Ser Thr Asn Tyr Asn Gln His Ala Met
                485                 490                 495
Val Phe Phe Lys Lys Val Val Gln Asn Arg Glu Tyr Phe Trp Ile Thr
            500                 505                 510
Leu Tyr Gly Arg Thr Lys Glu Leu Thr Ser Glu Leu Lys Glu Asn Phe
        515                 520                 525
Ile Arg Phe Ser Lys Ser Leu Gly Leu Pro Glu Asn His Ile Val Phe
        530                 535                 540
Pro Val Pro Ile Asp Gln Cys Ile Asp Gly Gly Gly Gly Ser Gly
545                 550                 555                 560
Gly Gly Ser Gln Asp Ser Thr Ser Asp Leu Ile Pro Ala Pro Pro
                565                 570                 575
Leu Ser Lys Val Pro Leu Gln Gln Asn Phe Gln Asp Asn Gln Phe His
            580                 585                 590
Gly Lys Trp Tyr Val Leu Gly Met Ala Gly Asn Phe His Leu Arg Glu
        595                 600                 605
Asp Lys Asp Pro Ser Lys Met Pro Ala Thr Ile Tyr Glu Leu Lys Glu
    610                 615                 620
```

```
Asp Lys Ser Tyr Asp Val Thr His Val Pro Phe Trp Ala Lys Lys Cys
625                 630                 635                 640

Ala Tyr Lys Thr Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
            660                 665                 670

Arg Val Val Ser Thr Asn Tyr Asn Gln His Ala Met Val Phe Ser Lys
            675                 680                 685

Gly Val Trp Gln Asn Arg Glu Thr Phe Val Ile Thr Leu Tyr Gly Arg
        690                 695                 700

Ala Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755
```

<210> SEQ ID NO 153
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0530.04N16(N65D)
      (G4S)2 S0530.07G09(N65D) (G4S)2 S0522.05M06 (N65D) Cterm StrepII
      His

<400> SEQUENCE: 153

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Ala Ile Tyr Glu Leu Lys Glu Asp Lys Ser Tyr
        50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Leu
```

```
              210                 215                 220
Ala Gly Asn Gly Trp Leu Arg Glu Asp Glu Asp Pro Leu Lys Met Met
225                 230                 235                 240

Ala Ala Val Tyr Glu Leu Arg Glu Asp Lys Ser Tyr Asp Val Thr Val
                245                 250                 255

Val Asp Phe Glu Leu Glu Cys Arg Tyr Met Thr Glu Thr Phe Val
            260                 265                 270

Pro Gly Asn Gln Pro Gly Glu Phe Thr Leu Gly Asp Ile Lys Ser Ser
        275                 280                 285

Pro Gly Trp Thr Ser Gln Leu Val Arg Val Ser Thr Asn Tyr Asn
    290                 295                 300

Gln His Ala Met Val Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
                340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
    370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
                405                 410                 415

Ala Arg Arg Glu Asp Lys Asp Pro Met Lys Met Met Ala Thr Ile Tyr
                420                 425                 430

Glu Leu Lys Glu Asp Lys Ser Tyr Asp Val Thr Glu Val Arg Phe Arg
                435                 440                 445

His Lys Lys Cys Lys Tyr Asp Ile Val Thr Phe Val Pro Gly Ser Gln
450                 455                 460

Pro Gly Glu Phe Thr Leu Gly Leu Ile Lys Ser Asp Pro Gly Gln Thr
465                 470                 475                 480

Pro Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
                500                 505                 510

Leu Tyr Gly Arg Thr Lys Glu Leu Thr Ser Glu Leu Lys Glu Asn Phe
            515                 520                 525

Ile Arg Phe Ser Lys Ser Leu Gly Leu Pro Glu Asn His Ile Val Phe
            530                 535                 540

Pro Val Pro Ile Asp Gln Cys Ile Asp Gly Gly Gly Gly Ser Gly
545                 550                 555                 560

Gly Gly Ser Gln Asp Ser Thr Ser Asp Leu Ile Pro Ala Pro Pro
            565                 570                 575

Leu Ser Lys Val Pro Leu Gln Gln Asn Phe Gln Asp Asn Gln Phe His
            580                 585                 590

Gly Lys Trp Tyr Val Val Gly His Ala Gly Asn Gln Trp Leu Arg Gly
            595                 600                 605

Asp Tyr Asp Pro Arg Lys Met Trp Ala Thr Ile Tyr Glu Leu Lys Glu
        610                 615                 620

Asp Lys Ser Tyr Asp Val Thr Asp Val Asp Phe Ala Ile Glu Lys Cys
625                 630                 635                 640
```

His Tyr Arg Ile Thr Thr Phe Val Pro Gly Ser Gln Pro Gly Glu Phe
                645                 650                 655

Thr Phe Gly Asn Ile Lys Ser His Pro Gly Gly Thr Ser Gly Leu Ala
            660                 665                 670

Arg Val Val Ser Thr Asn Tyr Asn Gln His Ala Met Val Phe Phe Lys
        675                 680                 685

Phe Val Ile Gln Asn Arg Glu Ala Phe Phe Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755

<210> SEQ ID NO 154
<211> LENGTH: 752
<212> TYPE: PRT
<213> ORGANISM: Artificial Sequence
<220> FEATURE:
<223> OTHER INFORMATION: S0474.01H22(N65Q;T54A) GQPKAAPS
      S0466.09E05(N65Q) GQPKAAPS S0466.13C10(N65Q) GQPKAAPS
      S0455.04F09(N65Q) StrepII, His6

<400> SEQUENCE: 154

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gln Pro Lys Ala Ala Pro Ser Gln Asp Ser Thr Ser Asp
            180                 185                 190

Leu Ile Pro Ala Pro Pro Leu Ser Lys Val Pro Leu Gln Gln Asn Phe
    195                 200                 205

Gln Asp Asn Gln Phe His Gly Lys Trp Tyr Val Val Gly Leu Ala Gly
    210                 215                 220

```
Asn Gly Trp Leu Arg Glu Asp Lys Asp Pro Val Lys Met Met Ala Thr
225                 230                 235                 240

Ile Tyr Glu Leu Lys Glu Asp Lys Ser Tyr Gln Val Thr Val Val Asp
                245                 250                 255

Phe Glu Leu Lys Lys Cys Arg Tyr Met Ile Glu Thr Phe Val Pro Gly
                260                 265                 270

Ser Gln Pro Gly Glu Phe Thr Leu Gly Asp Ile Lys Ser Phe Pro Gly
                275                 280                 285

Trp Thr Ser Gln Leu Val Arg Val Ser Thr Asn Tyr Asn Gln His
290                 295                 300

Ala Met Val Phe Phe Lys Gly Val Tyr Gln Asn Arg Glu Trp Phe His
305                 310                 315                 320

Ile Thr Leu Tyr Gly Arg Thr Lys Glu Leu Thr Ser Glu Leu Lys Glu
                325                 330                 335

Asn Phe Ile Arg Phe Ser Lys Ser Leu Gly Leu Pro Glu Asn His Ile
                340                 345                 350

Val Phe Pro Val Pro Ile Asp Gln Cys Ile Asp Gly Gly Gln Pro Lys
                355                 360                 365

Ala Ala Pro Ser Gln Asp Ser Thr Ser Asp Leu Ile Pro Ala Pro Pro
370                 375                 380

Leu Ser Lys Val Pro Leu Gln Gln Asn Phe Gln Asp Asn Gln Phe His
385                 390                 395                 400

Gly Lys Trp Tyr Val Gly Glu Ala Gly Asn Leu Ala Leu Arg Glu
                405                 410                 415

Asp Lys Asp Pro Lys Lys Met Met Ala Thr Ile Tyr Glu Leu Lys Glu
                420                 425                 430

Asp Lys Ser Tyr Gln Val Thr Glu Val Arg Phe Arg His Lys Lys Cys
                435                 440                 445

Gln Tyr Asp Ile Ala Thr Phe Val Pro Gly Ser Gln Pro Gly Glu Phe
                450                 455                 460

Thr Leu Gly Leu Ile Lys Ser Asp Pro Gly Gln Thr Ser Glu Leu Val
465                 470                 475                 480

Arg Val Val Ser Thr Asn Tyr Asn Gln His Ala Met Val Phe Phe Lys
                485                 490                 495

Lys Val Val Gln Asn Arg Glu Phe Phe Trp Ile Thr Leu Tyr Gly Arg
                500                 505                 510

Thr Lys Glu Leu Thr Ser Glu Leu Lys Glu Asn Phe Ile Arg Phe Ser
                515                 520                 525

Lys Ser Leu Gly Leu Pro Glu Asn His Ile Val Phe Pro Val Pro Ile
530                 535                 540

Asp Gln Cys Ile Asp Gly Gly Gln Pro Lys Ala Ala Pro Ser Gln Asp
545                 550                 555                 560

Ser Thr Ser Asp Leu Ile Pro Ala Pro Pro Leu Ser Lys Val Pro Leu
                565                 570                 575

Gln Gln Asn Phe Gln Asp Asn Gln Phe His Gly Lys Trp Tyr Val Val
                580                 585                 590

Gly Met Ala Gly Asn Phe His Leu Arg Glu Asp Lys Asp Pro Ser Lys
                595                 600                 605

Met Pro Ala Thr Ile Tyr Glu Leu Lys Glu Asp Lys Ser Tyr Gln Val
                610                 615                 620

Thr His Val Pro Phe Trp Ala Lys Lys Cys Ala Tyr Lys Ile Ile Thr
625                 630                 635                 640

Phe Val Pro Gly Ser Gln Pro Gly Glu Phe Thr Leu Gly Ala Ile Lys
```

```
                        645                 650                 655
            Ser Gly Pro Gly Met Thr Ser Trp Leu Val Arg Val Val Ser Thr Asn
                        660                 665                 670

Tyr Asn Gln His Ala Met Val Phe Phe Lys Gly Val Trp Gln Asn Arg
                        675                 680                 685

Glu Thr Phe Val Ile Thr Leu Tyr Gly Arg Thr Lys Glu Leu Thr Ser
                        690                 695                 700

Glu Leu Lys Glu Asn Phe Ile Arg Phe Ser Lys Ser Leu Gly Leu Pro
            705                 710                 715                 720

Glu Asn His Ile Val Phe Pro Val Pro Ile Asp Gln Cys Ile Asp Gly
                        725                 730                 735

Ser Ala Trp Ser His Pro Gln Phe Glu Lys His His His His His His
                        740                 745                 750

<210> SEQ ID NO 155
<211> LENGTH: 752
<212> TYPE: PRT
<213> ORGANISM: Artificial Sequence
<220> FEATURE:
<223> OTHER INFORMATION: S0474.01H22(N65Q;T54A) GQPKAAPS
      S0466.09E05(N65Q) GQPKAAPS S0466.13C10(N65Q) GQPKAAPS
      S0455.04F09(N65Q) StrepII, His6

<400> SEQUENCE: 155

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gln Pro Lys Ala Ala Pro Ser Gln Asp Ser Thr Ser Asp
            180                 185                 190

Leu Ile Pro Ala Pro Pro Leu Ser Lys Val Pro Leu Gln Gln Asn Phe
        195                 200                 205

Gln Asp Asn Gln Phe His Gly Lys Trp Tyr Val Val Gly Leu Ala Gly
    210                 215                 220

Asn Gly Trp Leu Arg Glu Asp Lys Asp Pro Val Lys Met Met Ala Thr
225                 230                 235                 240

Ile Tyr Glu Leu Lys Glu Asp Lys Ser Tyr Gln Val Thr Val Val Asp
                245                 250                 255
```

```
Phe Glu Leu Lys Lys Cys Arg Tyr Met Ile Glu Thr Phe Val Pro Gly
            260                 265                 270

Ser Gln Pro Gly Glu Phe Thr Leu Gly Asp Ile Lys Ser Phe Pro Gly
            275                 280                 285

Trp Thr Ser Gln Leu Val Arg Val Val Ser Thr Asn Tyr Asn Gln His
290                 295                 300

Ala Met Val Phe Phe Lys Gly Val Tyr Gln Asn Arg Glu Trp Phe His
305                 310                 315                 320

Ile Thr Leu Tyr Gly Arg Thr Lys Glu Leu Thr Ser Glu Leu Lys Glu
                325                 330                 335

Asn Phe Ile Arg Phe Ser Lys Ser Leu Gly Leu Pro Glu Asn His Ile
                340                 345                 350

Val Phe Pro Val Pro Ile Asp Gln Cys Ile Asp Gly Gly Gln Pro Lys
            355                 360                 365

Ala Ala Pro Ser Gln Asp Ser Thr Ser Asp Leu Ile Pro Ala Pro Pro
370                 375                 380

Leu Ser Lys Val Pro Leu Gln Gln Asn Phe Gln Asp Asn Gln Phe His
385                 390                 395                 400

Gly Lys Trp Tyr Val Gly Glu Ala Gly Asn Leu Ala Leu Arg Glu
                405                 410                 415

Asp Lys Asp Pro Lys Lys Met Met Ala Thr Ile Tyr Glu Leu Lys Glu
                420                 425                 430

Asp Lys Ser Tyr Gln Val Thr Glu Val Arg Phe Arg His Lys Lys Cys
            435                 440                 445

Gln Tyr Asp Ile Ala Thr Phe Val Pro Gly Ser Gln Pro Gly Glu Phe
            450                 455                 460

Thr Leu Gly Leu Ile Lys Ser Asp Pro Gly Gln Thr Ser Glu Leu Val
465                 470                 475                 480

Arg Val Val Ser Thr Asn Tyr Asn Gln His Ala Met Val Phe Phe Lys
                485                 490                 495

Lys Val Val Gln Asn Arg Glu Phe Phe Trp Ile Thr Leu Tyr Gly Arg
            500                 505                 510

Thr Lys Glu Leu Thr Ser Glu Leu Lys Glu Asn Phe Ile Arg Phe Ser
            515                 520                 525

Lys Ser Leu Gly Leu Pro Glu Asn His Ile Val Phe Pro Val Pro Ile
530                 535                 540

Asp Gln Cys Ile Asp Gly Gly Gln Pro Lys Ala Ala Pro Ser Gln Asp
545                 550                 555                 560

Ser Thr Ser Asp Leu Ile Pro Ala Pro Pro Leu Ser Lys Val Pro Leu
                565                 570                 575

Gln Gln Asn Phe Gln Asp Asn Gln Phe His Gly Lys Trp Tyr Val Val
            580                 585                 590

Gly Met Ala Gly Asn Phe His Leu Arg Glu Asp Lys Asp Pro Ser Lys
            595                 600                 605

Met Pro Ala Thr Ile Tyr Glu Leu Lys Glu Asp Lys Ser Tyr Gln Val
            610                 615                 620

Thr His Val Pro Phe Trp Ala Lys Lys Cys Ala Tyr Lys Ile Ile Thr
625                 630                 635                 640

Phe Val Pro Gly Ser Gln Pro Gly Glu Phe Thr Leu Gly Ala Ile Lys
            645                 650                 655

Ser Gly Pro Gly Met Thr Ser Trp Leu Val Arg Val Val Ser Thr Asn
            660                 665                 670
```

```
Tyr Asn Gln His Ala Met Val Phe Phe Lys Gly Val Trp Gln Asn Arg
            675                 680                 685

Glu Thr Phe Val Ile Thr Leu Tyr Gly Arg Thr Lys Glu Leu Thr Ser
        690                 695                 700

Glu Leu Lys Glu Asn Phe Ile Arg Phe Ser Lys Ser Leu Gly Leu Pro
705                 710                 715                 720

Glu Asn His Ile Val Phe Pro Val Pro Ile Asp Gln Cys Ile Asp Gly
                725                 730                 735

Ser Ala Trp Ser His Pro Gln Phe Glu Lys His His His His His His
            740                 745                 750

<210> SEQ ID NO 156
<211> LENGTH: 746
<212> TYPE: PRT
<213> ORGANISM: Artificial Sequence
<220> FEATURE:
<223> OTHER INFORMATION: S0474.01H22(N65Q;T54A) ASTKGP S0466.09E05(N65Q)
      ASTKGP S0466.13C10(N65Q) ASTKGP  S0455.04F09(N65Q) StrepII, His6

<400> SEQUENCE: 156

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ala Ser Thr Lys Gly Pro Gln Asp Ser Thr Ser Asp Leu Ile
            180                 185                 190

Pro Ala Pro Pro Leu Ser Lys Val Pro Leu Gln Gln Asn Phe Gln Asp
        195                 200                 205

Asn Gln Phe His Gly Lys Trp Tyr Val Val Gly Leu Ala Gly Asn Gly
    210                 215                 220

Trp Leu Arg Glu Asp Lys Asp Pro Val Lys Met Met Ala Thr Ile Tyr
225                 230                 235                 240

Glu Leu Lys Glu Asp Lys Ser Tyr Gln Val Thr Val Val Asp Phe Glu
                245                 250                 255

Leu Lys Lys Cys Arg Tyr Met Ile Glu Thr Phe Val Pro Gly Ser Gln
            260                 265                 270

Pro Gly Glu Phe Thr Leu Gly Asp Ile Lys Ser Phe Pro Gly Trp Thr
        275                 280                 285
```

-continued

```
Ser Gln Leu Val Arg Val Val Ser Thr Asn Tyr Asn Gln His Ala Met
    290                 295                 300

Val Phe Phe Lys Gly Val Tyr Gln Asn Arg Glu Trp Phe His Ile Thr
305                 310                 315                 320

Leu Tyr Gly Arg Thr Lys Glu Leu Thr Ser Glu Leu Lys Glu Asn Phe
                325                 330                 335

Ile Arg Phe Ser Lys Ser Leu Gly Leu Pro Glu Asn His Ile Val Phe
                340                 345                 350

Pro Val Pro Ile Asp Gln Cys Ile Asp Gly Ala Ser Thr Lys Gly Pro
            355                 360                 365

Gln Asp Ser Thr Ser Asp Leu Ile Pro Ala Pro Leu Ser Lys Val
    370                 375                 380

Pro Leu Gln Gln Asn Phe Gln Asp Asn Gln Phe His Gly Lys Trp Tyr
385                 390                 395                 400

Val Val Gly Glu Ala Gly Asn Leu Ala Leu Arg Glu Asp Lys Asp Pro
                405                 410                 415

Lys Lys Met Met Ala Thr Ile Tyr Glu Leu Lys Glu Asp Lys Ser Tyr
            420                 425                 430

Gln Val Thr Glu Val Arg Phe Arg His Lys Lys Cys Gln Tyr Asp Ile
        435                 440                 445

Ala Thr Phe Val Pro Gly Ser Gln Pro Gly Glu Phe Thr Leu Gly Leu
    450                 455                 460

Ile Lys Ser Asp Pro Gly Gln Thr Ser Glu Leu Val Arg Val Val Ser
465                 470                 475                 480

Thr Asn Tyr Asn Gln His Ala Met Val Phe Phe Lys Lys Val Val Gln
                485                 490                 495

Asn Arg Glu Phe Phe Trp Ile Thr Leu Tyr Gly Arg Thr Lys Glu Leu
                500                 505                 510

Thr Ser Glu Leu Lys Glu Asn Phe Ile Arg Phe Ser Lys Ser Leu Gly
            515                 520                 525

Leu Pro Glu Asn His Ile Val Phe Pro Val Pro Ile Asp Gln Cys Ile
    530                 535                 540

Asp Gly Ala Ser Thr Lys Gly Pro Gln Asp Ser Thr Ser Asp Leu Ile
545                 550                 555                 560

Pro Ala Pro Pro Leu Ser Lys Val Pro Leu Gln Gln Asn Phe Gln Asp
                565                 570                 575

Asn Gln Phe His Gly Lys Trp Tyr Val Val Gly Met Ala Gly Asn Phe
            580                 585                 590

His Leu Arg Glu Asp Lys Asp Pro Ser Lys Met Pro Ala Thr Ile Tyr
    595                 600                 605

Glu Leu Lys Glu Asp Lys Ser Tyr Gln Val Thr His Val Pro Phe Trp
610                 615                 620

Ala Lys Lys Cys Ala Tyr Lys Ile Ile Thr Phe Val Pro Gly Ser Gln
                625                 630                 635                 640

Pro Gly Glu Phe Thr Leu Gly Ala Ile Lys Ser Gly Pro Gly Met Thr
                645                 650                 655

Ser Trp Leu Val Arg Val Val Ser Thr Asn Tyr Asn Gln His Ala Met
                660                 665                 670

Val Phe Phe Lys Gly Val Trp Gln Asn Arg Glu Thr Phe Val Ile Thr
            675                 680                 685

Leu Tyr Gly Arg Thr Lys Glu Leu Thr Ser Glu Leu Lys Glu Asn Phe
    690                 695                 700
```

Ile Arg Phe Ser Lys Ser Leu Gly Leu Pro Glu Asn His Ile Val Phe
705                 710                 715                 720

Pro Val Pro Ile Asp Gln Cys Ile Asp Gly Ser Ala Trp Ser His Pro
            725                 730                 735

Gln Phe Glu Lys His His His His His His
            740                 745

<210> SEQ ID NO 157
<211> LENGTH: 749
<212> TYPE: PRT
<213> ORGANISM: Artificial Sequence
<220> FEATURE:
<223> OTHER INFORMATION: S0474.01H22(N65Q;T54A) ASTKGPS
      S0466.09E05(N65Q) ASTKGPS S0466.13C10(N65Q) ASTKGPS
      S0455.04F09(N65Q) StrepII, His6

<400> SEQUENCE: 157

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ala Ser Thr Lys Gly Pro Ser Gln Asp Ser Thr Ser Asp Leu
            180                 185                 190

Ile Pro Ala Pro Pro Leu Ser Lys Val Pro Leu Gln Gln Asn Phe Gln
        195                 200                 205

Asp Asn Gln Phe His Gly Lys Trp Tyr Val Val Gly Leu Ala Gly Asn
210                 215                 220

Gly Trp Leu Arg Glu Asp Lys Asp Pro Val Lys Met Met Ala Thr Ile
225                 230                 235                 240

Tyr Glu Leu Lys Glu Asp Lys Ser Tyr Gln Val Thr Val Val Asp Phe
                245                 250                 255

Glu Leu Lys Lys Cys Arg Tyr Met Ile Glu Thr Phe Val Pro Gly Ser
            260                 265                 270

Gln Pro Gly Glu Phe Thr Leu Gly Asp Ile Lys Ser Phe Pro Gly Trp
        275                 280                 285

Thr Ser Gln Leu Val Arg Val Val Ser Thr Asn Tyr Asn Gln His Ala
290                 295                 300

Met Val Phe Phe Lys Gly Val Tyr Gln Asn Arg Glu Trp Phe His Ile

```
305                 310                 315                 320
Thr Leu Tyr Gly Arg Thr Lys Glu Leu Thr Ser Glu Leu Lys Glu Asn
                325                 330                 335
Phe Ile Arg Phe Ser Lys Ser Leu Gly Leu Pro Glu Asn His Ile Val
                340                 345                 350
Phe Pro Val Pro Ile Asp Gln Cys Ile Asp Gly Ala Ser Thr Lys Gly
                355                 360                 365
Pro Ser Gln Asp Ser Thr Ser Asp Leu Ile Pro Ala Pro Pro Leu Ser
            370                 375                 380
Lys Val Pro Leu Gln Gln Asn Phe Gln Asp Asn Gln Phe His Gly Lys
385                 390                 395                 400
Trp Tyr Val Val Gly Glu Ala Gly Asn Leu Ala Leu Arg Glu Asp Lys
                405                 410                 415
Asp Pro Lys Lys Met Met Ala Thr Ile Tyr Glu Leu Lys Glu Asp Lys
                420                 425                 430
Ser Tyr Gln Val Thr Glu Val Arg Phe Arg His Lys Lys Cys Gln Tyr
                435                 440                 445
Asp Ile Ala Thr Phe Val Pro Gly Ser Gln Pro Gly Glu Phe Thr Leu
            450                 455                 460
Gly Leu Ile Lys Ser Asp Pro Gly Gln Thr Ser Glu Leu Val Arg Val
465                 470                 475                 480
Val Ser Thr Asn Tyr Asn Gln His Ala Met Val Phe Phe Lys Lys Val
                485                 490                 495
Val Gln Asn Arg Glu Phe Phe Trp Ile Thr Leu Tyr Gly Arg Thr Lys
                500                 505                 510
Glu Leu Thr Ser Glu Leu Lys Glu Asn Phe Ile Arg Phe Ser Lys Ser
                515                 520                 525
Leu Gly Leu Pro Glu Asn His Ile Val Phe Pro Val Pro Ile Asp Gln
            530                 535                 540
Cys Ile Asp Gly Ala Ser Thr Lys Gly Pro Ser Gln Asp Ser Thr Ser
545                 550                 555                 560
Asp Leu Ile Pro Ala Pro Pro Leu Ser Lys Val Pro Leu Gln Gln Asn
                565                 570                 575
Phe Gln Asp Asn Gln Phe His Gly Lys Trp Tyr Val Val Gly Met Ala
                580                 585                 590
Gly Asn Phe His Leu Arg Glu Asp Lys Asp Pro Ser Lys Met Pro Ala
                595                 600                 605
Thr Ile Tyr Glu Leu Lys Glu Asp Lys Ser Tyr Gln Val Thr His Val
                610                 615                 620
Pro Phe Trp Ala Lys Lys Cys Ala Tyr Lys Ile Ile Thr Phe Val Pro
625                 630                 635                 640
Gly Ser Gln Pro Gly Glu Phe Thr Leu Gly Ala Ile Lys Ser Gly Pro
                645                 650                 655
Gly Met Thr Ser Trp Leu Val Arg Val Val Ser Thr Asn Tyr Asn Gln
                660                 665                 670
His Ala Met Val Phe Phe Lys Gly Val Trp Gln Asn Arg Glu Thr Phe
                675                 680                 685
Val Ile Thr Leu Tyr Gly Arg Thr Lys Glu Leu Thr Ser Glu Leu Lys
            690                 695                 700
Glu Asn Phe Ile Arg Phe Ser Lys Ser Leu Gly Leu Pro Glu Asn His
705                 710                 715                 720
Ile Val Phe Pro Val Pro Ile Asp Gln Cys Ile Asp Gly Ser Ala Trp
                725                 730                 735
```

Ser His Pro Gln Phe Glu Lys His His His His His
            740                 745

<210> SEQ ID NO 158
<211> LENGTH: 746
<212> TYPE: PRT
<213> ORGANISM: Artificial Sequence
<220> FEATURE:
<223> OTHER INFORMATION: S0474.01H22(N65Q;T54A) QPKAAP S0466.09E05(N65Q)
      QPKAAP S0466.13C10(N65Q) QPKAAP S0455.04F09(N65Q) StrepII, His6

<400> SEQUENCE: 158

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gln Pro Lys Ala Ala Pro Gln Asp Ser Thr Ser Asp Leu Ile
            180                 185                 190

Pro Ala Pro Pro Leu Ser Lys Val Pro Leu Gln Gln Asn Phe Gln Asp
        195                 200                 205

Asn Gln Phe His Gly Lys Trp Tyr Val Val Gly Leu Ala Gly Asn Gly
    210                 215                 220

Trp Leu Arg Glu Asp Lys Asp Pro Val Lys Met Met Ala Thr Ile Tyr
225                 230                 235                 240

Glu Leu Lys Glu Asp Lys Ser Tyr Gln Val Thr Val Val Asp Phe Glu
                245                 250                 255

Leu Lys Lys Cys Arg Tyr Met Ile Glu Thr Phe Val Pro Gly Ser Gln
            260                 265                 270

Pro Gly Glu Phe Thr Leu Gly Asp Ile Lys Ser Phe Pro Gly Trp Thr
        275                 280                 285

Ser Gln Leu Val Arg Val Val Ser Thr Asn Tyr Asn Gln His Ala Met
    290                 295                 300

Val Phe Phe Lys Gly Val Tyr Gln Asn Arg Glu Trp Phe His Ile Thr
305                 310                 315                 320

Leu Tyr Gly Arg Thr Lys Glu Leu Thr Ser Glu Leu Lys Glu Asn Phe
                325                 330                 335

Ile Arg Phe Ser Lys Ser Leu Gly Leu Pro Glu Asn His Ile Val Phe

```
                 340                 345                 350
Pro Val Pro Ile Asp Gln Cys Ile Asp Gly Gln Pro Lys Ala Ala Pro
                355                 360                 365
Gln Asp Ser Thr Ser Asp Leu Ile Pro Ala Pro Pro Leu Ser Lys Val
            370                 375                 380
Pro Leu Gln Gln Asn Phe Gln Asp Asn Gln Phe His Gly Lys Trp Tyr
385                 390                 395                 400
Val Val Gly Glu Ala Gly Asn Leu Ala Leu Arg Glu Asp Lys Asp Pro
                405                 410                 415
Lys Lys Met Met Ala Thr Ile Tyr Glu Leu Lys Glu Asp Lys Ser Tyr
                420                 425                 430
Gln Val Thr Glu Val Arg Phe Arg His Lys Lys Cys Gln Tyr Asp Ile
            435                 440                 445
Ala Thr Phe Val Pro Gly Ser Gln Pro Gly Glu Phe Thr Leu Gly Leu
            450                 455                 460
Ile Lys Ser Asp Pro Gly Gln Thr Ser Glu Leu Val Arg Val Val Ser
465                 470                 475                 480
Thr Asn Tyr Asn Gln His Ala Met Val Phe Phe Lys Lys Val Val Gln
                485                 490                 495
Asn Arg Glu Phe Phe Trp Ile Thr Leu Tyr Gly Arg Thr Lys Glu Leu
                500                 505                 510
Thr Ser Glu Leu Lys Glu Asn Phe Ile Arg Phe Ser Lys Ser Leu Gly
            515                 520                 525
Leu Pro Glu Asn His Ile Val Phe Pro Val Pro Ile Asp Gln Cys Ile
            530                 535                 540
Asp Gly Gln Pro Lys Ala Ala Pro Gln Asp Ser Thr Ser Asp Leu Ile
545                 550                 555                 560
Pro Ala Pro Pro Leu Ser Lys Val Pro Leu Gln Gln Asn Phe Gln Asp
                565                 570                 575
Asn Gln Phe His Gly Lys Trp Tyr Val Val Gly Met Ala Gly Asn Phe
            580                 585                 590
His Leu Arg Glu Asp Lys Asp Pro Ser Lys Met Pro Ala Thr Ile Tyr
            595                 600                 605
Glu Leu Lys Glu Asp Lys Ser Tyr Gln Val Thr His Val Pro Phe Trp
            610                 615                 620
Ala Lys Lys Cys Ala Tyr Lys Ile Ile Thr Phe Val Pro Gly Ser Gln
625                 630                 635                 640
Pro Gly Glu Phe Thr Leu Gly Ala Ile Lys Ser Gly Pro Gly Met Thr
                645                 650                 655
Ser Trp Leu Val Arg Val Val Ser Thr Asn Tyr Asn Gln His Ala Met
            660                 665                 670
Val Phe Phe Lys Gly Val Trp Gln Asn Arg Glu Thr Phe Val Ile Thr
            675                 680                 685
Leu Tyr Gly Arg Thr Lys Glu Leu Thr Ser Glu Leu Lys Glu Asn Phe
            690                 695                 700
Ile Arg Phe Ser Lys Ser Leu Gly Leu Pro Glu Asn His Ile Val Phe
705                 710                 715                 720
Pro Val Pro Ile Asp Gln Cys Ile Asp Gly Ser Ala Trp Ser His Pro
                725                 730                 735
Gln Phe Glu Lys His His His His His His
            740                 745

<210> SEQ ID NO 159
```

```
<211> LENGTH: 749
<212> TYPE: PRT
<213> ORGANISM: Artificial Sequence
<220> FEATURE:
<223> OTHER INFORMATION: S0474.01H22(N65Q;T54A) GQPKAAP
      S0466.09E05(N65Q) GQPKAAP S0466.13C10(N65Q) GQPKAAP
      S0455.04F09(N65Q) StrepII, His6

<400> SEQUENCE: 159
```

| | | | | | | | | | | | | | | |
|---|---|---|---|---|---|---|---|---|---|---|---|---|---|---|
|Gln|Asp|Ser|Thr|Ser|Asp|Leu|Ile|Pro|Ala|Pro|Pro|Leu|Ser|Lys|Val|
|1| | | |5| | | | |10| | | | |15| |

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gln Pro Lys Ala Ala Pro Gln Asp Ser Thr Ser Asp Leu
            180                 185                 190

Ile Pro Ala Pro Pro Leu Ser Lys Val Pro Leu Gln Gln Asn Phe Gln
        195                 200                 205

Asp Asn Gln Phe His Gly Lys Trp Tyr Val Val Gly Leu Ala Gly Asn
    210                 215                 220

Gly Trp Leu Arg Glu Asp Lys Asp Pro Val Lys Met Met Ala Thr Ile
225                 230                 235                 240

Tyr Glu Leu Lys Glu Asp Lys Ser Tyr Gln Val Thr Val Val Asp Phe
                245                 250                 255

Glu Leu Lys Lys Cys Arg Tyr Met Ile Glu Thr Phe Val Pro Gly Ser
            260                 265                 270

Gln Pro Gly Glu Phe Thr Leu Gly Asp Ile Lys Ser Phe Pro Gly Trp
        275                 280                 285

Thr Ser Gln Leu Val Arg Val Val Ser Thr Asn Tyr Asn Gln His Ala
    290                 295                 300

Met Val Phe Phe Lys Gly Val Tyr Gln Asn Arg Glu Trp Phe His Ile
305                 310                 315                 320

Thr Leu Tyr Gly Arg Thr Lys Glu Leu Thr Ser Glu Leu Lys Glu Asn
                325                 330                 335

Phe Ile Arg Phe Ser Lys Ser Leu Gly Leu Pro Glu Asn His Ile Val
            340                 345                 350

Phe Pro Val Pro Ile Asp Gln Cys Ile Asp Gly Gly Gln Pro Lys Ala
        355                 360                 365

```
Ala Pro Gln Asp Ser Thr Ser Asp Leu Ile Pro Ala Pro Pro Leu Ser
    370                 375                 380

Lys Val Pro Leu Gln Gln Asn Phe Gln Asp Asn Gln Phe His Gly Lys
385                 390                 395                 400

Trp Tyr Val Val Gly Glu Ala Gly Asn Leu Ala Leu Arg Glu Asp Lys
                405                 410                 415

Asp Pro Lys Lys Met Met Ala Thr Ile Tyr Glu Leu Lys Glu Asp Lys
            420                 425                 430

Ser Tyr Gln Val Thr Glu Val Arg Phe Arg His Lys Lys Cys Gln Tyr
        435                 440                 445

Asp Ile Ala Thr Phe Val Pro Gly Ser Gln Pro Gly Glu Phe Thr Leu
    450                 455                 460

Gly Leu Ile Lys Ser Asp Pro Gly Gln Thr Ser Glu Leu Val Arg Val
465                 470                 475                 480

Val Ser Thr Asn Tyr Asn Gln His Ala Met Val Phe Phe Lys Lys Val
                485                 490                 495

Val Gln Asn Arg Glu Phe Phe Trp Ile Thr Leu Tyr Gly Arg Thr Lys
            500                 505                 510

Glu Leu Thr Ser Glu Leu Lys Glu Asn Phe Ile Arg Phe Ser Lys Ser
        515                 520                 525

Leu Gly Leu Pro Glu Asn His Ile Val Phe Pro Val Pro Ile Asp Gln
    530                 535                 540

Cys Ile Asp Gly Gly Gln Pro Lys Ala Ala Pro Gln Asp Ser Thr Ser
545                 550                 555                 560

Asp Leu Ile Pro Ala Pro Pro Leu Ser Lys Val Pro Leu Gln Gln Asn
                565                 570                 575

Phe Gln Asp Asn Gln Phe His Gly Lys Trp Tyr Val Val Gly Met Ala
            580                 585                 590

Gly Asn Phe His Leu Arg Glu Asp Lys Asp Pro Ser Lys Met Pro Ala
        595                 600                 605

Thr Ile Tyr Glu Leu Lys Glu Asp Lys Ser Tyr Gln Val Thr His Val
    610                 615                 620

Pro Phe Trp Ala Lys Lys Cys Ala Tyr Lys Ile Ile Thr Phe Val Pro
625                 630                 635                 640

Gly Ser Gln Pro Gly Glu Phe Thr Leu Gly Ala Ile Lys Ser Gly Pro
                645                 650                 655

Gly Met Thr Ser Trp Leu Val Arg Val Val Ser Thr Asn Tyr Asn Gln
            660                 665                 670

His Ala Met Val Phe Phe Lys Gly Val Trp Gln Asn Arg Glu Thr Phe
        675                 680                 685

Val Ile Thr Leu Tyr Gly Arg Thr Lys Glu Leu Thr Ser Glu Leu Lys
    690                 695                 700

Glu Asn Phe Ile Arg Phe Ser Lys Ser Leu Gly Leu Pro Glu Asn His
705                 710                 715                 720

Ile Val Phe Pro Val Pro Ile Asp Gln Cys Ile Asp Gly Ser Ala Trp
                725                 730                 735

Ser His Pro Gln Phe Glu Lys His His His His His His
            740                 745

<210> SEQ ID NO 160
<211> LENGTH: 752
<212> TYPE: PRT
<213> ORGANISM: Artificial Sequence
<220> FEATURE:
<223> OTHER INFORMATION: S0474.01H22(N65Q;T54A) GQPKAAPS
```

S0466.09E05(N65Q) GQPKAAPS  S0466.13C10(N65Q) GQPKAAPS
S0455.04F09(N65Q) StrepII, His6

<400> SEQUENCE: 160

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gln Pro Lys Ala Ala Pro Ser Gln Asp Ser Thr Ser Asp
            180                 185                 190

Leu Ile Pro Ala Pro Pro Leu Ser Lys Val Pro Leu Gln Gln Asn Phe
        195                 200                 205

Gln Asp Asn Gln Phe His Gly Lys Trp Tyr Val Val Gly Leu Ala Gly
    210                 215                 220

Asn Gly Trp Leu Arg Glu Asp Lys Asp Pro Val Lys Met Met Ala Thr
225                 230                 235                 240

Ile Tyr Glu Leu Lys Glu Asp Lys Ser Tyr Gln Val Thr Val Val Asp
                245                 250                 255

Phe Glu Leu Lys Lys Cys Arg Tyr Met Ile Glu Thr Phe Val Pro Gly
            260                 265                 270

Ser Gln Pro Gly Glu Phe Thr Leu Gly Asp Ile Lys Ser Phe Pro Gly
        275                 280                 285

Trp Thr Ser Gln Leu Val Arg Val Val Ser Thr Asn Tyr Asn Gln His
    290                 295                 300

Ala Met Val Phe Phe Lys Gly Val Tyr Gln Asn Arg Glu Trp Phe His
305                 310                 315                 320

Ile Thr Leu Tyr Gly Arg Thr Lys Glu Leu Thr Ser Glu Leu Lys Glu
                325                 330                 335

Asn Phe Ile Arg Phe Ser Lys Ser Leu Gly Leu Pro Glu Asn His Ile
            340                 345                 350

Val Phe Pro Val Pro Ile Asp Gln Cys Ile Asp Gly Gly Gln Pro Lys
        355                 360                 365

Ala Ala Pro Ser Gln Asp Ser Thr Ser Asp Leu Ile Pro Ala Pro Pro
    370                 375                 380

Leu Ser Lys Val Pro Leu Gln Gln Asn Phe Gln Asp Asn Gln Phe His
385                 390                 395                 400

Gly Lys Trp Tyr Val Val Gly Glu Ala Gly Asn Leu Ala Leu Arg Glu
            405                 410                 415

Asp Lys Asp Pro Lys Lys Met Met Ala Thr Ile Tyr Glu Leu Lys Glu
        420                 425                 430

Asp Lys Ser Tyr Gln Val Thr Glu Val Arg Phe Arg His Lys Lys Cys
    435                 440                 445

Gln Tyr Asp Ile Ala Thr Phe Val Pro Gly Ser Gln Pro Gly Glu Phe
450                 455                 460

Thr Leu Gly Leu Ile Lys Ser Asp Pro Gly Gln Thr Ser Glu Leu Val
465                 470                 475                 480

Arg Val Val Ser Thr Asn Tyr Asn Gln His Ala Met Val Phe Phe Lys
                485                 490                 495

Lys Val Val Gln Asn Arg Glu Phe Phe Trp Ile Thr Leu Tyr Gly Arg
            500                 505                 510

Thr Lys Glu Leu Thr Ser Glu Leu Lys Glu Asn Phe Ile Arg Phe Ser
        515                 520                 525

Lys Ser Leu Gly Leu Pro Glu Asn His Ile Val Phe Pro Val Pro Ile
    530                 535                 540

Asp Gln Cys Ile Asp Gly Gln Pro Lys Ala Ala Pro Ser Gln Asp
545                 550                 555                 560

Ser Thr Ser Asp Leu Ile Pro Ala Pro Leu Ser Lys Val Pro Leu
                565                 570                 575

Gln Gln Asn Phe Gln Asp Asn Gln Phe His Gly Lys Trp Tyr Val Val
            580                 585                 590

Gly Met Ala Gly Asn Phe His Leu Arg Glu Asp Lys Asp Pro Ser Lys
        595                 600                 605

Met Pro Ala Thr Ile Tyr Glu Leu Lys Glu Asp Lys Ser Tyr Gln Val
    610                 615                 620

Thr His Val Pro Phe Trp Ala Lys Lys Cys Ala Tyr Lys Ile Ile Thr
625                 630                 635                 640

Phe Val Pro Gly Ser Gln Pro Gly Glu Phe Thr Leu Gly Ala Ile Lys
                645                 650                 655

Ser Gly Pro Gly Met Thr Ser Trp Leu Val Arg Val Val Ser Thr Asn
            660                 665                 670

Tyr Asn Gln His Ala Met Val Phe Phe Lys Gly Val Trp Gln Asn Arg
        675                 680                 685

Glu Thr Phe Val Ile Thr Leu Tyr Gly Arg Thr Lys Glu Leu Thr Ser
    690                 695                 700

Glu Leu Lys Glu Asn Phe Ile Arg Phe Ser Lys Ser Leu Gly Leu Pro
705                 710                 715                 720

Glu Asn His Ile Val Phe Pro Val Pro Ile Asp Gln Cys Ile Asp Gly
                725                 730                 735

Ser Ala Trp Ser His Pro Gln Phe Glu Lys His His His His His His
            740                 745                 750

<210> SEQ ID NO 161
<211> LENGTH: 743
<212> TYPE: PRT
<213> ORGANISM: Artificial Sequence
<220> FEATURE:
<223> OTHER INFORMATION: S0474.01H22(N65Q;T54A) GGSGG S0466.09E05(N65Q)
      GGSGG S0466.13C10(N65Q) GGSGG S0455.04F09(N65Q) StrepII, His6

<400> SEQUENCE: 161

Gln Asp Ser Thr Ser Asp Leu Ile Pro Ala Pro Pro Leu Ser Lys Val

```
1               5                   10                  15
Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
                35                  40                  45

Gly Lys Met Asn Ala Ala Ile Tyr Glu Leu Lys Glu Asp Lys Ser Tyr
                50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
                115                 120                 125

Asn Arg Glu Ile Phe Trp Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Ser Gly Gly Gln Asp Ser Thr Ser Asp Leu Ile Pro
                180                 185                 190

Ala Pro Pro Leu Ser Lys Val Pro Leu Gln Gln Asn Phe Gln Asp Asn
                195                 200                 205

Gln Phe His Gly Lys Trp Tyr Val Val Gly Leu Ala Gly Asn Gly Trp
                210                 215                 220

Leu Arg Glu Asp Lys Asp Pro Val Lys Met Met Ala Thr Ile Tyr Glu
225                 230                 235                 240

Leu Lys Glu Asp Lys Ser Tyr Gln Val Thr Val Val Asp Phe Glu Leu
                245                 250                 255

Lys Lys Cys Arg Tyr Met Ile Glu Thr Phe Val Pro Gly Ser Gln Pro
                260                 265                 270

Gly Glu Phe Thr Leu Gly Asp Ile Lys Ser Phe Pro Gly Trp Thr Ser
                275                 280                 285

Gln Leu Val Arg Val Val Ser Thr Asn Tyr Asn Gln His Ala Met Val
                290                 295                 300

Phe Phe Lys Gly Val Tyr Gln Asn Arg Glu Trp Phe His Ile Thr Leu
305                 310                 315                 320

Tyr Gly Arg Thr Lys Glu Leu Thr Ser Glu Leu Lys Glu Asn Phe Ile
                325                 330                 335

Arg Phe Ser Lys Ser Leu Gly Leu Pro Glu Asn His Ile Val Phe Pro
                340                 345                 350

Val Pro Ile Asp Gln Cys Ile Asp Gly Gly Ser Gly Gly Gln Asp
                355                 360                 365

Ser Thr Ser Asp Leu Ile Pro Ala Pro Pro Leu Ser Lys Val Pro Leu
                370                 375                 380

Gln Gln Asn Phe Gln Asp Asn Gln Phe His Gly Lys Trp Tyr Val Val
385                 390                 395                 400

Gly Glu Ala Gly Asn Leu Ala Leu Arg Glu Asp Lys Asp Pro Lys Lys
                405                 410                 415

Met Met Ala Thr Ile Tyr Glu Leu Lys Glu Asp Lys Ser Tyr Gln Val
                420                 425                 430
```

```
Thr Glu Val Arg Phe Arg His Lys Lys Cys Gln Tyr Asp Ile Ala Thr
            435                 440                 445
Phe Val Pro Gly Ser Gln Pro Gly Glu Phe Thr Leu Gly Leu Ile Lys
        450                 455                 460
Ser Asp Pro Gly Gln Thr Ser Glu Leu Val Arg Val Ser Thr Asn
465                 470                 475                 480
Tyr Asn Gln His Ala Met Val Phe Phe Lys Val Val Gln Asn Arg
                485                 490                 495
Glu Phe Phe Trp Ile Thr Leu Tyr Gly Arg Thr Lys Glu Leu Thr Ser
            500                 505                 510
Glu Leu Lys Glu Asn Phe Ile Arg Phe Ser Lys Ser Leu Gly Leu Pro
        515                 520                 525
Glu Asn His Ile Val Phe Pro Val Pro Ile Asp Gln Cys Ile Asp Gly
    530                 535                 540
Gly Gly Ser Gly Gly Gln Asp Ser Thr Ser Asp Leu Ile Pro Ala Pro
545                 550                 555                 560
Pro Leu Ser Lys Val Pro Leu Gln Gln Asn Phe Gln Asp Asn Gln Phe
                565                 570                 575
His Gly Lys Trp Tyr Val Val Gly Met Ala Gly Asn Phe His Leu Arg
            580                 585                 590
Glu Asp Lys Asp Pro Ser Lys Met Pro Ala Thr Ile Tyr Glu Leu Lys
        595                 600                 605
Glu Asp Lys Ser Tyr Gln Val Thr His Val Pro Phe Trp Ala Lys Lys
    610                 615                 620
Cys Ala Tyr Lys Ile Ile Thr Phe Val Pro Gly Ser Gln Pro Gly Glu
625                 630                 635                 640
Phe Thr Leu Gly Ala Ile Lys Ser Gly Pro Gly Met Thr Ser Trp Leu
                645                 650                 655
Val Arg Val Val Ser Thr Asn Tyr Asn Gln His Ala Met Val Phe Phe
            660                 665                 670
Lys Gly Val Trp Gln Asn Arg Glu Thr Phe Val Ile Thr Leu Tyr Gly
        675                 680                 685
Arg Thr Lys Glu Leu Thr Ser Glu Leu Lys Glu Asn Phe Ile Arg Phe
    690                 695                 700
Ser Lys Ser Leu Gly Leu Pro Glu Asn His Ile Val Phe Pro Val Pro
705                 710                 715                 720
Ile Asp Gln Cys Ile Asp Gly Ser Ala Trp Ser His Pro Gln Phe Glu
                725                 730                 735
Lys His His His His His His
            740

<210> SEQ ID NO 162
<211> LENGTH: 749
<212> TYPE: PRT
<213> ORGANISM: Artificial Sequence
<220> FEATURE:
<223> OTHER INFORMATION: S0474.01H22(N65Q;T54A)SGGSG S0466.09E05(N65Q)
      SGGSG S0466.13C10(N65Q) SGGSG S0455.04F09(N65Q) StrepII, His6

<400> SEQUENCE: 162

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Val Ala Gly Asn Thr Ile Leu Arg Glu Asp Lys Asp Pro
```

```
                35                  40                  45
Gly Lys Met Asn Ala Ala Ile Tyr Glu Leu Lys Glu Asp Lys Ser Tyr
 50                  55                  60
Gln Val Thr Asp Val Arg Phe Ile Arg Lys Lys Cys His Tyr Tyr Ile
 65                  70                  75                  80
Asp Thr Phe Val Pro Gly Ser Gln Pro Gly Glu Phe Thr Leu Gly Asn
                 85                  90                  95
Ile Lys Ser Tyr Pro Gly Thr Thr Ser Gln Leu Val Arg Val Val Ser
                100                 105                 110
Thr Asn Tyr Asn Gln His Ala Met Val Phe Phe Lys Ile Val Arg Gln
                115                 120                 125
Asn Arg Glu Ile Phe Trp Ile Thr Leu Tyr Gly Arg Thr Lys Glu Leu
130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Gln Asp Ser Thr Ser Asp Leu
                180                 185                 190
Ile Pro Ala Pro Pro Leu Ser Lys Val Pro Leu Gln Gln Asn Phe Gln
                195                 200                 205
Asp Asn Gln Phe His Gly Lys Trp Tyr Val Val Gly Leu Ala Gly Asn
210                 215                 220
Gly Trp Leu Arg Glu Asp Lys Asp Pro Val Lys Met Met Ala Thr Ile
225                 230                 235                 240
Tyr Glu Leu Lys Glu Asp Lys Ser Tyr Gln Val Thr Val Val Asp Phe
                245                 250                 255
Glu Leu Lys Lys Cys Arg Tyr Met Ile Glu Thr Phe Val Pro Gly Ser
                260                 265                 270
Gln Pro Gly Glu Phe Thr Leu Gly Asp Ile Lys Ser Phe Pro Gly Trp
                275                 280                 285
Thr Ser Gln Leu Val Arg Val Val Ser Thr Asn Tyr Asn Gln His Ala
290                 295                 300
Met Val Phe Phe Lys Gly Val Tyr Gln Asn Arg Glu Trp Phe His Ile
305                 310                 315                 320
Thr Leu Tyr Gly Arg Thr Lys Glu Leu Thr Ser Glu Leu Lys Glu Asn
                325                 330                 335
Phe Ile Arg Phe Ser Lys Ser Leu Gly Leu Pro Glu Asn His Ile Val
                340                 345                 350
Phe Pro Val Pro Ile Asp Gln Cys Ile Asp Gly Gly Gly Gly Ser Gly
                355                 360                 365
Gly Gly Gln Asp Ser Thr Ser Asp Leu Ile Pro Ala Pro Pro Leu Ser
                370                 375                 380
Lys Val Pro Leu Gln Gln Asn Phe Gln Asp Asn Gln Phe His Gly Lys
385                 390                 395                 400
Trp Tyr Val Val Gly Glu Ala Gly Asn Leu Ala Leu Arg Glu Asp Lys
                405                 410                 415
Asp Pro Lys Lys Met Met Ala Thr Ile Tyr Glu Leu Lys Glu Asp Lys
                420                 425                 430
Ser Tyr Gln Val Thr Glu Val Arg Phe Arg His Lys Lys Cys Gln Tyr
                435                 440                 445
Asp Ile Ala Thr Phe Val Pro Gly Ser Gln Pro Gly Glu Phe Thr Leu
450                 455                 460
```

Gly Leu Ile Lys Ser Asp Pro Gly Gln Thr Ser Glu Leu Val Arg Val
465                 470                 475                 480

Val Ser Thr Asn Tyr Asn Gln His Ala Met Val Phe Phe Lys Lys Val
            485                 490                 495

Val Gln Asn Arg Glu Phe Phe Trp Ile Thr Leu Tyr Gly Arg Thr Lys
        500                 505                 510

Glu Leu Thr Ser Glu Leu Lys Glu Asn Phe Ile Arg Phe Ser Lys Ser
    515                 520                 525

Leu Gly Leu Pro Glu Asn His Ile Val Phe Pro Val Pro Ile Asp Gln
530                 535                 540

Cys Ile Asp Gly Gly Gly Ser Gly Gly Gly Gln Asp Ser Thr Ser
545                 550                 555                 560

Asp Leu Ile Pro Ala Pro Pro Leu Ser Lys Val Pro Leu Gln Gln Asn
                565                 570                 575

Phe Gln Asp Asn Gln Phe His Gly Lys Trp Tyr Val Val Gly Met Ala
            580                 585                 590

Gly Asn Phe His Leu Arg Glu Asp Lys Asp Pro Ser Lys Met Pro Ala
        595                 600                 605

Thr Ile Tyr Glu Leu Lys Glu Asp Lys Ser Tyr Gln Val Thr His Val
    610                 615                 620

Pro Phe Trp Ala Lys Lys Cys Ala Tyr Lys Ile Ile Thr Phe Val Pro
625                 630                 635                 640

Gly Ser Gln Pro Gly Glu Phe Thr Leu Gly Ala Ile Lys Ser Gly Pro
                645                 650                 655

Gly Met Thr Ser Trp Leu Val Arg Val Val Ser Thr Asn Tyr Asn Gln
            660                 665                 670

His Ala Met Val Phe Phe Lys Gly Val Trp Gln Asn Arg Glu Thr Phe
        675                 680                 685

Val Ile Thr Leu Tyr Gly Arg Thr Lys Glu Leu Thr Ser Glu Leu Lys
    690                 695                 700

Glu Asn Phe Ile Arg Phe Ser Lys Ser Leu Gly Leu Pro Glu Asn His
705                 710                 715                 720

Ile Val Phe Pro Val Pro Ile Asp Gln Cys Ile Asp Gly Ser Ala Trp
                725                 730                 735

Ser His Pro Gln Phe Glu Lys His His His His His His
            740                 745

<210> SEQ ID NO 163
<211> LENGTH: 749
<212> TYPE: PRT
<213> ORGANISM: Artificial Sequence
<220> FEATURE:
<223> OTHER INFORMATION: S0474.01H22(N65Q;T54A) GGGSGGG
      S0466.09E05(N65Q) GGGSGGG S0466.13C10(N65Q) GGGSGGG
      S0455.04F09(N65Q) StrepII, His6

<400> SEQUENCE: 163

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

-continued

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gln Asp Ser Thr Ser Asp Leu
                180                 185                 190

Ile Pro Ala Pro Pro Leu Ser Lys Val Pro Leu Gln Gln Asn Phe Gln
            195                 200                 205

Asp Asn Gln Phe His Gly Lys Trp Tyr Val Val Gly Leu Ala Gly Asn
        210                 215                 220

Gly Trp Leu Arg Glu Asp Lys Asp Pro Val Lys Met Met Ala Thr Ile
225                 230                 235                 240

Tyr Glu Leu Lys Glu Asp Lys Ser Tyr Gln Val Thr Val Val Asp Phe
                245                 250                 255

Glu Leu Lys Lys Cys Arg Tyr Met Ile Glu Thr Phe Val Pro Gly Ser
            260                 265                 270

Gln Pro Gly Glu Phe Thr Leu Gly Asp Ile Lys Ser Phe Pro Gly Trp
        275                 280                 285

Thr Ser Gln Leu Val Arg Val Val Ser Thr Asn Tyr Asn Gln His Ala
290                 295                 300

Met Val Phe Phe Lys Gly Val Tyr Gln Asn Arg Glu Trp Phe His Ile
305                 310                 315                 320

Thr Leu Tyr Gly Arg Thr Lys Glu Leu Thr Ser Glu Leu Lys Glu Asn
                325                 330                 335

Phe Ile Arg Phe Ser Lys Ser Leu Gly Leu Pro Glu Asn His Ile Val
            340                 345                 350

Phe Pro Val Pro Ile Asp Gln Cys Ile Asp Gly Gly Gly Gly Ser Gly
        355                 360                 365

Gly Gly Gln Asp Ser Thr Ser Asp Leu Ile Pro Ala Pro Pro Leu Ser
370                 375                 380

Lys Val Pro Leu Gln Gln Asn Phe Gln Asp Asn Gln Phe His Gly Lys
385                 390                 395                 400

Trp Tyr Val Val Gly Glu Ala Gly Asn Leu Ala Leu Arg Glu Asp Lys
                405                 410                 415

Asp Pro Lys Lys Met Met Ala Thr Ile Tyr Glu Leu Lys Glu Asp Lys
            420                 425                 430

Ser Tyr Gln Val Thr Glu Val Arg Phe Arg His Lys Lys Cys Gln Tyr
        435                 440                 445

Asp Ile Ala Thr Phe Val Pro Gly Ser Gln Pro Gly Glu Phe Thr Leu
450                 455                 460

Gly Leu Ile Lys Ser Asp Pro Gly Gln Thr Ser Glu Leu Val Arg Val
465                 470                 475                 480

Val Ser Thr Asn Tyr Asn Gln His Ala Met Val Phe Phe Lys Lys Val

```
                    485                 490                 495

Val Gln Asn Arg Glu Phe Phe Trp Ile Thr Leu Tyr Gly Arg Thr Lys
            500                 505                 510

Glu Leu Thr Ser Glu Leu Lys Glu Asn Phe Ile Arg Phe Ser Lys Ser
        515                 520                 525

Leu Gly Leu Pro Glu Asn His Ile Val Phe Val Pro Ile Asp Gln
    530                 535                 540

Cys Ile Asp Gly Gly Gly Ser Gly Gly Gln Asp Ser Thr Ser
545                 550                 555                 560

Asp Leu Ile Pro Ala Pro Pro Leu Ser Lys Val Pro Leu Gln Gln Asn
                565                 570                 575

Phe Gln Asp Asn Gln Phe His Gly Lys Trp Tyr Val Val Gly Met Ala
            580                 585                 590

Gly Asn Phe His Leu Arg Glu Asp Lys Asp Pro Ser Lys Met Pro Ala
        595                 600                 605

Thr Ile Tyr Glu Leu Lys Glu Asp Lys Ser Tyr Gln Val Thr His Val
    610                 615                 620

Pro Phe Trp Ala Lys Lys Cys Ala Tyr Lys Ile Ile Thr Phe Val Pro
625                 630                 635                 640

Gly Ser Gln Pro Gly Glu Phe Thr Leu Gly Ala Ile Lys Ser Gly Pro
                645                 650                 655

Gly Met Thr Ser Trp Leu Val Arg Val Val Ser Thr Asn Tyr Asn Gln
            660                 665                 670

His Ala Met Val Phe Phe Lys Gly Val Trp Gln Asn Arg Glu Thr Phe
        675                 680                 685

Val Ile Thr Leu Tyr Gly Arg Thr Lys Glu Leu Thr Ser Glu Leu Lys
    690                 695                 700

Glu Asn Phe Ile Arg Phe Ser Lys Ser Leu Gly Leu Pro Glu Asn His
705                 710                 715                 720

Ile Val Phe Pro Val Pro Ile Asp Gln Cys Ile Asp Gly Ser Ala Trp
                725                 730                 735

Ser His Pro Gln Phe Glu Lys His His His His His His
            740                 745

<210> SEQ ID NO 164
<211> LENGTH: 752
<212> TYPE: PRT
<213> ORGANISM: Artificial Sequence
<220> FEATURE:
<223> OTHER INFORMATION: S0474.01H22(N65Q;T54A)GGSGGSGG
      S0466.09E05(N65Q) GGSGGSGG S0466.13C10(N65Q)GGSGGSGG
      S0455.04F09(N65Q) StrepII, His6

<400> SEQUENCE: 164

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95
```

```
Ile Lys Ser Tyr Pro Gly Thr Ser Gln Leu Val Arg Val Ser
            100                 105             110

Thr Asn Tyr Asn Gln His Ala Met Val Phe Lys Ile Val Arg Gln
        115             120             125

Asn Arg Glu Ile Phe Trp Ile Thr Leu Tyr Gly Arg Thr Lys Glu Leu
    130             135             140

Thr Ser Glu Leu Lys Glu Asn Phe Ile Arg Phe Ser Lys Ser Leu Gly
145             150             155                 160

Leu Pro Glu Asn His Ile Val Phe Pro Val Pro Ile Asp Gln Cys Ile
                165             170             175

Asp Gly Gly Gly Ser Gly Gly Ser Gly Gly Gln Asp Ser Thr Ser Asp
            180             185             190

Leu Ile Pro Ala Pro Pro Leu Ser Lys Val Pro Leu Gln Gln Asn Phe
        195             200             205

Gln Asp Asn Gln Phe His Gly Lys Trp Tyr Val Val Gly Leu Ala Gly
    210             215             220

Asn Gly Trp Leu Arg Glu Asp Lys Asp Pro Val Lys Met Met Ala Thr
225             230             235                 240

Ile Tyr Glu Leu Lys Glu Asp Lys Ser Tyr Gln Val Thr Val Val Asp
                245             250             255

Phe Glu Leu Lys Lys Cys Arg Tyr Met Ile Glu Thr Phe Val Pro Gly
            260             265             270

Ser Gln Pro Gly Glu Phe Thr Leu Gly Asp Ile Lys Ser Phe Pro Gly
        275             280             285

Trp Thr Ser Gln Leu Val Arg Val Val Ser Thr Asn Tyr Asn Gln His
    290             295             300

Ala Met Val Phe Phe Lys Gly Val Tyr Gln Asn Arg Glu Trp Phe His
305             310             315                 320

Ile Thr Leu Tyr Gly Arg Thr Lys Glu Leu Thr Ser Glu Leu Lys Glu
                325             330             335

Asn Phe Ile Arg Phe Ser Lys Ser Leu Gly Leu Pro Glu Asn His Ile
            340             345             350

Val Phe Pro Val Pro Ile Asp Gln Cys Ile Asp Gly Gly Gly Ser Gly
        355             360             365

Gly Ser Gly Gly Gln Asp Ser Thr Ser Asp Leu Ile Pro Ala Pro Pro
    370             375             380

Leu Ser Lys Val Pro Leu Gln Gln Asn Phe Gln Asp Asn Gln Phe His
385             390             395                 400

Gly Lys Trp Tyr Val Val Gly Glu Ala Gly Asn Leu Ala Leu Arg Glu
                405             410             415

Asp Lys Asp Pro Lys Lys Met Met Ala Thr Ile Tyr Glu Leu Lys Glu
            420             425             430

Asp Lys Ser Tyr Gln Val Thr Glu Val Arg Phe Arg His Lys Lys Cys
        435             440             445

Gln Tyr Asp Ile Ala Thr Phe Val Pro Gly Ser Gln Pro Gly Glu Phe
    450             455             460

Thr Leu Gly Leu Ile Lys Ser Asp Pro Gly Gln Thr Ser Glu Leu Val
465             470             475                 480

Arg Val Val Ser Thr Asn Tyr Asn Gln His Ala Met Val Phe Phe Lys
                485             490             495

Lys Val Val Gln Asn Arg Glu Phe Phe Trp Ile Thr Leu Tyr Gly Arg
            500             505             510
```

```
Thr Lys Glu Leu Thr Ser Glu Leu Lys Glu Asn Phe Ile Arg Phe Ser
            515                 520                 525

Lys Ser Leu Gly Leu Pro Glu Asn His Ile Val Phe Pro Val Pro Ile
        530                 535                 540

Asp Gln Cys Ile Asp Gly Gly Ser Gly Gly Ser Gly Gly Gln Asp
545                 550                 555                 560

Ser Thr Ser Asp Leu Ile Pro Ala Pro Pro Leu Ser Lys Val Pro Leu
                565                 570                 575

Gln Gln Asn Phe Gln Asp Asn Gln Phe His Gly Lys Trp Tyr Val Val
            580                 585                 590

Gly Met Ala Gly Asn Phe His Leu Arg Glu Asp Lys Asp Pro Ser Lys
        595                 600                 605

Met Pro Ala Thr Ile Tyr Glu Leu Lys Glu Asp Lys Ser Tyr Gln Val
    610                 615                 620

Thr His Val Pro Phe Trp Ala Lys Lys Cys Ala Tyr Lys Ile Ile Thr
625                 630                 635                 640

Phe Val Pro Gly Ser Gln Pro Gly Glu Phe Thr Leu Gly Ala Ile Lys
                645                 650                 655

Ser Gly Pro Gly Met Thr Ser Trp Leu Val Arg Val Val Ser Thr Asn
            660                 665                 670

Tyr Asn Gln His Ala Met Val Phe Phe Lys Gly Val Trp Gln Asn Arg
        675                 680                 685

Glu Thr Phe Val Ile Thr Leu Tyr Gly Arg Thr Lys Glu Leu Thr Ser
    690                 695                 700

Glu Leu Lys Glu Asn Phe Ile Arg Phe Ser Lys Ser Leu Gly Leu Pro
705                 710                 715                 720

Glu Asn His Ile Val Phe Pro Val Pro Ile Asp Gln Cys Ile Asp Gly
                725                 730                 735

Ser Ala Trp Ser His Pro Gln Phe Glu Lys His His His His His His
            740                 745                 750

<210> SEQ ID NO 165
<211> LENGTH: 755
<212> TYPE: PRT
<213> ORGANISM: Artificial Sequence
<220> FEATURE:
<223> OTHER INFORMATION: S0474.01H22(N65Q;T54A) GGGSGGSGGG
      S0466.09E05(N65Q) GGGSGGSGGG S0466.13C10(N65Q) GGGSGGSGGG
      S0455.04F09(N65Q) StrepII, His6

<400> SEQUENCE: 165

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
```

-continued

```
            115                 120                 125
Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Ser Gly Gly Ser Gly Gly Gln Asp Ser Thr Ser
                180                 185                 190      Ser

Asp Leu Ile Pro Ala Pro Pro Leu Ser Lys Val Pro Leu Gln Gln Asn
        195                 200                 205

Phe Gln Asp Asn Gln Phe His Gly Lys Trp Tyr Val Val Gly Leu Ala
        210                 215                 220

Gly Asn Gly Trp Leu Arg Glu Asp Lys Asp Pro Val Lys Met Met Ala
225                 230                 235                 240

Thr Ile Tyr Glu Leu Lys Glu Asp Lys Ser Tyr Gln Val Thr Val Val
                245                 250                 255

Asp Phe Glu Leu Lys Lys Cys Arg Tyr Met Ile Glu Thr Phe Val Pro
        260                 265                 270

Gly Ser Gln Pro Gly Glu Phe Thr Leu Gly Asp Ile Lys Ser Phe Pro
        275                 280                 285

Gly Trp Thr Ser Gln Leu Val Arg Val Val Ser Thr Asn Tyr Asn Gln
290                 295                 300

His Ala Met Val Phe Phe Lys Gly Val Tyr Gln Asn Arg Glu Trp Phe
305                 310                 315                 320

His Ile Thr Leu Tyr Gly Arg Thr Lys Glu Leu Thr Ser Glu Leu Lys
                325                 330                 335

Glu Asn Phe Ile Arg Phe Ser Lys Ser Leu Gly Leu Pro Glu Asn His
        340                 345                 350

Ile Val Phe Pro Val Pro Ile Asp Gln Cys Ile Asp Gly Gly Ser
        355                 360                 365           Ser

Gly Gly Ser Gly Gly Gly Gln Asp Ser Thr Ser Asp Leu Ile Pro Ala
370                 375                 380

Pro Pro Leu Ser Lys Val Pro Leu Gln Gln Asn Phe Gln Asp Asn Gln
385                 390                 395                 400

Phe His Gly Lys Trp Tyr Val Val Gly Glu Ala Gly Asn Leu Ala Leu
                405                 410                 415

Arg Glu Asp Lys Asp Pro Lys Lys Met Met Ala Thr Ile Tyr Glu Leu
        420                 425                 430

Lys Glu Asp Lys Ser Tyr Gln Val Thr Glu Val Arg Phe Arg His Lys
        435                 440                 445

Lys Cys Gln Tyr Asp Ile Ala Thr Phe Val Pro Gly Ser Gln Pro Gly
        450                 455                 460

Glu Phe Thr Leu Gly Leu Ile Lys Ser Asp Pro Gly Gln Thr Ser Glu
465                 470                 475                 480

Leu Val Arg Val Val Ser Thr Asn Tyr Asn Gln His Ala Met Val Phe
                485                 490                 495

Phe Lys Lys Val Val Gln Asn Arg Glu Phe Phe Trp Ile Thr Leu Tyr
        500                 505                 510

Gly Arg Thr Lys Glu Leu Thr Ser Glu Leu Lys Glu Asn Phe Ile Arg
        515                 520                 525

Phe Ser Lys Ser Leu Gly Leu Pro Glu Asn His Ile Val Phe Pro Val
530                 535                 540
```

-continued

```
Pro Ile Asp Gln Cys Ile Asp Gly Gly Gly Ser Gly Gly Ser Gly Gly
545                 550                 555                 560

Gly Gln Asp Ser Thr Ser Asp Leu Ile Pro Ala Pro Pro Leu Ser Lys
                565                 570                 575

Val Pro Leu Gln Gln Asn Phe Gln Asp Asn Gln Phe His Gly Lys Trp
            580                 585                 590

Tyr Val Val Gly Met Ala Gly Asn Phe His Leu Arg Glu Asp Lys Asp
        595                 600                 605

Pro Ser Lys Met Pro Ala Thr Ile Tyr Glu Leu Lys Glu Asp Lys Ser
    610                 615                 620

Tyr Gln Val Thr His Val Pro Phe Trp Ala Lys Lys Cys Ala Tyr Lys
625                 630                 635                 640

Ile Ile Thr Phe Val Pro Gly Ser Gln Pro Gly Glu Phe Thr Leu Gly
                645                 650                 655

Ala Ile Lys Ser Gly Pro Gly Met Thr Ser Trp Leu Val Arg Val Val
                660                 665                 670

Ser Thr Asn Tyr Asn Gln His Ala Met Val Phe Phe Lys Gly Val Trp
            675                 680                 685

Gln Asn Arg Glu Thr Phe Val Ile Thr Leu Tyr Gly Arg Thr Lys Glu
        690                 695                 700

Leu Thr Ser Glu Leu Lys Glu Asn Phe Ile Arg Phe Ser Lys Ser Leu
705                 710                 715                 720

Gly Leu Pro Glu Asn His Ile Val Phe Pro Val Pro Ile Asp Gln Cys
                725                 730                 735

Ile Asp Gly Ser Ala Trp Ser His Pro Gln Phe Glu Lys His His His
                740                 745                 750

His His His
        755

<210> SEQ ID NO 166
<211> LENGTH: 755
<212> TYPE: PRT
<213> ORGANISM: Artificial Sequence
<220> FEATURE:
<223> OTHER INFORMATION: S0474.01H22(N65Q;T54A)GGGSGGSGGG
      S0466.09E05(N65Q) GGGSGGSGGG S0466.13C10(N65Q)GGGSGGSGGG
      S0455.04F09(N65Q) StrepII, His6

<400> SEQUENCE: 166

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125
```

```
Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly Gly Gly Ser Gly Gly Ser Gly Gly Gln Asp Ser Thr Ser
            180                 185                 190

Asp Leu Ile Pro Ala Pro Pro Leu Ser Lys Val Pro Leu Gln Gln Asn
            195                 200                 205

Phe Gln Asp Asn Gln Phe His Gly Lys Trp Tyr Val Val Gly Leu Ala
210                 215                 220

Gly Asn Gly Trp Leu Arg Glu Asp Lys Asp Pro Val Lys Met Met Ala
225                 230                 235                 240

Thr Ile Tyr Glu Leu Lys Glu Asp Lys Ser Tyr Gln Val Thr Val Val
                245                 250                 255

Asp Phe Glu Leu Lys Lys Cys Arg Tyr Met Ile Glu Thr Phe Val Pro
            260                 265                 270

Gly Ser Gln Pro Gly Glu Phe Thr Leu Gly Asp Ile Lys Ser Phe Pro
            275                 280                 285

Gly Trp Thr Ser Gln Leu Val Arg Val Val Ser Thr Asn Tyr Asn Gln
290                 295                 300

His Ala Met Val Phe Phe Lys Gly Val Tyr Gln Asn Arg Glu Trp Phe
305                 310                 315                 320

His Ile Thr Leu Tyr Gly Arg Thr Lys Glu Leu Thr Ser Glu Leu Lys
                325                 330                 335

Glu Asn Phe Ile Arg Phe Ser Lys Ser Leu Gly Leu Pro Glu Asn His
            340                 345                 350

Ile Val Phe Pro Val Pro Ile Asp Gln Cys Ile Asp Gly Gly Gly Ser
            355                 360                 365

Gly Gly Ser Gly Gly Gly Gln Asp Ser Thr Ser Asp Leu Ile Pro Ala
370                 375                 380

Pro Pro Leu Ser Lys Val Pro Leu Gln Gln Asn Phe Gln Asp Asn Gln
385                 390                 395                 400

Phe His Gly Lys Trp Tyr Val Val Gly Glu Ala Gly Asn Leu Ala Leu
            405                 410                 415

Arg Glu Asp Lys Asp Pro Lys Lys Met Met Ala Thr Ile Tyr Glu Leu
            420                 425                 430

Lys Glu Asp Lys Ser Tyr Gln Val Thr Glu Val Arg Phe Arg His Lys
            435                 440                 445

Lys Cys Gln Tyr Asp Ile Ala Thr Phe Val Pro Gly Ser Gln Pro Gly
            450                 455                 460

Glu Phe Thr Leu Gly Leu Ile Lys Ser Asp Pro Gly Gln Thr Ser Glu
465                 470                 475                 480

Leu Val Arg Val Val Ser Thr Asn Tyr Asn Gln His Ala Met Val Phe
                485                 490                 495

Phe Lys Lys Val Val Gln Asn Arg Glu Phe Phe Trp Ile Thr Leu Tyr
            500                 505                 510

Gly Arg Thr Lys Glu Leu Thr Ser Glu Leu Lys Glu Asn Phe Ile Arg
            515                 520                 525

Phe Ser Lys Ser Leu Gly Leu Pro Glu Asn His Ile Val Phe Pro Val
            530                 535                 540

Pro Ile Asp Gln Cys Ile Asp Gly Gly Gly Ser Gly Gly Ser Gly Gly
```

-continued

```
545                 550                 555                 560
Gly Gln Asp Ser Thr Ser Asp Leu Ile Pro Ala Pro Leu Ser Lys
                565                 570                 575

Val Pro Leu Gln Gln Asn Phe Gln Asp Asn Gln Phe His Gly Lys Trp
                580                 585                 590

Tyr Val Val Gly Met Ala Gly Asn Phe His Leu Arg Glu Asp Lys Asp
                595                 600                 605

Pro Ser Lys Met Pro Ala Thr Ile Tyr Glu Leu Lys Glu Asp Lys Ser
                610                 615                 620

Tyr Gln Val Thr His Val Pro Phe Trp Ala Lys Lys Cys Ala Tyr Lys
625                 630                 635                 640

Ile Ile Thr Phe Val Pro Gly Ser Gln Pro Gly Glu Phe Thr Leu Gly
                645                 650                 655

Ala Ile Lys Ser Gly Pro Gly Met Thr Ser Trp Leu Val Arg Val Val
                660                 665                 670

Ser Thr Asn Tyr Asn Gln His Ala Met Val Phe Phe Lys Gly Val Trp
                675                 680                 685

Gln Asn Arg Glu Thr Phe Val Ile Thr Leu Tyr Gly Arg Thr Lys Glu
                690                 695                 700

Leu Thr Ser Glu Leu Lys Glu Asn Phe Ile Arg Phe Ser Lys Ser Leu
705                 710                 715                 720

Gly Leu Pro Glu Asn His Ile Val Phe Pro Val Pro Ile Asp Gln Cys
                725                 730                 735

Ile Asp Gly Ser Ala Trp Ser His Pro Gln Phe Glu Lys His His His
                740                 745                 750

His His His
        755

<210> SEQ ID NO 167
<211> LENGTH: 728
<212> TYPE: PRT
<213> ORGANISM: Artificial Sequence
<220> FEATURE:
<223> OTHER INFORMATION: S0474.01H22(N65D;T54A) S0510.05H10(N65D)
      S0510.11H24(N65D) S0455.04F09(N65D) StrepII His tag

<400> SEQUENCE: 167

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Ala Ile Tyr Glu Leu Lys Glu Asp Lys Ser Tyr
        50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
                115                 120                 125

Asn Arg Glu Ile Phe Trp Ile Thr Leu Tyr Gly Arg Thr Lys Glu Leu
                130                 135                 140
```

-continued

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gln Asp Ser Thr Ser Asp Leu Ile Pro Ala Pro Pro Leu Ser
            180                 185                 190

Lys Val Pro Leu Gln Gln Asn Phe Gln Asp Asn Gln Phe His Gly Lys
        195                 200                 205

Trp Tyr Val Val Gly Leu Ala Gly Asn Gly Trp Leu Arg Glu Asp Lys
    210                 215                 220

Asp Pro Leu Lys Met Met Ala Thr Ile Tyr Glu Leu Lys Glu Asp Lys
225                 230                 235                 240

Ser Tyr Asp Val Thr Val Asp Phe Glu Leu Lys Lys Cys Arg Tyr
                245                 250                 255

Met Ile Glu Thr Phe Val Pro Gly Ser Gln Pro Gly Glu Phe Thr Leu
                260                 265                 270

Gly Asp Ile Lys Ser Ser Pro Gly Trp Thr Ser Gln Leu Val Arg Val
            275                 280                 285

Val Ser Thr Asn Tyr Asn Gln His Ala Met Val Phe Phe Lys Gly Val
    290                 295                 300

Tyr Gln Asn Arg Glu Trp Phe His Ile Thr Leu Tyr Gly Arg Thr Lys
305                 310                 315                 320

Glu Leu Thr Ser Glu Leu Lys Glu Asn Phe Ile Arg Phe Ser Lys Ser
                325                 330                 335

Leu Gly Leu Pro Glu Asn His Ile Val Phe Pro Val Pro Ile Asp Gln
            340                 345                 350

Cys Ile Asp Gly Gln Asp Ser Thr Ser Asp Leu Ile Pro Ala Pro Pro
        355                 360                 365

Leu Ser Lys Val Pro Leu Gln Gln Asn Phe Gln Asp Asn Gln Phe His
    370                 375                 380

Gly Lys Trp Tyr Val Val Gly Glu Ala Gly Asn Leu Ala Leu Arg Glu
385                 390                 395                 400

Asp Lys Asp Pro Met Lys Met Met Ala Thr Ile Tyr Glu Leu Lys Glu
                405                 410                 415

Asp Lys Ser Tyr Asp Val Thr Glu Val Arg Phe Arg Gln Lys Lys Cys
            420                 425                 430

Lys Tyr Asp Ile Val Thr Phe Val Pro Gly Ser Gln Pro Gly Glu Phe
        435                 440                 445

Thr Leu Gly Leu Ile Lys Ser Asp Pro Gly Gln Thr Ser Glu Leu Val
    450                 455                 460

Arg Val Val Ser Thr Asn Tyr Asn Gln His Ala Met Val Phe Phe Lys
465                 470                 475                 480

Lys Val Val Gln Asn Arg Glu Tyr Phe Trp Ile Thr Leu Tyr Gly Arg
                485                 490                 495

Thr Lys Glu Leu Thr Ser Glu Leu Lys Glu Asn Phe Ile Arg Phe Ser
            500                 505                 510

Lys Ser Leu Gly Leu Pro Glu Asn His Ile Val Phe Pro Val Pro Ile
        515                 520                 525

Asp Gln Cys Ile Asp Gly Asp Ser Thr Ser Asp Leu Ile Pro Ala
    530                 535                 540

Pro Pro Leu Ser Lys Val Pro Leu Gln Gln Asn Phe Gln Asp Asn Gln
545                 550                 555                 560

Phe His Gly Lys Trp Tyr Val Val Gly Met Ala Gly Asn Phe His Leu
```

```
                565                 570                 575
Arg Glu Asp Lys Asp Pro Ser Lys Met Pro Ala Thr Ile Tyr Glu Leu
            580                 585                 590

Lys Glu Asp Lys Ser Tyr Asp Val Thr His Val Pro Phe Trp Ala Lys
        595                 600                 605

Lys Cys Ala Tyr Lys Ile Ile Thr Phe Val Pro Gly Ser Gln Pro Gly
    610                 615                 620

Glu Phe Thr Leu Gly Ala Ile Lys Ser Gly Pro Gly Met Thr Ser Trp
625                 630                 635                 640

Leu Val Arg Val Val Ser Thr Asn Tyr Asn Gln His Ala Met Val Phe
                645                 650                 655

Phe Lys Gly Val Trp Gln Asn Arg Glu Thr Phe Val Ile Thr Leu Tyr
            660                 665                 670

Gly Arg Thr Lys Glu Leu Thr Ser Glu Leu Lys Glu Asn Phe Ile Arg
        675                 680                 685

Phe Ser Lys Ser Leu Gly Leu Pro Glu Asn His Ile Val Phe Pro Val
    690                 695                 700

Pro Ile Asp Gln Cys Ile Asp Gly Ser Ala Trp Ser His Pro Gln Phe
705                 710                 715                 720

Glu Lys His His His His His His
                725

<210> SEQ ID NO 168
<211> LENGTH: 731
<212> TYPE: PRT
<213> ORGANISM: Artificial Sequence
<220> FEATURE:
<223> OTHER INFORMATION: S0474.01H22(N65D;T54A) (G) S0510.05H10(N65D)
      (G) S0510.11H24(N65D) (G) S0455.04F09(N65D) StrepII His tag

<400> SEQUENCE: 168

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gln Asp Ser Thr Ser Asp Leu Ile Pro Ala Pro Pro Leu
            180                 185                 190
```

```
Ser Lys Val Pro Leu Gln Gln Asn Phe Gln Asp Asn Gln Phe His Gly
        195                 200                 205

Lys Trp Tyr Val Val Gly Leu Ala Gly Asn Gly Trp Leu Arg Glu Asp
210                 215                 220

Lys Asp Pro Leu Lys Met Met Ala Thr Ile Tyr Glu Leu Lys Glu Asp
225                 230                 235                 240

Lys Ser Tyr Asp Val Thr Val Asp Phe Glu Leu Lys Lys Cys Arg
                245                 250                 255

Tyr Met Ile Glu Thr Phe Val Pro Gly Ser Gln Pro Gly Glu Phe Thr
                260                 265                 270

Leu Gly Asp Ile Lys Ser Ser Pro Gly Trp Thr Ser Gln Leu Val Arg
                275                 280                 285

Val Val Ser Thr Asn Tyr Asn Gln His Ala Met Val Phe Phe Lys Gly
        290                 295                 300

Val Tyr Gln Asn Arg Glu Trp Phe His Ile Thr Leu Tyr Gly Arg Thr
305                 310                 315                 320

Lys Glu Leu Thr Ser Glu Leu Lys Glu Asn Phe Ile Arg Phe Ser Lys
                325                 330                 335

Ser Leu Gly Leu Pro Glu Asn His Ile Val Phe Pro Val Pro Ile Asp
                340                 345                 350

Gln Cys Ile Asp Gly Gly Gln Asp Ser Thr Ser Asp Leu Ile Pro Ala
                355                 360                 365

Pro Pro Leu Ser Lys Val Pro Leu Gln Gln Asn Phe Gln Asp Asn Gln
        370                 375                 380

Phe His Gly Lys Trp Tyr Val Val Gly Glu Ala Gly Asn Leu Ala Leu
385                 390                 395                 400

Arg Glu Asp Lys Asp Pro Met Lys Met Met Ala Thr Ile Tyr Glu Leu
                405                 410                 415

Lys Glu Asp Lys Ser Tyr Asp Val Thr Glu Val Arg Phe Arg Gln Lys
                420                 425                 430

Lys Cys Lys Tyr Asp Ile Val Thr Phe Val Pro Gly Ser Gln Pro Gly
        435                 440                 445

Glu Phe Thr Leu Gly Leu Ile Lys Ser Asp Pro Gly Gln Thr Ser Glu
450                 455                 460

Leu Val Arg Val Val Ser Thr Asn Tyr Asn Gln His Ala Met Val Phe
465                 470                 475                 480

Phe Lys Lys Val Val Gln Asn Arg Glu Tyr Phe Trp Ile Thr Leu Tyr
                485                 490                 495

Gly Arg Thr Lys Glu Leu Thr Ser Glu Leu Lys Glu Asn Phe Ile Arg
                500                 505                 510

Phe Ser Lys Ser Leu Gly Leu Pro Glu Asn His Ile Val Phe Pro Val
        515                 520                 525

Pro Ile Asp Gln Cys Ile Asp Gly Gly Gln Asp Ser Thr Ser Asp Leu
530                 535                 540

Ile Pro Ala Pro Pro Leu Ser Lys Val Pro Leu Gln Gln Asn Phe Gln
545                 550                 555                 560

Asp Asn Gln Phe His Gly Lys Trp Tyr Val Val Gly Met Ala Gly Asn
                565                 570                 575

Phe His Leu Arg Glu Asp Lys Asp Pro Ser Lys Met Pro Ala Thr Ile
                580                 585                 590

Tyr Glu Leu Lys Glu Asp Lys Ser Tyr Asp Val Thr His Val Pro Phe
                595                 600                 605

Trp Ala Lys Lys Cys Ala Tyr Lys Ile Ile Thr Phe Val Pro Gly Ser
```

```
                610                 615                 620
Gln Pro Gly Glu Phe Thr Leu Gly Ala Ile Lys Ser Gly Pro Gly Met
625                 630                 635                 640

Thr Ser Trp Leu Val Arg Val Val Ser Thr Asn Tyr Asn Gln His Ala
                645                 650                 655

Met Val Phe Phe Lys Gly Val Trp Gln Asn Arg Glu Thr Phe Val Ile
            660                 665                 670

Thr Leu Tyr Gly Arg Thr Lys Glu Leu Thr Ser Glu Leu Lys Glu Asn
        675                 680                 685

Phe Ile Arg Phe Ser Lys Ser Leu Gly Leu Pro Glu Asn His Ile Val
    690                 695                 700

Phe Pro Val Pro Ile Asp Gln Cys Ile Asp Gly Ser Ala Trp Ser His
705                 710                 715                 720

Pro Gln Phe Glu Lys His His His His His His
                725                 730

<210> SEQ ID NO 169
<211> LENGTH: 737
<212> TYPE: PRT
<213> ORGANISM: Artificial Sequence
<220> FEATURE:
<223> OTHER INFORMATION: S0474.01H22(N65D;T54A) (G)3 S0510.05H10(N65D)
      (G)3 S0510.11H24(N65D) (G)3 S0455.04F09(N65D) StrepII His tag

<400> SEQUENCE: 169

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gln Asp Ser Thr Ser Asp Leu Ile Pro Ala Pro
            180                 185                 190

Pro Leu Ser Lys Val Pro Leu Gln Gln Asn Phe Gln Asp Asn Gln Phe
        195                 200                 205

His Gly Lys Trp Tyr Val Val Gly Leu Ala Gly Asn Gly Trp Leu Arg
    210                 215                 220

Glu Asp Lys Asp Pro Leu Lys Met Met Ala Thr Ile Tyr Glu Leu Lys
225                 230                 235                 240
```

-continued

```
Glu Asp Lys Ser Tyr Asp Val Thr Val Val Asp Phe Glu Leu Lys Lys
            245                 250                 255
Cys Arg Tyr Met Ile Glu Thr Phe Val Pro Gly Ser Gln Pro Gly Glu
        260                 265                 270
Phe Thr Leu Gly Asp Ile Lys Ser Ser Pro Gly Trp Thr Ser Gln Leu
    275                 280                 285
Val Arg Val Val Ser Thr Asn Tyr Asn Gln His Ala Met Val Phe Phe
290                 295                 300
Lys Gly Val Tyr Gln Asn Arg Glu Trp Phe His Ile Thr Leu Tyr Gly
305                 310                 315                 320
Arg Thr Lys Glu Leu Thr Ser Glu Leu Lys Glu Asn Phe Ile Arg Phe
                325                 330                 335
Ser Lys Ser Leu Gly Leu Pro Glu Asn His Ile Val Phe Pro Val Pro
            340                 345                 350
Ile Asp Gln Cys Ile Asp Gly Gly Gly Gln Asp Ser Thr Ser Asp
        355                 360                 365
Leu Ile Pro Ala Pro Pro Leu Ser Lys Val Pro Leu Gln Gln Asn Phe
    370                 375                 380
Gln Asp Asn Gln Phe His Gly Lys Trp Tyr Val Val Gly Glu Ala Gly
385                 390                 395                 400
Asn Leu Ala Leu Arg Glu Asp Lys Asp Pro Met Lys Met Met Ala Thr
                405                 410                 415
Ile Tyr Glu Leu Lys Glu Asp Lys Ser Tyr Asp Val Thr Glu Val Arg
            420                 425                 430
Phe Arg Gln Lys Lys Cys Lys Tyr Asp Ile Val Thr Phe Val Pro Gly
        435                 440                 445
Ser Gln Pro Gly Glu Phe Thr Leu Gly Leu Ile Lys Ser Asp Pro Gly
    450                 455                 460
Gln Thr Ser Glu Leu Val Arg Val Val Ser Thr Asn Tyr Asn Gln His
465                 470                 475                 480
Ala Met Val Phe Phe Lys Lys Val Val Gln Asn Arg Glu Tyr Phe Trp
                485                 490                 495
Ile Thr Leu Tyr Gly Arg Thr Lys Glu Leu Thr Ser Glu Leu Lys Glu
            500                 505                 510
Asn Phe Ile Arg Phe Ser Lys Ser Leu Gly Leu Pro Glu Asn His Ile
        515                 520                 525
Val Phe Pro Val Pro Ile Asp Gln Cys Ile Asp Gly Gly Gly Gln
    530                 535                 540
Asp Ser Thr Ser Asp Leu Ile Pro Ala Pro Pro Leu Ser Lys Val Pro
545                 550                 555                 560
Leu Gln Gln Asn Phe Gln Asp Asn Gln Phe His Gly Lys Trp Tyr Val
                565                 570                 575
Val Gly Met Ala Gly Asn Phe His Leu Arg Glu Asp Lys Asp Pro Ser
            580                 585                 590
Lys Met Pro Ala Thr Ile Tyr Glu Leu Lys Glu Asp Lys Ser Tyr Asp
        595                 600                 605
Val Thr His Val Pro Phe Trp Ala Lys Lys Cys Ala Tyr Lys Ile Ile
    610                 615                 620
Thr Phe Val Pro Gly Ser Gln Pro Gly Glu Phe Thr Leu Gly Ala Ile
625                 630                 635                 640
Lys Ser Gly Pro Gly Met Thr Ser Trp Leu Val Arg Val Val Ser Thr
                645                 650                 655
Asn Tyr Asn Gln His Ala Met Val Phe Phe Lys Gly Val Trp Gln Asn
```

-continued

```
                660                 665                 670
Arg Glu Thr Phe Val Ile Thr Leu Tyr Gly Arg Thr Lys Glu Leu Thr
            675                 680                 685

Ser Glu Leu Lys Glu Asn Phe Ile Arg Phe Ser Lys Ser Leu Gly Leu
        690                 695                 700

Pro Glu Asn His Ile Val Phe Pro Val Pro Ile Asp Gln Cys Ile Asp
705                 710                 715                 720

Gly Ser Ala Trp Ser His Pro Gln Phe Glu Lys His His His His
                725                 730                 735

His
```

<210> SEQ ID NO 170
<211> LENGTH: 743
<212> TYPE: PRT
<213> ORGANISM: Artificial Sequence
<220> FEATURE:
<223> OTHER INFORMATION: S0474.01H22(N65D;T54A) (GSGSG)
     S0510.05H10(N65D) (GSGSG) S0510.11H24(N65D) (GSGSG)
     S0455.04F09(N65D) StrepII His tag

<400> SEQUENCE: 170

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Ser Gly Ser Gly Gln Asp Ser Thr Ser Asp Leu Ile Pro
            180                 185                 190

Ala Pro Pro Leu Ser Lys Val Pro Leu Gln Gln Asn Phe Gln Asp Asn
        195                 200                 205

Gln Phe His Gly Lys Trp Tyr Val Val Gly Leu Ala Gly Asn Gly Trp
    210                 215                 220

Leu Arg Glu Asp Lys Asp Pro Leu Lys Met Met Ala Thr Ile Tyr Glu
225                 230                 235                 240

Leu Lys Glu Asp Lys Ser Tyr Asp Val Thr Val Asp Phe Glu Leu
                245                 250                 255

Lys Lys Cys Arg Tyr Met Ile Glu Thr Phe Val Pro Gly Ser Gln Pro
            260                 265                 270
```

-continued

```
Gly Glu Phe Thr Leu Gly Asp Ile Lys Ser Ser Pro Gly Trp Thr Ser
            275                 280                 285
Gln Leu Val Arg Val Val Ser Thr Asn Tyr Asn Gln His Ala Met Val
        290                 295                 300
Phe Phe Lys Gly Val Tyr Gln Asn Arg Glu Trp Phe His Ile Thr Leu
305                 310                 315                 320
Tyr Gly Arg Thr Lys Glu Leu Thr Ser Glu Leu Lys Glu Asn Phe Ile
                325                 330                 335
Arg Phe Ser Lys Ser Leu Gly Leu Pro Glu Asn His Ile Val Phe Pro
            340                 345                 350
Val Pro Ile Asp Gln Cys Ile Asp Gly Gly Ser Gly Ser Gly Gln Asp
        355                 360                 365
Ser Thr Ser Asp Leu Ile Pro Ala Pro Pro Leu Ser Lys Val Pro Leu
370                 375                 380
Gln Gln Asn Phe Gln Asp Asn Gln Phe His Gly Lys Trp Tyr Val Val
385                 390                 395                 400
Gly Glu Ala Gly Asn Leu Ala Leu Arg Glu Asp Lys Asp Pro Met Lys
                405                 410                 415
Met Met Ala Thr Ile Tyr Glu Leu Lys Glu Asp Lys Ser Tyr Asp Val
            420                 425                 430
Thr Glu Val Arg Phe Arg Gln Lys Lys Cys Lys Tyr Asp Ile Val Thr
        435                 440                 445
Phe Val Pro Gly Ser Gln Pro Gly Glu Phe Thr Leu Gly Leu Ile Lys
        450                 455                 460
Ser Asp Pro Gly Gln Thr Ser Glu Leu Val Arg Val Val Ser Thr Asn
465                 470                 475                 480
Tyr Asn Gln His Ala Met Val Phe Phe Lys Val Val Gln Asn Arg
                485                 490                 495
Glu Tyr Phe Trp Ile Thr Leu Tyr Gly Arg Thr Lys Glu Leu Thr Ser
            500                 505                 510
Glu Leu Lys Glu Asn Phe Ile Arg Phe Ser Lys Ser Leu Gly Leu Pro
        515                 520                 525
Glu Asn His Ile Val Phe Pro Val Pro Ile Asp Gln Cys Ile Asp Gly
        530                 535                 540
Gly Ser Gly Ser Gly Gln Asp Ser Thr Ser Asp Leu Ile Pro Ala Pro
545                 550                 555                 560
Pro Leu Ser Lys Val Pro Leu Gln Gln Asn Phe Gln Asp Asn Gln Phe
                565                 570                 575
His Gly Lys Trp Tyr Val Val Gly Met Ala Gly Asn Phe His Leu Arg
            580                 585                 590
Glu Asp Lys Asp Pro Ser Lys Met Pro Ala Thr Ile Tyr Glu Leu Lys
        595                 600                 605
Glu Asp Lys Ser Tyr Asp Val Thr His Val Pro Phe Trp Ala Lys Lys
        610                 615                 620
Cys Ala Tyr Lys Ile Ile Thr Phe Val Pro Gly Ser Gln Pro Gly Glu
625                 630                 635                 640
Phe Thr Leu Gly Ala Ile Lys Ser Gly Pro Gly Met Thr Ser Trp Leu
                645                 650                 655
Val Arg Val Val Ser Thr Asn Tyr Asn Gln His Ala Met Val Phe Phe
            660                 665                 670
Lys Gly Val Trp Gln Asn Arg Glu Thr Phe Val Ile Thr Leu Tyr Gly
        675                 680                 685
Arg Thr Lys Glu Leu Thr Ser Glu Leu Lys Glu Asn Phe Ile Arg Phe
```

```
                690               695               700
Ser Lys Ser Leu Gly Leu Pro Glu Asn His Ile Val Phe Pro Val Pro
705                 710               715               720

Ile Asp Gln Cys Ile Asp Gly Ser Ala Trp Ser His Pro Gln Phe Glu
                725               730               735

Lys His His His His His His
            740

<210> SEQ ID NO 171
<211> LENGTH: 743
<212> TYPE: PRT
<213> ORGANISM: Artificial Sequence
<220> FEATURE:
<223> OTHER INFORMATION: S0474.01H22(N65D;T54A) (G2SG2)
      S0510.05H10(N65D) (G2SG2) S0510.11H24(N65D) (G2SG2)
      S0455.04F09(N65D) StrepII His tag

<400> SEQUENCE: 171

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Ser Gly Gly Gln Asp Ser Thr Ser Asp Leu Ile Pro
            180                 185                 190

Ala Pro Pro Leu Ser Lys Val Pro Leu Gln Gln Asn Phe Gln Asp Asn
        195                 200                 205

Gln Phe His Gly Lys Trp Tyr Val Val Gly Leu Ala Gly Asn Gly Trp
    210                 215                 220

Leu Arg Glu Asp Lys Asp Pro Leu Lys Met Met Ala Thr Ile Tyr Glu
225                 230                 235                 240

Leu Lys Glu Asp Lys Ser Tyr Asp Val Thr Val Val Asp Phe Glu Leu
                245                 250                 255

Lys Lys Cys Arg Tyr Met Ile Glu Thr Phe Val Pro Gly Ser Gln Pro
            260                 265                 270

Gly Glu Phe Thr Leu Gly Asp Ile Lys Ser Ser Pro Gly Trp Thr Ser
        275                 280                 285

Gln Leu Val Arg Val Val Ser Thr Asn Tyr Asn Gln His Ala Met Val
    290                 295                 300
```

```
Phe Phe Lys Gly Val Tyr Gln Asn Arg Glu Trp Phe His Ile Thr Leu
305                 310                 315                 320

Tyr Gly Arg Thr Lys Glu Leu Thr Ser Glu Leu Lys Glu Asn Phe Ile
                325                 330                 335

Arg Phe Ser Lys Ser Leu Gly Leu Pro Glu Asn His Ile Val Phe Pro
            340                 345                 350

Val Pro Ile Asp Gln Cys Ile Asp Gly Gly Ser Gly Gly Gln Asp
        355                 360                 365

Ser Thr Ser Asp Leu Ile Pro Ala Pro Pro Leu Ser Lys Val Pro Leu
    370                 375                 380

Gln Gln Asn Phe Gln Asp Asn Gln Phe His Gly Lys Trp Tyr Val Val
385                 390                 395                 400

Gly Glu Ala Gly Asn Leu Ala Leu Arg Glu Asp Lys Asp Pro Met Lys
                405                 410                 415

Met Met Ala Thr Ile Tyr Glu Leu Lys Glu Asp Lys Ser Tyr Asp Val
                420                 425                 430

Thr Glu Val Arg Phe Arg Gln Lys Lys Cys Lys Tyr Asp Ile Val Thr
            435                 440                 445

Phe Val Pro Gly Ser Gln Pro Gly Glu Phe Thr Leu Gly Leu Ile Lys
        450                 455                 460

Ser Asp Pro Gly Gln Thr Ser Glu Leu Val Arg Val Val Ser Thr Asn
465                 470                 475                 480

Tyr Asn Gln His Ala Met Val Phe Phe Lys Lys Val Val Gln Asn Arg
                485                 490                 495

Glu Tyr Phe Trp Ile Thr Leu Tyr Gly Arg Thr Lys Glu Leu Thr Ser
            500                 505                 510

Glu Leu Lys Glu Asn Phe Ile Arg Phe Ser Lys Ser Leu Gly Leu Pro
        515                 520                 525

Glu Asn His Ile Val Phe Pro Val Pro Ile Asp Gln Cys Ile Asp Gly
    530                 535                 540

Gly Gly Ser Gly Gly Gln Asp Ser Thr Ser Asp Leu Ile Pro Ala Pro
545                 550                 555                 560

Pro Leu Ser Lys Val Pro Leu Gln Gln Asn Phe Gln Asp Asn Gln Phe
                565                 570                 575

His Gly Lys Trp Tyr Val Val Gly Met Ala Gly Asn Phe His Leu Arg
            580                 585                 590

Glu Asp Lys Asp Pro Ser Lys Met Pro Ala Thr Ile Tyr Glu Leu Lys
        595                 600                 605

Glu Asp Lys Ser Tyr Asp Val Thr His Val Pro Phe Trp Ala Lys Lys
    610                 615                 620

Cys Ala Tyr Lys Ile Ile Thr Phe Val Pro Gly Ser Gln Pro Gly Glu
625                 630                 635                 640

Phe Thr Leu Gly Ala Ile Lys Ser Gly Pro Gly Met Thr Ser Trp Leu
                645                 650                 655

Val Arg Val Val Ser Thr Asn Tyr Asn Gln His Ala Met Val Phe Phe
            660                 665                 670

Lys Gly Val Trp Gln Asn Arg Glu Thr Phe Val Ile Thr Leu Tyr Gly
        675                 680                 685

Arg Thr Lys Glu Leu Thr Ser Glu Leu Lys Glu Asn Phe Ile Arg Phe
    690                 695                 700

Ser Lys Ser Leu Gly Leu Pro Glu Asn His Ile Val Phe Pro Val Pro
705                 710                 715                 720
```

```
Ile Asp Gln Cys Ile Asp Gly Ser Ala Trp Ser His Pro Gln Phe Glu
            725                 730                 735

Lys His His His His His His
            740
```

```
<210> SEQ ID NO 172
<211> LENGTH: 746
<212> TYPE: PRT
<213> ORGANISM: Artificial Sequence
<220> FEATURE:
<223> OTHER INFORMATION: S0474.01H22(N65D;T54A) (GSG2SG)
      S0510.05H10(N65D) (GSG2SG) S0510.11H24(N65D) (GSG2SG)
      S0455.04F09(N65D) StrepII His tag

<400> SEQUENCE: 172
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Ser Gly Gly Ser Gly Gln Asp Ser Thr Ser Asp Leu Ile
            180                 185                 190

Pro Ala Pro Pro Leu Ser Lys Val Pro Leu Gln Gln Asn Phe Gln Asp
        195                 200                 205

Asn Gln Phe His Gly Lys Trp Tyr Val Val Gly Leu Ala Gly Asn Gly
    210                 215                 220

Trp Leu Arg Glu Asp Lys Asp Pro Leu Lys Met Met Ala Thr Ile Tyr
225                 230                 235                 240

Glu Leu Lys Glu Asp Lys Ser Tyr Asp Val Thr Val Asp Phe Glu
                245                 250                 255

Leu Lys Lys Cys Arg Tyr Met Ile Glu Thr Phe Val Pro Gly Ser Gln
        260                 265                 270

Pro Gly Glu Phe Thr Leu Gly Asp Ile Lys Ser Ser Pro Gly Trp Thr
    275                 280                 285

Ser Gln Leu Val Arg Val Val Ser Thr Asn Tyr Asn Gln His Ala Met
290                 295                 300

Val Phe Phe Lys Gly Val Tyr Gln Asn Arg Glu Trp Phe His Ile Thr
305                 310                 315                 320

Leu Tyr Gly Arg Thr Lys Glu Leu Thr Ser Glu Leu Lys Glu Asn Phe
```

```
                325                 330                 335
Ile Arg Phe Ser Lys Ser Leu Gly Leu Pro Glu Asn His Ile Val Phe
            340                 345                 350
Pro Val Pro Ile Asp Gln Cys Ile Asp Gly Ser Gly Gly Ser Gly
            355                 360                 365
Gln Asp Ser Thr Ser Asp Leu Ile Pro Ala Pro Pro Leu Ser Lys Val
            370                 375                 380
Pro Leu Gln Gln Asn Phe Gln Asp Asn Gln Phe His Gly Lys Trp Tyr
385                 390                 395                 400
Val Val Gly Glu Ala Gly Asn Leu Ala Leu Arg Glu Asp Lys Asp Pro
                405                 410                 415
Met Lys Met Met Ala Thr Ile Tyr Glu Leu Lys Glu Asp Lys Ser Tyr
            420                 425                 430
Asp Val Thr Glu Val Arg Phe Arg Gln Lys Lys Cys Lys Tyr Asp Ile
            435                 440                 445
Val Thr Phe Val Pro Gly Ser Gln Pro Gly Glu Phe Thr Leu Gly Leu
            450                 455                 460
Ile Lys Ser Asp Pro Gly Gln Thr Ser Glu Leu Val Arg Val Val Ser
465                 470                 475                 480
Thr Asn Tyr Asn Gln His Ala Met Val Phe Phe Lys Lys Val Val Gln
                485                 490                 495
Asn Arg Glu Tyr Phe Trp Ile Thr Leu Tyr Gly Arg Thr Lys Glu Leu
            500                 505                 510
Thr Ser Glu Leu Lys Glu Asn Phe Ile Arg Phe Ser Lys Ser Leu Gly
            515                 520                 525
Leu Pro Glu Asn His Ile Val Phe Pro Val Pro Ile Asp Gln Cys Ile
            530                 535                 540
Asp Gly Gly Ser Gly Gly Ser Gly Gln Asp Ser Thr Ser Asp Leu Ile
545                 550                 555                 560
Pro Ala Pro Pro Leu Ser Lys Val Pro Leu Gln Gln Asn Phe Gln Asp
                565                 570                 575
Asn Gln Phe His Gly Lys Trp Tyr Val Val Gly Met Ala Gly Asn Phe
            580                 585                 590
His Leu Arg Glu Asp Lys Asp Pro Ser Lys Met Pro Ala Thr Ile Tyr
            595                 600                 605
Glu Leu Lys Glu Asp Lys Ser Tyr Asp Val Thr His Val Pro Phe Trp
            610                 615                 620
Ala Lys Lys Cys Ala Tyr Lys Ile Ile Thr Phe Val Pro Gly Ser Gln
625                 630                 635                 640
Pro Gly Glu Phe Thr Leu Gly Ala Ile Lys Ser Gly Pro Gly Met Thr
                645                 650                 655
Ser Trp Leu Val Arg Val Val Ser Thr Asn Tyr Asn Gln His Ala Met
            660                 665                 670
Val Phe Phe Lys Gly Val Trp Gln Asn Arg Glu Thr Phe Val Ile Thr
            675                 680                 685
Leu Tyr Gly Arg Thr Lys Glu Leu Thr Ser Glu Leu Lys Glu Asn Phe
            690                 695                 700
Ile Arg Phe Ser Lys Ser Leu Gly Leu Pro Glu Asn His Ile Val Phe
705                 710                 715                 720
Pro Val Pro Ile Asp Gln Cys Ile Asp Gly Ser Ala Trp Ser His Pro
                725                 730                 735
Gln Phe Glu Lys His His His His His His
            740                 745
```

<210> SEQ ID NO 173
<211> LENGTH: 749
<212> TYPE: PRT
<213> ORGANISM: Artificial Sequence
<220> FEATURE:
<223> OTHER INFORMATION: S0474.01H22(N65D;T54A) (G2SGSG2)
    S0510.05H10(N65D) (G2SGSG2) S0510.11H24(N65D) (G2SGSG2)
    S0455.04F09(N65D) StrepII His tag

<400> SEQUENCE: 173

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Ser Gly Ser Gly Gly Gln Asp Ser Thr Ser Asp Leu
            180                 185                 190

Ile Pro Ala Pro Pro Leu Ser Lys Val Pro Leu Gln Gln Asn Phe Gln
        195                 200                 205

Asp Asn Gln Phe His Gly Lys Trp Tyr Val Val Gly Leu Ala Gly Asn
    210                 215                 220

Gly Trp Leu Arg Glu Asp Lys Asp Pro Leu Lys Met Met Ala Thr Ile
225                 230                 235                 240

Tyr Glu Leu Lys Glu Asp Lys Ser Tyr Asp Val Thr Val Val Asp Phe
                245                 250                 255

Glu Leu Lys Lys Cys Arg Tyr Met Ile Glu Thr Phe Val Pro Gly Ser
            260                 265                 270

Gln Pro Gly Glu Phe Thr Leu Gly Asp Ile Lys Ser Ser Pro Gly Trp
        275                 280                 285

Thr Ser Gln Leu Val Arg Val Val Ser Thr Asn Tyr Asn Gln His Ala
    290                 295                 300

Met Val Phe Phe Lys Gly Val Tyr Gln Asn Arg Glu Trp Phe His Ile
305                 310                 315                 320

Thr Leu Tyr Gly Arg Thr Lys Glu Leu Thr Ser Glu Leu Lys Glu Asn
                325                 330                 335

Phe Ile Arg Phe Ser Lys Ser Leu Gly Leu Pro Glu Asn His Ile Val
            340                 345                 350

```
Phe Pro Val Pro Ile Asp Gln Cys Ile Asp Gly Gly Ser Gly Ser
            355                 360                 365

Gly Gly Gln Asp Ser Thr Ser Asp Leu Ile Pro Ala Pro Pro Leu Ser
370                 375                 380

Lys Val Pro Leu Gln Gln Asn Phe Gln Asp Asn Gln Phe His Gly Lys
385                 390                 395                 400

Trp Tyr Val Val Gly Glu Ala Gly Asn Leu Ala Leu Arg Glu Asp Lys
                405                 410                 415

Asp Pro Met Lys Met Met Ala Thr Ile Tyr Glu Leu Lys Glu Asp Lys
            420                 425                 430

Ser Tyr Asp Val Thr Glu Val Arg Phe Arg Gln Lys Lys Cys Lys Tyr
        435                 440                 445

Asp Ile Val Thr Phe Val Pro Gly Ser Gln Pro Gly Glu Phe Thr Leu
    450                 455                 460

Gly Leu Ile Lys Ser Asp Pro Gly Gln Thr Ser Glu Leu Val Arg Val
465                 470                 475                 480

Val Ser Thr Asn Tyr Asn Gln His Ala Met Val Phe Phe Lys Lys Val
                485                 490                 495

Val Gln Asn Arg Glu Tyr Phe Trp Ile Thr Leu Tyr Gly Arg Thr Lys
            500                 505                 510

Glu Leu Thr Ser Glu Leu Lys Glu Asn Phe Ile Arg Phe Ser Lys Ser
        515                 520                 525

Leu Gly Leu Pro Glu Asn His Ile Val Phe Pro Val Pro Ile Asp Gln
    530                 535                 540

Cys Ile Asp Gly Gly Ser Gly Ser Gly Gln Asp Ser Thr Ser
545                 550                 555                 560

Asp Leu Ile Pro Ala Pro Pro Leu Ser Lys Val Pro Leu Gln Gln Asn
                565                 570                 575

Phe Gln Asp Asn Gln Phe His Gly Lys Trp Tyr Val Val Gly Met Ala
            580                 585                 590

Gly Asn Phe His Leu Arg Glu Asp Lys Asp Pro Ser Lys Met Pro Ala
        595                 600                 605

Thr Ile Tyr Glu Leu Lys Glu Asp Lys Ser Tyr Asp Val Thr His Val
    610                 615                 620

Pro Phe Trp Ala Lys Lys Cys Ala Tyr Lys Ile Ile Thr Phe Val Pro
625                 630                 635                 640

Gly Ser Gln Pro Gly Glu Phe Thr Leu Gly Ala Ile Lys Ser Gly Pro
                645                 650                 655

Gly Met Thr Ser Trp Leu Val Arg Val Val Ser Thr Asn Tyr Asn Gln
            660                 665                 670

His Ala Met Val Phe Phe Lys Gly Val Trp Gln Asn Arg Glu Thr Phe
        675                 680                 685

Val Ile Thr Leu Tyr Gly Arg Thr Lys Glu Leu Thr Ser Glu Leu Lys
    690                 695                 700

Glu Asn Phe Ile Arg Phe Ser Lys Ser Leu Gly Leu Pro Glu Asn His
705                 710                 715                 720

Ile Val Phe Pro Val Pro Ile Asp Gln Cys Ile Asp Gly Ser Ala Trp
                725                 730                 735

Ser His Pro Gln Phe Glu Lys His His His His His
            740                 745

<210> SEQ ID NO 174
<211> LENGTH: 749
<212> TYPE: PRT
```

-continued

<213> ORGANISM: Artificial Sequence
<220> FEATURE:
<223> OTHER INFORMATION: S0474.01H22(N65D;T54A) (G3SG3)
    S0510.05H10(N65D) (G3SG3) S0510.11H24(N65D) (G3SG3)
    S0455.04F09(N65D) StrepII His tag

<400> SEQUENCE: 174

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Ser Gly Gly Gly Gln Asp Ser Thr Ser Asp Leu
            180                 185                 190

Ile Pro Ala Pro Pro Leu Ser Lys Val Pro Leu Gln Gln Asn Phe Gln
        195                 200                 205

Asp Asn Gln Phe His Gly Lys Trp Tyr Val Val Gly Leu Ala Gly Asn
210                 215                 220

Gly Trp Leu Arg Glu Asp Lys Asp Pro Leu Lys Met Met Ala Thr Ile
225                 230                 235                 240

Tyr Glu Leu Lys Glu Asp Lys Ser Tyr Asp Val Thr Val Val Asp Phe
                245                 250                 255

Glu Leu Lys Lys Cys Arg Tyr Met Ile Glu Thr Phe Val Pro Gly Ser
            260                 265                 270

Gln Pro Gly Glu Phe Thr Leu Gly Asp Ile Lys Ser Ser Pro Gly Trp
        275                 280                 285

Thr Ser Gln Leu Val Arg Val Ser Thr Asn Tyr Asn Gln His Ala
290                 295                 300

Met Val Phe Phe Lys Gly Val Tyr Gln Asn Arg Glu Trp Phe His Ile
305                 310                 315                 320

Thr Leu Tyr Gly Arg Thr Lys Glu Leu Thr Ser Glu Leu Lys Glu Asn
            325                 330                 335

Phe Ile Arg Phe Ser Lys Ser Leu Gly Leu Pro Glu Asn His Ile Val
        340                 345                 350

Phe Pro Val Pro Ile Asp Gln Cys Ile Asp Gly Gly Gly Ser Gly
        355                 360                 365

Gly Gly Gln Asp Ser Thr Ser Asp Leu Ile Pro Ala Pro Pro Leu Ser
370                 375                 380

Lys Val Pro Leu Gln Gln Asn Phe Gln Asp Asn Gln Phe His Gly Lys
385                 390                 395                 400

Trp Tyr Val Val Gly Glu Ala Gly Asn Leu Ala Leu Arg Glu Asp Lys
            405                 410                 415

Asp Pro Met Lys Met Met Ala Thr Ile Tyr Glu Leu Lys Glu Asp Lys
        420                 425                 430

Ser Tyr Asp Val Thr Glu Val Arg Phe Arg Gln Lys Lys Cys Lys Tyr
    435                 440                 445

Asp Ile Val Thr Phe Val Pro Gly Ser Gln Pro Gly Glu Phe Thr Leu
450                 455                 460

Gly Leu Ile Lys Ser Asp Pro Gly Gln Thr Ser Glu Leu Val Arg Val
465                 470                 475                 480

Val Ser Thr Asn Tyr Asn Gln His Ala Met Val Phe Phe Lys Lys Val
            485                 490                 495

Val Gln Asn Arg Glu Tyr Phe Trp Ile Thr Leu Tyr Gly Arg Thr Lys
        500                 505                 510

Glu Leu Thr Ser Glu Leu Lys Glu Asn Phe Ile Arg Phe Ser Lys Ser
    515                 520                 525

Leu Gly Leu Pro Glu Asn His Ile Val Phe Pro Val Pro Ile Asp Gln
530                 535                 540

Cys Ile Asp Gly Gly Gly Ser Gly Gly Gly Gln Asp Ser Thr Ser
545                 550                 555                 560

Asp Leu Ile Pro Ala Pro Pro Leu Ser Lys Val Pro Leu Gln Gln Asn
            565                 570                 575

Phe Gln Asp Asn Gln Phe His Gly Lys Trp Tyr Val Val Gly Met Ala
        580                 585                 590

Gly Asn Phe His Leu Arg Glu Asp Lys Asp Pro Ser Lys Met Pro Ala
    595                 600                 605

Thr Ile Tyr Glu Leu Lys Glu Asp Lys Ser Tyr Asp Val Thr His Val
610                 615                 620

Pro Phe Trp Ala Lys Lys Cys Ala Tyr Lys Ile Ile Thr Phe Val Pro
625                 630                 635                 640

Gly Ser Gln Pro Gly Glu Phe Thr Leu Gly Ala Ile Lys Ser Gly Pro
            645                 650                 655

Gly Met Thr Ser Trp Leu Val Arg Val Val Ser Thr Asn Tyr Asn Gln
        660                 665                 670

His Ala Met Val Phe Phe Lys Gly Val Trp Gln Asn Arg Glu Thr Phe
    675                 680                 685

Val Ile Thr Leu Tyr Gly Arg Thr Lys Glu Leu Thr Ser Glu Leu Lys
690                 695                 700

Glu Asn Phe Ile Arg Phe Ser Lys Ser Leu Gly Leu Pro Glu Asn His
705                 710                 715                 720

Ile Val Phe Pro Val Pro Ile Asp Gln Cys Ile Asp Gly Ser Ala Trp
            725                 730                 735

Ser His Pro Gln Phe Glu Lys His His His His His
        740                 745

<210> SEQ ID NO 175
<211> LENGTH: 752
<212> TYPE: PRT
<213> ORGANISM: Artificial Sequence
<220> FEATURE:
<223> OTHER INFORMATION: S0474.01H22(N65D;T54A) (G2SG2SG2)
      S0510.05H10(N65D) (G2SG2SG2) S0510.11H24(N65D) (G2SG2SG2)
      S0455.04F09(N65D) StrepII His tag

<400> SEQUENCE: 175

| | | | | | | | | | | | | | | |
|---|---|---|---|---|---|---|---|---|---|---|---|---|---|---|
|Gln|Asp|Ser|Thr|Ser|Asp|Leu|Ile|Pro|Ala|Pro|Pro|Leu|Ser|Lys|Val|
|1| | | |5| | | | |10| | | | |15| |
|Pro|Leu|Gln|Gln|Asn|Phe|Gln|Asp|Asn|Gln|Phe|His|Gly|Lys|Trp|Tyr|
| | | |20| | | | |25| | | | |30| | |
|Val|Val|Gly|Val|Ala|Gly|Asn|Thr|Ile|Leu|Arg|Glu|Asp|Lys|Asp|Pro|
| | | |35| | | | |40| | | | |45| | |
|Gly|Lys|Met|Asn|Ala|Ala|Ile|Tyr|Glu|Leu|Lys|Glu|Asp|Lys|Ser|Tyr|
| |50| | | | |55| | | | |60| | | | |
|Asp|Val|Thr|Asp|Val|Arg|Phe|Ile|Arg|Lys|Lys|Cys|His|Tyr|Tyr|Ile|
|65| | | | |70| | | | |75| | | | |80|
|Asp|Thr|Phe|Val|Pro|Gly|Ser|Gln|Pro|Gly|Glu|Phe|Thr|Leu|Gly|Asn|
| | | | |85| | | | |90| | | | |95| |
|Ile|Lys|Ser|Tyr|Pro|Gly|Thr|Thr|Ser|Gln|Leu|Val|Arg|Val|Val|Ser|
| | | |100| | | | |105| | | | |110| | |
|Thr|Asn|Tyr|Asn|Gln|His|Ala|Met|Val|Phe|Phe|Lys|Ile|Val|Arg|Gln|
| | | |115| | | | |120| | | | |125| | |
|Asn|Arg|Glu|Ile|Phe|Trp|Ile|Thr|Leu|Tyr|Gly|Arg|Thr|Lys|Glu|Leu|
| |130| | | | |135| | | | |140| | | | |
|Thr|Ser|Glu|Leu|Lys|Glu|Asn|Phe|Ile|Arg|Phe|Ser|Lys|Ser|Leu|Gly|
|145| | | | |150| | | | |155| | | | |160|
|Leu|Pro|Glu|Asn|His|Ile|Val|Phe|Pro|Val|Pro|Ile|Asp|Gln|Cys|Ile|
| | | | |165| | | | |170| | | | |175| |
|Asp|Gly|Gly|Gly|Ser|Gly|Gly|Ser|Gly|Gly|Gln|Asp|Ser|Thr|Ser|Asp|
| | | |180| | | | |185| | | | |190| | |
|Leu|Ile|Pro|Ala|Pro|Pro|Leu|Ser|Lys|Val|Pro|Leu|Gln|Gln|Asn|Phe|
| | | |195| | | | |200| | | | |205| | |
|Gln|Asp|Asn|Gln|Phe|His|Gly|Lys|Trp|Tyr|Val|Val|Gly|Leu|Ala|Gly|
| |210| | | | |215| | | | |220| | | | |
|Asn|Gly|Trp|Leu|Arg|Glu|Asp|Lys|Asp|Pro|Leu|Lys|Met|Met|Ala|Thr|
|225| | | | |230| | | | |235| | | | |240|
|Ile|Tyr|Glu|Leu|Lys|Glu|Asp|Lys|Ser|Tyr|Asp|Val|Thr|Val|Val|Asp|
| | | | |245| | | | |250| | | | |255| |
|Phe|Glu|Leu|Lys|Lys|Cys|Arg|Tyr|Met|Ile|Glu|Thr|Phe|Val|Pro|Gly|
| | | | |260| | | | |265| | | | |270| |
|Ser|Gln|Pro|Gly|Glu|Phe|Thr|Leu|Gly|Asp|Ile|Lys|Ser|Ser|Pro|Gly|
| | | |275| | | | |280| | | | |285| | |
|Trp|Thr|Ser|Gln|Leu|Val|Arg|Val|Val|Ser|Thr|Asn|Tyr|Asn|Gln|His|
| |290| | | | |295| | | | |300| | | | |
|Ala|Met|Val|Phe|Phe|Lys|Gly|Val|Tyr|Gln|Asn|Arg|Glu|Trp|Phe|His|
|305| | | | |310| | | | |315| | | | |320|
|Ile|Thr|Leu|Tyr|Gly|Arg|Thr|Lys|Glu|Leu|Thr|Ser|Glu|Leu|Lys|Glu|
| | | | |325| | | | |330| | | | |335| |
|Asn|Phe|Ile|Arg|Phe|Ser|Lys|Ser|Leu|Gly|Leu|Pro|Glu|Asn|His|Ile|
| | | |340| | | | |345| | | | |350| | |
|Val|Phe|Pro|Val|Pro|Ile|Asp|Gln|Cys|Ile|Asp|Gly|Gly|Ser|Gly|
| | | |355| | | | |360| | | | |365| | |
|Gly|Ser|Gly|Gly|Gln|Asp|Ser|Thr|Ser|Asp|Leu|Ile|Pro|Ala|Pro|Pro|
| |370| | | | |375| | | | |380| | | | |
|Leu|Ser|Lys|Val|Pro|Leu|Gln|Gln|Asn|Phe|Gln|Asp|Asn|Gln|Phe|His|
|385| | | | |390| | | | |395| | | | |400|
|Gly|Lys|Trp|Tyr|Val|Val|Gly|Glu|Ala|Gly|Asn|Leu|Ala|Leu|Arg|Glu|

```
                405                 410                 415
Asp Lys Asp Pro Met Lys Met Met Ala Thr Ile Tyr Glu Leu Lys Glu
            420                 425                 430

Asp Lys Ser Tyr Asp Val Thr Glu Val Arg Phe Arg Gln Lys Lys Cys
            435                 440                 445

Lys Tyr Asp Ile Val Thr Phe Val Pro Gly Ser Gln Pro Gly Glu Phe
450                 455                 460

Thr Leu Gly Leu Ile Lys Ser Asp Pro Gly Gln Thr Ser Glu Leu Val
465                 470                 475                 480

Arg Val Val Ser Thr Asn Tyr Asn Gln His Ala Met Val Phe Phe Lys
            485                 490                 495

Lys Val Val Gln Asn Arg Glu Tyr Phe Trp Ile Thr Leu Tyr Gly Arg
            500                 505                 510

Thr Lys Glu Leu Thr Ser Glu Leu Lys Glu Asn Phe Ile Arg Phe Ser
            515                 520                 525

Lys Ser Leu Gly Leu Pro Glu Asn His Ile Val Phe Pro Val Pro Ile
530                 535                 540

Asp Gln Cys Ile Asp Gly Gly Ser Gly Gly Ser Gly Gly Gln Asp
545                 550                 555                 560

Ser Thr Ser Asp Leu Ile Pro Ala Pro Pro Leu Ser Lys Val Pro Leu
            565                 570                 575

Gln Gln Asn Phe Gln Asp Asn Gln Phe His Gly Lys Trp Tyr Val Val
            580                 585                 590

Gly Met Ala Gly Asn Phe His Leu Arg Glu Asp Lys Asp Pro Ser Lys
            595                 600                 605

Met Pro Ala Thr Ile Tyr Glu Leu Lys Glu Asp Lys Ser Tyr Asp Val
610                 615                 620

Thr His Val Pro Phe Trp Ala Lys Lys Cys Ala Tyr Lys Ile Ile Thr
625                 630                 635                 640

Phe Val Pro Gly Ser Gln Pro Gly Glu Phe Thr Leu Gly Ala Ile Lys
            645                 650                 655

Ser Gly Pro Gly Met Thr Ser Trp Leu Val Arg Val Val Ser Thr Asn
            660                 665                 670

Tyr Asn Gln His Ala Met Val Phe Phe Lys Gly Val Trp Gln Asn Arg
            675                 680                 685

Glu Thr Phe Val Ile Thr Leu Tyr Gly Arg Thr Lys Glu Leu Thr Ser
            690                 695                 700

Glu Leu Lys Glu Asn Phe Ile Arg Phe Ser Lys Ser Leu Gly Leu Pro
705                 710                 715                 720

Glu Asn His Ile Val Phe Pro Val Pro Ile Asp Gln Cys Ile Asp Gly
            725                 730                 735

Ser Ala Trp Ser His Pro Gln Phe Glu Lys His His His His His His
            740                 745                 750

<210> SEQ ID NO 176
<211> LENGTH: 758
<212> TYPE: PRT
<213> ORGANISM: Artificial Sequence
<220> FEATURE:
<223> OTHER INFORMATION: S0474.01H22(N65D;T54A) (G3SG2SG3)
      S0510.05H10(N65D) (G3SG2SG3) S0510.11H24(N65D) (G3SG2SG3)
      S0455.04F09(N65D) StrepII His tag

<400> SEQUENCE: 176

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
             20                  25                  30
Val Val Gly Val Ala Gly Asn Thr Ile Leu Arg Glu Asp Lys Asp Pro
         35                  40                  45
Gly Lys Met Asn Ala Ala Ile Tyr Glu Leu Lys Glu Asp Lys Ser Tyr
 50                  55                  60
Asp Val Thr Asp Val Arg Phe Ile Arg Lys Lys Cys His Tyr Tyr Ile
 65                  70                  75                  80
Asp Thr Phe Val Pro Gly Ser Gln Pro Gly Glu Phe Thr Leu Gly Asn
                 85                  90                  95
Ile Lys Ser Tyr Pro Gly Thr Thr Ser Gln Leu Val Arg Val Val Ser
            100                 105                 110
Thr Asn Tyr Asn Gln His Ala Met Val Phe Phe Lys Ile Val Arg Gln
            115                 120                 125
Asn Arg Glu Ile Phe Trp Ile Thr Leu Tyr Gly Arg Thr Lys Glu Leu
130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Gly Gln Asp Ser Thr
                180                 185                 190
Ser Asp Leu Ile Pro Ala Pro Pro Leu Ser Lys Val Pro Leu Gln Gln
            195                 200                 205
Asn Phe Gln Asp Asn Gln Phe His Gly Lys Trp Tyr Val Val Gly Leu
            210                 215                 220
Ala Gly Asn Gly Trp Leu Arg Glu Asp Lys Asp Pro Leu Lys Met Met
225                 230                 235                 240
Ala Thr Ile Tyr Glu Leu Lys Glu Asp Lys Ser Tyr Asp Val Thr Val
                245                 250                 255
Val Asp Phe Glu Leu Lys Lys Cys Arg Tyr Met Ile Glu Thr Phe Val
            260                 265                 270
Pro Gly Ser Gln Pro Gly Glu Phe Thr Leu Gly Asp Ile Lys Ser Ser
            275                 280                 285
Pro Gly Trp Thr Ser Gln Leu Val Arg Val Val Ser Thr Asn Tyr Asn
290                 295                 300
Gln His Ala Met Val Phe Phe Lys Gly Val Tyr Gln Asn Arg Glu Trp
305                 310                 315                 320
Phe His Ile Thr Leu Tyr Gly Arg Thr Lys Glu Leu Thr Ser Glu Leu
                325                 330                 335
Lys Glu Asn Phe Ile Arg Phe Ser Lys Ser Leu Gly Leu Pro Glu Asn
            340                 345                 350
His Ile Val Phe Pro Val Pro Ile Asp Gln Cys Ile Asp Gly Gly Gly
            355                 360                 365
Gly Ser Gly Gly Ser Gly Gly Gln Asp Ser Thr Ser Asp Leu Ile
370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                405                 410                 415
Ala Leu Arg Glu Asp Lys Asp Pro Met Lys Met Met Ala Thr Ile Tyr
            420                 425                 430
```

-continued

Glu Leu Lys Glu Asp Lys Ser Tyr Asp Val Thr Glu Val Arg Phe Arg
            435                 440                 445

Gln Lys Lys Cys Lys Tyr Asp Ile Val Thr Phe Val Pro Gly Ser Gln
    450                 455                 460

Pro Gly Glu Phe Thr Leu Gly Leu Ile Lys Ser Asp Pro Gly Gln Thr
465                 470                 475                 480

Ser Glu Leu Val Arg Val Ser Thr Asn Tyr Asn Gln His Ala Met
                485                 490                 495

Val Phe Phe Lys Lys Val Val Gln Asn Arg Glu Tyr Phe Trp Ile Thr
                500                 505                 510

Leu Tyr Gly Arg Thr Lys Glu Leu Thr Ser Glu Leu Lys Glu Asn Phe
    515                 520                 525

Ile Arg Phe Ser Lys Ser Leu Gly Leu Pro Glu Asn His Ile Val Phe
    530                 535                 540

Pro Val Pro Ile Asp Gln Cys Ile Asp Gly Gly Gly Ser Gly Gly
545                 550                 555                 560

Ser Gly Gly Gly Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe His
        580                 585                 590

Gly Lys Trp Tyr Val Val Gly Met Ala Gly Asn Phe His Leu Arg Glu
    595                 600                 605

Asp Lys Asp Pro Ser Lys Met Pro Ala Thr Ile Tyr Glu Leu Lys Glu
        610                 615                 620

Asp Lys Ser Tyr Asp Val Thr His Val Pro Phe Trp Ala Lys Lys Cys
625                 630                 635                 640

Ala Tyr Lys Ile Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
            660                 665                 670

Arg Val Val Ser Thr Asn Tyr Asn Gln His Ala Met Val Phe Phe Lys
    675                 680                 685

Gly Val Trp Gln Asn Arg Glu Thr Phe Val Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
        740                 745                 750

His His His His His His
        755

<210> SEQ ID NO 177
<211> LENGTH: 754
<212> TYPE: PRT
<213> ORGANISM: Artificial Sequence
<220> FEATURE:
<223> OTHER INFORMATION: S0474.01H22(N65D;T54A) (G4S)2 S0512.17L07(N39S_
      N65D_T136A) (G4S)2 S0510.10A04_stop103Q(N65D)
      (G4S)2-S0455.04F23(N65D) StrepII His tag

<400> SEQUENCE: 177

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr

```
            20                  25                  30
Val Val Gly Val Ala Gly Asn Thr Ile Leu Arg Glu Asp Lys Asp Pro
            35                  40                  45
Gly Lys Met Asn Ala Ala Ile Tyr Glu Leu Lys Glu Asp Lys Ser Tyr
            50                  55                  60
Asp Val Thr Asp Val Arg Phe Ile Arg Lys Lys Cys His Tyr Tyr Ile
65                  70                  75                  80
Asp Thr Phe Val Pro Gly Ser Gln Pro Gly Glu Phe Thr Leu Gly Asn
                    85                  90                  95
Ile Lys Ser Tyr Pro Gly Thr Thr Ser Gln Leu Val Arg Val Val Ser
            100                 105                 110
Thr Asn Tyr Asn Gln His Ala Met Val Phe Phe Lys Ile Val Arg Gln
            115                 120                 125
Asn Arg Glu Ile Phe Trp Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                    165                 170                 175
Asp Gly Gly Gly Gly Ser Gly Gly Gly Ser Gln Asp Ser Thr
            180                 185                 190
Ser Asp Leu Ile Pro Ala Pro Pro Leu Ser Lys Val Pro Leu Gln Gln
            195                 200                 205
Asn Phe Gln Asp Asn Gln Phe His Gly Lys Trp Tyr Val Val Gly Trp
            210                 215                 220
Ala Gly Ser Thr Thr Leu Arg Glu Asp Lys Asp Pro Pro Lys Met Pro
225                 230                 235                 240
Ala Thr Ile Tyr Glu Leu Lys Glu Asp Lys Ser Tyr Asp Val Thr Asp
                    245                 250                 255
Val Gln Phe Pro Glu Lys Lys Cys Ile Tyr Ser Thr Ile Thr Phe Val
            260                 265                 270
Pro Gly Ser Gln Pro Gly Glu Phe Thr Leu Gly Gly Ile Lys Ser Ser
            275                 280                 285
Pro Gly Gln Thr Ser His Leu Val Arg Val Val Ser Thr Asn Tyr Asn
            290                 295                 300
Gln His Ala Met Val Phe Phe Lys Tyr Val Ile Gln Asn Arg Glu Gly
305                 310                 315                 320
Phe Asn Ile Ala Leu Tyr Gly Arg Thr Lys Glu Leu Thr Ser Glu Leu
                    325                 330                 335
Lys Glu Asn Phe Ile Arg Phe Ser Lys Ser Leu Gly Leu Pro Glu Asn
            340                 345                 350
His Ile Val Phe Pro Val Pro Ile Asp Gln Cys Ile Asp Gly Gly Gly
            355                 360                 365
Gly Gly Ser Gly Gly Gly Ser Gln Asp Ser Thr Ser Asp Leu Ile
            370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                    405                 410                 415
Ala Leu Arg Glu Asp Lys Asp Pro Lys Lys Met Met Ala Thr Ile Tyr
            420                 425                 430
Glu Leu Lys Glu Asp Lys Ser Tyr Asp Val Thr Glu Val Arg Phe Arg
            435                 440                 445
```

Tyr Lys Lys Cys Gln Tyr Asp Ile Val Thr Phe Val Pro Gly Ser Gln
            450                 455                 460

Pro Gly Glu Phe Thr Leu Ser Glu Pro Gly Gln Thr Ser Glu Leu Val
465                 470                 475                 480

Arg Val Val Ser Thr Asn Tyr Asn Gln His Ala Met Val Phe Phe Lys
                485                 490                 495

Lys Val Val Gln Asn Arg Glu Phe Phe Trp Ile Thr Leu Tyr Gly Arg
            500                 505                 510

Thr Lys Glu Leu Thr Ser Glu Leu Lys Glu Asn Phe Ile Arg Phe Ser
        515                 520                 525

Lys Ser Leu Gly Leu Pro Glu Asn His Ile Val Phe Pro Val Pro Ile
530                 535                 540

Asp Gln Cys Ile Asp Gly Gly Gly Gly Ser Gly Gly Gly Ser
545                 550                 555                 560

Gln Asp Ser Thr Ser Asp Leu Ile Pro Ala Pro Pro Leu Ser Lys Val
                565                 570                 575

Pro Leu Gln Gln Asn Phe Gln Asp Asn Gln Phe His Gly Lys Trp Tyr
            580                 585                 590

Val Val Gly His Ala Gly Asn Gln Trp Leu Arg Glu Asp Lys Asp Pro
        595                 600                 605

Arg Lys Met Trp Ala Thr Ile Tyr Glu Leu Lys Glu Asp Lys Ser Tyr
610                 615                 620

Asp Val Thr Asp Val Asp Phe Ala Ile Lys Lys Cys His Tyr Arg Ile
625                 630                 635                 640

Thr Thr Phe Val Pro Gly Ser Gln Pro Gly Glu Phe Thr Leu Gly Asn
                645                 650                 655

Ile Lys Ser His Pro Gly Gly Thr Ser Gly Leu Val Arg Val Val Ser
            660                 665                 670

Thr Asn Tyr Asn Gln His Ala Met Val Phe Phe Lys Phe Val Ile Gln
        675                 680                 685

Asn Arg Glu Ala Phe Phe Ile Thr Leu Tyr Gly Arg Thr Lys Glu Leu
690                 695                 700

Thr Ser Glu Leu Lys Glu Asn Phe Ile Arg Phe Ser Lys Ser Leu Gly
705                 710                 715                 720

Leu Pro Glu Asn His Ile Val Phe Pro Val Pro Ile Asp Gln Cys Ile
                725                 730                 735

Asp Gly Ser Ala Trp Ser His Pro Gln Phe Glu Lys His His His
            740                 745                 750

His His

<210> SEQ ID NO 178
<211> LENGTH: 754
<212> TYPE: PRT
<213> ORGANISM: Artificial Sequence
<220> FEATURE:
<223> OTHER INFORMATION: S0474.01H22(N65D;T54A) (G4S)2 S0512.17L07(N39S_
    N65D_T136A) (G4S)2-S0510.10A04_stop103Q(N65D)
    (G4S)2-S0455.04F09(N65D)StrepII His tag

<400> SEQUENCE: 178

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro

```
            35                  40                  45
Gly Lys Met Asn Ala Ala Ile Tyr Glu Leu Lys Glu Asp Lys Ser Tyr
 50                  55                  60
Asp Val Thr Asp Val Arg Phe Ile Arg Lys Lys Cys His Tyr Tyr Ile
 65                  70                  75                  80
Asp Thr Phe Val Pro Gly Ser Gln Pro Gly Glu Phe Thr Leu Gly Asn
                     85                  90                  95
Ile Lys Ser Tyr Pro Gly Thr Thr Ser Gln Leu Val Arg Val Val Ser
                    100                 105                 110
Thr Asn Tyr Asn Gln His Ala Met Val Phe Phe Lys Ile Val Arg Gln
                    115                 120                 125
Asn Arg Glu Ile Phe Trp Ile Thr Leu Tyr Gly Arg Thr Lys Glu Leu
                    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                    165                 170                 175
Asp Gly Gly Gly Gly Ser Gly Gly Gly Ser Gln Asp Ser Thr
                    180                 185                 190
Ser Asp Leu Ile Pro Ala Pro Pro Leu Ser Lys Val Pro Leu Gln Gln
                    195                 200                 205
Asn Phe Gln Asp Asn Gln Phe His Gly Lys Trp Tyr Val Val Gly Trp
                    210                 215                 220
Ala Gly Ser Thr Thr Leu Arg Glu Asp Lys Asp Pro Pro Lys Met Pro
225                 230                 235                 240
Ala Thr Ile Tyr Glu Leu Lys Glu Asp Lys Ser Tyr Asp Val Thr Asp
                    245                 250                 255
Val Gln Phe Pro Glu Lys Lys Cys Ile Tyr Ser Thr Ile Thr Phe Val
                    260                 265                 270
Pro Gly Ser Gln Pro Gly Glu Phe Thr Leu Gly Gly Ile Lys Ser Ser
                    275                 280                 285
Pro Gly Gln Thr Ser His Leu Val Arg Val Val Ser Thr Asn Tyr Asn
                    290                 295                 300
Gln His Ala Met Val Phe Phe Lys Tyr Val Ile Gln Asn Arg Glu Gly
305                 310                 315                 320
Phe Asn Ile Ala Leu Tyr Gly Arg Thr Lys Glu Leu Thr Ser Glu Leu
                    325                 330                 335
Lys Glu Asn Phe Ile Arg Phe Ser Lys Ser Leu Gly Leu Pro Glu Asn
                    340                 345                 350
His Ile Val Phe Pro Val Pro Ile Asp Gln Cys Ile Asp Gly Gly Gly
                    355                 360                 365
Gly Gly Ser Gly Gly Gly Ser Gln Asp Ser Thr Ser Asp Leu Ile
                    370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                    405                 410                 415
Ala Leu Arg Glu Asp Lys Asp Pro Lys Lys Met Met Ala Thr Ile Tyr
                    420                 425                 430
Glu Leu Lys Glu Asp Lys Ser Tyr Asp Val Thr Glu Val Arg Phe Arg
                    435                 440                 445
Tyr Lys Lys Cys Gln Tyr Asp Ile Val Thr Phe Val Pro Gly Ser Gln
                    450                 455                 460
```

Pro Gly Glu Phe Thr Leu Ser Glu Pro Gly Gln Thr Ser Glu Leu Val
465                 470                 475                 480

Arg Val Val Ser Thr Asn Tyr Asn Gln His Ala Met Val Phe Phe Lys
            485                 490                 495

Lys Val Val Gln Asn Arg Glu Phe Phe Trp Ile Thr Leu Tyr Gly Arg
        500                 505                 510

Thr Lys Glu Leu Thr Ser Glu Leu Lys Glu Asn Phe Ile Arg Phe Ser
    515                 520                 525

Lys Ser Leu Gly Leu Pro Glu Asn His Ile Val Phe Pro Val Pro Ile
530                 535                 540

Asp Gln Cys Ile Asp Gly Gly Gly Gly Ser Gly Gly Gly Gly Ser
545                 550                 555                 560

Gln Asp Ser Thr Ser Asp Leu Ile Pro Ala Pro Pro Leu Ser Lys Val
            565                 570                 575

Pro Leu Gln Gln Asn Phe Gln Asp Asn Gln Phe His Gly Lys Trp Tyr
        580                 585                 590

Val Val Gly Met Ala Gly Asn Phe His Leu Arg Glu Asp Lys Asp Pro
    595                 600                 605

Ser Lys Met Pro Ala Thr Ile Tyr Glu Leu Lys Glu Asp Lys Ser Tyr
610                 615                 620

Asp Val Thr His Val Pro Phe Trp Ala Lys Lys Cys Ala Tyr Lys Ile
625                 630                 635                 640

Ile Thr Phe Val Pro Gly Ser Gln Pro Gly Glu Phe Thr Leu Gly Ala
            645                 650                 655

Ile Lys Ser Gly Pro Gly Met Thr Ser Trp Leu Val Arg Val Val Ser
        660                 665                 670

Thr Asn Tyr Asn Gln His Ala Met Val Phe Phe Lys Gly Val Trp Gln
    675                 680                 685

Asn Arg Glu Thr Phe Val Ile Thr Leu Tyr Gly Arg Thr Lys Glu Leu
690                 695                 700

Thr Ser Glu Leu Lys Glu Asn Phe Ile Arg Phe Ser Lys Ser Leu Gly
705                 710                 715                 720

Leu Pro Glu Asn His Ile Val Phe Pro Val Pro Ile Asp Gln Cys Ile
            725                 730                 735

Asp Gly Ser Ala Trp Ser His Pro Gln Phe Glu Lys His His His His
        740                 745                 750

His His

<210> SEQ ID NO 179
<211> LENGTH: 754
<212> TYPE: PRT
<213> ORGANISM: Artificial Sequence
<220> FEATURE:
<223> OTHER INFORMATION: S0474.01H22(N65D;T54A) (G4S)2 S0510.05H10(N65D)
      (G4S)2 S0510.10A04_stop103Q(N65D) (G4S)2 S0455.04F23(N65D) StrepII
      His tag

<400> SEQUENCE: 179

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr

-continued

```
                50                  55                  60
Asp Val Thr Asp Val Arg Phe Ile Arg Lys Lys Cys His Tyr Tyr Ile
 65                  70                  75                  80
Asp Thr Phe Val Pro Gly Ser Gln Pro Gly Glu Phe Thr Leu Gly Asn
                 85                  90                  95
Ile Lys Ser Tyr Pro Gly Thr Thr Ser Gln Leu Val Arg Val Val Ser
                100                 105                 110
Thr Asn Tyr Asn Gln His Ala Met Val Phe Phe Lys Ile Val Arg Gln
                115                 120                 125
Asn Arg Glu Ile Phe Trp Ile Thr Leu Tyr Gly Arg Thr Lys Glu Leu
130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Gly Ser Gly Gly Gly Ser Gln Asp Ser Thr
                180                 185                 190
Ser Asp Leu Ile Pro Ala Pro Pro Leu Ser Lys Val Pro Leu Gln Gln
                195                 200                 205
Asn Phe Gln Asp Asn Gln Phe His Gly Lys Trp Tyr Val Val Gly Leu
210                 215                 220
Ala Gly Asn Gly Trp Leu Arg Glu Asp Lys Asp Pro Leu Lys Met Met
225                 230                 235                 240
Ala Thr Ile Tyr Glu Leu Lys Glu Asp Lys Ser Tyr Asp Val Thr Val
                245                 250                 255
Val Asp Phe Glu Leu Lys Lys Cys Arg Tyr Met Ile Glu Thr Phe Val
                260                 265                 270
Pro Gly Ser Gln Pro Gly Glu Phe Thr Leu Gly Asp Ile Lys Ser Ser
                275                 280                 285
Pro Gly Trp Thr Ser Gln Leu Val Arg Val Val Ser Thr Asn Tyr Asn
                290                 295                 300
Gln His Ala Met Val Phe Phe Lys Gly Val Tyr Gln Asn Arg Glu Trp
305                 310                 315                 320
Phe His Ile Thr Leu Tyr Gly Arg Thr Lys Glu Leu Thr Ser Glu Leu
                325                 330                 335
Lys Glu Asn Phe Ile Arg Phe Ser Lys Ser Leu Gly Leu Pro Glu Asn
                340                 345                 350
His Ile Val Phe Pro Val Pro Ile Asp Gln Cys Ile Asp Gly Gly Gly
                355                 360                 365
Gly Gly Ser Gly Gly Gly Ser Gln Asp Ser Thr Ser Asp Leu Ile
                370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                405                 410                 415
Ala Leu Arg Glu Asp Lys Asp Pro Lys Lys Met Met Ala Thr Ile Tyr
                420                 425                 430
Glu Leu Lys Glu Asp Lys Ser Tyr Asp Val Thr Glu Val Arg Phe Arg
                435                 440                 445
Tyr Lys Lys Cys Gln Tyr Asp Ile Val Thr Phe Val Pro Gly Ser Gln
                450                 455                 460
Pro Gly Glu Phe Thr Leu Ser Glu Pro Gly Gln Thr Ser Glu Leu Val
465                 470                 475                 480
```

```
Arg Val Val Ser Thr Asn Tyr Asn Gln His Ala Met Val Phe Phe Lys
                485                 490                 495

Lys Val Val Gln Asn Arg Glu Phe Phe Trp Ile Thr Leu Tyr Gly Arg
            500                 505                 510

Thr Lys Glu Leu Thr Ser Glu Leu Lys Glu Asn Phe Ile Arg Phe Ser
        515                 520                 525

Lys Ser Leu Gly Leu Pro Glu Asn His Ile Val Phe Pro Val Pro Ile
    530                 535                 540

Asp Gln Cys Ile Asp Gly Gly Gly Gly Ser Gly Gly Gly Gly Ser
545                 550                 555                 560

Gln Asp Ser Thr Ser Asp Leu Ile Pro Ala Pro Pro Leu Ser Lys Val
                565                 570                 575

Pro Leu Gln Gln Asn Phe Gln Asp Asn Gln Phe His Gly Lys Trp Tyr
            580                 585                 590

Val Val Gly His Ala Gly Asn Gln Trp Leu Arg Glu Asp Lys Asp Pro
        595                 600                 605

Arg Lys Met Trp Ala Thr Ile Tyr Glu Leu Lys Glu Asp Lys Ser Tyr
    610                 615                 620

Asp Val Thr Asp Val Asp Phe Ala Ile Lys Lys Cys His Tyr Arg Ile
625                 630                 635                 640

Thr Thr Phe Val Pro Gly Ser Gln Pro Gly Glu Phe Thr Leu Gly Asn
                645                 650                 655

Ile Lys Ser His Pro Gly Gly Thr Ser Gly Leu Val Arg Val Val Ser
            660                 665                 670

Thr Asn Tyr Asn Gln His Ala Met Val Phe Phe Lys Phe Val Ile Gln
        675                 680                 685

Asn Arg Glu Ala Phe Phe Ile Thr Leu Tyr Gly Arg Thr Lys Glu Leu
    690                 695                 700

Thr Ser Glu Leu Lys Glu Asn Phe Ile Arg Phe Ser Lys Ser Leu Gly
705                 710                 715                 720

Leu Pro Glu Asn His Ile Val Phe Pro Val Pro Ile Asp Gln Cys Ile
                725                 730                 735

Asp Gly Ser Ala Trp Ser His Pro Gln Phe Glu Lys His His His His
            740                 745                 750

His His

<210> SEQ ID NO 180
<211> LENGTH: 754
<212> TYPE: PRT
<213> ORGANISM: Artificial Sequence
<220> FEATURE:
<223> OTHER INFORMATION: S0474.01H22(N65D;T54A) (G4S)2-S0510.05H10(N65D)
      (G4S)2 S0510.10A04_stop103Q(N65D) (G4S)2-S0455.04F09(N65D) StrepII
      His tag

<400> SEQUENCE: 180

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
```

-continued

```
                65                  70                  75                  80
Asp Thr Phe Val Pro Gly Ser Gln Pro Gly Glu Phe Thr Leu Gly Asn
                    85                  90                  95
Ile Lys Ser Tyr Pro Gly Thr Thr Ser Gln Leu Val Arg Val Val Ser
                100                 105                 110
Thr Asn Tyr Asn Gln His Ala Met Val Phe Phe Lys Ile Val Arg Gln
                115                 120                 125
Asn Arg Glu Ile Phe Trp Ile Thr Leu Tyr Gly Arg Thr Lys Glu Leu
130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Ser Gln Asp Ser Thr
                180                 185                 190
Ser Asp Leu Ile Pro Ala Pro Pro Leu Ser Lys Val Pro Leu Gln Gln
                195                 200                 205
Asn Phe Gln Asp Asn Gln Phe His Gly Lys Trp Tyr Val Val Gly Leu
                210                 215                 220
Ala Gly Asn Gly Trp Leu Arg Glu Asp Lys Asp Pro Leu Lys Met Met
225                 230                 235                 240
Ala Thr Ile Tyr Glu Leu Lys Glu Asp Lys Ser Tyr Asp Val Thr Val
                245                 250                 255
Val Asp Phe Glu Leu Lys Lys Cys Arg Tyr Met Ile Glu Thr Phe Val
                260                 265                 270
Pro Gly Ser Gln Pro Gly Glu Phe Thr Leu Gly Asp Ile Lys Ser Ser
                275                 280                 285
Pro Gly Trp Thr Ser Gln Leu Val Arg Val Val Ser Thr Asn Tyr Asn
                290                 295                 300
Gln His Ala Met Val Phe Phe Lys Gly Val Tyr Gln Asn Arg Glu Trp
305                 310                 315                 320
Phe His Ile Thr Leu Tyr Gly Arg Thr Lys Glu Leu Thr Ser Glu Leu
                325                 330                 335
Lys Glu Asn Phe Ile Arg Phe Ser Lys Ser Leu Gly Leu Pro Glu Asn
                340                 345                 350
His Ile Val Phe Pro Val Pro Ile Asp Gln Cys Ile Asp Gly Gly Gly
                355                 360                 365
Gly Gly Ser Gly Gly Gly Ser Gln Asp Ser Thr Ser Asp Leu Ile
                370                 375                 380
Pro Ala Pro Pro Leu Ser Lys Val Pro Leu Gln Gln Asn Phe Gln Asp
385                 390                 395                 400
Asn Gln Phe His Gly Lys Trp Tyr Val Val Gly Glu Ala Gly Asn Leu
                    405                 410                 415
Ala Leu Arg Glu Asp Lys Asp Pro Lys Lys Met Met Ala Thr Ile Tyr
                420                 425                 430
Glu Leu Lys Glu Asp Lys Ser Tyr Asp Val Thr Glu Val Arg Phe Arg
                435                 440                 445
Tyr Lys Lys Cys Gln Tyr Asp Ile Val Thr Phe Val Pro Gly Ser Gln
                450                 455                 460
Pro Gly Glu Phe Thr Leu Ser Glu Pro Gly Gln Thr Ser Glu Leu Val
465                 470                 475                 480
Arg Val Val Ser Thr Asn Tyr Asn Gln His Ala Met Val Phe Phe Lys
                485                 490                 495
```

-continued

```
Lys Val Val Gln Asn Arg Glu Phe Phe Trp Ile Thr Leu Tyr Gly Arg
                500                 505                 510

Thr Lys Glu Leu Thr Ser Glu Leu Lys Glu Asn Phe Ile Arg Phe Ser
            515                 520                 525

Lys Ser Leu Gly Leu Pro Glu Asn His Ile Val Phe Pro Val Pro Ile
        530                 535                 540

Asp Gln Cys Ile Asp Gly Gly Gly Gly Ser Gly Gly Gly Gly Ser
545                 550                 555                 560

Gln Asp Ser Thr Ser Asp Leu Ile Pro Ala Pro Pro Leu Ser Lys Val
                565                 570                 575

Pro Leu Gln Gln Asn Phe Gln Asp Asn Gln Phe His Gly Lys Trp Tyr
            580                 585                 590

Val Val Gly Met Ala Gly Asn Phe His Leu Arg Glu Asp Lys Asp Pro
        595                 600                 605

Ser Lys Met Pro Ala Thr Ile Tyr Glu Leu Lys Glu Asp Lys Ser Tyr
    610                 615                 620

Asp Val Thr His Val Pro Phe Trp Ala Lys Lys Cys Ala Tyr Lys Ile
625                 630                 635                 640

Ile Thr Phe Val Pro Gly Ser Gln Pro Gly Glu Phe Thr Leu Gly Ala
                645                 650                 655

Ile Lys Ser Gly Pro Gly Met Thr Ser Trp Leu Val Arg Val Val Ser
            660                 665                 670

Thr Asn Tyr Asn Gln His Ala Met Val Phe Phe Lys Gly Val Trp Gln
        675                 680                 685

Asn Arg Glu Thr Phe Val Ile Thr Leu Tyr Gly Arg Thr Lys Glu Leu
    690                 695                 700

Thr Ser Glu Leu Lys Glu Asn Phe Ile Arg Phe Ser Lys Ser Leu Gly
705                 710                 715                 720

Leu Pro Glu Asn His Ile Val Phe Pro Val Pro Ile Asp Gln Cys Ile
                725                 730                 735

Asp Gly Ser Ala Trp Ser His Pro Gln Phe Glu Lys His His His
            740                 745                 750

His His
```

<210> SEQ ID NO 181
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0512.17L07(N39S_
N65D_T136A) (G4S)2 S0510.11H24(N65D) (G4S)2 S0455.04F23(N65D)
StrepII His tag

<400> SEQUENCE: 181

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
```

-continued

```
                85                  90                  95
Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
                180                 185                 190

Ser Asp Leu Ile Pro Ala Pro Pro Leu Ser Lys Val Pro Leu Gln Gln
            195                 200                 205

Asn Phe Gln Asp Asn Gln Phe His Gly Lys Trp Tyr Val Val Gly Trp
            210                 215                 220

Ala Gly Ser Thr Thr Leu Arg Glu Asp Lys Asp Pro Pro Lys Met Pro
225                 230                 235                 240

Ala Thr Ile Tyr Glu Leu Lys Glu Asp Lys Ser Tyr Asp Val Thr Asp
                245                 250                 255

Val Gln Phe Pro Glu Lys Lys Cys Ile Tyr Ser Thr Ile Thr Phe Val
            260                 265                 270

Pro Gly Ser Gln Pro Gly Glu Phe Thr Leu Gly Gly Ile Lys Ser Ser
            275                 280                 285

Pro Gly Gln Thr Ser His Leu Val Arg Val Val Ser Thr Asn Tyr Asn
            290                 295                 300

Gln His Ala Met Val Phe Phe Lys Tyr Val Ile Gln Asn Arg Glu Gly
305                 310                 315                 320

Phe Asn Ile Ala Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
                370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
                405                 410                 415

Ala Leu Arg Glu Asp Lys Asp Pro Met Lys Met Ala Thr Ile Tyr
            420                 425                 430

Glu Leu Lys Glu Asp Lys Ser Tyr Asp Val Thr Glu Val Arg Phe Arg
            435                 440                 445

Gln Lys Lys Cys Lys Tyr Asp Ile Val Thr Phe Val Pro Gly Ser Gln
            450                 455                 460

Pro Gly Glu Phe Thr Leu Gly Leu Ile Lys Ser Asp Pro Gly Gln Thr
465                 470                 475                 480

Ser Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
            500                 505                 510
```

```
Leu Tyr Gly Arg Thr Lys Glu Leu Thr Ser Glu Leu Lys Glu Asn Phe
            515                 520                 525

Ile Arg Phe Ser Lys Ser Leu Gly Leu Pro Glu Asn His Ile Val Phe
        530                 535                 540

Pro Val Pro Ile Asp Gln Cys Ile Asp Gly Gly Gly Gly Ser Gly
545                 550                 555                 560

Gly Gly Gly Ser Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe His
            580                 585                 590

Gly Lys Trp Tyr Val Val Gly His Ala Gly Asn Gln Trp Leu Arg Glu
        595                 600                 605

Asp Lys Asp Pro Arg Lys Met Trp Ala Thr Ile Tyr Glu Leu Lys Glu
    610                 615                 620

Asp Lys Ser Tyr Asp Val Thr Asp Val Asp Phe Ala Ile Lys Lys Cys
625                 630                 635                 640

His Tyr Arg Ile Thr Thr Phe Val Pro Gly Ser Gln Pro Gly Glu Phe
                645                 650                 655

Thr Leu Gly Asn Ile Lys Ser His Pro Gly Gly Thr Ser Gly Leu Val
            660                 665                 670

Arg Val Val Ser Thr Asn Tyr Asn Gln His Ala Met Val Phe Phe Lys
        675                 680                 685

Phe Val Ile Gln Asn Arg Glu Ala Phe Phe Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755

<210> SEQ ID NO 182
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0512.17L07(N39S_
      N65D_T136A) (G4S)2-S0510.11H24(N65D) (G4S)2-S0455.04F09(N65D)
      StrepII His tag

<400> SEQUENCE: 182

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95
```

```
Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
                180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Trp
        210                 215                 220

Ala Gly Ser Thr Thr Leu Arg Glu Asp Lys Asp Pro Pro Lys Met Pro
225                 230                 235                 240

Ala Thr Ile Tyr Glu Leu Lys Glu Asp Lys Ser Tyr Asp Val Thr Asp
                245                 250                 255

Val Gln Phe Pro Glu Lys Lys Cys Ile Tyr Ser Thr Ile Thr Phe Val
            260                 265                 270

Pro Gly Ser Gln Pro Gly Glu Phe Thr Leu Gly Gly Ile Lys Ser Ser
        275                 280                 285

Pro Gly Gln Thr Ser His Leu Val Arg Val Val Ser Thr Asn Tyr Asn
290                 295                 300

Gln His Ala Met Val Phe Phe Lys Tyr Val Ile Gln Asn Arg Glu Gly
305                 310                 315                 320

Phe Asn Ile Ala Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
        355                 360                 365

Gly Gly Ser Gly Gly Gly Ser Gln Asp Ser Thr Ser Asp Leu Ile
370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
                405                 410                 415

Ala Leu Arg Glu Asp Lys Asp Pro Met Lys Met Ala Thr Ile Tyr
            420                 425                 430

Glu Leu Lys Glu Asp Lys Ser Tyr Asp Val Thr Glu Val Arg Phe Arg
        435                 440                 445

Gln Lys Lys Cys Lys Tyr Asp Ile Val Thr Phe Val Pro Gly Ser Gln
450                 455                 460

Pro Gly Glu Phe Thr Leu Gly Leu Ile Lys Ser Asp Pro Gly Gln Thr
465                 470                 475                 480

Ser Glu Leu Val Arg Val Ser Thr Asn Tyr Asn Gln His Ala Met
                485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Thr Ser Glu Leu Lys Glu Asn Phe
```

```
                    515                 520                 525

Ile Arg Phe Ser Lys Ser Leu Gly Leu Pro Glu Asn His Ile Val Phe
530                 535                 540

Pro Val Pro Ile Asp Gln Cys Ile Asp Gly Gly Gly Gly Ser Gly
545                 550                 555                 560

Gly Gly Gly Ser Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe His
            580                 585                 590

Gly Lys Trp Tyr Val Val Gly Met Ala Gly Asn Phe His Leu Arg Glu
        595                 600                 605

Asp Lys Asp Pro Ser Lys Met Pro Ala Thr Ile Tyr Glu Leu Lys Glu
    610                 615                 620

Asp Lys Ser Tyr Asp Val Thr His Val Pro Phe Trp Ala Lys Lys Cys
625                 630                 635                 640

Ala Tyr Lys Ile Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
            660                 665                 670

Arg Val Val Ser Thr Asn Tyr Asn Gln His Ala Met Val Phe Phe Lys
        675                 680                 685

Gly Val Trp Gln Asn Arg Glu Thr Phe Val Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755

<210> SEQ ID NO 183
<211> LENGTH: 758
<212> TYPE: PRT
<213> ORGANISM: Artificial Sequence
<220> FEATURE:
<223> OTHER INFORMATION: S0474.01H22(N65D;T54A) (G4S)2 S0510.05H10(N65D)
      (G4S)2 S0510.11H24(N65D) (G4S)2 S0455.04F23(N65D) StrepII His tag

<400> SEQUENCE: 183

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Ser Gln Leu Val Arg Val Val Ser
            100                 105                 110
```

```
Thr Asn Tyr Asn Gln His Ala Met Val Phe Lys Ile Val Arg Gln
            115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Leu
    210                 215                 220

Ala Gly Asn Gly Trp Leu Arg Glu Asp Lys Asp Pro Leu Lys Met Met
225                 230                 235                 240

Ala Thr Ile Tyr Glu Leu Lys Glu Asp Lys Ser Tyr Asp Val Thr Val
                245                 250                 255

Val Asp Phe Glu Leu Lys Lys Cys Arg Tyr Met Ile Glu Thr Phe Val
            260                 265                 270

Pro Gly Ser Gln Pro Gly Glu Phe Thr Leu Gly Asp Ile Lys Ser Ser
        275                 280                 285

Pro Gly Trp Thr Ser Gln Leu Val Arg Val Val Ser Thr Asn Tyr Asn
    290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
            340                 345                 350

His Ile Val Phe Pro Val Pro Ile Asp Gln Cys Ile Asp Gly Gly Gly
        355                 360                 365

Gly Gly Ser Gly Gly Gly Ser Gln Asp Ser Thr Ser Asp Leu Ile
    370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
                405                 410                 415

Ala Leu Arg Glu Asp Lys Asp Pro Met Lys Met Met Ala Thr Ile Tyr
            420                 425                 430

Glu Leu Lys Glu Asp Lys Ser Tyr Asp Val Thr Glu Val Arg Phe Arg
        435                 440                 445

Gln Lys Lys Cys Lys Tyr Asp Ile Val Thr Phe Val Pro Gly Ser Gln
    450                 455                 460

Pro Gly Glu Phe Thr Leu Gly Leu Ile Lys Ser Asp Pro Gly Gln Thr
465                 470                 475                 480

Ser Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Thr Ser Glu Leu Lys Glu Asn Phe
        515                 520                 525

Ile Arg Phe Ser Lys Ser Leu Gly Leu Pro Glu Asn His Ile Val Phe
```

```
                530                 535                 540
Pro Val Pro Ile Asp Gln Cys Ile Asp Gly Gly Gly Gly Ser Gly
545                 550                 555                 560

Gly Gly Gly Ser Gln Asp Ser Thr Ser Asp Leu Ile Pro Ala Pro Pro
                565                 570                 575

Leu Ser Lys Val Pro Leu Gln Gln Asn Phe Gln Asp Asn Gln Phe His
                580                 585                 590

Gly Lys Trp Tyr Val Val Gly His Ala Gly Asn Gln Trp Leu Arg Glu
                595                 600                 605

Asp Lys Asp Pro Arg Lys Met Trp Ala Thr Ile Tyr Glu Leu Lys Glu
                610                 615                 620

Asp Lys Ser Tyr Asp Val Thr Asp Val Asp Phe Ala Ile Lys Lys Cys
625                 630                 635                 640

His Tyr Arg Ile Thr Thr Phe Val Pro Gly Ser Gln Pro Gly Glu Phe
                645                 650                 655

Thr Leu Gly Asn Ile Lys Ser His Pro Gly Gly Thr Ser Gly Leu Val
                660                 665                 670

Arg Val Val Ser Thr Asn Tyr Asn Gln His Ala Met Val Phe Phe Lys
                675                 680                 685

Phe Val Ile Gln Asn Arg Glu Ala Phe Ile Thr Leu Tyr Gly Arg
                690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
                740                 745                 750

His His His His His His
                755

<210> SEQ ID NO 184
<211> LENGTH: 758
<212> TYPE: PRT
<213> ORGANISM: Artificial Sequence
<220> FEATURE:
<223> OTHER INFORMATION: S0474.01H22(N65D;T54A)(G4S)2 S0510.05H10(N65D)
      (G4S)2 S0510.11H24(N65D) (G4S)2 S0455.04F09(N65D)StrepII His tag

<400> SEQUENCE: 184

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Ala Ile Tyr Glu Leu Lys Glu Asp Lys Ser Tyr
        50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
                115                 120                 125
```

```
Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
                180                 185                 190

Ser Asp Leu Ile Pro Ala Pro Leu Ser Lys Val Pro Leu Gln Gln
        195                 200                 205

Asn Phe Gln Asp Asn Gln Phe His Gly Lys Trp Tyr Val Val Gly Leu
210                 215                 220

Ala Gly Asn Gly Trp Leu Arg Glu Asp Lys Asp Pro Leu Lys Met Met
225                 230                 235                 240

Ala Thr Ile Tyr Glu Leu Lys Glu Asp Lys Ser Tyr Asp Val Thr Val
                245                 250                 255

Val Asp Phe Glu Leu Lys Lys Cys Arg Tyr Met Ile Glu Thr Phe Val
                260                 265                 270

Pro Gly Ser Gln Pro Gly Glu Phe Thr Leu Gly Asp Ile Lys Ser Ser
            275                 280                 285

Pro Gly Trp Thr Ser Gln Leu Val Arg Val Val Ser Thr Asn Tyr Asn
        290                 295                 300

Gln His Ala Met Val Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
                340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
        370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
            405                 410                 415

Ala Leu Arg Glu Asp Lys Asp Pro Met Lys Met Met Ala Thr Ile Tyr
            420                 425                 430

Glu Leu Lys Glu Asp Lys Ser Tyr Asp Val Thr Glu Val Arg Phe Arg
        435                 440                 445

Gln Lys Lys Cys Lys Tyr Asp Ile Val Thr Phe Val Pro Gly Ser Gln
450                 455                 460

Pro Gly Glu Phe Thr Leu Gly Leu Ile Lys Ser Asp Pro Gly Gln Thr
465                 470                 475                 480

Ser Glu Leu Val Arg Val Val Ser Thr Asn Tyr Asn Gln His Ala Met
                485                 490                 495

Val Phe Phe Lys Lys Val Val Gln Asn Arg Glu Tyr Phe Trp Ile Thr
            500                 505                 510

Leu Tyr Gly Arg Thr Lys Glu Leu Thr Ser Glu Leu Lys Glu Asn Phe
            515                 520                 525

Ile Arg Phe Ser Lys Ser Leu Gly Leu Pro Glu Asn His Ile Val Phe
        530                 535                 540

Pro Val Pro Ile Asp Gln Cys Ile Asp Gly Gly Gly Gly Ser Gly
```

```
                545                 550                 555                 560
Gly Gly Gly Ser Gln Asp Ser Thr Ser Asp Leu Ile Pro Ala Pro Pro
                565                 570                 575
Leu Ser Lys Val Pro Leu Gln Gln Asn Phe Gln Asp Asn Gln Phe His
                580                 585                 590
Gly Lys Trp Tyr Val Val Gly Met Ala Gly Asn Phe His Leu Arg Glu
                595                 600                 605
Asp Lys Asp Pro Ser Lys Met Pro Ala Thr Ile Tyr Glu Leu Lys Glu
            610                 615                 620
Asp Lys Ser Tyr Asp Val Thr His Val Pro Phe Trp Ala Lys Lys Cys
625                 630                 635                 640
Ala Tyr Lys Ile Ile Thr Phe Val Pro Gly Ser Gln Pro Gly Glu Phe
                645                 650                 655
Thr Leu Gly Ala Ile Lys Ser Gly Pro Gly Met Thr Ser Trp Leu Val
                660                 665                 670
Arg Val Val Ser Thr Asn Tyr Asn Gln His Ala Met Val Phe Phe Lys
            675                 680                 685
Gly Val Trp Gln Asn Arg Glu Thr Phe Val Ile Thr Leu Tyr Gly Arg
        690                 695                 700
Thr Lys Glu Leu Thr Ser Glu Leu Lys Glu Asn Phe Ile Arg Phe Ser
705                 710                 715                 720
Lys Ser Leu Gly Leu Pro Glu Asn His Ile Val Phe Pro Val Pro Ile
                725                 730                 735
Asp Gln Cys Ile Asp Gly Ser Ala Trp Ser His Pro Gln Phe Glu Lys
            740                 745                 750
His His His His His His
        755

<210> SEQ ID NO 185
<211> LENGTH: 758
<212> TYPE: PRT
<213> ORGANISM: Artificial Sequence
<220> FEATURE:
<223> OTHER INFORMATION: S0474.01H22(N65Q;T54A) (G4S)2 S0466.09E05(N65Q)
      (G4S)2 S0466.13C10(N65Q) (G4S)2 S0455.04F09(N65Q) StrepII, His6

<400> SEQUENCE: 185

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Val Ala Gly Asn Thr Ile Leu Arg Glu Asp Lys Asp Pro
        35                  40                  45
Gly Lys Met Asn Ala Ala Ile Tyr Glu Leu Lys Glu Asp Lys Ser Tyr
    50                  55                  60
Gln Val Thr Asp Val Arg Phe Ile Arg Lys Lys Cys His Tyr Tyr Ile
65                  70                  75                  80
Asp Thr Phe Val Pro Gly Ser Gln Pro Gly Glu Phe Thr Leu Gly Asn
                85                  90                  95
Ile Lys Ser Tyr Pro Gly Thr Thr Ser Gln Leu Val Arg Val Val Ser
            100                 105                 110
Thr Asn Tyr Asn Gln His Ala Met Val Phe Phe Lys Ile Val Arg Gln
        115                 120                 125
Asn Arg Glu Ile Phe Trp Ile Thr Leu Tyr Gly Arg Thr Lys Glu Leu
    130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly Gly Gly Gly Gly Ser Gly Gly Gly Ser Gln Asp Ser Thr
                180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Leu
    210                 215                 220

Ala Gly Asn Gly Trp Leu Arg Glu Asp Lys Asp Pro Val Lys Met Met
225                 230                 235                 240

Ala Thr Ile Tyr Glu Leu Lys Glu Asp Lys Ser Tyr Gln Val Thr Val
            245                 250                 255

Val Asp Phe Glu Leu Lys Lys Cys Arg Tyr Met Ile Glu Thr Phe Val
        260                 265                 270

Pro Gly Ser Gln Pro Gly Glu Phe Thr Leu Gly Asp Ile Lys Ser Phe
    275                 280                 285

Pro Gly Trp Thr Ser Gln Leu Val Arg Val Val Ser Thr Asn Tyr Asn
290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
            325                 330                 335

Lys Glu Asn Phe Ile Arg Phe Ser Lys Ser Leu Gly Leu Pro Glu Asn
        340                 345                 350

His Ile Val Phe Pro Val Pro Ile Asp Gln Cys Ile Asp Gly Gly Gly
    355                 360                 365

Gly Gly Ser Gly Gly Gly Ser Gln Asp Ser Thr Ser Asp Leu Ile
370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
            405                 410                 415

Ala Leu Arg Glu Asp Lys Asp Pro Lys Lys Met Met Ala Thr Ile Tyr
        420                 425                 430

Glu Leu Lys Glu Asp Lys Ser Tyr Gln Val Thr Glu Val Arg Phe Arg
    435                 440                 445

His Lys Lys Cys Gln Tyr Asp Ile Ala Thr Phe Val Pro Gly Ser Gln
450                 455                 460

Pro Gly Glu Phe Thr Leu Gly Leu Ile Lys Ser Asp Pro Gly Gln Thr
465                 470                 475                 480

Ser Glu Leu Val Arg Val Val Ser Thr Asn Tyr Asn Gln His Ala Met
            485                 490                 495

Val Phe Phe Lys Lys Val Val Gln Asn Arg Glu Phe Phe Trp Ile Thr
        500                 505                 510

Leu Tyr Gly Arg Thr Lys Glu Leu Thr Ser Glu Leu Lys Glu Asn Phe
    515                 520                 525

Ile Arg Phe Ser Lys Ser Leu Gly Leu Pro Glu Asn His Ile Val Phe
530                 535                 540

Pro Val Pro Ile Asp Gln Cys Ile Asp Gly Gly Gly Gly Ser Gly
545                 550                 555                 560

Gly Gly Ser Gln Asp Ser Thr Ser Asp Leu Ile Pro Ala Pro Pro
```

565                 570                 575
Leu Ser Lys Val Pro Leu Gln Gln Asn Phe Gln Asp Asn Gln Phe His
                  580                 585                 590

Gly Lys Trp Tyr Val Val Gly Met Ala Gly Asn Phe His Leu Arg Glu
              595                 600                 605

Asp Lys Asp Pro Ser Lys Met Pro Ala Thr Ile Tyr Glu Leu Lys Glu
          610                 615                 620

Asp Lys Ser Tyr Gln Val Thr His Val Pro Phe Trp Ala Lys Lys Cys
625                 630                 635                 640

Ala Tyr Lys Ile Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
            660                 665                 670

Arg Val Val Ser Thr Asn Tyr Asn Gln His Ala Met Val Phe Phe Lys
        675                 680                 685

Gly Val Trp Gln Asn Arg Glu Thr Phe Val Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
        755

<210> SEQ ID NO 186
<211> LENGTH: 758
<212> TYPE: PRT
<213> ORGANISM: Artificial Sequence
<220> FEATURE:
<223> OTHER INFORMATION: S0475.06L06(N65Q;S79F) (G4S)2 S0466.09E05(N65Q)
      (G4S)2 S0466.13C10(N65Q) (G4S)2 S0455.04F09(N65Q) StrepII His tag

<400> SEQUENCE: 186

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Gln Val Thr Glu Val Arg Phe His Asn Lys Lys Cys Asn Tyr Phe Ile
65                  70                  75                  80

Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110

Thr Asn Tyr Asn Gln His Ala Met Val Phe Phe Lys Asn Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

-continued

Leu Pro Glu Asn His Ile Val Phe Pro Val Pro Ile Asp Gln Cys Ile
            165                 170                 175

Asp Gly Gly Gly Gly Ser Gly Gly Gly Ser Gln Asp Ser Thr
        180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Leu
    210                 215                 220

Ala Gly Asn Gly Trp Leu Arg Glu Asp Lys Pro Val Lys Met Met
225                 230                 235                 240

Ala Thr Ile Tyr Glu Leu Lys Glu Asp Lys Ser Tyr Gln Val Thr Val
            245                 250                 255

Val Asp Phe Glu Leu Lys Lys Cys Arg Tyr Met Ile Glu Thr Phe Val
            260                 265                 270

Pro Gly Ser Gln Pro Gly Glu Phe Thr Leu Gly Asp Ile Lys Ser Phe
        275                 280                 285

Pro Gly Trp Thr Ser Gln Leu Val Arg Val Val Ser Thr Asn Tyr Asn
        290                 295                 300

Gln His Ala Met Val Phe Phe Lys Gly Val Tyr Gln Asn Arg Glu Trp
305                 310                 315                 320

Phe His Ile Thr Leu Tyr Gly Arg Thr Lys Glu Leu Thr Ser Glu Leu
            325                 330                 335

Lys Glu Asn Phe Ile Arg Phe Ser Lys Ser Leu Gly Leu Pro Glu Asn
                340                 345                 350

His Ile Val Phe Pro Val Pro Ile Asp Gln Cys Ile Asp Gly Gly Gly
            355                 360                 365

Gly Gly Ser Gly Gly Gly Ser Gln Asp Ser Thr Ser Asp Leu Ile
    370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Glu Ala Gly Asn Leu
            405                 410                 415

Ala Leu Arg Glu Asp Lys Asp Pro Lys Lys Met Met Ala Thr Ile Tyr
            420                 425                 430

Glu Leu Lys Glu Asp Lys Ser Tyr Gln Val Thr Glu Val Arg Phe Arg
        435                 440                 445

His Lys Lys Cys Gln Tyr Asp Ile Ala Thr Phe Val Pro Gly Ser Gln
    450                 455                 460

Pro Gly Glu Phe Thr Leu Gly Leu Ile Lys Ser Asp Pro Gly Gln Thr
465                 470                 475                 480

Ser Glu Leu Val Arg Val Val Ser Thr Asn Tyr Asn Gln His Ala Met
            485                 490                 495

Val Phe Phe Lys Lys Val Val Gln Asn Arg Glu Phe Phe Trp Ile Thr
            500                 505                 510

Leu Tyr Gly Arg Thr Lys Glu Leu Thr Ser Glu Leu Lys Glu Asn Phe
        515                 520                 525

Ile Arg Phe Ser Lys Ser Leu Gly Leu Pro Glu Asn His Ile Val Phe
        530                 535                 540

Pro Val Pro Ile Asp Gln Cys Ile Asp Gly Gly Gly Gly Ser Gly
545                 550                 555                 560

Gly Gly Ser Gln Asp Ser Thr Ser Asp Leu Ile Pro Ala Pro Pro
            565                 570                 575

Leu Ser Lys Val Pro Leu Gln Gln Asn Phe Gln Asp Asn Gln Phe His

-continued

```
                580                 585                 590
Gly Lys Trp Tyr Val Val Gly Met Ala Gly Asn Phe His Leu Arg Glu
            595                 600                 605

Asp Lys Asp Pro Ser Lys Met Pro Ala Thr Ile Tyr Glu Leu Lys Glu
        610                 615                 620

Asp Lys Ser Tyr Gln Val Thr His Val Pro Phe Trp Ala Lys Lys Cys
625                 630                 635                 640

Ala Tyr Lys Ile Ile Thr Phe Val Pro Gly Ser Gln Pro Gly Glu Phe
                645                 650                 655

Thr Leu Gly Ala Ile Lys Ser Gly Pro Gly Met Thr Ser Trp Leu Val
            660                 665                 670

Arg Val Val Ser Thr Asn Tyr Asn Gln His Ala Met Val Phe Phe Lys
        675                 680                 685

Gly Val Trp Gln Asn Arg Glu Thr Phe Val Ile Thr Leu Tyr Gly Arg
    690                 695                 700

Thr Lys Glu Leu Thr Ser Glu Leu Lys Glu Asn Phe Ile Arg Phe Ser
705                 710                 715                 720

Lys Ser Leu Gly Leu Pro Glu Asn His Ile Val Phe Pro Val Pro Ile
                725                 730                 735

Asp Gln Cys Ile Asp Gly Ser Ala Trp Ser His Pro Gln Phe Glu Lys
            740                 745                 750

His His His His His His
            755
```

FUSION MOLECULES

I. RELATED APPLICATIONS

This application claims the benefit of European Application No. EP15306106.4 filed on Jul. 7, 2015, which is incorporated by reference herein in its entirety.

II. SEQUENCE LISTING

The instant application contains a Sequence Listing which has been submitted electronically in ASCII format and is hereby incorporated by reference in its entirety. Said ASCII copy, created on Jun. 20, 2016, is named DE2015-080 PCT SeqEN_St 25 v0616 and is 500,881 bytes in size.

III. TECHNICAL FIELD OF THE INVENTION

The present invention relates to fusion molecules that have binding specificity for pyoverdine type I, II and III and pyochelin and can be used in various applications, including diagnostic and/or therapeutic applications, for example, to inhibit or reduce growth of *P. aeruginosa* and/or to prevent or treat *P. aeruginosa* biofilm infection as well as diseases or disorders associated with *P. aeruginosa* biofilm infection. The present invention also concerns methods of producing the fusion molecules described herein as well as compositions and kits comprising such fusion molecules. The present invention further relates to nucleic acid molecules encoding the fusion molecules described herein.

IV. BACKGROUND OF THE INVENTION

*Pseudomonas aeruginosa* (*P. aeruginosa*) is an opportunistic pathogen that causes acute infections, primarily in association with tissue injuries. *P. aeruginosa* forms biofilms on indwelling devices and on the pulmonary tissues of patients with the genetic disorder, cystic fibrosis. Biofilm infections are difficult to treat with conventional antibiotic therapies. However, research has demonstrated that iron is essential for proper biofilm formation by *P. aeruginosa*, and therefore iron-uptake systems are potential targets for anti-*Pseudomonas* therapies.

*P. aeruginosa* is able to scavenge iron from the host environment by using the secreted iron-binding siderophores, pyochelin and pyoverdine. Pyoverdine (Pvd) is a peptide-linked hydroxamate- and catecholate-type ligand, and pyochelin (Pch) is a derivatized conjugate of salicylate and two molecules of cysteine and having phenol, carboxylate, and amine ligand functionalities. Both Pvd and Pch have demonstrated roles in *P. aeruginosa* virulence with some indication of synergism. Double-deficient mutants unable to make either siderophore are much more attenuated in virulence than either single-deficient mutant unable to make just one of the two siderophores (Takase et al., Infection and Immunity, April 2000, p. 1834-1839). Furthermore, pyoverdine acts as a signalling molecule to control production of several virulence factors as well as pyoverdine itself; while it has been proposed that pyochelin may be part of a system for obtaining divalent metals such as ferrous iron and zinc for *P. aeruginosa*'s pathogenicity, in addition to ferric iron (Visca et al., 1992).

Three structurally different pyoverdine types or groups have been identified from several *P. aeruginosa* strains: from *P. aeruginosa* ATCC 15692 (Briskot et al., 1989, Liebigs Ann Chem, p. 375-384), from *P. aeruginosa* ATCC 27853 (Tappe et al., 1993, J. Prakt-Chem., 335, p. 83-87) and from a natural isolate, *P. aeruginosa* R (Gipp et al., 1991, Z. Naturforsch, 46c, p. 534-541). Moreover, comparative biological investigations on 88 clinical isolates and the two collection strains mentioned above revealed three different strain-specific pyoverdine-mediated iron uptake systems (Cornells et al., 1989, Infect Immun., 57, p. 3491-3497; Meyer et al., 1997, Microbiology, 143, p. 35-43) according to the reference strains: *P. aeruginosa* ATCC 15692 (Type I Pvd or Pvd I), *P. aeruginosa* ATCC 27853 (Type II Pvd or Pvd II) and the clinical isolates *P. aeruginosa* R and pa6 (Type III Pvd or Pvd III).

Each pyoverdine type has three members (subtypes) differing in the side chain which is succinyl (s), succinamide (sa) or α-ketoglutaryl (αKG), namely, Pvd type I succinyl, Pvd type I succinamide, Pvd type I α-ketoglutaryl, Pvd type II succinyl, Pvd type II succinamide, Pvd type II α-ketoglutaryl, Pvd type III succinyl, Pvd type III succinamide and Pvd type III α-ketoglutaryl.

Each *P. aeruginosa* strain expresses one Pvd type i.e. *P. aeruginosa* ATCC 15692 expresses Type I Pvd, *P. aeruginosa* ATCC 27853 expresses Type II Pvd and *P. aeruginosa* R and pa6 expresses Type III Pvd, whereby each Pvd type includes all three members of the respective type, and each said strain also expresses pyochelin.

The inventors have identified the pyoverdines and pyochelin as targets which are crucial for *P. aeruginosa*'s pathogenicity and developed specific inhibitors for such targets, i.e. for each type of Pvd including for every type the three members (subtypes) differing in the side chain (Pvd I s, Pvd I sa, Pvd I αKG, Pvd II s, Pvd II sa, Pvd II αKG, Pvd III s, Pvd III sa, Pvd III αKG) as well as for Pch, and in every case to the free siderophore as well as to the siderophore with bound iron without creating the strong selective pressure imposed by conventional antibiotics (see also EP 15 305 242.8).

The biofilm mode of growth is believed to be critical for persistent *P. aeruginosa* infections (Costerton et al., 1999; Singh et al., 2000) and the dual expression of Pvd and Pch genes is necessary for normal biofilm development (Banin et al., 2005). Given that *P. aeruginosa* produces an impressive array of virulence factors, all playing a role in its pathogenicity, a strategy to efficiently inhibit *P. aeruginosa* virulence is to target several virulence factors.

V. SUMMARY OF THE INVENTION

In one aspect, the present invention relates to a fusion molecule having binding specificity for pyoverdine type I, II and III and pyochelin, comprising (a) a first polypeptide comprising or consisting of a first human neutrophil gelatinase-associated lipocalin (hNGAL) mutein that binds pyoverdine type I;

(b) a second polypeptide comprising or consisting of a second hNGAL mutein that binds pyoverdine type II;

(c) a third polypeptide comprising or consisting of a third hNGAL mutein that binds pyoverdine type III; and (d) a fourth polypeptide comprising or consisting of a fourth hNGAL mutein that binds pyochelin;

wherein the first, second, third and fourth polypeptides are covalently linked.

In one embodiment, the hNGAL mutein comprises a mutated amino acid residue at one or more positions corresponding to positions of the linear polypeptide sequence of the mature hNGAL (SEQ ID NO: 1).

In one embodiment, the hNGAL mutein comprises a mutated amino acid residue at one or more positions corresponding to positions 28, 34, 36, 39-42, 44-47, 49, 52, 54-55, 65, 68, 70, 72-75, 77, 79-81, 87, 96, 100, 103, 106, 108, 123, 125, 127, 132, 134, 141 and 145 of the linear polypeptide sequence of the mature hNGAL (SEQ ID NO: 1).

In one embodiment, the first hNGAL mutein comprises a mutated amino acid residue at one or more positions corresponding to positions 28, 36, 39-41, 46, 49, 52, 54, 55, 59, 65, 68, 70, 72-75, 77, 79-81, 87, 96, 100, 103, 106, 125, 127, 132, 134, and 136 of the linear polypeptide sequence of the mature hNGAL (SEQ ID NO: 1).

In one embodiment, the second hNGAL mutein comprises a mutated amino acid residue at one or more positions corresponding to positions 28, 36, 40, 41, 49, 52, 54, 65, 68, 70, 72-75, 77, 79, 81, 87, 96, 100, 103, 106, 125, 127, 132 and 134 of the linear polypeptide sequence of the mature hNGAL (SEQ ID NO: 1).

In one embodiment, the third hNGAL mutein comprises a mutated amino acid residue at one or more positions corresponding to positions 28, 36, 40-42, 45-47, 49, 52, 65, 68, 70, 72, 73, 77, 79, 81, 87, 96, 100, 103, 105, 106, 125, 127, 132, 134 and 145 of the linear polypeptide sequence of the mature hNGAL (SEQ ID NO: 1).

In one embodiment, the fourth hNGAL mutein comprises a mutated amino acid residue at one or more positions corresponding to positions 28, 34, 36, 40, 41, 44-46, 49, 52, 54, 65, 68, 70, 72-74, 77, 79-81, 87, 96, 100, 103, 106, 108, 123, 125, 127, 132, 134 and 141 of the linear polypeptide sequence of the mature hNGAL (SEQ ID NO: 1).

```
                                                (SEQ ID NO: 1)
QDSTSDLIPAPPLSKVPLQQNFQDNQFQGKWYVVGLAGNAILREDKDPQK

MYATIYELKEDKSYNVTSVLFRKKKCDYWIRTFVPGCQPGEFTLGNIKSY

PGLTSYLVRVVSTNYNQHAMVFFKKVSQNREYFKITLYGRTKELTSELKE

NFIRFSKSLGLPENHIVFPVPIDQCIDG
```

In one embodiment, the hNGAL mutein binds pyoverdine type I, pyoverdine type II, pyoverdine type III and pyochelin, respectively, with a dissociation constant $K_D$ of 200 nM or lower.

In one embodiment, the first, second, third and fourth polypeptides are covalently linked via linker molecules.

In one embodiment, the linker molecules are peptide linkers.

In one embodiment, the fusion molecule further comprises a multimerization domain allowing the multimerization of the fusion molecule.

In one embodiment, the multimerization domain is a dimerization domain allowing the dimerization of the fusion molecule.

In one embodiment, the dimerization domain is selected from the group consisting of an Fc domain, an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an uteroglobin dimerization domain and variants or fragments of any one of the foregoing.

In one embodiment, the Fc domain is a human IgG4-Fc domain.

In one embodiment, the fusion molecule has a general formula selected from the group consisting of $$N'-X_1-L_1-X_2-L_2-X_3-L_3-X_4-C' \quad (I),$$

$$N'-X_1-L_1-X_2-L_2-X_3-L_3-X_4-L_4-MD-C' \quad (II),$$

$$N'-MD-L_1-X_1-L_2-X_2-L_3-X_3-L_4-X_4-C' \quad (III),$$

$$N'-X_1-L_1-X_2-L_2-MD-L_3-X_3-L_4-X_4-C' \quad (IV),$$

$$N'-X_1-L_1-MD-L_2-X_2-L_3-X_3-L_4-X_4-C' \quad (V), \text{ and}$$

$$N'-X_1-L_1-X_2-L_2-X_3-L_3-MD-L_4-X_4-C' \quad (VI)$$

wherein $X_1$, $X_2$, $X_3$ and $X_4$ are, at each occurrence, selected from the group consisting of the first, second, third and fourth polypeptides, with the proviso that the fusion molecule comprises each of the first, second, third and fourth polypeptides;

MD comprises a multimerization domain; and $L_1$, $L_2$, $L_3$ and $L_4$ are, at each occurrence, independently selected from a covalent bond and a linker molecule.

In one embodiment, the fusion molecule is present as a multimeric (e.g., dimeric) complex.

In one embodiment, the fusion molecule further comprises at least one label or tag allowing the detection and/or isolation of the fusion molecule.

In one embodiment, the fusion molecule further comprises one or more modifications increasing the stability of the fusion molecule and/or extending the serum half-life of the fusion molecule.

In one embodiment, the fusion molecule inhibits or reduces iron-uptake by *P. aeruginosa* through pyochelin and/or pyoverdine.

In one embodiment, the fusion molecule inhibits or reduces virulence factor expression by *P. aeruginosa*.

In one embodiment, the fusion molecule inhibits or reduces pyochelin- and/or pyoverdine-mediated signaling.

In one embodiment, the fusion molecule inhibits or reduces *P. aeruginosa* bacterial growth.

In one embodiment, the fusion molecule is associated with or conjugated/fused to a pharmaceutically active agent.

In one embodiment, the pharmaceutically active agent is selected from the group consisting of an antibiotic, a cytostatic agent, a toxin, a metal or metal compound/complex, a chelating agent, a hapten and an antibody.

In a further aspect, the present invention relates to a nucleic acid molecule comprising a nucleotide sequence encoding the fusion molecule as defined above.

In one embodiment, the nucleic acid molecule is operably linked to a regulatory sequence to allow expression of the nucleic acid molecule.

In one embodiment, the nucleic acid molecule is comprised in a vector.

In another aspect, the present invention relates to a host cell containing a nucleic acid molecule as defined above.

In yet another aspect, the present invention relates to a method of producing the fusion molecule as defined above, wherein the fusion molecule is produced (i) by culturing a host cell as defined above under conditions that allow the expression of the fusion molecule and by isolating the fusion molecule from the host cell or its culture medium, or (ii) by in vitro translating a nucleic acid molecule as defined above.

In a further aspect, the present invention relates to a pharmaceutical composition comprising a fusion molecule as defined above, a nucleic acid molecule as defined above, or a cell as defined above.

In one embodiment, the pharmaceutical composition further comprises a pharmaceutically acceptable carrier and/or excipient.

In one embodiment, the pharmaceutical composition further comprises an additional pharmaceutically active agent.

In one embodiment, the additional pharmaceutically active agent is selected from the group consisting of an antibiotic, a cytostatic agent, a toxin, a metal or metal compound/complex, a chelating agent, a hapten and an antibody.

In yet another aspect, the present invention relates to a kit comprising a fusion molecule as defined above, a nucleic acid molecule as defined above, a cell as defined above, or a pharmaceutical composition as defined above.

In yet another aspect, the present invention relates to a fusion molecule as defined above, a nucleic acid molecule as defined above, a cell as defined above, or a pharmaceutical composition as defined above for use as a medicament.

In yet another aspect, the present invention relates to a fusion molecule as defined above, a nucleic acid molecule as defined above, a cell as defined above, or a pharmaceutical composition as defined above for use in the prevention or treatment of *P. aeruginosa* biofilm infection in a subject.

In yet another aspect, the present invention relates to a fusion molecule as defined above, a nucleic acid molecule as defined above, a cell as defined above, or a pharmaceutical composition as defined above for use in the prevention or treatment of a disease or disorder associated with or caused by *P. aeruginosa* biofilm infection in a subject.

In yet another aspect, the present invention relates to a method of preventing or treating *P. aeruginosa* biofilm infection in a subject, comprising administering an effective amount of a fusion molecule as defined above, a nucleic acid molecule as defined above, a cell as defined above, or a pharmaceutical composition as defined above to the subject.

In yet another aspect, the present invention relates to a method of preventing or treating a disease or disorder associated with or caused by *P. aeruginosa* biofilm infection in a subject, comprising administering an effective amount of a fusion molecule as defined above, a nucleic acid molecule as defined above, a cell as defined above, or a pharmaceutical composition as defined above to the subject.

In one embodiment, the *P. aeruginosa* biofilm infection is acute infection.

In one embodiment, the *P. aeruginosa* biofilm infection is chronic infection.

VI. DESCRIPTION OF THE FIGURES

FIG. 1A: shows the structure of the *P. aeruginosa* siderophore Pvd type I (see Birskot et al., 1989).

Figure 1B:
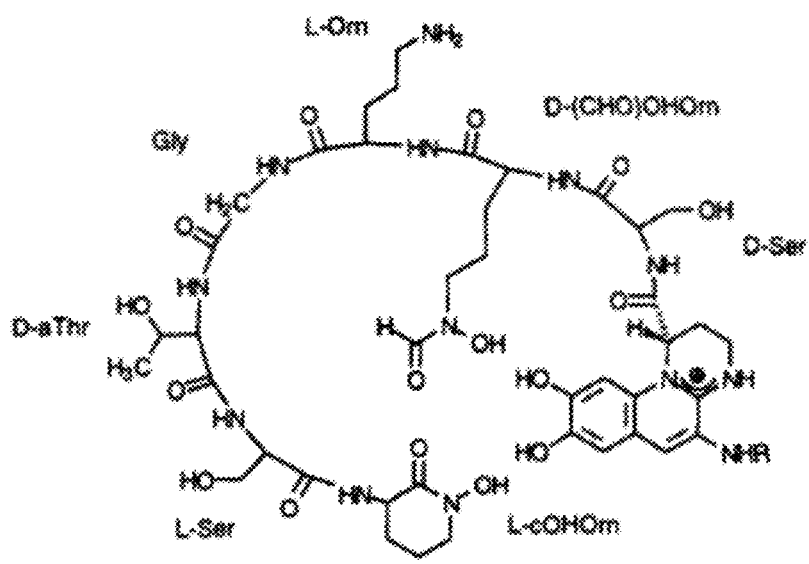

FIG. 1B: shows the structure of the *P. aeruginosa* siderophore Pvd type II (see Birskot et al., 1989).

Figure 1C:
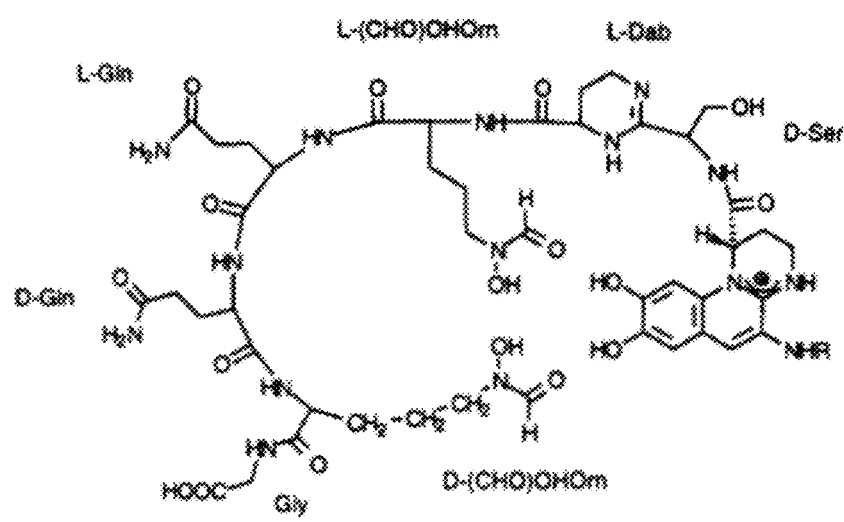

FIG. 1C: shows the structure of the *P. aeruginosa* siderophore Pvd type III (Gipp et al., 1991).

Figure 1D:
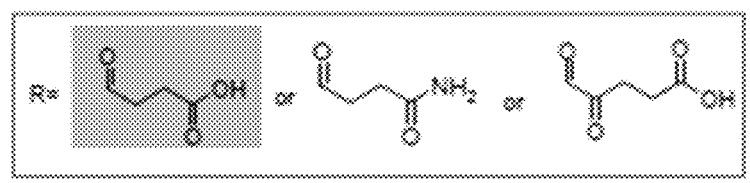

FIG. 1D: shows that the substitution group R attached to the chromophore part of Pvd can be a succinyl, succinamide or α-ketoglutaryl side chain.

Figure 1E:
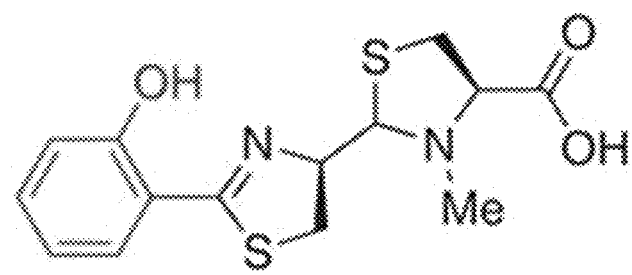

FIG. 1E: shows the structure of pyochelin (Brandel et al., 2011).

Figure 2A:
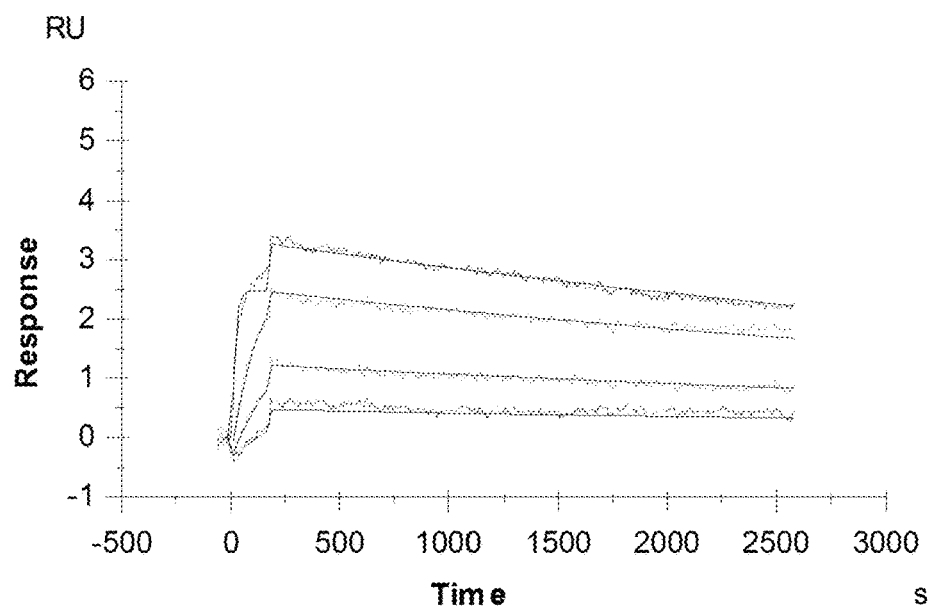

FIG. 2A: provides typical measurements of on-rate and off-rate by surface plasmon resonance for Pvd I s (+Fe) binding to the lipocalin mutein SEQ ID NO: 16.

Figure 2B:
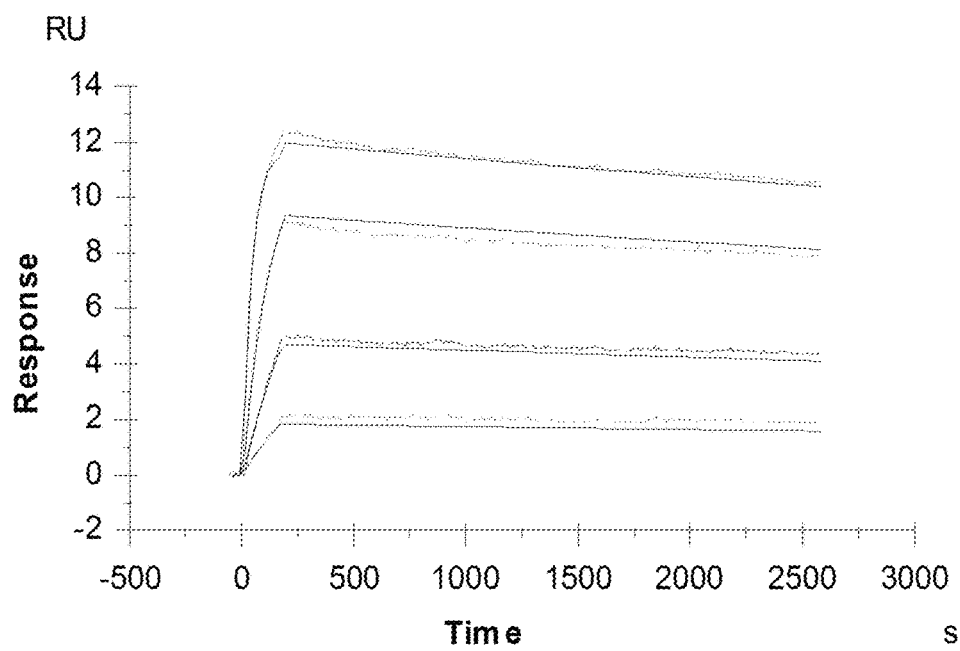

FIG. 2B: provides typical measurements of on-rate and off-rate by surface plasmon resonance for Pvd II s (+Fe) binding to the lipocalin mutein SEQ ID NO: 36.

Figure 2C:
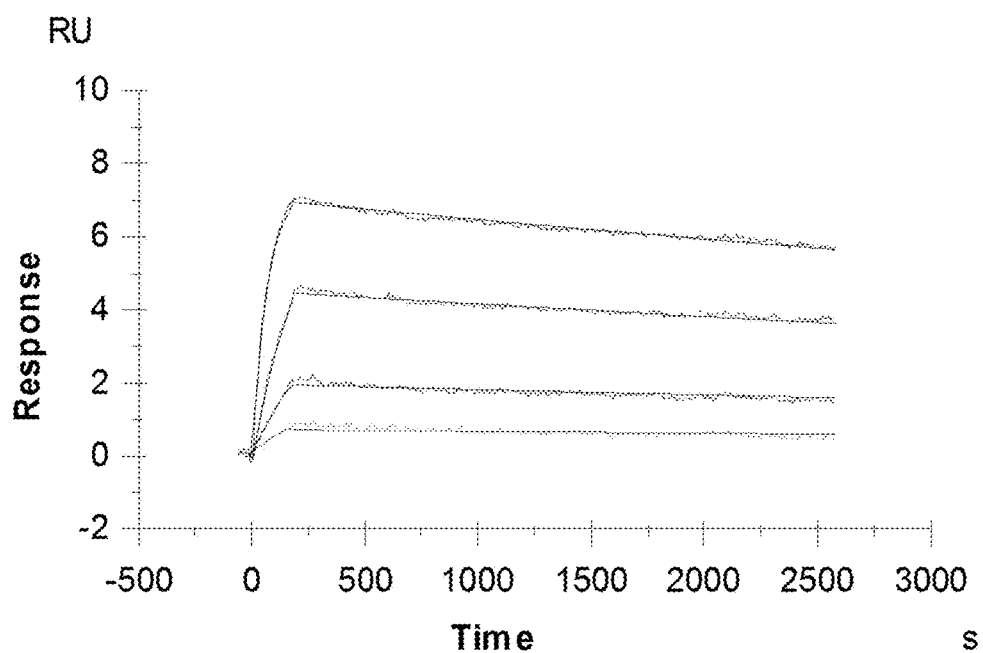

FIG. 2C: provides typical measurements of on-rate and off-rate by surface plasmon resonance for Pvd III (+Fe) binding to the lipocalin mutein SEQ ID NO: 53.

Figure 2D:
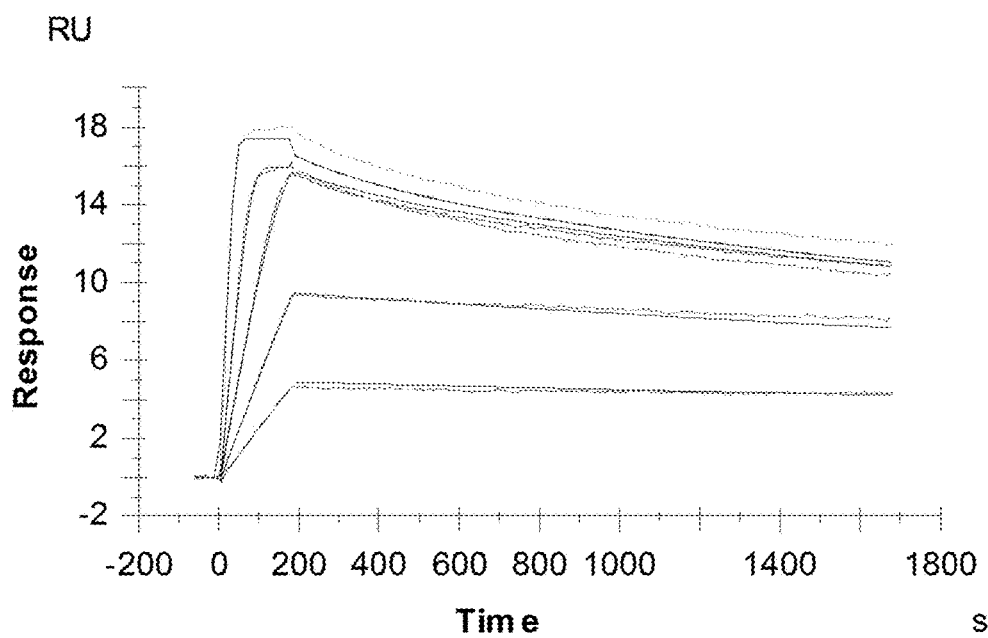

FIG. 2D: provides typical measurements of on-rate and off-rate by surface plasmon resonance for pyochelin (+Fe) binding to SEQ ID NO: 62.

Figure 2E:
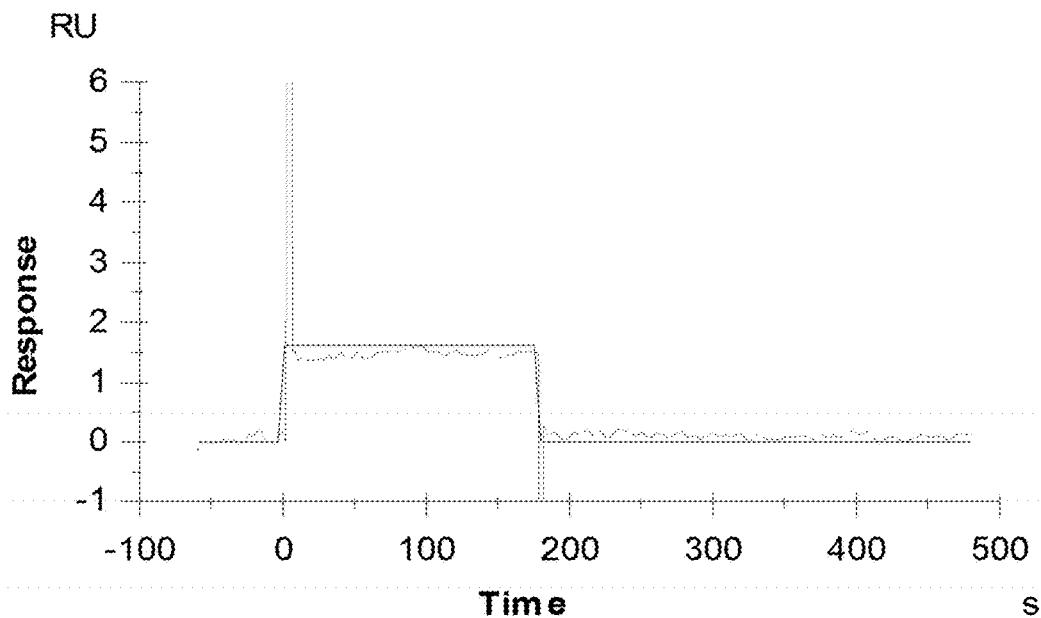

FIG. 2E: shows absence of binding of Pvd I s (+Fe) at 1200 nM to the negative control SEQ ID NO: 64.

Figure 2F:
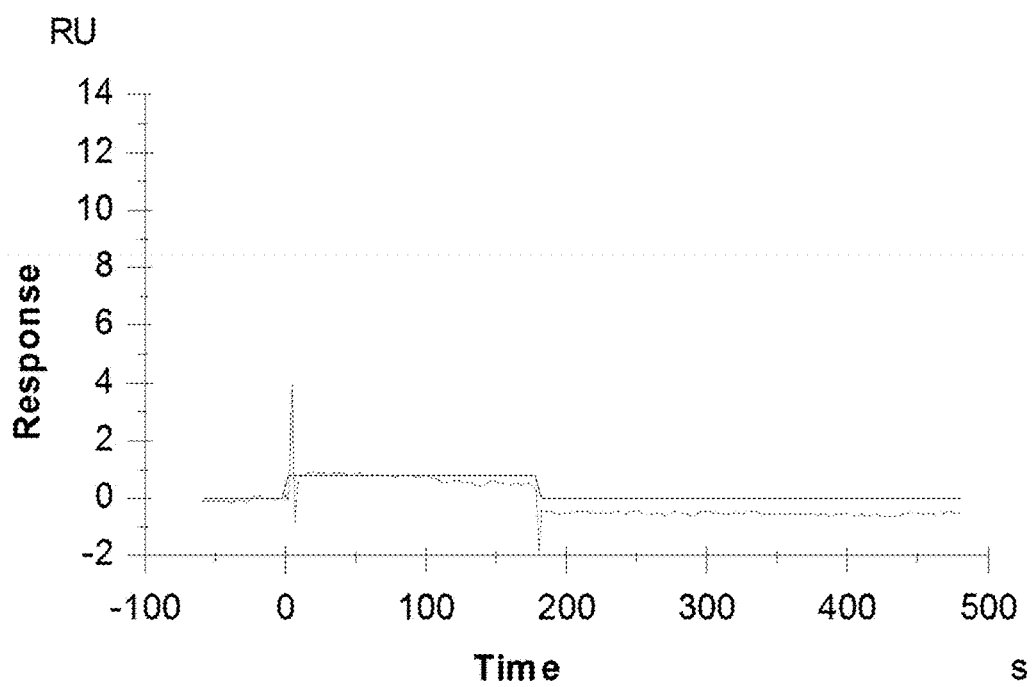

FIG. 2F: shows absence of binding of Pvd II s (+Fe) at 1200 nM to the negative control SEQ ID NO: 64.

Figure 2G:
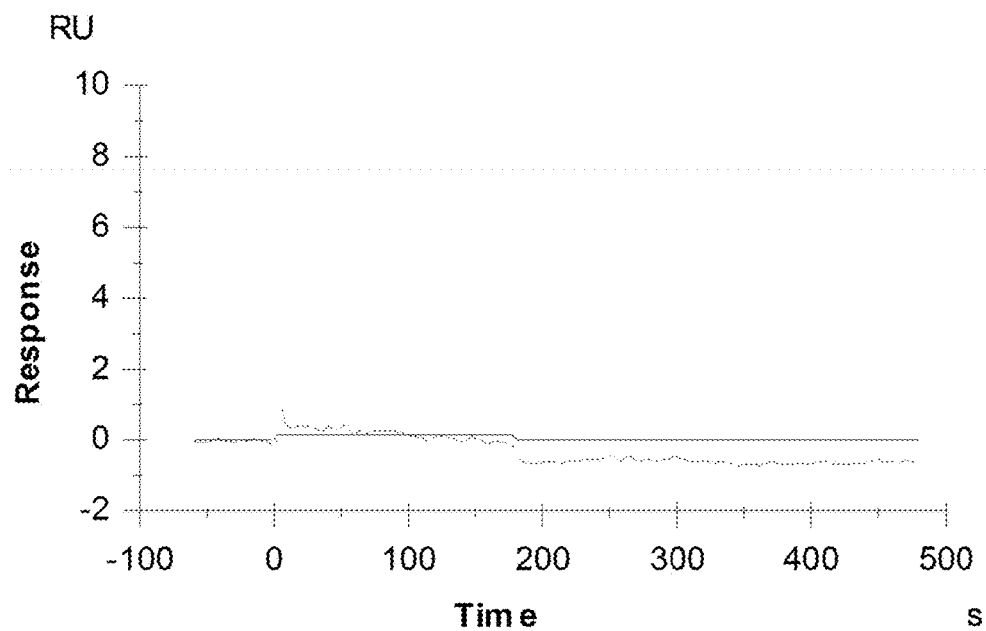

FIG. 2G: shows absence of binding of Pvd III s (+Fe) at 1200 nM to the negative control SEQ ID NO: 64.

Figure 2H:
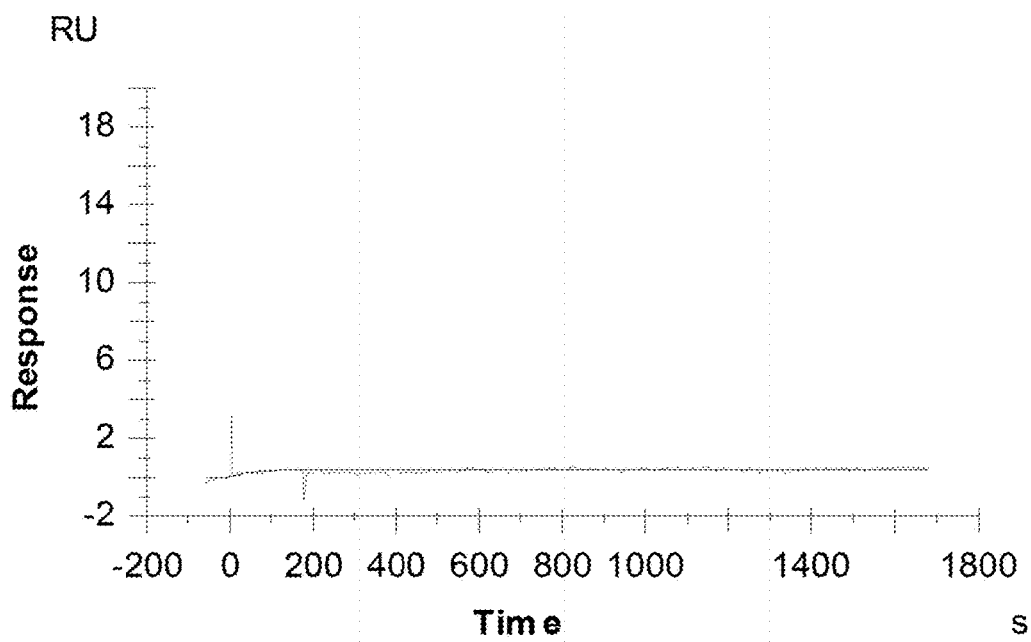

FIG. 2H: shows absence of binding of pyochelin (+Fe) at 200 nM to the negative control SEQ ID NO: 64.

Figure 3:
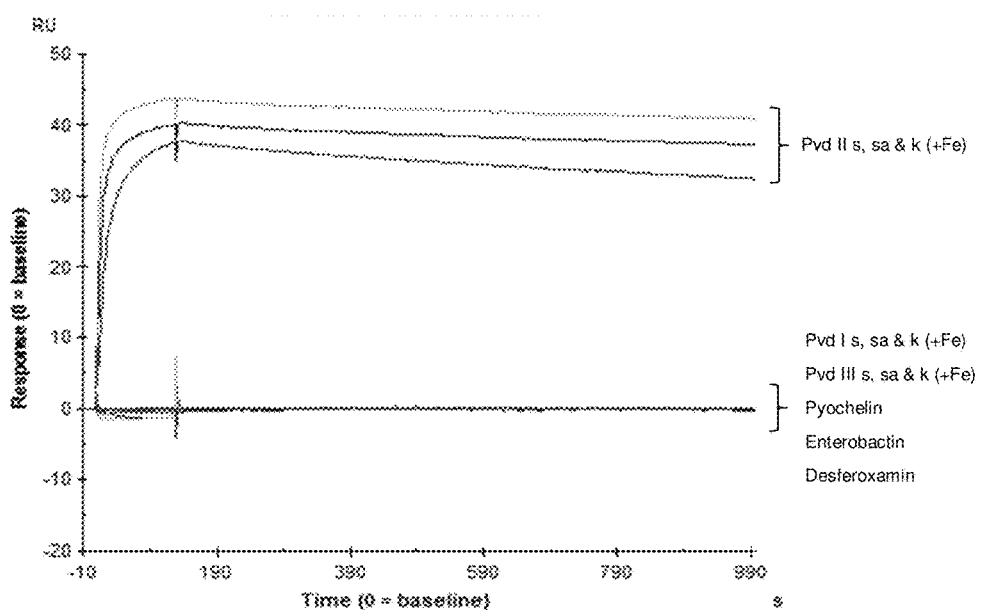

FIG. 3: shows an exemplary specificity and crossreactivity profile for the lipocalin mutein SEQ ID NO: 35 as determined by surface plasmon resonance. Specific binding to pyoverdine II succinyl, succinamide and α-ketoglutaryl is demonstrated, while absence of binding to pyoverdines of type I and type III, pyochelin, enterobactin and desferoxamin is shown. High concentrations of 2 µM are used for all analytes.

Figure 4A:
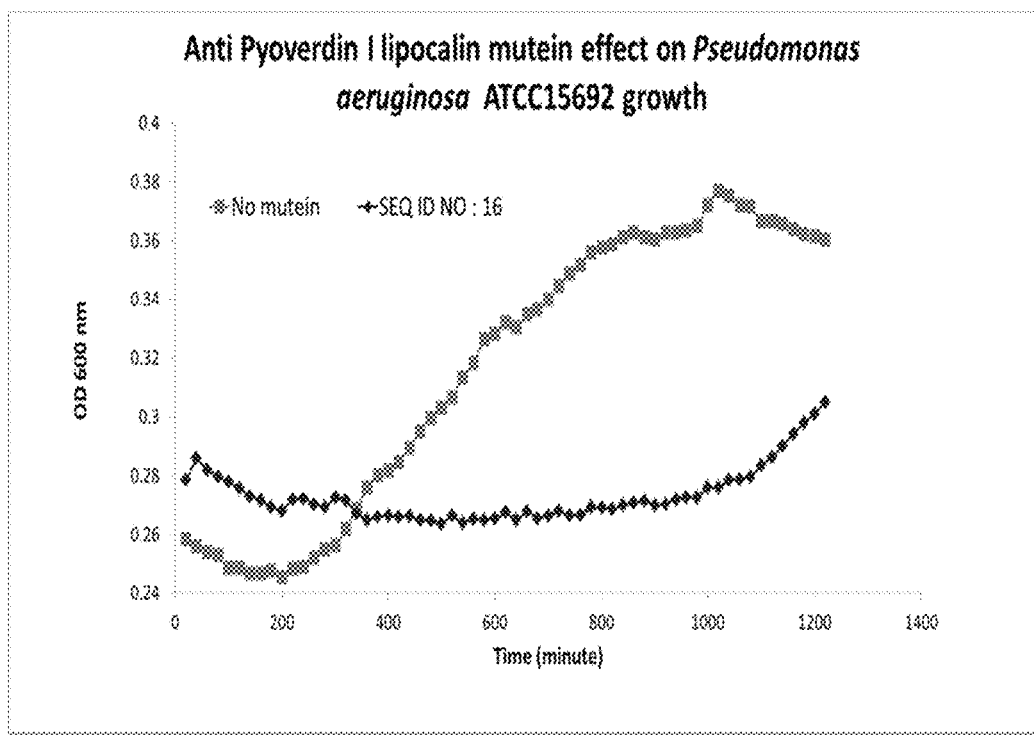

FIG. 4A: Pvd I-specific mutein SEQ ID NO: 16 shows growth inhibition of a Pvd I specific *P. aeruginosa* strain (ATCC27853) compared to the control culture growing without mutein.

Figure 4B:
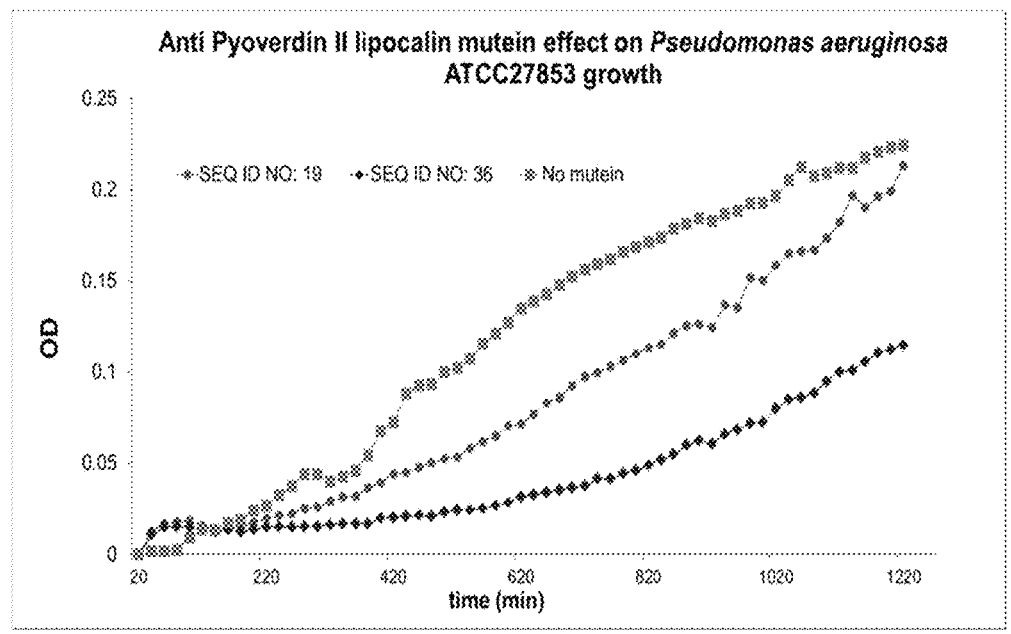

FIG. 4B: Pvd II-specific muteins SEQ ID NOs: 19 and 36 show growth inhibition of a Pvd II specific *P. aeruginosa* strain (ATCC15692) compared to the control culture growing without mutein. SEQ ID NO: 36 has a higher binding affinity compared to SEQ ID NO: 19 and shows a greater growth inhibition.

Figure 4C:
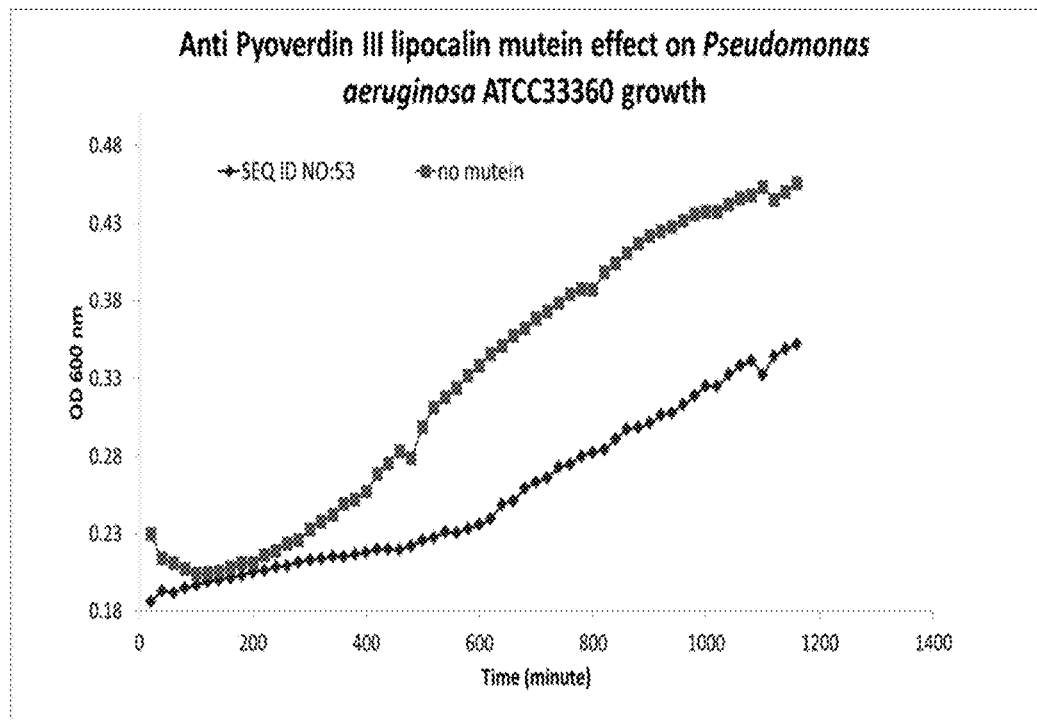

FIG. 4C: Pvd III-specific mutein SEQ ID NO: 53 shows growth inhibition of a Pvd III specific *P. aeruginosa* strain (ATCC33360) compared to the control culture growing without mutein.

Figure 4D:
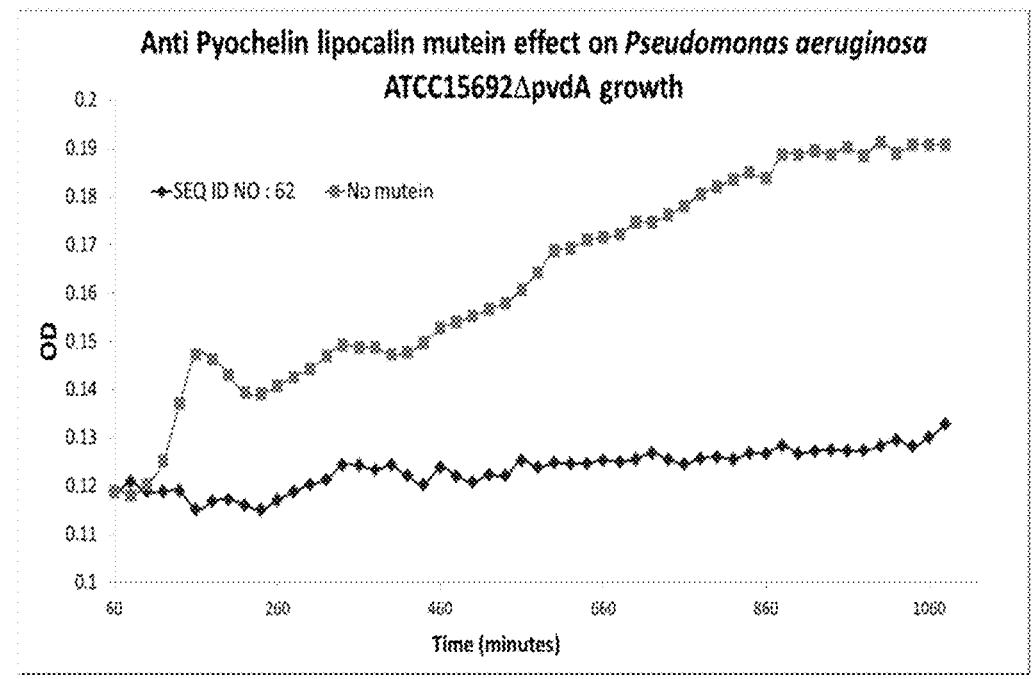

FIG. 4D: Pch-specific mutein SEQ ID NO: 62 shows growth inhibition of a Pvd I knock out *P. aeruginosa* strain (ATCC15692 ΔpvdA) relying on Pch for iron uptake compared to the control culture growing without mutein. 10 µM lipocalin muteins were applied in the assay.

Figure 5:
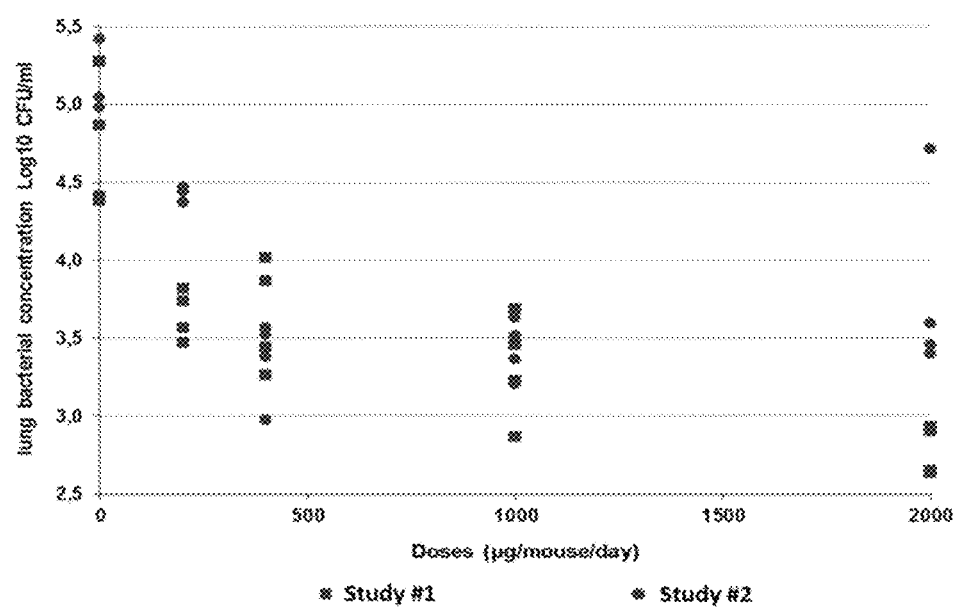

FIG. 5: shows in a *P. aeruginosa*-induced lung infection model in mice that administration of SEQ ID NO: 19, 1 hour before and at time of bacteria challenge, prevents the development of infection in mice in a dose-dependent manner. A significant prevention effect was observed starting from SEQ ID NO: 19 at 200 µg/mouse, with a maximal effect at 2000 µg/mouse.

Figures 6, 7:
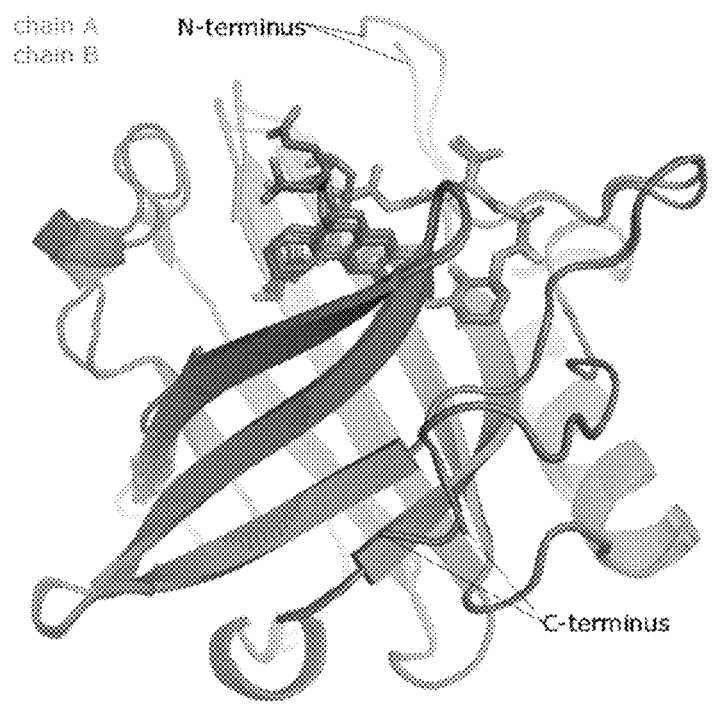

FIG. 6: shows the amino acid sequence expressed for crystallisation (SEQ ID NO: 129), including a start methionine at position 1, a lysine at position 2, a hexahistidine tag at position 3-8, a linker region of amino acids DYDIPTT at position 9-15 (SEQ ID NO: 132), the tobacco etch viral (TEV) protease cleavage site ENLYFQG at position 16-22 (SEQ ID NO: 133) followed by the amino acid sequence of the mutein of interest from position 23 onwards.

FIG. 7: shows the SEQ ID NO: 31—Pvd-Fe complex structure. An overlay of two SEQ ID NO: 31 molecules i.e. chain A and chain B from an asymmetric unit is shown.

Figure 8:
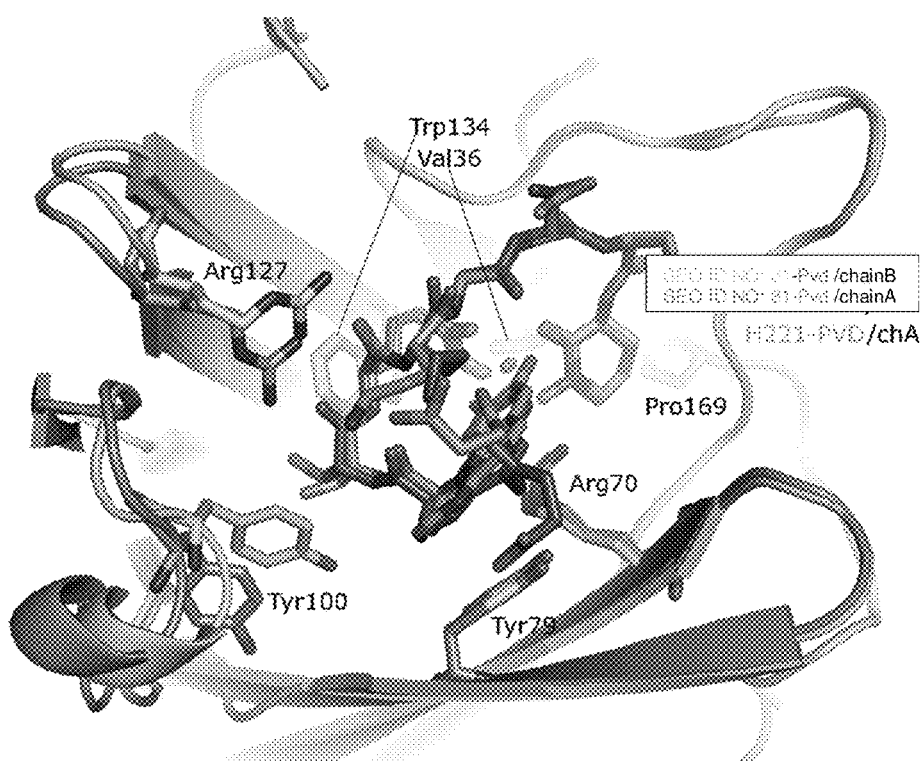

FIG. 8: shows SEQ ID NO: 31 and Pvd-Fe interactions. Two molecules from asymmetric unit are overlaid. Side chains interacting with Pvd-Fe are depicted.

Figure 9:
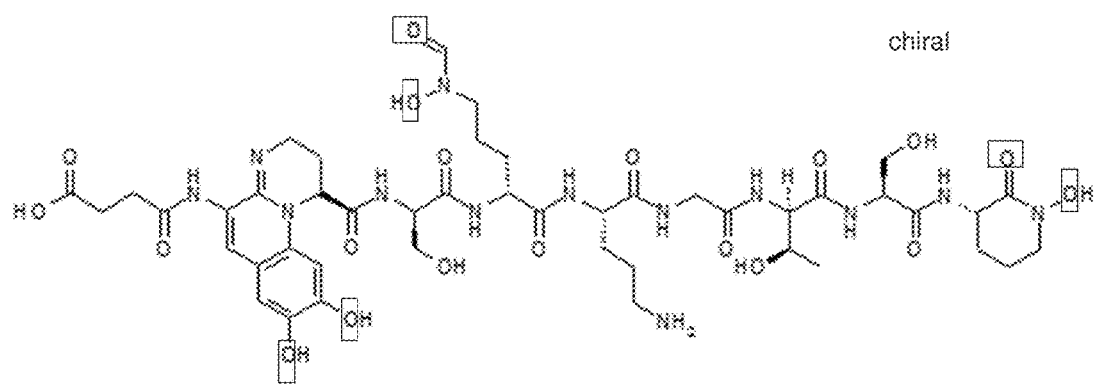

FIG. 9: shows the Pvd composition. Oxygen atoms involved in iron binding are boxed.

Figure 10A:
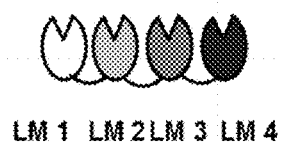

FIG. 10A: shows the structure of a fusion molecule according to the present invention. Lipocalin muteins one, two, three and four (LM 1, 2, 3, 4) were genetically fused via linker molecules (here: peptide linkers of the sequence $(G_4S)_2$; see SEQ ID NO: 141), wherein LM 1 (SEQ ID NO: 34 or 36) bound to the pyoverdine II group siderophores with bound iron ion and without complexed iron ion, LM 2 (SEQ ID NO: 16 or 17) bound to the pyoverdine I group siderophores with bound iron ion and without complexed iron ion, LM 3 (SEQ ID NO: 50 or 53) bound to the pyoverdine III group siderophores with bound iron ion and without complexed iron ion and LM 4 (SEQ ID NO: 62 or 63) bound to pyochelin siderophore with bound iron ion and without complexed iron ion. The fusion molecule construct (SEQ ID NO: 134 or 135) comprised binding capacity to all *P. aeruginosa* siderophores in one molecule and had one binding moiety for each Pvd group and one for pyochelin.

Figure 10B:
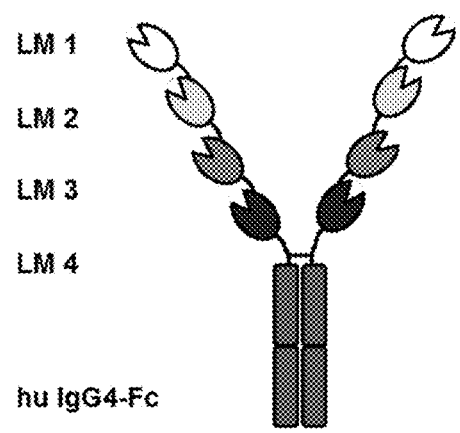

FIG. 10B: shows the structure of an Fc-fusion molecule construct according to the present invention. Lipocalin muteins one, two, three and four (LM 1, 2, 3, 4) were genetically fused via linker molecules (here: peptide linkers of the sequence $(G_4S)_2$; see SEQ ID NO: 141) to the N-terminus of the human IgG4-Fc domain (hu IgG4-Fc; SEQ ID NO: 140), wherein LM 1 (SEQ ID NO: 34 or 36) bound to the pyoverdine II group siderophores with bound iron ion and without complexed iron ion, LM 2 (SEQ ID NO: 16 or 17) bound to the pyoverdine I group siderophores with bound iron ion and without complexed iron ion, LM 3 (SEQ ID NO: 50 or 53) bound to the pyoverdine III group siderophores with bound iron ion and without complexed iron ion and LM 4 (SEQ ID NO: 62 or 63) bound to pyochelin siderophore with bound iron ion and without complexed iron ion. The Fc-fusion molecule construct (SEQ ID NO: 136 or 137) comprised binding capacity to all *P. aeruginosa* siderophores in one molecule and had two binding moieties for each Pvd group and for pyochelin.

Figure 10C:
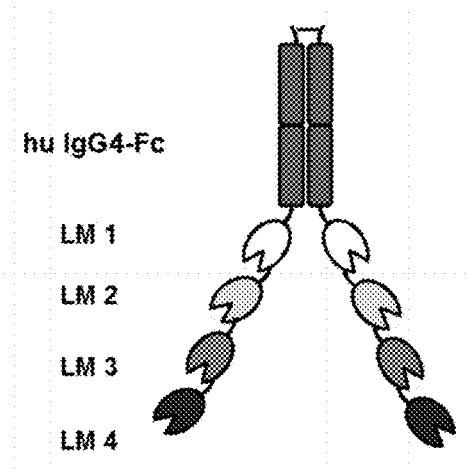

FIG. 10C: shows the structure of an Fc-fusion molecule construct according to the present invention. Lipocalin muteins one, two, three and four (LM 1, 2, 3, 4) were genetically fused via linker molecules (here: peptide linkers of the sequence $(G_4S)_2$; see SEQ ID NO: 141) to the C-terminus of the human IgG4-Fc domain (hu IgG4-Fc; SEQ ID NO: 140), wherein LM 1 (SEQ ID NO: 34) bound to the pyoverdine II group siderophores with bound iron ion and without complexed iron ion, LM 2 (SEQ ID NO: 17) bound to the pyoverdine I group siderophores with bound iron ion and without complexed iron ion, LM 3 (SEQ ID NO: 50) bound to the pyoverdine III group siderophores with bound iron ion and without complexed iron ion and LM 4 (SEQ ID NO: 63) bound to pyochelin siderophore with bound iron ion and without complexed iron ion. The Fc-fusion molecule construct (SEQ ID NO: 138) comprised binding capacity to all *P. aeruginosa* siderophores in one molecule and had two binding moieties for each Pvd group and for pyochelin.

Figure 10D:
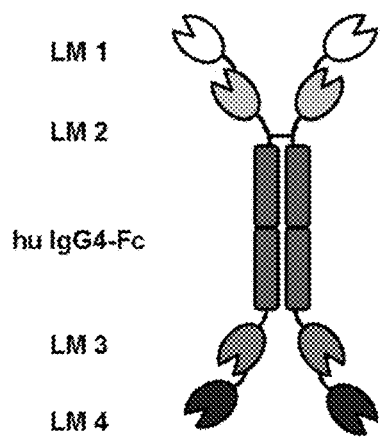

FIG. 10D: shows the structure of an Fc-fusion molecule construct according to the present invention. Lipocalin muteins one and two and three and four (LM 1, 2, 3, 4) were genetically fused via linker molecules (here: peptide linkers of the sequence $(G_4S)_2$; see SEQ ID NO: 141). LM 1 and LM 2 were genetically fused to the N-terminus of the human IgG4-Fc domain (hu IgG4-Fc; SEQ ID NO: 140), and LM 3 and LM 4 were genetically fused to the C-terminus of the human IgG4-Fc domain (hu IgG4-Fc; SEQ ID NO: 140), wherein LM 1 (SEQ ID NO: 34) bound to the pyoverdine II group siderophores with bound iron ion and without complexed iron ion, LM 2 (SEQ ID NO: 17) bound to the pyoverdine I group siderophores with bound iron ion and without complexed iron ion, LM 3 (SEQ ID NO: 50) bound to the pyoverdine III group siderophores with bound iron ion and without complexed iron ion and LM 4 (SEQ ID NO: 63) bound to pyochelin siderophore with bound iron ion and without complexed iron ion. The Fc-fusion molecule construct (SEQ ID NO: 139) comprised binding capacity to all *P. aeruginosa* siderophores in one molecule and had two binding moieties for each Pvd group and for pyochelin.

Figure 11:
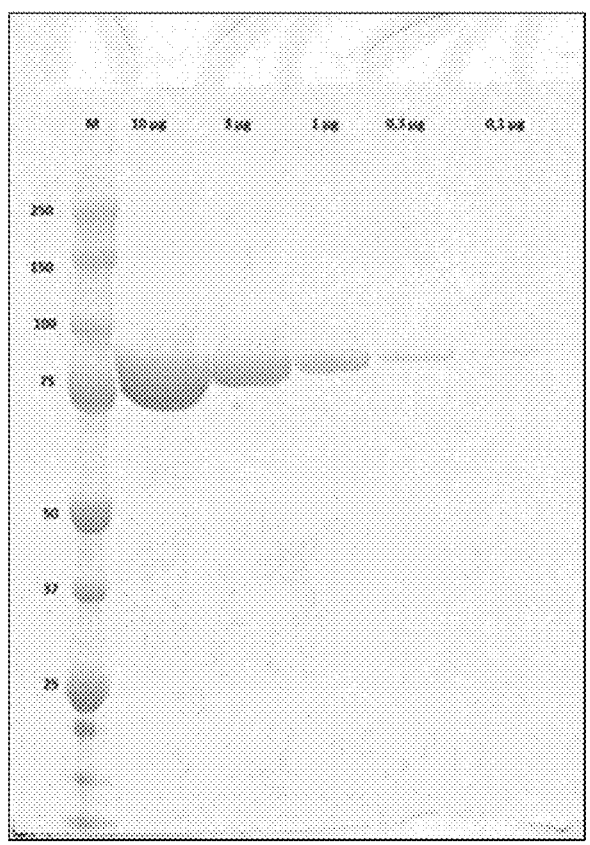

FIG. 11: shows a Coomassie-stained SDS-PAGE gel of a purified fusion molecule (here: SEQ ID NO: 134).

Figure 12:
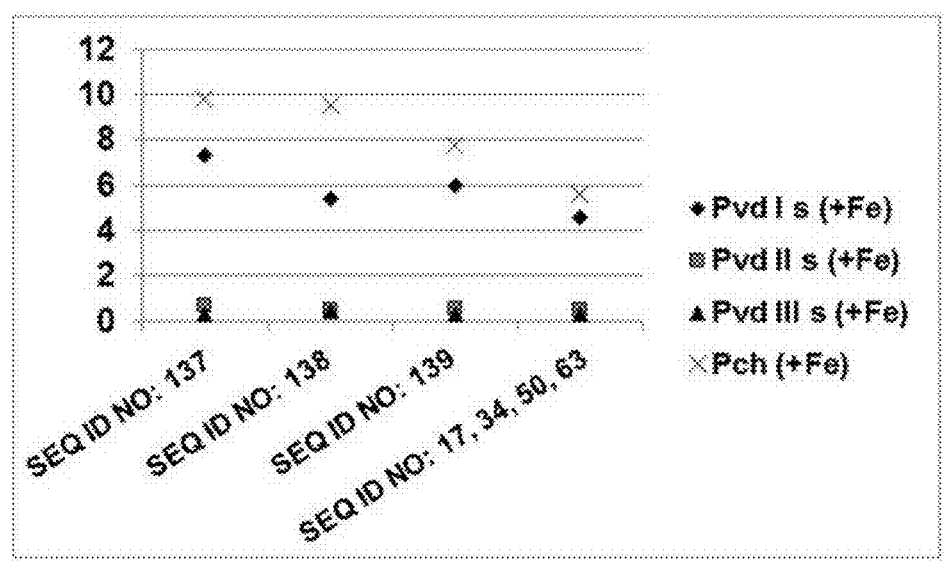

FIG. 12: shows binding of the different Fc-fusion molecule constructs of SEQ ID NOs: 137, 138 and 139 and of the respective single lipocalin muteins of SEQ ID NOs: 17, 34, 50 and 63 to the iron-loaded succinyl variants of the different pyoverdine groups and to iron-loaded pyochelin in solution, as determined in an ELISA based assay. All Fc-fusion molecule formats were active in binding to the single targets and had $IC_{50}$ values comparable to those of single lipocalin muteins.

Figure 13:
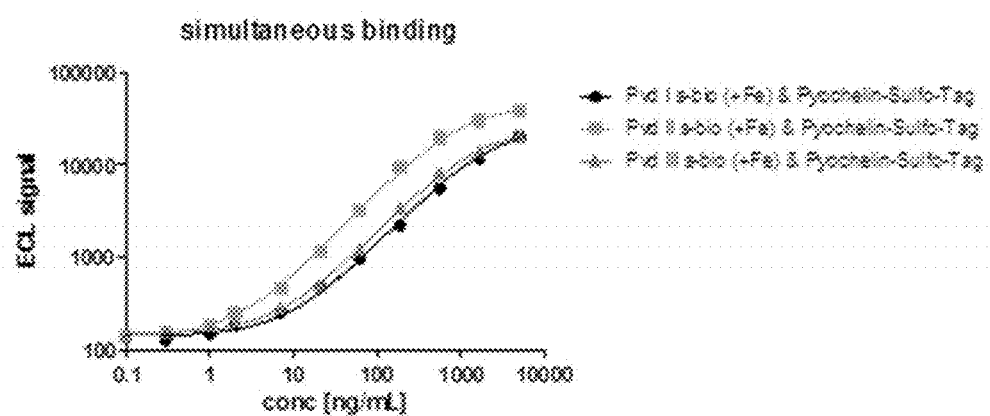

FIG. 13: shows that fusion molecules (here: SEQ ID NO: 134) are capable of simultaneous engagement of pyoverdine and pyochelin. Biotinylated pyoverdine from each of the respective groups (I, II and III) with a succinyl residue was captured on neutravidin coated MSD plates, and the fusion molecule was allowed to bind. Bound fusion molecule was detected via Sulfo-tag labeled pyochelin.

Figure 14A:
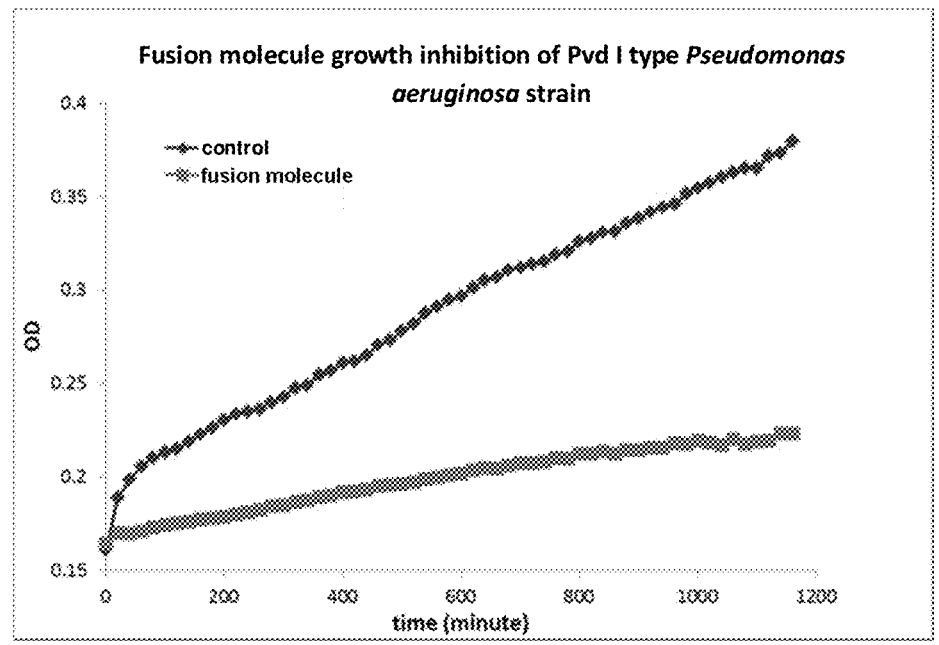

FIG. 14A: shows that fusion molecule SEQ ID NO: 134 is capable of inhibiting growth of a strain producing Pvd I in iron-limited medium.

Figure 14B:
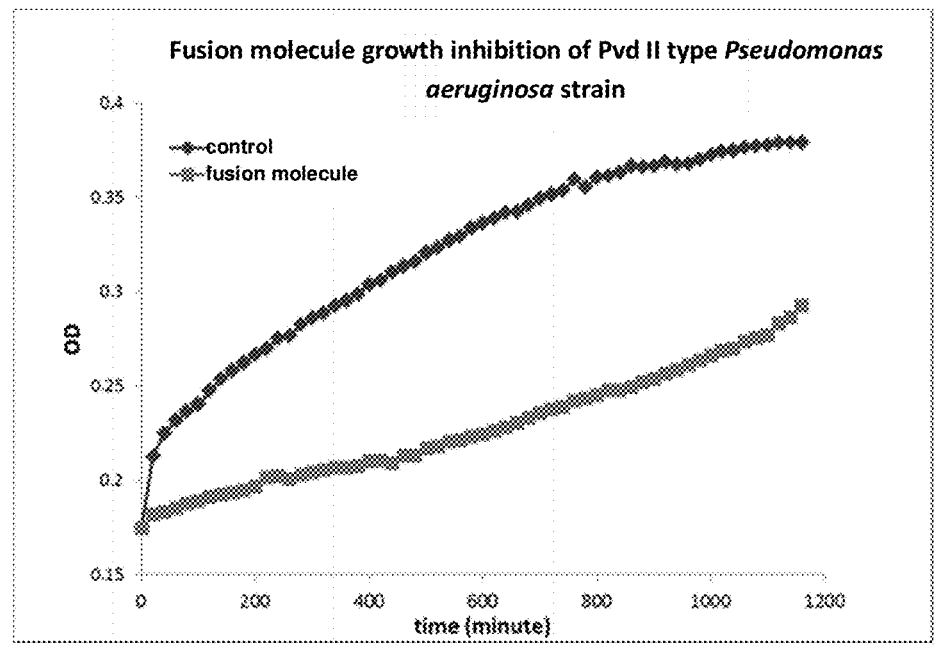

FIG. 14B: shows that fusion molecule SEQ ID NO: 134 is capable of inhibiting growth of a strain producing Pvd II in iron-limited medium.

Figure 14C:
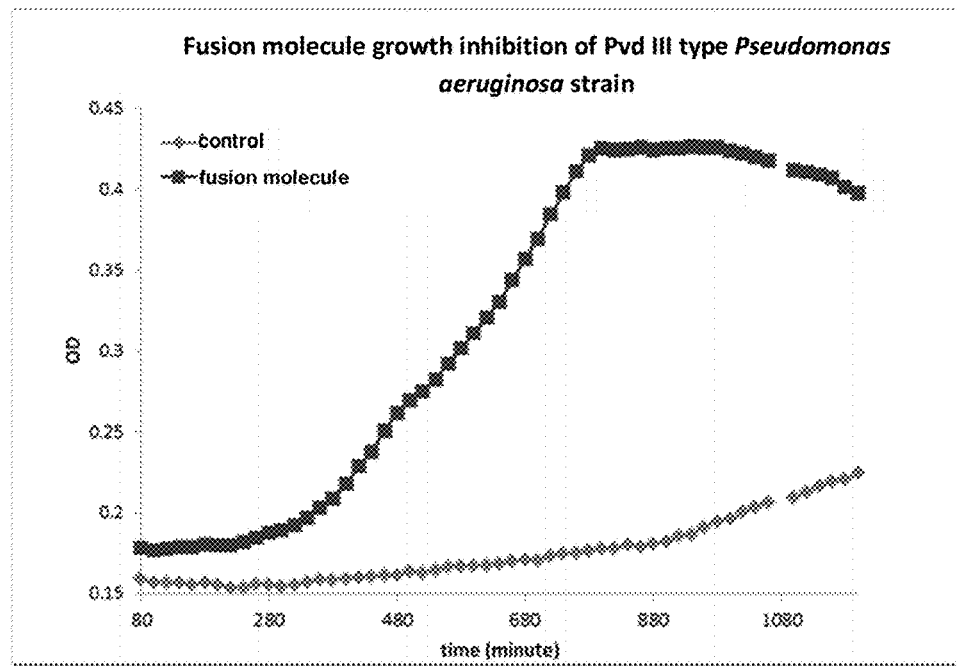

FIG. 14C: shows that fusion molecule SEQ ID NO: 134 is capable of inhibiting growth of a strain producing Pvd III in iron-limited medium.

Figure 14D:
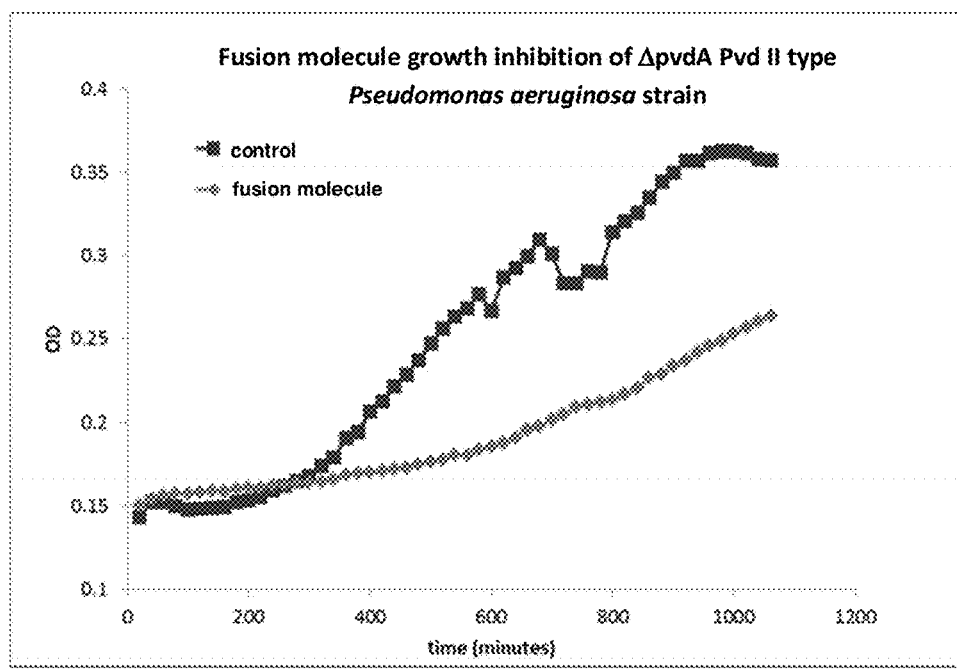

FIG. 14D: shows that fusion molecule SEQ ID NO: 134 is capable of inhibiting growth of a ΔpvdA PvdII knock out strain in iron-limited medium.

Figure 15:
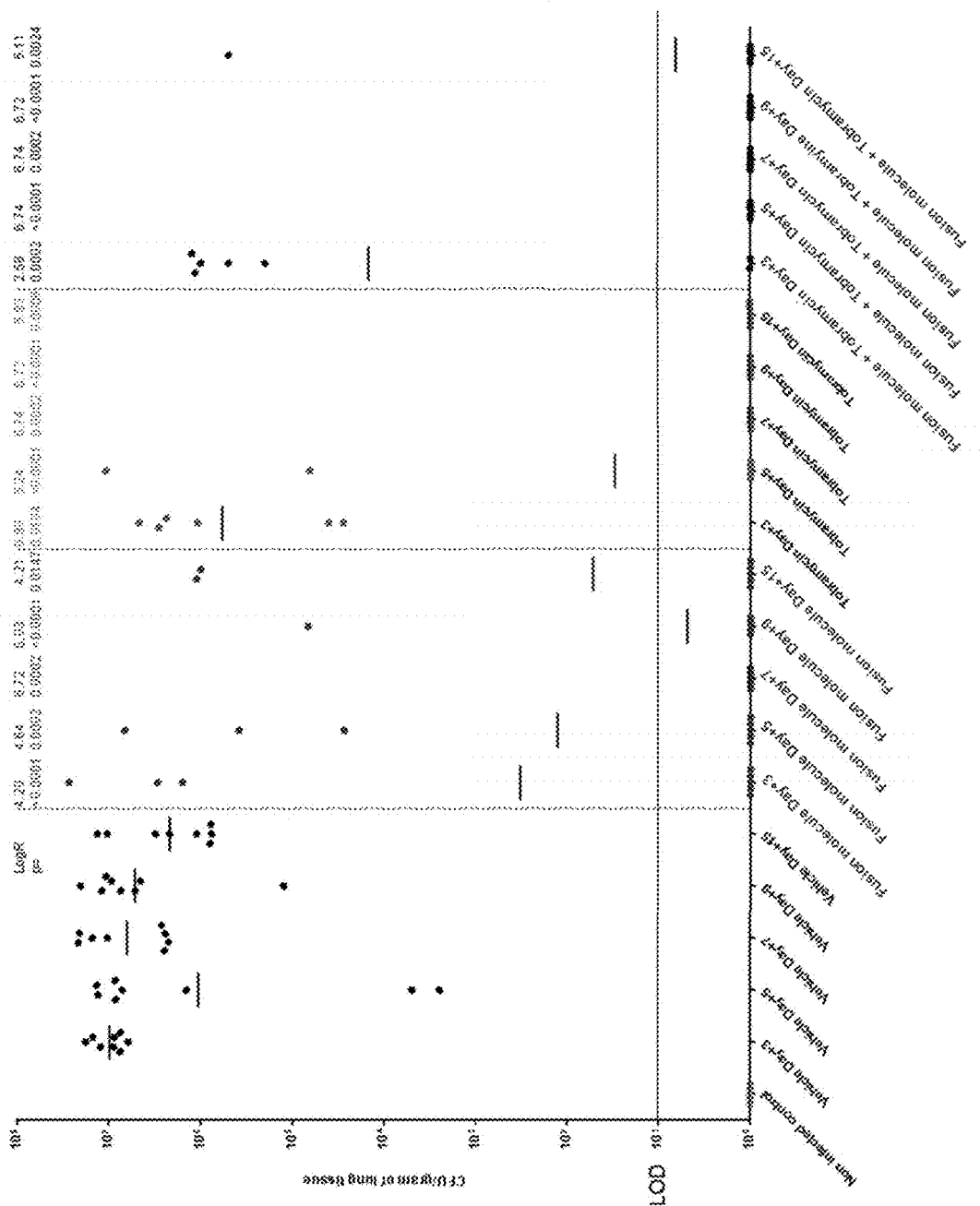

FIG. 15: shows that fusion molecules (here: SEQ ID NO: 134, referred to as RA10680550) significantly reduce *P. aeruginosa* lung burden (CFU/gram of lung tissue) in a chronic model of infection after a single dose at day 3 and that no relapse occurs up to day 15. It further shows that the fusion molecules do not antagonize Tobramycin activity, and that, in a combination therapy, the two activities synergize. The geometric mean burden of each treatment is indicated by the horizontal bar. Above each column the $Log_{10}$ reduction (Log R) of that treatment group compared to the vehicle is recorded (LOD=limit of detection).

Figure 16:
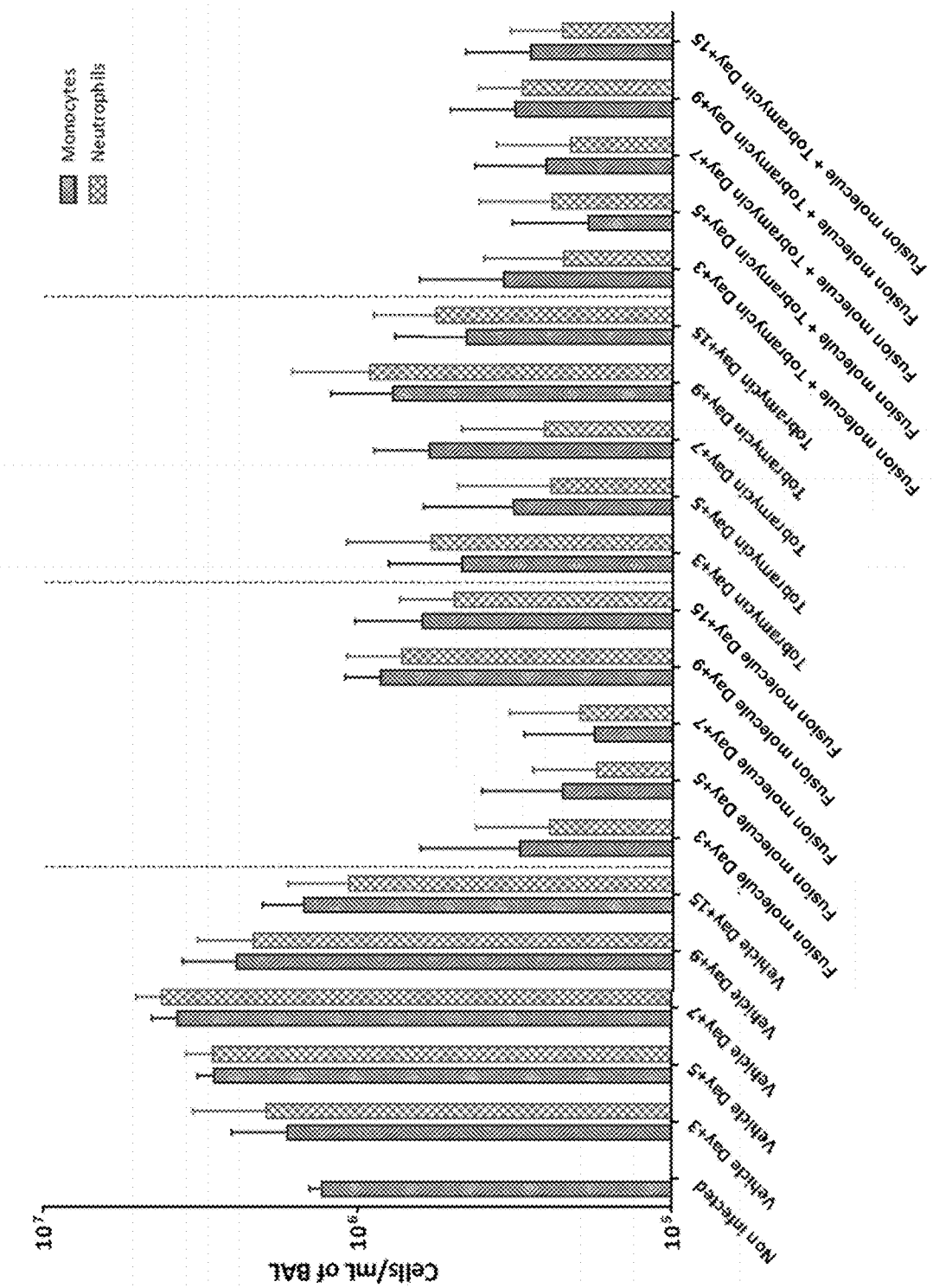

FIG. 16: shows that fusion molecules (here: SEQ ID NO: 134, also referred to as RA10680550) block the increase of total white cell count in the lung of infected rats and thereby increases the clearance of infection. The Tobramycin/fusion molecule combination shows a clear benefit versus each of the single treatments. Absolute BAL white blood cell (monocytes and neutrophils) counts mean+SD (cells per ml of BAL) at days 3, 5, 7, 9 and 15 post infection (Log scale).

Figure 17A:
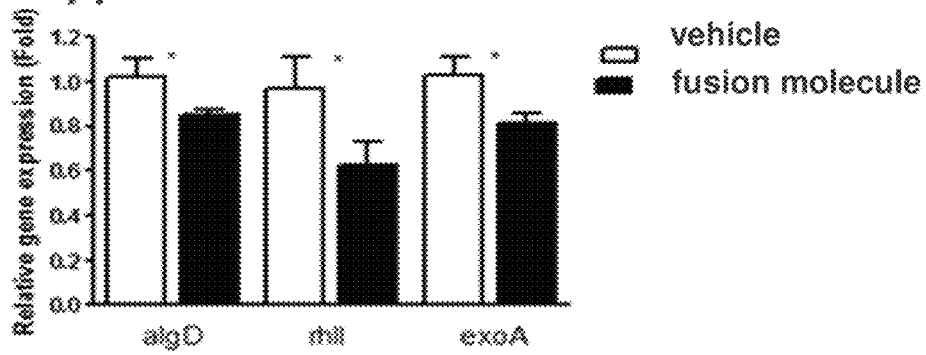

FIG. 17A: shows that fusion molecules decrease virulence factor expression during the early phase of colonization. The tested fusion molecule of SEQ ID NO: 134 shows a significant effect on the virulence gene expression of rhII of *P. aeruginosa*. rhII is involved in quorum sensing by producing N-butanoyl homoserine lactone (BHL). BHL binds to its receptor RhIR, thereby inducing expression of a complement of genes, including their own loci (completing the autoinducing circuits).

Figure 17B:
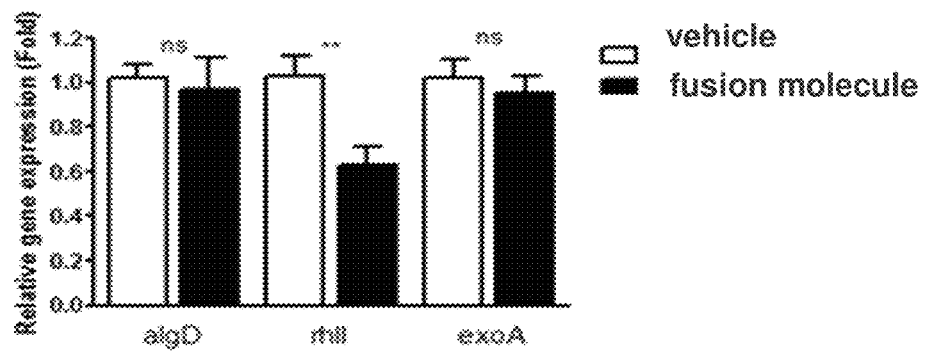

FIG. 17B: shows that fusion molecules decrease virulence factor expression during the established colonization. The tested fusion molecule of SEQ ID NO: 134 shows a significant effect on the virulence gene expression of rhII of *P. aeruginosa*.

Figure 18:
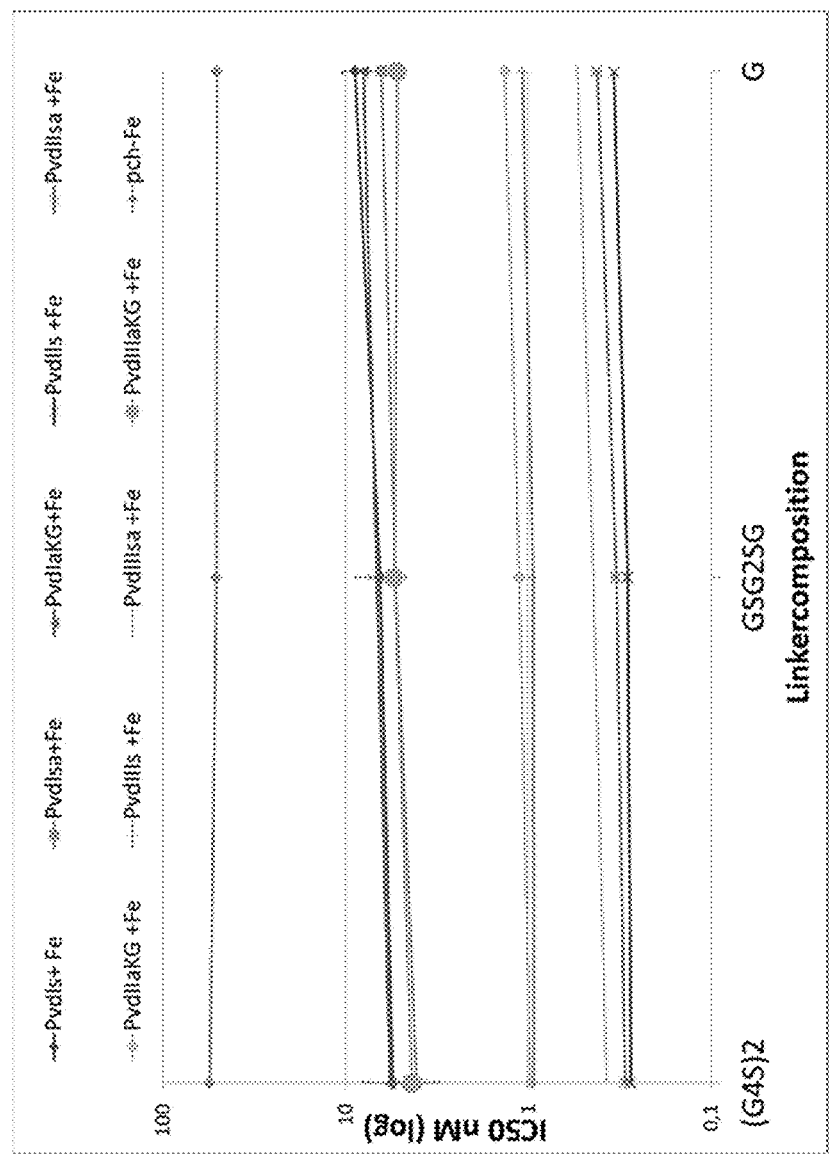

FIG. 18: shows that the binding capacity of fusion molecules is not influenced by the length of the linker molecule separating the four lipocalin muteins. The tested linker molecules were glycine, GSGGSG (SEQ ID NO: 142) and (G4S)$_2$ (SEQ ID NO: 141).

Figure 19A:
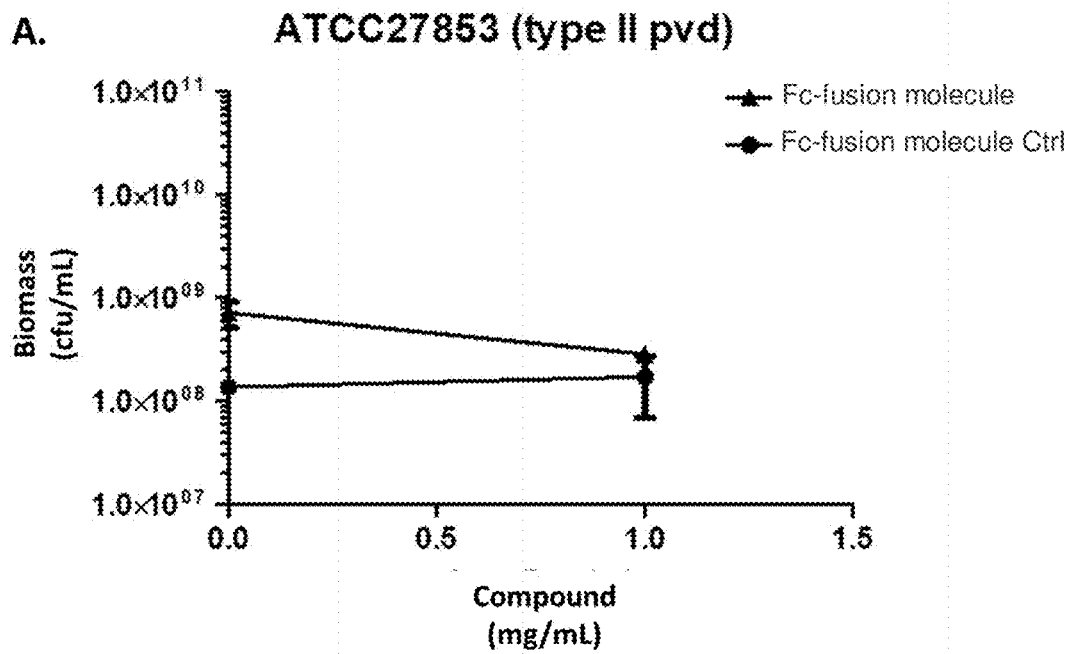

FIG. 19A: shows the effect of Fc-fusion molecule SEQ ID NO: 136 on the biomass of exponentially growing *P. aeruginosa* strain ATCC27853 in an iron-starved medium. Means and s.e.m. values are plotted.

Figure 19B:
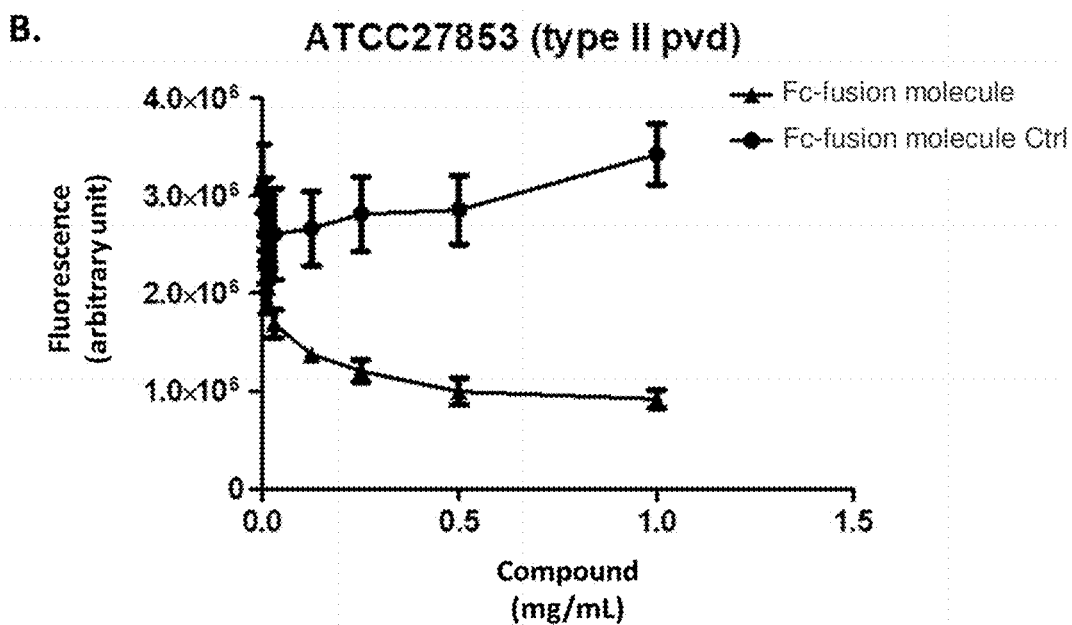

FIG. 19B: shows that Fc-fusion molecule SEQ ID NO: 136 prevents the production of pyoverdine by exponentially growing *P. aeruginosa* strain ATCC27853 in an iron-starved medium.

Figure 19C:
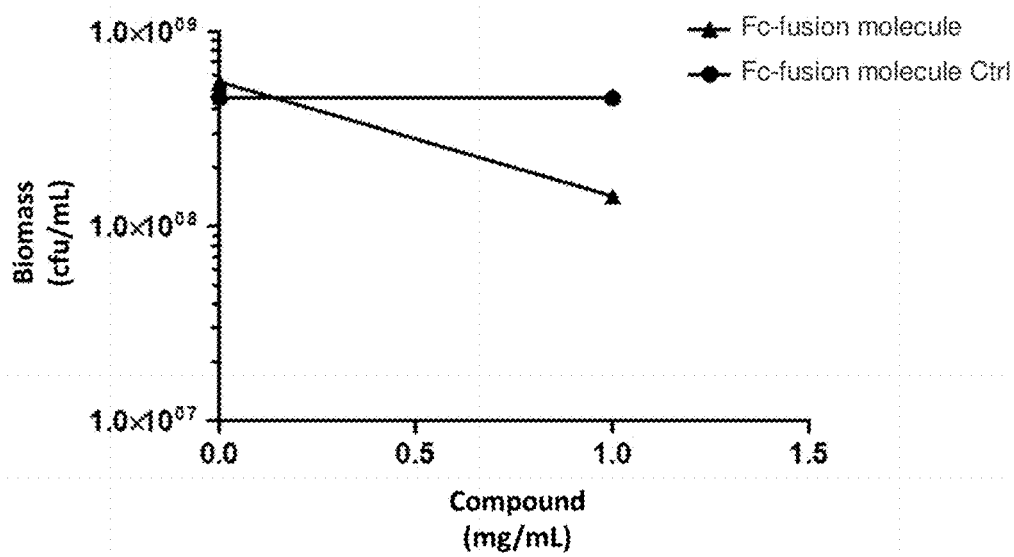

FIG. 19C: shows the effect of Fc-fusion molecule SEQ ID NO: 136 on the biomass of exponentially growing *P. aeruginosa* strain ATCC15692 in an iron-starved medium. Means and s.e.m. values are plotted.

Figure 19D:
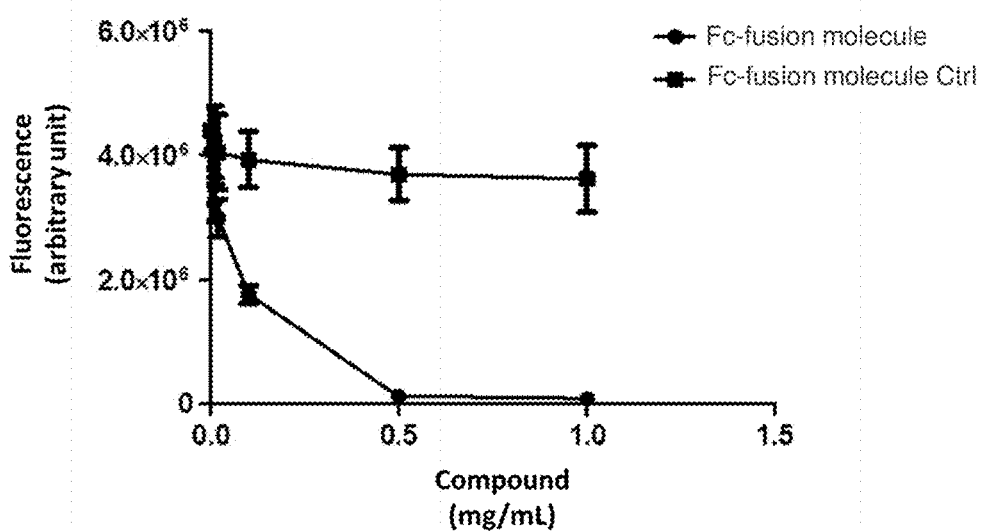

FIG. 19D: shows that Fc-fusion molecule SEQ ID NO: 136 prevents the production of pyoverdine by exponentially growing *P. aeruginosa* strain ATCC15692 in an iron-starved medium.

Figure 19E:
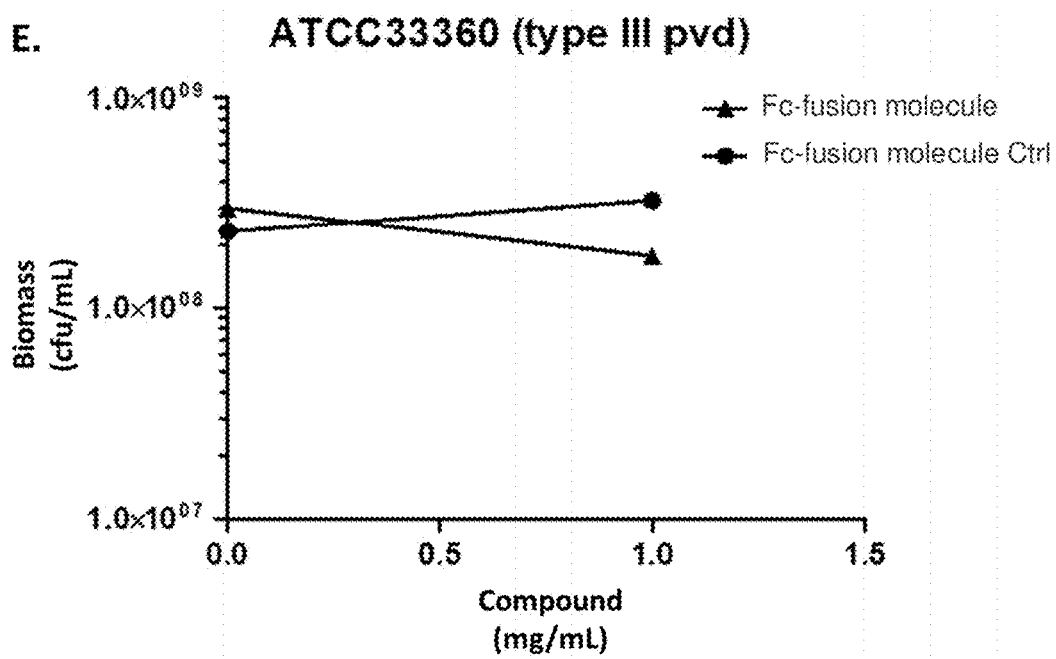

FIG. 19E: shows the effect of Fc-fusion molecule SEQ ID NO: 136 on the biomass of exponentially growing *P. aeruginosa* strain ATCC33360 in an iron-starved medium. Means and s.e.m. values are plotted.

Figure 19F:
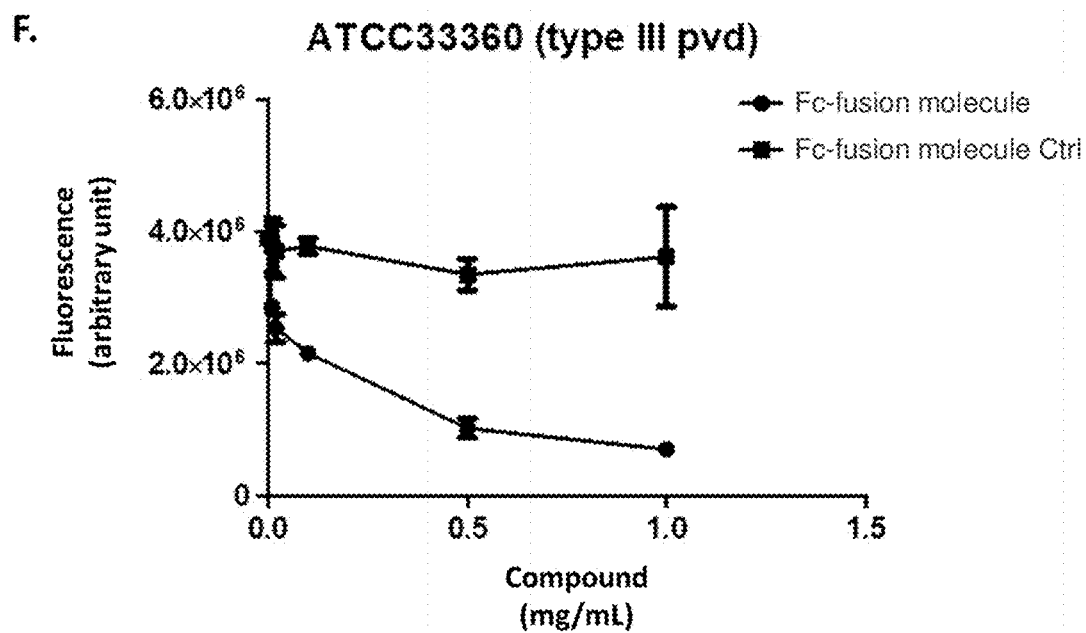

FIG. 19F: shows that Fc-fusion molecule SEQ ID NO: 136 prevents the production of pyoverdine by exponentially growing *P. aeruginosa* strain ATCC33360 in an iron-starved medium.

Figure 20A:
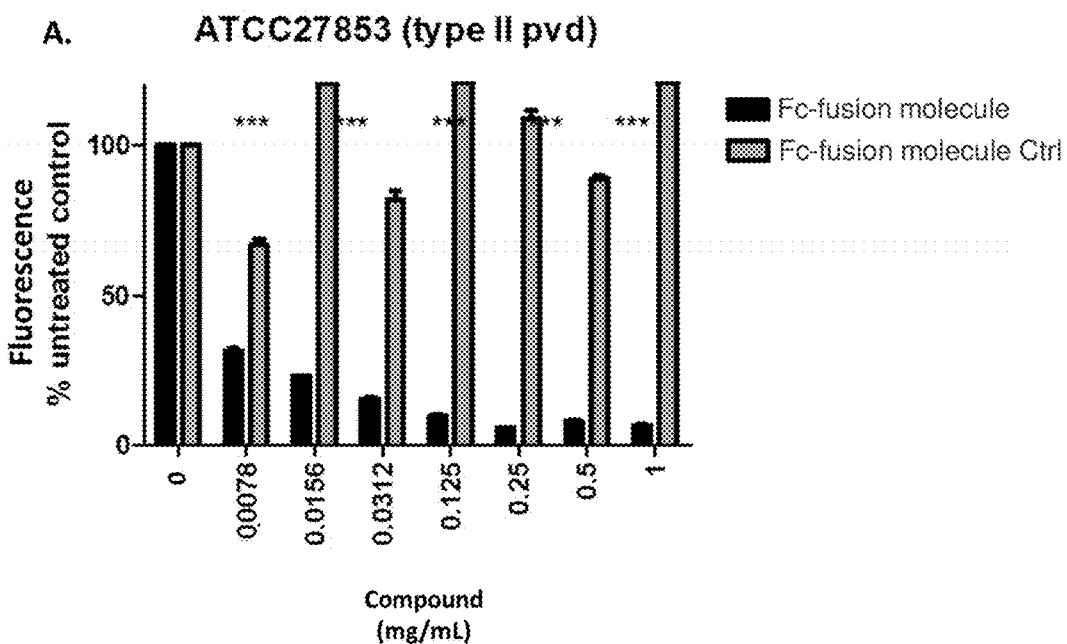

FIG. 20A: shows that Fc-fusion molecule SEQ ID NO: 136 prevents the production of pyoverdine by exponentially growing strain ATCC27853 in an iron-starved medium, wherein the relative pyoverdine fluorescence is normalized relative to the biomass.

Figure 20B:
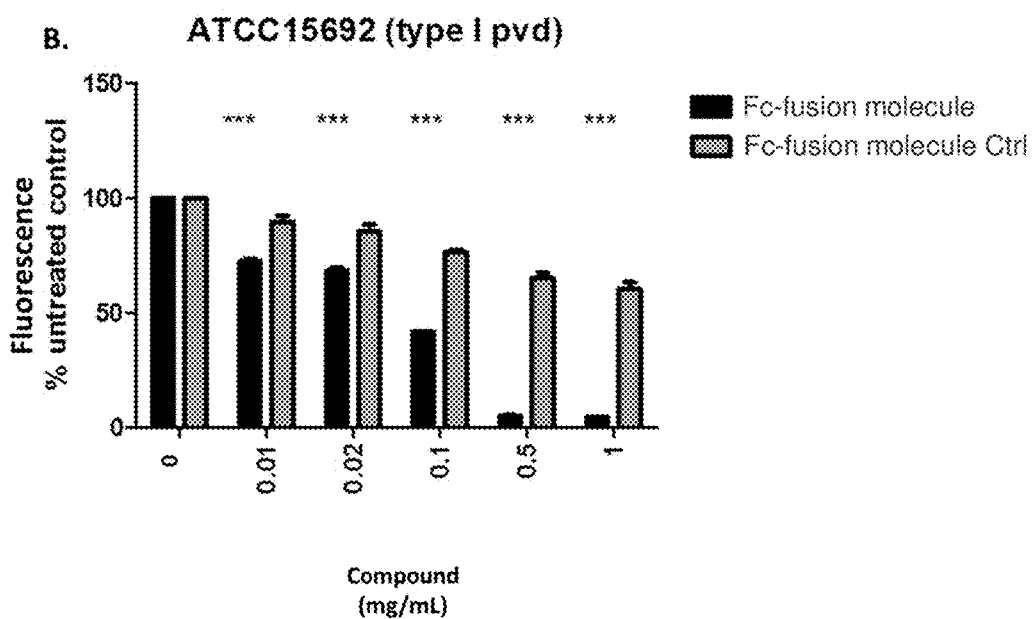

FIG. 20B: shows that Fc-fusion molecule SEQ ID NO: 136 prevents the production of pyoverdine by exponentially growing strain ATCC15692 in an iron-starved medium, wherein the relative pyoverdine fluorescence is normalized relative to the biomass.

Figure 20C:
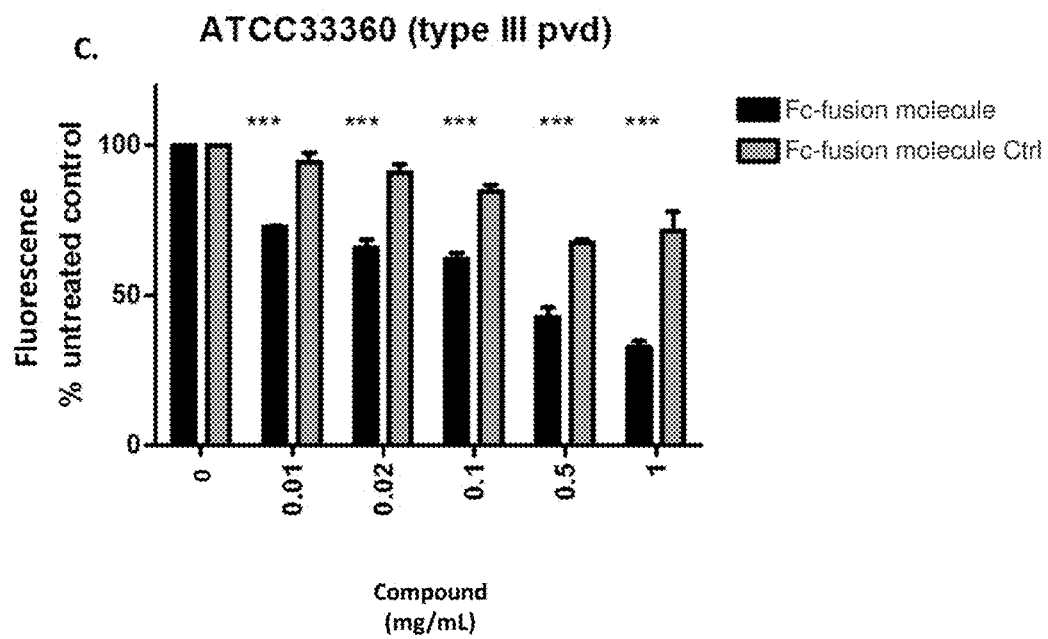

FIG. 20C: shows that Fc-fusion molecule SEQ ID NO: 136 prevents the production of pyoverdine by exponentially growing strain ATCC33360 in an iron-starved medium, wherein the relative pyoverdine fluorescence is normalized relative to the biomass.

Figure 21:
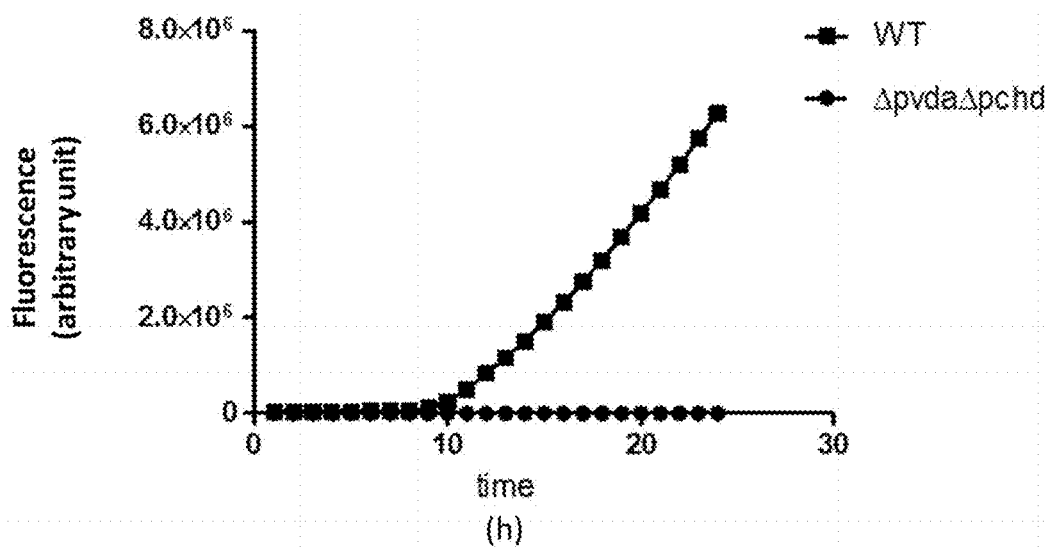

FIG. 21: shows that the effects shown in FIGS. 19A-F and 20A-C are pyoverdine-specific. The mean values of fluorescence in cultures of strain ATCC27853 and in a pvdA/pchD double mutant strain of ATCC27853 show that the mutant strain unable to synthesize these siderophores does not exhibit any fluorescence signal.

Figure 22:
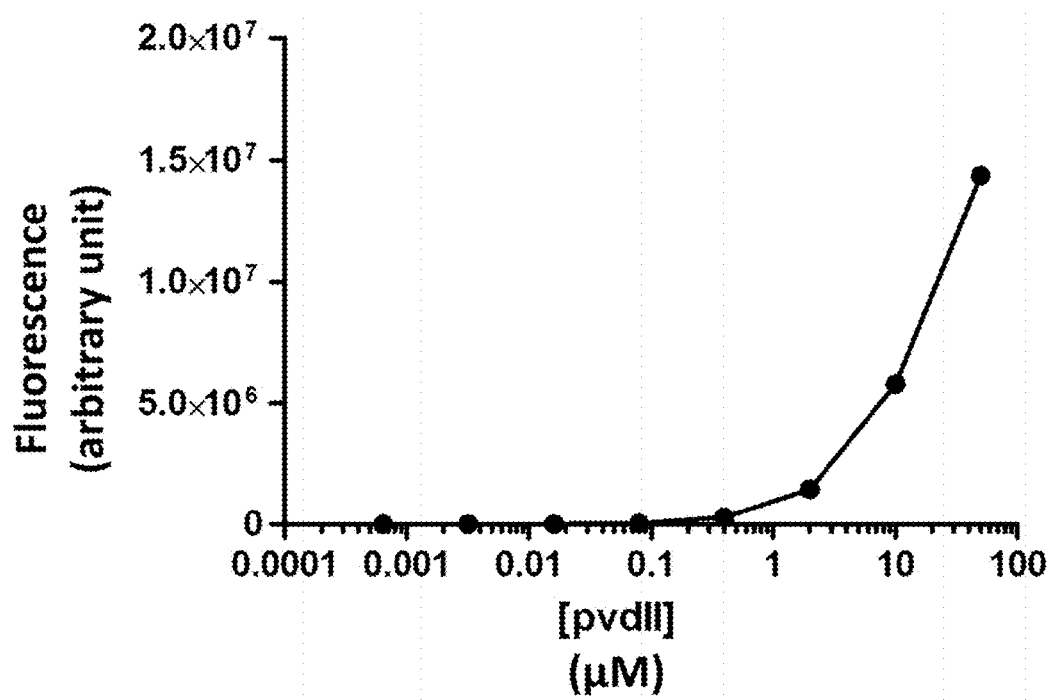

FIG. 22: shows that the effects shown in FIGS. 19A-F and 20A-C are pyoverdine-specific (see also FIG. 21). To normalize the fluorescence signal, purified pyoverdine II obtained from the supernatant of wild-type ATCC27853 was used to spike the cultures prior to fluorescence signal acquisition, and a calibration curve was obtained.

Figure 23:
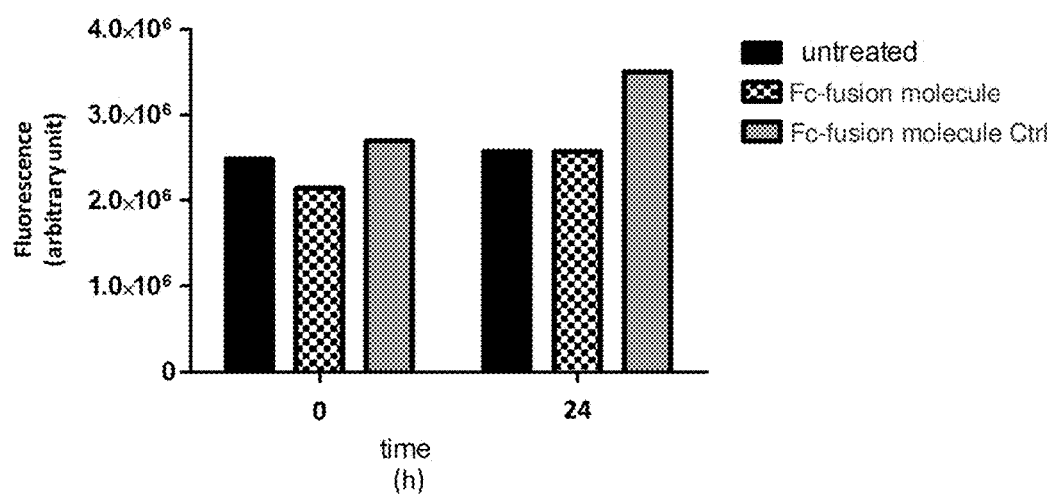

FIG. 23: shows that the drop in fluorescence signal in the presence of an Fc-fusion molecule was not due to fluorescence quenching upon pyoverdine binding by the compound. The Fc-fusion molecule (SEQ ID NO: 136) was added extemporaneously to a culture supernatant containing pyoverdine (obtained with a filtered 24 hours-culture of ATCC27853), and fluorescence was read immediately and after 24 h. As shown by the mean values of fluorescence observed in this experiment, no fluorescence quenching was detectable.

Figure 24A:
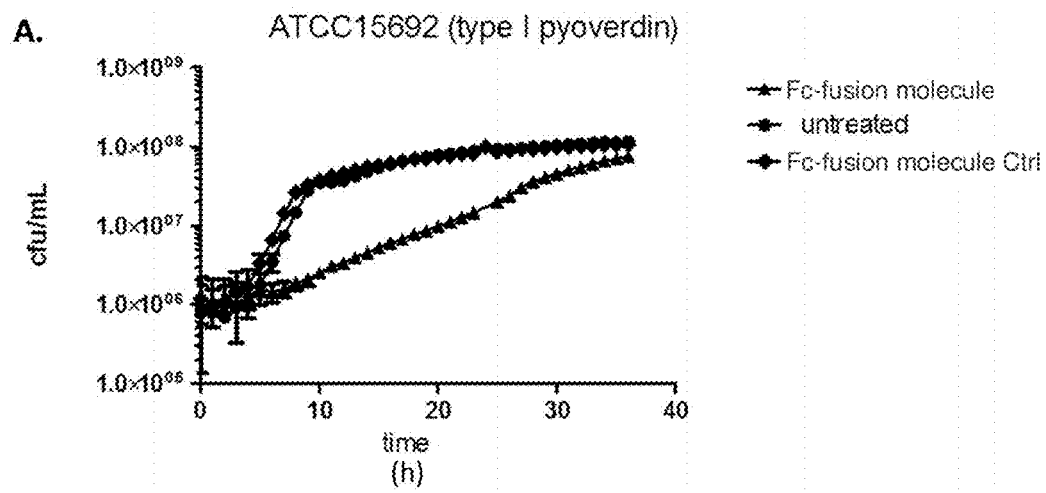

FIG. 24A: shows that Fc-fusion molecules influence the kinetics of bacterial growth. The impact of 1 mg/mL treatment with an Fc-fusion molecule (SEQ ID NO: 136) on strain ATCC15692 is shown as means and s.e.m. of cfu/mL.

Figure 24B:
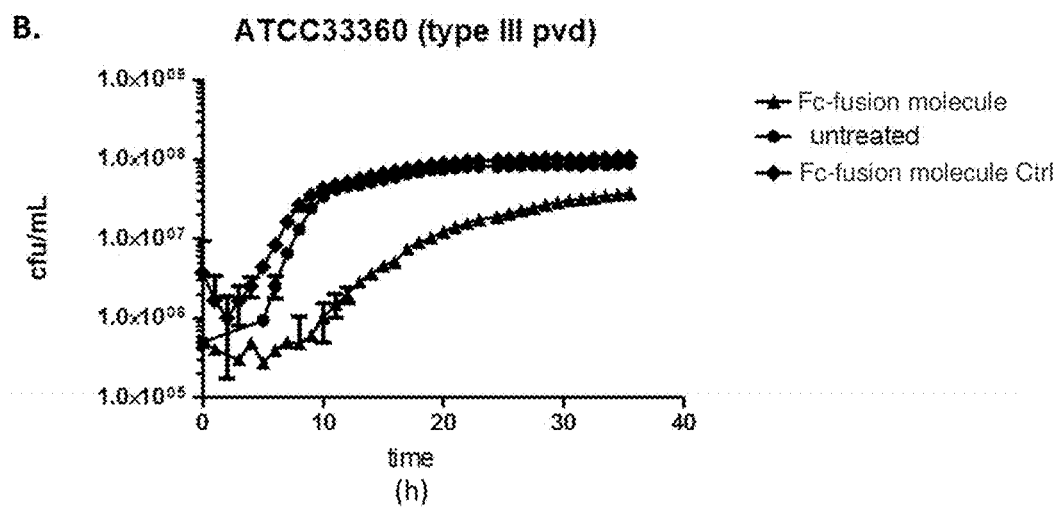

FIG. 24B: shows that Fc-fusion molecules influence the kinetics of bacterial growth. The impact of 1 mg/mL treatment with an Fc-fusion molecule (SEQ ID NO: 136) on strain ATCC33360 is shown as means and s.e.m. of cfu/mL.

Figure 25:
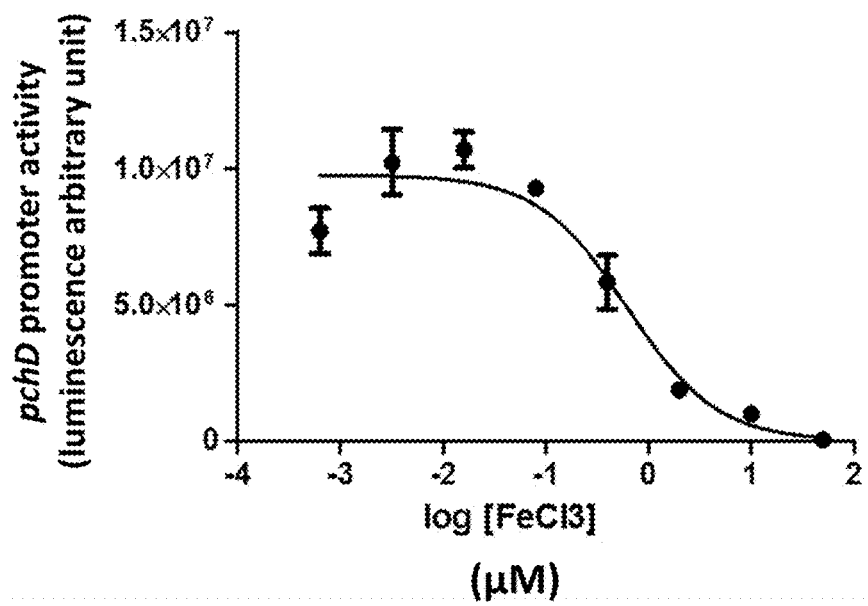

FIG. 25: shows the impact of iron concentration on Ppchd transcriptional activity. The means and s.e.m. of the observed luminescence show that pchD promoter expression was induced in the C-MS medium without addition of iron and repressed by iron addition, thereby validating the functionality of the reporter fusion.

Figure 26:
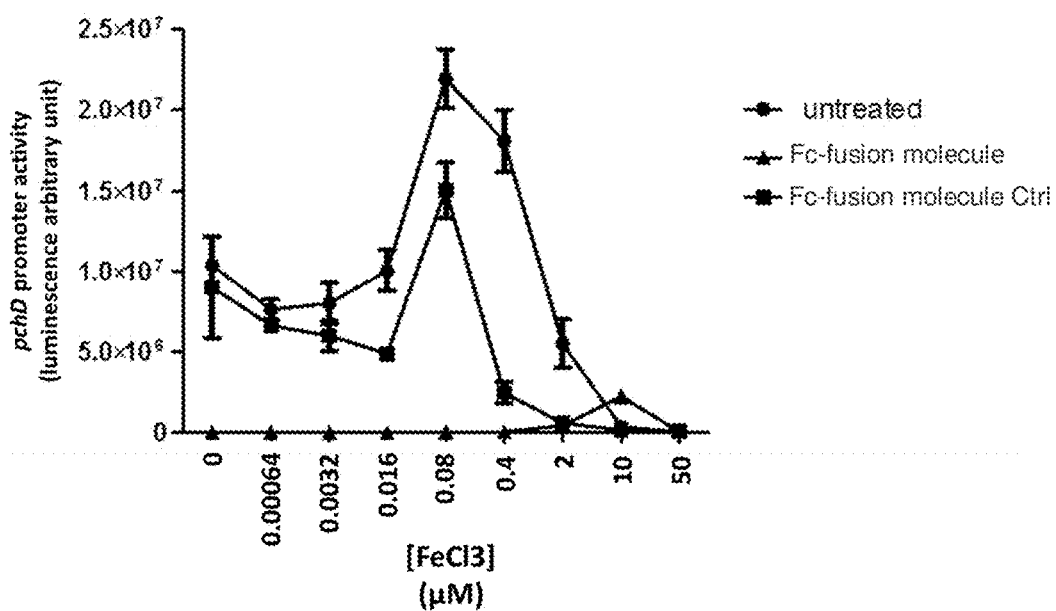

FIG. 26: shows the impact of treatment with an Fc-fusion molecule (SEQ ID NO: 136) on Ppchd transcriptional activity in the presence of various amounts of supplementary iron. The means and s.e.m. of the observed luminescence show that promoter activity was abolished in the presence of the Fc-fusion molecule regardless of the amount of supplemented iron, whereas the control Fc-fusion molecule had no effect.

Figure 27:
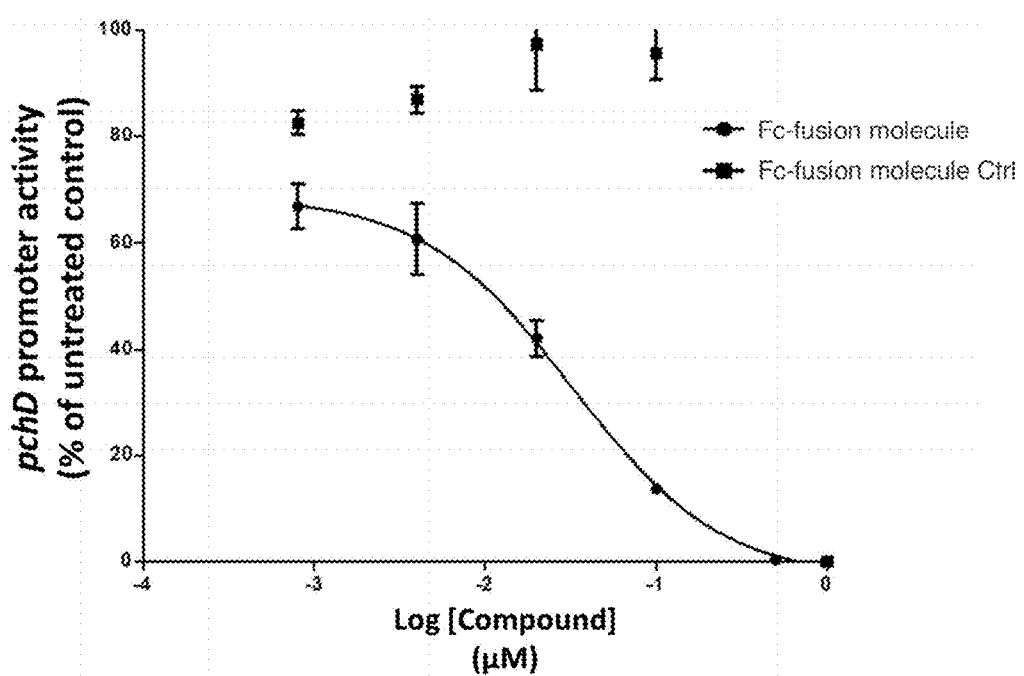

FIG. 27: shows the impact of a range of doses of an Fc-fusion molecule (SEQ ID NO: 136) on PpchD transcriptional activity tested with no iron supplement. The points of means and s.e.m. of the observed luminescence were fitted to a standard dose-response curve and yielded an IC$_{50}$ value of 0.03 mg/mL (95% CI: 0.02-0.05) for the Fc-fusion molecule, whereas it was undefined for the isotypic control Fc-fusion molecule.

VII. DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and exemplary embodiments should not be construed to limit the present invention to only the explicitly described embodiments. This description should be understood to support and encompass embodiments which combine the explicitly described embodiments with any number of the disclosed and/or exemplary elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kolbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (Sambrook, J. et al. (2001) Molecular Cloning: A Laboratory Manual, 3rd Ed., Cold Spring Harbor Laboratory Press, Cold Spring Harbor, N.Y.).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

A. Fusion Molecules

The present invention provides fusion molecules having binding specificity for pyoverdine type I, II and III and pyochelin, comprising (a) a first polypeptide comprising or consisting of a first human neutrophil gelatinase-associated lipocalin (hNGAL) mutein that binds pyoverdine type I;

(b) a second polypeptide comprising or consisting of a second hNGAL mutein that binds pyoverdine type II;

(c) a third polypeptide comprising or consisting of a third hNGAL mutein that binds pyoverdine type III; and (d) a fourth polypeptide comprising or consisting of a fourth hNGAL mutein that binds pyochelin;

wherein the first, second, third and fourth polypeptides are covalently linked.

The term "fusion molecule" generally refers to molecules created by joining two or more distinct molecules (e.g., (poly-)peptides or proteins), particularly head-to-tail (e.g., N-terminus to C-terminus or vice versa), resulting in a single molecule with functional properties derived from each of the original molecules (e.g., (poly-)peptides or proteins). In one embodiment, the fusion molecule is a fusion protein.

The term "binding specificity", as used herein, refers to the ability of a ligand (e.g., the fusion molecule of the invention) to discriminate between the target(s) (e.g., pyoverdine type I, II and III and pyochelin) and one or more reference targets, since binding specificity is not an absolute, but a relative property. Specific binding can be determined, for example, in accordance with Western blots, ELISA-, RIA-, ECL-, IRMA-tests, FACS, IHC and peptide scans.

As used herein, "pyoverdine" means a fluorescent siderophore that is produced by the Gram-negative bacterium *Pseudomonas aeruginosa* under iron-deficient growth conditions and has high affinity for iron. Pyoverdines are composed of three structural parts: a dihydroxyquinoline chromophore, a side chain and a variable peptidic chain. The peptide chain moiety is involved in receptor recognition and binding. Three different Pvds, differing in their peptide chain, have been identified (types I-III; FIG. 1A-D). The size and amino acid composition of pyoverdine types are unique to each species, as well as the pyoverdine recognition specificity. Three *P. aeruginosa* strains can be distinguished, each producing a different pyoverdine type and a cognate FpvA receptor. Each type has three members (subtypes) differing in the side chain which is succinyl, succinamide or α-ketoglutaryl, namely, Pvd type I succinyl, Pvd type I succinamide, Pvd type I α-ketoglutaryl, Pvd type II succinyl, Pvd type II succinamide, Pvd type II α-ketoglutaryl, Pvd type III succinyl, Pvd type III succinamide and Pvd type III α-ketoglutaryl.

As used herein, "pyochelin" means a thiazoline derivatized conjugate of salicylate and two molecules of cysteine and having phenol, carboxylate, and amine ligand functionalities, produced by *P. aeruginosa* and solubilizing ferric iron. Pyochelin is a structurally unique siderophore possessing phenolate, but neither a hydroxamate nor a catecholate moiety (FIG. 1E).

The term "neutrophil gelatinase-associated lipocalin (hNGAL)" (also referred to as "human lipocalin 2" or "human Lcn 2" or "human NGAL" or simply "lipocalin"), as used herein, refers to the mature human neutrophil gelatinase-associated lipocalin (NGAL) with the SWISS-PROT/UniProt Data Bank Accession Number P80188. A human NGAL (hNGAL) mutein may also be designated herein as "lipocalin mutein" or simply "mutein". The amino acid sequence shown in SWISS-PROT/UniProt Data Bank Accession Number P80188 may be used as a particular "reference sequence". In one embodiment, the amino acid sequence shown in SEQ ID NO: 1 is used as reference sequence. Wild-type hNGAL does not bind to pyoverdines or pyochelin. The natural ligand of wild-type hNGAL is enterobactin, which docks into the calyx of hNGAL with high affinity.

As used herein, a "mutein," a "mutated" entity (whether protein or nucleic acid), or "mutant" refers to a modified version of a naturally occurring (wild-type) nucleic acid or protein or protein reference sequence/scaffold comprising an exchange, deletion, or insertion of one or more nucleotides or amino acids, compared to the naturally occurring (wild-type) nucleic acid or protein reference sequence/scaffold. Said term also includes fragments of a mutein and variants as described herein. Muteins for use in the fusion molecules of the invention, fragments or variants thereof may retain the function of binding to pyoverdine or pyochelin as described herein.

In one embodiment, the hNGAL muteins comprised by the first, second, third and fourth polypeptides are specific for or specifically bind to pyoverdine type I, II and III and pyochelin, respectively.

When used herein in the context of hNGAL muteins that bind to pyoverdine or pyochelin, the term "specific for" includes that the mutein is directed against, binds to, or reacts with pyoverdine or pyochelin, respectively. Thus, being directed to, binding to or reacting with includes that the mutein specifically binds to pyoverdine or pyochelin, respectively. The term "specifically" in this context means that the mutein reacts with a pyoverdine protein or a pyochelin protein, as described herein, but essentially not with another protein. The term "another protein" includes any non-pyoverdine or non-pyochelin protein, respectively, including proteins closely related to or being homologous to pyoverdine or pyochelin against which the muteins disclosed herein are directed to. However, pyoverdine or pyochelin proteins, fragments and/or variants from species other than human such as those described in the context of the definition "subject" are not excluded by the term "another protein". The term "does not essentially bind" means that the mutein of the present disclosure does not bind another protein, i.e., shows a cross-reactivity of less than 30%, particularly 20%, more particularly 10%, even more particularly less than 9, 8, 7, 6 or 5%. Whether the mutein specifically reacts as defined herein above can easily be tested, inter alia, by comparing the reaction of a lipocalin mutein of the present disclosure with pyoverdine or pyochelin and the reaction of said mutein with (an) other protein(s). "Specific binding" can also be determined, for example, in accordance with Western blots, ELISA-, RIA-, ECL-, IRMA-tests, FACS, IHC and peptide scans.

In one embodiment, the hNGAL muteins comprised by the first, second, third and fourth polypeptides bind to pyoverdine type I, II and III and pyochelin, respectively, with detectable affinity.

As used herein, "detectable affinity" means the ability to bind to a selected target with a dissociation constant $K_D$ of generally about $10^{-5}$ M or lower, e.g., about $10^{-6}$ M or lower, or about $10^{-7}$ M or lower. Lower affinities (i.e., higher $K_D$ values) are generally no longer measurable with common methods such as ELISA and therefore of secondary importance.

As used herein, "binding affinity" of a protein of the disclosure (e.g. a mutein of human lipocalin 2) to a selected target (in the present case, pyoverdine or pyochelin), can be measured (and thereby $K_D$ values of a mutein-ligand complex be determined) by a multitude of methods known to those skilled in the art. Such methods include, but are not limited to, fluorescence titration, direct ELISA, competition ELISA, calorimetric methods, such as isothermal titration calorimetry (ITC), and surface plasmon resonance (Biacore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, direct ELISA, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA".

In some embodiments, the mutein specific for pyoverdine (type I, II or III) as used in the fusion molecule of the invention is able to bind pyoverdine (type I, II or III, respectively) with a dissociation constant $K_D$ of 200 nM or lower, or about 100 nM or lower, or about 50 nM or lower, or about 25 nM or lower, or about 15 nM or lower. In some embodiments, the mutein specific for pyochelin as used in the fusion molecule of the invention is able to bind pyochelin with a dissociation constant $K_D$ of 200 nM or lower, or about 100 nM or lower, or about 50 nM or lower, or about 25 nM or lower, or about 15 nM or lower. In some further particular embodiments, a mutein of the fusion molecule according to the present invention binds pyoverdine (type I, II or III) or pyochelin, respectively, with a dissociation constant for pyoverdine (type I, II or III, respectively) or pyochelin of about 10 nM or lower, or about 5 nM or lower, or about 2 nM or lower, or about 1 nM or lower, or about 0.1 nM or lower, or about 10 pM or lower.

In particular embodiments, the fusion molecule of the invention binds pyoverdine (type I, II and III) and pyochelin with a respective dissociation constant $K_D$ of 200 nM or lower, or about 100 nM or lower, or about 50 nM or lower, or about 25 nM or lower, or about 15 nM or lower, or about 10 nM or lower, or about 5 nM or lower, or about 2 nM or lower, or about 1 nM or lower, or about 0.1 nM or lower, or about 10 pM or lower.

In one embodiment, the $K_D$ value is determined by surface plasmon resonance (Biacore), by competition ELISA, or by "direct ELISA".

hNGAL muteins for use in the fusion molecules of the present invention as well as methods for their generation and identification are disclosed/described in detail in EP 15 305 242.8 and PCT/EP2016/053226 as well as in the section "hNGAL muteins" below.

In a particular embodiment, an hNGAL mutein that is specific for pyoverdine type I is shown in any one of SEQ ID NOs: 2-18 (e.g., SEQ ID NO: 16). In a particular embodiment, an hNGAL mutein that is specific for pyoverdine type II is shown in any one of SEQ ID NOs: 19-37 (e.g., SEQ ID NO: 36). In a particular embodiment, an hNGAL mutein that is specific for pyoverdine type III is shown in any one of SEQ ID NOs: 38-53 (e.g., SEQ ID NO: 53). In a particular embodiment, an hNGAL mutein that is specific for pyochelin is shown in any one of SEQ ID NOs: 54-63 (e.g., SEQ ID NO: 62).

The term "covalently linked", as used herein, refers to linkage via a covalent bond or via a covalent linker molecule. In one embodiment, the first, second, third and fourth polypeptides are covalently linked via linker molecules.

The term "linker molecules", as used herein, refers to molecules adapted to connect/link protein moieties, e.g., the first, second, third and fourth polypeptides as defined herein. A linker molecule in accordance with the present invention may have any size/length. In some embodiments, the linker molecule is long enough to provide an adequate degree of flexibility to prevent the connected/linked moieties from interfering with each other's activity, for example by steric hindrance, and to allow for proper protein folding. In some embodiments, the linker molecule is short enough to provide stability (e.g., proteolytic stability) in the cell. Suitable linker molecules are known to a person skilled in the art and include, for example, peptides as well as non-peptidic molecules, e.g., non-peptidic oligomers and polymers of suitable lengths. According to the present invention, the various linker molecules within a single fusion molecule described herein may be the same or different.

In one embodiment, the linker molecules are peptide linkers. A peptide linker in accordance with the present invention may have any length, i.e., it may comprise any number of amino acid residues. In some embodiments, the linker is long enough to provide an adequate degree of flexibility to prevent the connected/linked moieties from interfering with each other's activity, for example by steric hindrance, and to allow for proper protein folding. In some embodiments, the linker is short enough to provide stability (e.g., proteolytic stability) in the cell. In some embodiments, the peptide linkers have a length of 1 to 30 amino acids, or a length of 1 to 25 amino acids, or a length of 1 to 20 amino acids, or a length of 1 to 15 amino acids, or a length of 1 to 12 amino acids or a length of 1 to 10 amino acids. Thus, according to the present invention, a peptide linker may be composed of a single amino acid residue, e.g., glycine (Gly, G).

The amino acids of a peptide linker in accordance with the present invention may be selected from all naturally or non-naturally occurring amino acids, in particular from the amino acids glycine (Gly, G), serine (Ser, S) and threonine (Thr, T). In one embodiment, the peptide linker is a glycine-serine-threonine-rich linker or glycine-serine-rich linker, wherein at least 50%, or at least 60%, or at least 70%, or at least 80%, or at least 90% of the amino acids are a glycine or serine or threonine residue or a glycine or serine residue, respectively. In another embodiment, the amino acids are selected from glycine, serine and threonine, i.e., the peptide linker is exclusively composed of glycine, serine and threonine residues (referred to as a glycine-serine-threonine linker). In yet another embodiment, the peptide linker is exclusively composed of glycine and serine residues (referred to as a glycine-serine linker).

In one embodiment, the peptide linker is a glycine-serine linker and has a length of 1 to 30 amino acids, or a length of 1 to 25 amino acids, or a length of 1 to 20 amino acids, or a length of 1 to 15 amino acids, or a length of 1 to 12 amino acids or a length of 1 to 10 amino acids. Particular peptide linkers in accordance with the present invention have the general formula $(GGGGX)_n$, wherein X is, at each occurrence, independently selected from S and T, and n is an integer selected from 1 to 5, or 1 to 4, or 1 to 3, or 1 and 2. In one embodiment, the peptide linker has the amino acid sequence of SEQ ID NO: 141. In another embodiment, the peptide linker has the amino acid sequence of SEQ ID NO: 142.

In one embodiment, the fusion molecule further comprises a multimerization domain allowing the multimerization of the fusion molecule. Multimerization may occur by non-covalent interaction and/or covalent interaction, in particular via one or more disulfide bonds, between multiple (e.g., 2, 3 or 4, particularly 2 or 3, more particularly 2) multimerization domains.

Suitable multimerization domains are known to a person skilled in the art and include, for example, trimerization domains, such as a tenascin trimerization motif, a collectin trimerization domain and streptavidin, and dimerization domains, such as an Fc domain, an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an uteroglobin dimerization domain. In one embodiment, the Fc domain is a human IgG4-Fc domain, which, in a particular embodiment, comprises or consists of the amino acid sequence of SEQ ID NO: 140. Also included are variants or fragments of any one of the foregoing domains, e.g., domains that have been modified so as to extend their half-life and/or increase their efficiency, as long as they still allow multimerization (e.g., dimerization) of the fusion molecule, i.e. are functional. Suitable modifications are known to a person skilled in the art and include, but are not limited to, modifications of the Fc domain which increase its affinity for FcRn, as described, for example, in Zalevsky, J. et al. (2010), Nature Biotechnology, 28(2): 157-9 (e.g., N434S, V259I/V308F, M252Y/S254T/T256E, M428L/N434S, and V259I/V308F/M428L).

In one embodiment, the fusion molecule has a general formula selected from the group consisting of

 N'-X$_1$-L$_1$-X$_2$-L$_2$-X$_3$-L$_3$-X$_4$-C' (I),

 N'-X$_1$-L$_1$-X$_2$-L$_2$-X$_3$-L$_3$-X$_4$-L$_4$-MD-C' (II),

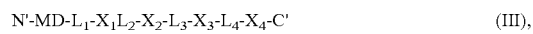 N'-MD-L$_1$-X$_1$L$_2$-X$_2$-L$_3$-X$_3$-L$_4$-X$_4$-C' (III),

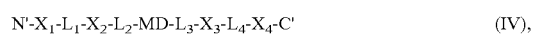 N'-X$_1$-L$_1$-X$_2$-L$_2$-MD-L$_3$-X$_3$-L$_4$-X$_4$-C' (IV),

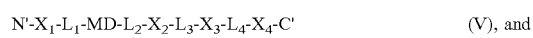 N'-X$_1$-L$_1$-MD-L$_2$-X$_2$-L$_3$-X$_3$-L$_4$-X$_4$-C' (V), and

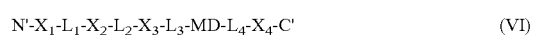 N'-X$_1$-L$_1$-X$_2$-L$_2$-X$_3$-L$_3$-MD-L$_4$-X$_4$-C' (VI)

wherein $X_1$, $X_2$, $X_3$ and $X_4$ are, at each occurrence, selected from the group consisting of the first, second, third and fourth polypeptides, with the proviso that the fusion molecule comprises each of the first, second, third and fourth polypeptides;

MD comprises a multimerization domain; and $L_1$, $L_2$, $L_3$ and $L_4$ are, at each occurrence, independently selected from a covalent bond and a linker molecule.

According to the present invention, $L_1$, $L_2$, $L_3$ and $L_4$ may be the same or different.

In one embodiment, the fusion molecule is present as a multimeric (e.g., dimeric) complex.

Therefore, in one aspect, the present invention also provides a multimere (or multimeric complex) comprising two or more fusion molecules described herein (e.g., a dimer or dimeric complex). Such complex may also be referred to as fusion molecule complex. In one embodiment, the two or more fusion molecules non-covalently or covalently (e.g., via disulfide bonds) associate to form the fusion molecule complex.

In one embodiment, the fusion molecule further comprises at least one label or tag allowing the detection and/or isolation of the fusion molecule.

A "label or tag allowing the detection and/or isolation of the fusion molecule" is meant to include any labels/tags known in the art for these purposes. They include affinity tags such as the Strep-Tag® or Strep-Tag® II (Schmidt, T. G. M. et al. (1996) J. Mol. Biol. 255, 753-766), the myc-tag, the FLAG-tag, the His6-tag or the HA-tag or proteins such as maltose binding protein (MBP) and glutathione-S-transferase (GST) as well as combinations thereof (e.g., Strep-Tag® or Strep-Tag® II and His-6-tag). Proteins with chromogenic or fluorescent properties such as the green fluorescent protein (GFP) or the yellow fluorescent protein (YFP) are suitable labels as well.

The amino acid sequence of a (poly)peptide label or tag may be introduced at any position within the amino acid sequence of the fusion molecule, and may, for example, take the shape of a loop within the encoded protein structure (e.g., within any of the peptide linkers described herein or even within the muteins as long as the label/tag does not interfere with their function), or it may be N-terminally or C-terminally fused. The label or tag may further contain a cleavage site that allows a removal of the label or tag from the fusion molecule. Similarly, non-peptidic labels or tags, e.g., fluorescent dyes, may be conjugated to the fusion molecule at any suitable site.

In general, it is possible to label the fusion molecules of the invention with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products.

The fusion molecule may also comprise an amino acid sequence for facilitating secretion of the molecule, such as an N-terminal secretion signal, or a signal sequence. The fusion molecule of the invention may further comprise a binding domain which serves, e.g., to enhance selectivity for a specific cell type. This can be achieved, e.g., by providing a binding domain that binds to a specific antigen expressed on the surface of said cell type.

In one embodiment, the fusion molecule further comprises one or more modifications increasing the stability of the fusion molecule and/or extending the serum half-life of the fusion molecule.

In one embodiment, "stability" of the fusion molecule relates to the "half-life" of the fusion molecule, e.g., in vivo. "Half-life" relates to the period of time which is needed to eliminate half of the activity, amount, or number of molecules.

The fusion molecule may in some embodiments be conjugated to a moiety that extends the serum half-life of the fusion molecule (in this regard see also PCT publication WO 2006/56464 A2 where such conjugation strategies are described with references to muteins of human neutrophil gelatinase-associated lipocalin with binding affinity for CTLA-4). The moiety that extends the serum half-life may be a polyalkylene glycol molecule, hydroxyethyl starch, polysialic acid, fatty acid molecules, such as palmitic acid (Vajo & Duckworth 2000, Pharmacol. Rev. 52, 1-9), an Fc part of an immunoglobulin, a CH3 domain of an immunoglobulin, a CH4 domain of an immunoglobulin, an albumin binding peptide, an albumin binding protein, or transferrin to name only a few. The albumin binding protein may be a bacterial albumin binding protein, an antibody, an antibody fragment including domain antibodies (see U.S. Pat. No. 6,696,245, for example), or a mutein with binding activity for albumin. Accordingly, suitable conjugation partners for extending the half-life of a fusion molecule of the invention include an albumin binding protein, for example, a bacterial albumin binding domain, such as the one of streptococcal protein G (König, T., & Skerra, A. (1998) J. Immunol. Methods 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) J Biol Chem 277, 35035-35043).

In other embodiments, albumin itself (Osborn, B. L. et al., 2002, J. Pharmacol. Exp. Ther. 303, 540-548), or a biological active fragment of albumin can be used as conjugation partner of a fusion molecule of the invention. The term "albumin" includes all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombuminq Novozymes Delta Ltd. (Nottingham, UK) can be conjugated or fused to a fusion molecule of the invention in order to extend the half-life of the fusion molecule.

If the albumin-binding protein is an antibody fragment it may be a domain antibody. Domain antibodies (dAbs) are engineered to allow precise control over biophysical properties and in vivo half-life to create the optimal safety and efficacy product profile. Domain antibodies are for example commercially available from Domantis Ltd. (Cambridge, UK and MA, USA).

Using transferrin as a moiety to extend the serum half-life of the fusion molecules of the invention, the fusion molecules can be genetically fused to the N- or C-terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of each of the at least four muteins linked to the Fc region of an antibody to improve pharmacokinetics, solubility, and production efficiency.

Yet another alternative to prolong the half-life of the fusion molecules of the invention is to fuse to the N- or C-terminus of the fusion molecules long, unstructured, flexible glycine-rich sequences (for example poly-glycine with about 20 to 80 consecutive glycine residues). This approach disclosed in WO 2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins J. Control. Release 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as, e.g., described in U.S. Pat. No. 6,500,930 or 6,620,413, carbohydrate oligo- and polymers such as starch or hydroxyethyl starch (HES) can be conjugated to a fusion molecule of the invention for the purpose of serum half-life extension.

In one embodiment, the fusion molecules of the invention are fused at their N-terminus and/or their C-terminus to a fusion partner which is a protein domain that extends the serum half-life of the fusion molecules. In further particular embodiments, the protein domain is an Fc part of an immunoglobulin, a CH3 domain of an immunoglobulin, a CH4 domain of an immunoglobulin, an albumin binding peptide, or an albumin binding protein.

In another embodiment, the fusion molecules of the invention are conjugated to a compound that extends the serum half-life of the fusion molecules. More particularly, the mutein is conjugated to a compound selected from the group consisting of a polyalkylene glycol molecule, a hydroxyethyl starch, an Fc part of an immunoglobulin, a CH3 domain of an immunoglobulin, a CH4 domain of an immunoglobulin, an albumin binding peptide, and an albumin binding protein.

In one embodiment, the fusion molecule inhibits or reduces iron-uptake by *P. aeruginosa* through pyochelin and/or pyoverdine.

In one embodiment, the fusion molecule reduces virulence factor expression by *P. aeruginosa*.

In one embodiment, the fusion molecule inhibits or reduces *P. aeruginosa* bacterial growth.

In one embodiment, the fusion molecule is associated with or conjugated/fused to a pharmaceutically active agent. Such conjugates can be produced by methods well known in the art.

In one embodiment, the pharmaceutically active agent is selected from the group consisting of an antibiotic, a cytostatic agent, a toxin, an enzyme, a metal or metal compound/complex, a chelating agent, a radionuclide, a small organic molecule, a therapeutically active peptide, a therapeutically active nucleic acid molecule, a hapten and an antibody.

Suitable antibiotics include Tobramycin, Azithromycin, Aztreonam, Colistin and carbapenems.

Suitable metals or metal compounds/complexes are gallium, gallium compounds and gallium-based complexes.

The term "small organic molecule", as used herein, refers to an organic molecule comprising at least two carbon atoms having a molecular weight in the range between 100 and 2000 Dalton. In some embodiments, the organic molecule comprises not more than 7 or 12 rotatable carbon bonds. In some embodiments, the organic molecule has a molecular weight in the range between 100 and 1000 Dalton, or <900 Dalton, and optionally including one or two metal atoms.

The term "therapeutically active peptide" refers, e.g., to peptides acting as agonists/antagonists of a cell surface receptor or peptides competing for a protein binding site on a given cellular target.

The term "therapeutically active nucleic acid molecule" refers, e.g., to antisense nucleic acid molecules, small interfering RNAs, micro RNAs or ribozymes.

In one embodiment, the fusion molecule comprises or consists of an amino acid sequence selected from the group consisting of SEQ ID NOs: 134 to 139 and SEQ ID NOs: 143 to 186, wherein, in particular embodiments, the amino acid sequences of SEQ ID NOs: 144 to 186 lack the (C-terminal) Strep-Tag® II and His6 tags. In one embodiment, the fusion molecule comprises or consists of the amino acid sequence of SEQ ID NO: 134 or SEQ ID NO: 136.

B. hNGAL Muteins for Use in the Fusion Molecules of the Present Invention

In some embodiments, an hNGAL mutein binding pyoverdine (type I, II or III) or pyochelin may include at least one amino acid substitution of a native cysteine residue (e.g., the cysteine residue at position 87 of the linear polypeptide sequence of human NGAL, SEQ ID NO: 1) by another amino acid, for example, a serine residue. In some other embodiments, a mutein binding pyoverdine or pyochelin may include one or more non-native cysteine residues substituting one or more amino acids of wild-type hNGAL. In a further particular embodiment, an hNGAL mutein according to the disclosure includes at least two amino acid substitutions of a native amino acid by a cysteine residue, thereby to form one or more cysteine bridges. In some embodiments, said cysteine bridge may connect at least two loop regions. The definition of these regions is used herein in accordance with Flower (Flower, 1996, Flower, et al., 2000) and Breustedt et al. (2005).

In some embodiments, an hNGAL mutein of the disclosure does not bind to enterobactin.

In one aspect, the present disclosure includes various hNGAL muteins that bind pyoverdine or pyochelin, e.g., with at least detectable affinity. In this sense, pyoverdine or pyochelin is regarded as a non-natural ligand of the reference wild-type hNGAL, where "non-natural ligand" refers to a compound that does not bind to wild-type human lipocalin 2 under physiological conditions. By engineering wild-type hNGAL with one or more mutations at certain sequence positions, the present inventors have demonstrated that high affinity and high specificity for the non-natural ligand, pyoverdine or pyochelin, is possible. In some embodiments, at 1, 2, 3, 4, 5, 6, 7, 8, 9, 10, 11, 12 or even more nucleotide triplet(s) encoding certain sequence positions on wild-type human lipocalin 2, a random mutagenesis may be carried out through substitution at these positions by a subset of nucleotide triplets.

The muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of hNGAL, such as sequence positions 28, 34, 36, 39-42, 44-47, 49, 52, 54, 55, 65, 68, 70, 72-75, 77, 79-81, 87, 96, 100, 103, 106, 108, 123, 125, 127, 132, 134, 141 and 145 of the linear polypeptide sequence of human NGAL (SEQ ID NO: 1). In some embodiments, the mutated amino acid residue represents a conservative substitution. In some embodiments, the mutated amino acid residue represents a non-conservative substitution. In some embodiments, the hNGAL mutein comprises a mutated amino acid residue at one or more positions corresponding to positions 28, 54, 65 and 87 of the linear polypeptide sequence of the mature hNGAL (SEQ ID NO: 1).

A mutein of the disclosure may include the wild-type (natural) amino acid sequence of the "parental" protein scaffold (such as hNGAL) outside the mutated amino acid sequence positions. In some embodiments, an hNGAL mutein according to the disclosure may also carry one or more amino acid mutations at a sequence position/positions as long as such a mutation does not substantially hamper or interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human lipocalin 2 as long as these deletions or insertion result in a stable folded/functional mutein (for example, hNGAL muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature hNGAL. As an illustrative example, the present disclosure also encompasses hNGAL muteins as defined above, in which four amino acid residues (G-N-I-K; positions 95-98; SEQ ID NO: 130) of the linear polypeptide sequence of the mature hNGAL have been deleted (e.g. SEQ ID NO: 46).

The amino acid sequence of an hNGAL mutein disclosed herein has a high sequence identity to the mature hNGAL (SEQ ID NO: 1) when compared to sequence identities with other lipocalins. In this general context, the amino acid sequence of a mutein of the disclosure is at least substantially similar to the amino acid sequence of the natural wild-type hNGAL, e.g., with the proviso that possibly there are gaps (as defined below) in an alignment that are the result of additions or deletions of amino acids. A respective sequence of a mutein of the disclosure, being substantially similar to the sequences of the mature hNGAL, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the mature hNGAL, e.g., with the proviso that the altered position or sequence is retained and that one or more gaps are possible.

a) hNGAL Muteins Specific for Pyoverdine

In one aspect, the present disclosure relates to specific-binding human lipocalin 2 (human Lcn2 or hNGAL) muteins specific for one type of pyoverdine, such as Pvd type I, Pvd type II or Pvd type III.

One embodiment of the current disclosure relates to a mutein that is capable of binding one type of pyoverdine, e.g., with detectable affinity, such as an affinity measured by a $K_D$ of about 200 nM or lower, such as about 150 nM or lower.

In one aspect, the current disclosure provides an hNGAL mutein that is capable of binding Pvd type I complexed with iron with a $K_D$ of about 20 nM or lower, such as 15 nM or lower, for example, when measured by Biacore T200 instrument in an assay essentially described in Example 6.

In some further embodiments, one or more hNGAL muteins of this disclosure are capable of binding Pvd type I succinyl, Pvd type I succinamide and Pvd type I α-ketoglutaryl with and without complexed iron, with an affinity measured by an $IC_{50}$ value of about 200 nM or lower, for example, when measured in an ELISA assay essentially described in Example 5.

In some embodiments, the mutein is capable of inhibiting iron uptake mediated by pyoverdine type I succinyl with an $IC_{50}$ value of about 150 nM or lower, for example, in a competition ELISA format essentially described in Example 7.

In some embodiments, the mutein is capable of inhibiting bacterial growth of Pvd I strain, for example, in an assay essentially described in Example 8.

In this regard, the disclosure relates to a polypeptide (e.g., a first polypeptide as referred to herein), wherein said polypeptide comprises or consists of an hNGAL mutein, and said hNGAL mutein in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at any one or more of sequence positions 28, 36, 39-41, 46, 49, 52, 54, 55, 59, 65, 68, 70, 72-75, 77, 79-81, 87, 96, 100, 103, 106, 125, 127, 132, 134 and 136 of SEQ ID NO: 1, and wherein said polypeptide binds Pvd type I, including Pvd type I succinyl, Pvd type I succinamide and Pvd type I α-ketoglutaryl.

In some embodiments, a Pvd-type-1-binding hNGAL mutein of the disclosure includes, at any one or more of the sequence positions 36, 40-41, 49, 52, 68, 70, 72, 73, 77, 79, 81, 96, 100, 103, 106, 125, 127, 132 and 134 of the linear polypeptide sequence of the mature hNGAL (SEQ ID NO: 1), one or more of the following mutated amino acid residues: Leu 36→Asn, Thr, Val, Trp or Phe; Ala 40→Gly, Asn, Thr or Phe; Ile 41→Arg, Ala, Thr, Phe or Trp; Gln 49→Ile, Leu, Val, Ala or Pro; Tyr 52→Met, Trp or Pro; Ser 68→Asp, Val or Glu; Leu 70→Gln, Trp, Asp or Thr; Arg 72→Trp, Ala, Ser, Leu, Pro or Glu; Lys 73→Asp, Leu, Ala, Glu or Asn; Asp 77→Arg, Leu, Tyr, Ser, Gln, Thr, Ile or Asn; Trp 79→Gln, Asp, Ser, Arg, Met or Glu; Arg 81→Gln, Gly, Ile, Glu, His or Asp; Asn 96→His, Ile, Gly, Tyr or Asp; Tyr 100→Lys, Glu, Asn, Ser, Phe or Tyr; Leu 103→Lys, Pro, Gln, His, Asp, Tyr, Glu, Trp or Asn; Tyr 106→His, Gln or Phe; Lys 125→Arg, Ser, Trp, Tyr, Val or Gly; Ser 127→Trp, Asn, Ala, Thr, Tyr, His, Ile, Val or Asp; Tyr 132→Trp, Asn, Gly or Lys; and Lys 134→Asn, His, Trp, Gly, Gln or Asp. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a Pvd-type-1-binding hNGAL mutein according to the disclosure may also comprise one or more or all of the following substitutions in comparison with the linear polypeptide sequence of the mature hNGAL: Gln 28→His; Lys 46→Glu; Thr 54→Val or Ala; Ile 55→Val; Lys 59→Arg; Asn 65→Asp or Gln; Ile 80→Thr; Cys 87→Ser or Asn; and Thr 136→Ala.

In some additional embodiments, an hNGAL mutein of the disclosure, which binds to Pvd type I, includes the following amino acid replacements in comparison with the linear polypeptide sequence of the mature hNGAL:
 (a) Gln 28→His; Leu 36→Asn; Ala 40→Gly; Ile 41→Trp; Gln 49→Ile; Tyr 52→Met; Ser 68→Val; Leu 70→Gln; Arg 72→Trp; Lys 73→Asp; Asp 77→Leu; Trp 79→Gln; Arg 81→Gln; Cys 87→Ser; Asn 96→His; Tyr 100→Lys; Leu 103→His; Tyr 106→His; Lys 125 Arg; Ser 127 Trp; Tyr 132 Trp; Lys 134 Asp;
 (b) Gln 28→His; Leu 36→Thr; Ala 40→Gly; Ile 41→Phe; Gln 49→Leu; Tyr 52→Trp; Leu 70→Trp;

Arg 72→Ala; Lys 73→Leu; Asp 77→Tyr; Trp 79→Asp; Arg 81→Gly; Cys 87→Ser; Asn 96→Ile; Tyr 100→Glu; Leu 103→His; Tyr 106→Gln; Lys 125→Trp; Ser 127 Asn; Tyr 132 Asn; Lys 134→Gln;

(c) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Arg 81→Ile; Cys 87→Ser; Asn 96→Gly; Tyr 100→Asn; Leu 103→Lys; Tyr 106→His; Lys 125 Tyr; Ser 127→Ala; Tyr 132→Gly; Lys 134→Asn;

(d) Gln 28→His; Leu 36→Phe; Ala 40→Asn; Ile 41→Arg; Gln 49→Pro; Tyr 52→Met; Ser 68→Asp; Leu 70→Thr; Arg 72→Glu; Lys 73→Ala; Asp 77→Arg; Trp 79→Arg; Arg 81→Ile; Cys 87→Ser; Asn 96→Tyr; Tyr 100→Lys; Leu 103→Pro; Tyr 106 Phe; Lys 125→Ser; Ser 127→Thr; Tyr 132→Trp; Lys 134→Gly;

(e) Gln 28→His; Ala 40→Gly; Ile 41→Trp; Gln 49→Val; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96 Asp; Tyr 100→Phe; Leu 103→Trp; Tyr 106→Gln; Lys 125→Gly; Ser 127 Tyr; Tyr 132 Trp; Lys 134→His;

(f) Gln 28→His; Leu 36→Val; Ala 40→Phe; Ile 41→Phe; Gln 49→Ala; Tyr 52→Pro; Ser 68→Glu; Leu 70→Trp; Arg 72→Leu; Lys 73→Asn; Asp 77→Gln; Trp 79→Glu; Arg 81→His; Cys 87→Ser; Asn 96→Tyr; Leu 103→Tyr; Tyr 106→His; Lys 125→Val; Ser 127→His; Tyr 132→Lys; Lys 134→Trp;

(g) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Ile; Tyr 132→Gly; Lys 134→Asn;

(h) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Asp; Asp 77→Ser; Trp 79→Ser; Arg 81→Ile; Cys 87→Ser; Asn 96→Gly; Tyr 100→Asn; Leu 103→Asp; Tyr 106→His; Lys 125 Tyr; Ser 127→Val; Tyr 132→Gly; Lys 134 Asn;

(i) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Glu; Asp 77→Thr; Trp 79→Ser; Arg 81→Ile; Cys 87→Ser; Asn 96→Asp; Tyr 100→Asn; Leu 103→Glu; Tyr 106→His; Lys 125→Tyr; Ser 127→Asp; Tyr 132→Gly; Lys 134→Asn;

(j) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Asp; Asp 77→Val; Trp 79→Ser; Arg 81→Ile; Cys 87→Ser; Asn 96→Gly; Tyr 100→Asn; Leu 103→Asn; Tyr 106→His; Lys 125 Tyr; Ser 127→Val; Tyr 132→Gly; Lys 134 Asn;

(k) Gln 28→His; Ala 40→Gly; Ile 41→Trp; Gln 49→Leu; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Ser; Leu 103→Trp; Tyr 106→Gln; Lys 125→Gly; Ser 127→Tyr; Tyr 132→Trp; Lys 134→His;

(l) Gln 28→His; Leu 36→Trp; Ala 40 Thr; Ile 41→Thr; Gln 49→Pro; Tyr 52→Pro; Thr 54→Val; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134 Asn;

(m) Gln 28→His; Ala 40→Gly; Ile 41→Trp; Lys 46→Glu; Gln 49→Leu; Tyr 52→Met; Thr 54→Ala; Ile 55→Val; Lys 59→Arg; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87 Asn; Asn 96 Asp; Tyr 100→Ser; Leu 103→Trp; Tyr 106→Gln; Lys 125→Gly; Ser 127→Tyr; Tyr 132 Trp; Lys 134→His;

(n) Leu 36→Trp; Asn 39→Asp; Ala 40 Thr; Ile 41→Thr; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127 Thr; Tyr 132→Gly; Lys 134 Asn; Thr 136→Ala;

(o) Leu 36→Trp; Ala 40 Thr; Ile 41→Ala; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134 Asn; Thr 136→Ala;

(p) Gln 28→His; Ala 40→Gly; Ile 41→Trp; Lys 46→Glu; Gln 49→Leu; Tyr 52→Met; Thr 54→Ala; Ile 55→Val; Lys 59→Arg; Asn 65→Asp; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→Ser; Leu 103 Trp; Tyr 106→Gln; Lys 125→Gly; Ser 127→Tyr; Tyr 132→Trp; Lys 134→His; or (q) Gln 28→His; Ala 40→Gly; Ile 41→Trp; Lys 46→Glu; Gln 49→Leu; Tyr 52→Met; Thr 54→Ala; Ile 55→Val; Lys 59→Arg; Asn 65→Gln; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→Ser; Leu 103 Trp; Tyr 106→Gln; Lys 125→Gly; Ser 127→Tyr; Tyr 132→Trp; Lys 134→His.

In the residual region, i.e. the region differing from sequence positions 28, 36, 39-41, 46, 49, 52, 54-55, 59, 65, 68, 70, 72-75, 77, 79-81, 87, 96, 100, 103, 106, 125, 127, 132, 134 and 136, an hNGAL mutein of the disclosure may include the wild-type (natural) amino acid sequence outside the mutated amino acid sequence positions.

In further particular embodiments, a mutein according to the current disclosure comprises an amino acid sequence selected from the group consisting of SEQ ID NOs: 2-18 or a Pvd-type-1-binding fragment or variant thereof.

The amino acid sequence of a Pvd-type-1-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 2-18.

The disclosure also includes structural homologues of an hNGAL mutein having an amino acid sequence selected from the group consisting of SEQ ID NOs: 2-18, which structural homologues have an amino acid sequence homology or sequence identity of more than about 60%, particularly more than 65%, more than 70%, more than 75%, more than 80%, more than 85%, more than 90%, more than 92% and most particularly more than 95% in relation to said hNGAL mutein.

A Pvd-type-1-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

In another aspect, the current disclosure provides an hNGAL mutein that binds Pvd type II complexed with iron with a $K_D$ of about 20 nM or lower, such as 5 nM or lower, for example, when measured by Biacore 1200 instrument in an assay essentially described in Example 6.

In some still further embodiments, one or more hNGAL muteins of this disclosure are capable of binding Pvd type II succinyl, Pvd type II succinamide and Pvd type II α-ketoglutaryl with and without complexed iron, with an affinity measured by an $IC_{50}$ value of about 200 nM or lower, for example, when measured in an ELISA assay essentially described in Example 5.

In some embodiments, the mutein is capable of inhibiting iron uptake mediated by pyoverdine type II succinyl with an $IC_{50}$ value of about 150 nM or lower, for example, in a competition ELISA format essentially described in Example 7.

In some embodiments, the mutein is capable of inhibiting bacterial growth of Pvd II strain, for example, in an assay essentially described in Example 8.

In some other embodiments, the mutein is capable of inhibiting or lessening growth of *P. aeruginosa* stains expressing pyoverdine type II, for example, in an assay essentially described in Example 10.

In this regard, the disclosure relates to a polypeptide (e.g., a second polypeptide as referred to herein), wherein said polypeptide comprises or consists of an hNGAL mutein, and said hNGAL mutein in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at any one or more of sequence positions 28, 36, 40, 41, 49, 52, 54, 65, 68, 70, 72-75, 77, 79, 81, 87, 96, 100, 103, 106, 125, 127, 132 and 134 of SEQ ID NO: 1, and wherein said polypeptide binds Pvd type II.

In some embodiments, a Pvd-type-II-binding hNGAL mutein of the disclosure includes, at any one or more of the sequence positions 36, 40, 41, 49, 52, 68, 70, 72-73, 77, 79, 81, 87, 96, 100, 103, 106, 125, 127, 132 and 134 of the linear polypeptide sequence of the mature hNGAL (SEQ ID NO: 1), one or more of the following mutated amino acid residues: Leu 36→Asn, Ile or Val; Ala 40→Glu, Gly, Asn, Thr or His; Ile 41→Arg, Val or Thr; Gln 49→Gly, Ala or Pro; Tyr 52→Asn, Gly, Trp or Pro; Ser 68→Asp, Arg or Glu; Leu 70→Arg or Trp; Arg 72→His, Ile, Ala, Ser or Gly; Lys 73→Asn, Met, Pro, Phe, Gln or Arg; Asp 77→His, Ile, Met, Lys, Gly or Asn; Trp 79→Ser, Tyr, Ala, Asp, Phe or Trp; Arg 81→Glu, Ser, Tyr or Asp; Asn 96→Met, Ile, Arg, Asp, Lys, Asn or Ala; Tyr 100→Lys, Glu, Asn, Ser, Phe or Tyr; Leu 103→Thr, Ile, Gln, Gly, Met, His, Trp or Val; Tyr 106→Met, Gln, Ala, Ile, Asn, Gly, Met or Phe; Lys 125→Ala, Ile or Asn; Ser 127→Lys, Arg, Ser, Met, Asp or Asn; Tyr 132→Met, Phe, Asn, Ala, Ile, Gly or Val; and Lys 134→Trp or Tyr. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a Pvd-type-II-binding hNGAL mutein according to the disclosure may also comprise one or more or all of the following substitutions in comparison with the linear polypeptide sequence of the mature hNGAL: Gln 28→His; Thr 54→Ala; Asn 65→Asp or Gln and Cys 87→Ser.

In some additional embodiments, an hNGAL mutein of the disclosure, which binds to Pvd type II, includes the following amino acid replacements in comparison with the linear polypeptide sequence of the mature hNGAL:

(a) Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Tyr 100→Asn; Leu 103→Gln; Tyr 106→Met; Ser 127p Lys; Tyr 132→Gly; Lys 134 Trp;

(b) Gln 28→His; Ala 40→Thr; Ile 41→Ile; Gln 49→Gly; Tyr 52→Asn; Ser 68→Asp; Leu 70→Arg; Arg 72→Ile; Lys 73→Met; Asp 77→His; Trp 79→Tyr; Arg 81→Glu; Cys 87→Ser; Asn 96→Ile; Tyr 100→Asn; Leu 103→Thr; Tyr 106→Gln; Lys 125→Ile; Ser 127→Arg; Tyr 132→Met; Lys 134→Trp;

(c) Gln 28→His; Leu 36→Ile; Ala 40 Thr; Ile 41→Val; Gln 49→Gly; Tyr 52→Pro; Ser 68→Glu; Leu 70→Arg; Arg 72→Ala; Lys 73→Pro; Asp 77→Ile; Trp 79→Ser; Arg 81→Ser; Cys 87→Ser; Asn 96→Met; Tyr 100→Ser; Leu 103→Gly; Tyr 106→Ala; Lys 125→Lys; Tyr 132→Val; Lys 134→Trp;

(d) Gln 28→His; Ala 40→Asn; Gln 49→Ala; Tyr 52→Pro; Ser 68→Glu; Leu 70→Arg; Arg 72→Ser; Lys 73→Gln; Asp 77→Met; Trp 79→Ala; Arg 81→Tyr; Cys 87→Ser; Asn 96→Arg; Tyr 100→Pro; Leu 103→Thr; Tyr 106→Ile; Lys 125→Lys; Ser 127p Met; Tyr 132→Phe; Lys 134 Trp;

(e) Gln 28→His; Ala 40→His; Gln 49→Ala; Tyr 52→Pro; Ser 68→Glu; Leu 70→Asp; Arg 72→Gly; Lys 73→Arg; Asp 77→His; Trp 79→Trp; Arg 81→Glu; Cys 87→Ser; Asn 96→Arg; Tyr 100→Asp; Leu 103→Met; Tyr 106→Phe; Lys 125→Ala; Ser 127→Asp; Tyr 132→Asn; Lys 134→Trp;

(f) Gln 28→His; Leu 36→Asn; Ala 40→Gly; Ile 41→Arg; Gln 49→Pro; Tyr 52→Trp; Ser 68→Arg; Leu 70→Trp; Arg 72→Asn; Lys 73→Gln; Asp 77→Lys; Trp 79→Asp; Arg 81→Glu; Cys 87→Ser; Asn 96→Asp; Tyr 100→Thr; Leu 103→Trp; Tyr 106→Asn; Lys 125→Asn; Ser 127→Met; Tyr 132→Ile; Lys 134→Tyr;

(g) Gln 28→His; Leu 36→Val; Ala 40 Thr; Ile 41→Thr; Gln 49→Gly; Tyr 52→Gly; Ser 68→Glu; Leu 70→Arg; Arg 72→Gly; Lys 73→Arg; Asp 77→Gly; Trp 79→Trp; Arg 81→Glu; Cys 87→Ser; Asn 96→Ala; Tyr 100→Trp; Leu 103→Ile; Tyr 106→Gly; Lys 125→Lys; Ser 127 Asn; Tyr 132→Val; Lys 134→Trp;

(h) Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

(i) Gln 28→His; Leu 36→Val; Ala 40→Thr; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Leu 103→Gln; Tyr 106→Met; Ser 127→Lys; Tyr 132→Val; Lys 134→Trp;

(j) Gln 28→His; Leu 36→Val; Ala 40→Thr; Ile 41→Val; Gln 49→Gly; Tyr 52→Pro; Ser 68→Glu; Leu 70→Arg; Arg 72→His; Asp 77→Asn; Trp 79→Phe; Arg 81→Glu; Cys 87→Ser; Asn 96→Lys; Tyr 100→His; Leu 103→Gln; Tyr 106→Met; Ser 127p Lys; Tyr 132→Ala; Lys 134→Trp;

(k) Gln 28→His; Leu 36→Val; Ala 40→Gly; Ile 41→Val; Gln 49→Gly; Tyr 52→Pro; Ser 68→Glu; Leu 70→Arg; Arg 72→His; Lys 73→Asn; Asp 77→Asn; Trp 79→Trp; Arg 81→Glu; Cys 87→Ser; Tyr 100→Asn; Leu 103→His; Tyr 106→Met; Ser 127p Lys; Tyr 132→Gly; Lys 134 Trp;

(l) Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Phe; Asp 77→His; Trp 79→Tyr; Arg 81→Asp; Cys 87→Ser; Leu 103→Met; Tyr 106→Gln; Lys 125→Ile; Ser 127 Arg; Tyr 132→Ile; Lys 134→Trp;

(m) Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127 Arg; Tyr 132→Ile; Lys 134→Trp;

(n) Gln 28→His; Leu 36→Val; Ala 40→Glu; Ile 41→Val; Gln 49→Gly; Tyr 52→Pro; Asn 65→Asp; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

(o) Gln 28→His; Leu 36→Val; Ala 40→Glu; Ile 41→Val; Gln 49→Gly; Tyr 52→Pro; Asn 65→Gln; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

(p) Gln 28→His; Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106 Gln; Lys 125→Ile; Ser 127→Arg; Tyr 132→Ile; Lys 134→Trp;

(q) Gln 28→His; Leu 36→Val; Ala 40→Thr; Ile 41→Ile; Gln 49→Gly; Tyr 52→Asn; Thr 54→Ala; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

(r) Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp; or (s) Gln 28→His; Leu 36→Val; Ala 40→Thr; Ile 41→Ile; Gln 49→Gly; Tyr 52→Asn; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127 Arg; Tyr 132→Ile; Lys 134→Trp.

In the residual region, i.e. the region differing from sequence positions 28, 36, 40-41, 49, 52, 54, 65, 68, 70, 72-75, 77, 79, 81, 87, 96, 100, 103, 106, 125, 127, 132 and 134, an hNGAL mutein of the disclosure may include the wild-type (natural) amino acid sequence outside the mutated amino acid sequence positions.

In further particular embodiments, a mutein according to the current disclosure comprises an amino acid sequence selected from the group consisting of SEQ ID NOs: 19-37 or a Pvd-type-II-binding fragment or variant thereof.

The amino acid sequence of a Pvd-type-II-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 19-37.

The disclosure also includes structural homologues of an hNGAL mutein having an amino acid sequence selected from the group consisting of SEQ ID NOs: 19-37, which structural homologues have an amino acid sequence homology or sequence identity of more than about 60%, particularly more than 65%, more than 70%, more than 75%, more than 80%, more than 85%, more than 90%, more than 92% and most particularly more than 95% in relation to said hNGAL mutein.

A Pvd-type-II-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

In still another aspect, the current disclosure provides an hNGAL mutein that binds Pvd type III complexed with iron with a $K_D$ of about 20 nM or lower, such as 10 nM or lower, for example, when measured by Biacore 1200 instrument in an assay essentially described in Example 6.

In some still further embodiments, one or more hNGAL muteins of this disclosure are capable of binding Pvd type III succinyl, Pvd type III succinamide and Pvd type III α-ketoglutaryl with and without complexed iron, with an affinity measured by an $IC_{50}$ value of about 200 nM or lower, for example, when measured in an ELISA assay essentially described in Example 5.

In some embodiments, the mutein is capable of inhibiting iron uptake mediated by pyoverdine type III with an $IC_{50}$ value of about 150 nM or lower, for example, in a competition ELISA format essentially described in Example 7.

In some embodiments, the mutein is capable of inhibiting bacterial growth of Pvd III strain, for example, in an assay essentially described in Example 8.

In this regard, the disclosure relates to a polypeptide (e.g., a third polypeptide as referred to herein), wherein said polypeptide comprises or consists of an hNGAL mutein, and said hNGAL mutein in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at any one or more of sequence positions 28, 36, 40-42, 45-47, 49, 52, 65, 68, 70, 72, 73, 77, 79, 81, 87, 96, 100, 103, 105, 106, 125, 127, 132, 134 and 145 of SEQ ID NO: 1, and wherein said polypeptide binds Pvd type III.

In some embodiments, a Pvd-type-III-binding hNGAL mutein of the disclosure includes, at any one or more of the sequence positions 36, 40, 41, 49, 52, 68, 70, 72, 73, 77, 79, 81, 96, 100, 103, 106, 125, 127, 132 and 134 of the linear polypeptide sequence of the mature hNGAL (SEQ ID NO: 1), one or more of the following mutated amino acid residues: Leu 36→Phe or Glu; Ala 40→Trp, Leu or Arg; Ile 41→Met, Arg, Ala, Leu or Trp; Gln 49→His, Ile, Arg, Lys, Met or Pro; Tyr 52→Asn, Tyr, Arg, Ser or Met; Ser 68→Asp, Asn, Glu or Gln; Leu 70→Lys, Asn or Arg; Arg 72→Leu, Arg, Gln or Tyr; Lys 73→His, Leu, Ala, Pro, Gln or Tyr; Asp 77→Ala, Ile, Lys, Gln or Arg; Trp 79→Ser or Asp; Arg 81→His, Ala, Ser or Val; Asn 96→Met, Ile, Arg, Gly, Leu or Val; Tyr 100→Ala, Ile, Asn, Pro or Asp; Leu 103→Gln, Gly, Phe or Pro; Tyr 106→Glu; Lys 125→Trp or Thr; Ser 127→Val, His, Ile, Phe or Ala; Tyr 132→Phe; and Lys 134→Trp, Gln or Glu. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a Pvd-type-III-binding hNGAL mutein according to the disclosure may also comprise one or more or all of the following substitutions in comparison with the linear polypeptide sequence of the mature hNGAL: Gln 28→His; Leu 42→Arg; Asp 45→Gly; Lys 46→Arg; Asp 47→Asn; Asn 65→Asp; Cys 87→Ser; Ser 105→Pro and Thr 145→Pro.

In some additional embodiments, an hNGAL mutein of the disclosure, which binds to Pvd type III, includes the following amino acid replacements in comparison with the linear polypeptide sequence of the mature hNGAL:

(a) Gln 28→His; Leu 36→Phe; Ala 40→Trp; Ile 41→Met; Gln 49→His; Tyr 52→Asn; Ser 68→Glu; Leu 70→Lys; Arg 72→Gln; Lys 73→Ala; Asp 77→Ile; Trp 79→Ser; Arg 81→His; Cys 87→Ser; Asn 96→Ile; Tyr 100→Asn; Leu 103→Gly; Tyr 106→Glu; Lys 125→Trp; Ser 127→His; Tyr 132→Phe; Lys 134→Gln;

(b) Gln 28→His; Leu 36→Phe; Ala 40→Arg; Ile 41→Trp; Gln 49→Ile; Tyr 52→Tyr; Ser 68→Gln; Leu 70→Asn; Arg 72→Trp; Lys 73→Leu; Asp 77→Ala; Trp 79→Ser; Arg 81→Ser; Cys 87→Ser; Asn 96→Arg; Tyr 100→Ile; Leu 103→Pro; Tyr 106→Glu; Lys 125→Thr; Ser 127→Ile; Tyr 132→Phe; Lys 134→Glu;

(c) Gln 28→His; Leu 36→Phe; Ala 40→Leu; Ile 41→Leu; Gln 49→Arg; Tyr 52→Arg; Ser 68→Asp; Leu 70→Arg; Arg 72→Leu; Lys 73→Tyr; Asp 77→Ile; Trp 79→Ser; Arg 81→Ala; Cys 87→Ser; Asn 96→Gly; Tyr 100→Ala; Leu 103→Phe; Tyr 106→Glu; Lys 125→Trp; Ser 127→Ala; Lys 134→Glu;

(d) Gln 28→His; Leu 36→Phe; Ala 40→Trp; Ile 41→Arg; Gln 49→Pro; Tyr 52→Ser; Ser 68→Asn; Leu 70→Arg; Arg 72→Trp; Lys 73→Pro; Asp 77→Arg; Trp 79→Ser; Arg 81→Ser; Cys 87→Ser; Asn 96→Met; Tyr 100→Pro; Leu 103→Gly; Tyr 106→Glu; Lys 125→Trp; Ser 127→Phe; Tyr 132→Phe; Lys 134→Glu;

(e) Gln 28→His; Leu 36→Glu; Ala 40→Leu; Ile 41→Ala; Gln 49→Lys; Tyr 52→Met; Ser 68→Glu; Leu 70→Arg; Lys 73→His; Asp 77→Gln; Trp 79→Asp; Arg 81→Ala; Cys 87→Ser; Asn 96→Leu; Tyr 100→Asp; Leu 103→Gln; Tyr 106→Glu; Ser 127→Val; Tyr 132→Phe; Lys 134→Trp;

(f) Gln 28→His; Leu 36→Glu; Ala 40→Leu; Ile 41→Ala; Gln 49→Met; Tyr 52→Met; Ser 68→Glu; Leu 70→Arg; Lys 73→Gln; Asp 77→Lys; Trp 79→Asp; Arg 81→Val; Cys 87→Ser; Asn 96→Leu; Tyr 100→Asp; Leu 103→Gln; Tyr 106→Glu; Ser 127→Val; Tyr 132→Phe; Lys 134→Trp;

(g) Gln 28→His; Leu 36→Glu; Ala 40→Leu; Ile 41→Thr; Gln 49→Met; Tyr 52→Met; Ser 68→Glu; Leu 70→Arg; Lys 73→Arg; Asp 77→Lys; Trp 79→Asp; Arg 81→Val; Cys 87→Ser; Asn 96→Val; Tyr 100→Asp; Leu 103→Gln; Tyr 106→Glu; Ser 127→Val; Tyr 132→Phe; Lys 134→Trp;

(h) Gln 28→His; Leu 36→Glu; Ala 40→Leu; Ile 41→Ala; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Tyr 106→Glu; Ser 127→Val; Tyr 132→Phe; Lys 134→Trp;

(i) Gln 28→His; Leu 36→Glu; Ala 40→Leu; Ile 41→Ala; Gln 49→Lys; Tyr 52→Met; Ser 68→Glu; Leu 70→Arg; Lys 73→Tyr; Asp 77→Gln; Trp 79→Asp; Arg 81→Val; Cys 87→Ser; Asn 96→— (e.g., deletion of the four amino acids Gly 95, Asn 96, Ile 97 and Lys 98); Tyr 100→Glu; Leu 103→Gln; Tyr 106→Glu; Ser 127→Val; Tyr 132→Phe; Lys 134 Trp;

(j) Gln 28→His; Leu 36→Glu; Ala 40→Leu; Ile 41→Ala; Leu 42→Arg; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

(k) Gln 28→His; Leu 36→Glu; Ala 40→Leu; Ile 41→Ala; Asp 47→Asn; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

(l) Gln 28→His; Leu 36→Glu; Ala 40→Leu; Ile 41→Ala; Asp 45→Gly; Lys 46→Arg; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

(m) Gln 28→His; Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

(n) Gln 28→His; Leu 36→Glu; Ala 40→Leu; Ile 41→Ala; Asp 47→Asn; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

(o) Gln 28→His; Leu 36→Glu; Ala 40→Leu; Ile 41→Ala; Asp 45→Gly; Lys 46→Arg; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr

100→Asp; Leu 103→Gln; Ser 105→Pro; Tyr 106→Glu; Ser 127→Val; Tyr 132→Phe; Lys 134→Trp; or (p) Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127 Val; Tyr 132→Phe; Lys 134→Trp.

In the residual region, i.e. the region differing from sequence positions 28, 36, 40-42, 45-47, 49, 52, 65, 68, 70, 72-73, 77, 79, 81, 87, 96, 100, 103, 105-106, 125, 127, 132, 134 and 145, an hNGAL mutein of the disclosure may include the wild-type (natural) amino acid sequence outside the mutated amino acid sequence positions.

In further particular embodiments, a mutein according to the current disclosure comprises an amino acid sequence selected from the group consisting of SEQ ID NOs: 38-53 or a Pvd-type-III-binding fragment or variant thereof.

The amino acid sequence of a Pvd-type-III-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 38-53.

The disclosure also includes structural homologues of an hNGAL mutein having an amino acid sequence selected from the group consisting of SEQ ID NOs: 38-53, which structural homologues have an amino acid sequence homology or sequence identity of more than about 60%, particularly more than 65%, more than 70%, more than 75%, more than 80%, more than 85%, more than 90%, more than 92% and most particularly more than 95% in relation to said hNGAL mutein.

A Pvd-type-III-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

b) Applications of Muteins Specific for Pyoverdine

Numerous possible applications for the pyoverdine-binding muteins of the disclosure, therefore, exist in medicine. In one further aspect, the disclosure relates to the use of a pyoverdine-binding mutein disclosed herein for detecting pyoverdine (type I, II or III) in a sample as well as a respective method of diagnosis.

The present disclosure also involves the use of one or more pyoverdine-binding muteins as described for complex formation with pyoverdine (type I, II or III).

Therefore, in another aspect of the disclosure, the disclosed muteins are used for the detection of pyoverdine (type I, II or III). Such use may include the steps of contacting one or more said muteins, under suitable conditions, with a sample suspected of containing pyoverdine, thereby allowing formation of a complex between the muteins and pyoverdine (type I, II or III), and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The pyoverdine-binding muteins disclosed herein may also be used for the separation of pyoverdine (type I, II or III). Such use may include the steps of contacting one or more said muteins, under suitable conditions, with a sample supposed to contain pyoverdine (type I, II and/or III), thereby allowing formation of a complex between the muteins and pyoverdine (type I, II or III), and separating the complex from the sample.

In the use of the disclosed muteins for the detection of pyoverdine as well as the separation of pyoverdine (type I, II or III), the muteins and/or pyoverdine or a domain or fragment thereof may be immobilized on a suitable solid phase.

In still another aspect, the present disclosure features a diagnostic or analytical kit comprising a pyoverdine-binding mutein according to the disclosure.

In addition to their use in diagnostics, in yet another aspect, the disclosure encompasses the use of a pyoverdine-binding mutein of the disclosure or a composition comprising such mutein for the binding of pyoverdine (type I, II or III) in a subject and/or inhibiting or lessening growth of *P. aeruginosa* in a subject.

In still another aspect, the present disclosure features a method of binding pyoverdine (type I, II or III) in a subject, comprising administering to said subject an effective amount of one or more pyoverdine-binding muteins of the disclosure or of one or more compositions comprising such muteins.

In still another aspect, the present disclosure involves a method for inhibiting or lessening growth of *P. aeruginosa* in a subject, comprising administering to said subject an effective amount of one or more pyoverdine-binding muteins of the disclosure or of one or more compositions comprising such muteins.

c) hNGAL Muteins Specific for Pyochelin

In one aspect, the present disclosure relates to an hNGAL mutein that binds pyochelin complexed with iron with a $K_D$ of about 20 nM or lower, such as 1 nM or lower, for example, when measured by Biacore 1200 instrument in an assay essentially described in Example 6.

In some still further embodiments, one or more hNGAL muteins of this disclosure are capable of binding pyochelin with complexed iron, with an affinity measured by an $IC_{50}$ value of about 500 nM or lower, for example, when measured in an ELISA assay essentially described in Example 5.

In some still further embodiments, one or more hNGAL muteins of this disclosure are capable of binding pyochelin without complexed iron, with an affinity measured by an $IC_{50}$ value of about 200 nM or lower, for example, when measured in an ELISA assay essentially described in Example 5.

In some still further embodiments, one or more hNGAL muteins of this disclosure are capable of binding pyochelin with and without complexed iron, with an affinity measured by an $IC_{50}$ value of about 200 nM or lower, for example, when measured in an ELISA assay essentially described in Example 5.

In some embodiments, the mutein is capable of inhibiting iron uptake mediated by pyochelin with an $IC_{50}$ value of about 150 nM or lower, for example, in a competition ELISA format essentially described in Example 7.

In some embodiments, the mutein is capable of inhibiting bacterial growth of Pvd I knock-out (ΔpvdA), for example, in an assay essentially described in Example 8.

In this regard, the disclosure relates to a polypeptide (e.g., a fourth polypeptide as referred to herein), wherein said polypeptide comprises or consists of an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at any one or more of sequence positions 28, 34, 36, 40, 41, 44-46, 49, 52, 54, 65, 68, 70, 72-74, 77, 79-81, 87, 96, 100, 103, 106, 108, 123, 125, 127, 132, 134 and 141 of SEQ ID NO:1, and wherein said polypeptide binds pyochelin.

In some embodiments, a pyochelin-binding hNGAL mutein of the disclosure includes, at any one or more of the sequence positions 36, 40, 41, 49, 52, 68, 70, 72, 73, 77, 79, 81, 87, 96, 100, 103, 106, 125, 127, 132 and 134 of the linear polypeptide sequence of the mature hNGAL (SEQ ID NO: 1), one or more of the following mutated amino acid residues: Leu 36→His, Met or Val; Ala 40→Ile, Gln, Tyr or Phe; Ile 41→Leu, His or Trp; Gln 49→His, Arg, Ser or Ala; Tyr 52→Leu, Trp or Pro; Ser 68→Asp or His; Leu 70→Arg or Trp; Arg 72→His, Ile, Ala, Ser or Gly; Lys 73→Asn, Met, Pro, Phe, Gln or Arg; Asp 77→Arg, Thr, Pro or Asp; Trp 79→Ala, Arg, Lys or Asp; Arg 81 Thr, Ile or Trp; Asn 96→Met, Asn, Pro or Ala; Tyr 100→Gly, His or Glu; Leu 103→Gly, Met, His or Gln; Tyr 106→Met, Gly, Arg or Trp; Lys 125→Trp, Phe, Gly or Leu; Ser 127→Arg, Trp, Asp or Ile; Tyr 132→Ala, Glu or Thr; and Lys 134→Leu, Val, Asn or Phe. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a pyochelin-binding hNGAL mutein according to the disclosure may also comprise one or more or all of the following substitutions in comparison with the linear polypeptide sequence of the mature hNGAL: Gln 28→His; Val 34→Leu; Glu 44→Gly; Asp 45→Gly; Lys→Arg or Tyr; Asn 65→Asp; Ile 80→Thr; Cys 87→Ser; Leu 94→Phe; Val 108→Ala; Phe 123→Ser and Thr 141→Ala.

In some additional embodiments, an hNGAL mutein of the disclosure, which binds to pyochelin, includes the following amino acid replacements in comparison with the linear polypeptide sequence of the mature hNGAL:

(a) Gln 28→His; Ala 40→Ile; Ile 41→Leu; Gln 49→His; Tyr 52→Leu; Ser 68→His; Leu 70→Thr; Arg 72→Lys; Lys 73→Trp; Asp 77→Ile; Trp 79→Ser; Arg 81→His; Cys 87→Ser; Asn 96→Met; Tyr 100→Asn; Leu 103→His; Tyr 106→Met; Lys 125→Trp; Ser 127→Asp; Tyr 132→Glu; Lys 134→Leu;

(b) Gln 28→His; Leu 36→His; Ala 40→Gln; Ile 41→Trp; Gln 49→Arg; Tyr 52→Trp; Ser 68→Asp; Leu 70→Asp; Arg 72→Ala; Lys 73→Ile; Asp 77→His; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

(c) Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Arg 81→Ile; Cys 87→Ser; Asn 96→Ala; Tyr 100→Gly; Leu 103→Met; Tyr 106→Trp; Lys 125→Gly; Ser 127→Trp; Tyr 132→Thru; Lys 134→Val;

(d) Gln 28→His; Leu 36→Val; Ala 40→Tyr; Ile 41→Trp; Gln 49→Ala; Ser 68→Asp; Leu 70→Arg; Arg 72 Trp; Lys 73→Arg; Asp 77→Arg; Trp 79→Asp; Arg 81 Trp; Cys 87→Ser; Asn 96→Pro; Tyr 100→Glu; Leu 103→Gln; Tyr 106→Arg; Lys 125→Leu; Ser 127→Arg; Tyr 132→Ala; Lys 134→Asn;

(e) Gln 28→His; Val 34→Leu; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val; Thr 141→Ala;

(f) Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val;

(g) Gln 28→His; Leu 36→His; Ala 40→Gln; Ile 41→Trp; Asp 45→Gly; Lys 46→Arg; Gln 49→Arg; Tyr 52→Trp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

(h) Gln 28→His; Leu 36→His; Ala 40→Gln; Ile 41→Trp; Glu 44→Gly; Lys 46→Tyr; Gln 49→Arg; Tyr 52→Trp; Ser 68→Asp; Leu 70→Asp; Arg 72→Ala; Lys 73→Ile; Lys 74→Glu; Asp 77→His; Trp 79→Arg; Arg 81→Thr; Cys 87→Ser; Leu 94→Phe; Tyr 100→His; Leu 103→Gly; Tyr 106→Gly; Val 108→Ala; Lys 125→Phe; Ser 127→Ile; Tyr 132→Ala; Lys 134→Phe; or (i) Leu 36→His; Ala 40→Gln; Ile 41→Trp; Asp 45→Gly; Lys 46→Arg; Gln 49→Arg; Tyr 52→Trp; Asn 65→Asp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe.

In the residual region, i.e. the region differing from sequence positions 28, 34, 36, 40, 41, 44-46, 49, 52, 54, 65, 68, 70, 72-74, 77, 79-81, 87, 96, 100, 103, 106, 108, 123, 125, 127, 132, 134 and 141, an hNGAL mutein of the disclosure may include the wild-type (natural) amino acid sequence outside the mutated amino acid sequence positions.

In further particular embodiments, a mutein according to the current disclosure comprises an amino acid sequence selected from the group consisting of SEQ ID NOs: 54-63 or a pyochelin-binding fragment or variant thereof.

The amino acid sequence of a pyochelin-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 54-63.

The disclosure also includes structural homologues of an hNGAL mutein having an amino acid sequence selected from the group consisting of SEQ ID NOs: 54-63, which structural homologues have an amino acid sequence homology or sequence identity of more than about 60%, particularly more than 65%, more than 70%, more than 75%, more than 80%, more than 85%, more than 90%, more than 92% and most particularly more than 95% in relation to said hNGAL mutein.

A pyochelin-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

d) Applications of Muteins Specific for Pyochelin

Numerous possible applications for the pyochelin-binding muteins of the disclosure, therefore, exist in medicine. In one further aspect, the disclosure relates to the use of such a mutein disclosed herein for detecting pyochelin in a sample as well as a respective method of diagnosis.

The present disclosure also involves the use of one or more muteins with binding-affinity for pyochelin as described for complex formation with pyochelin.

Therefore, in another aspect of the disclosure, the disclosed muteins are used for the detection of pyochelin. Such use may include the steps of contacting one or more said muteins, under suitable conditions, with a sample suspected of containing pyochelin, thereby allowing formation of a complex between the muteins and pyochelin, and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The muteins disclosed herein may also be used for the separation of pyochelin. Such use may include the steps of contacting one or more said muteins, under suitable conditions, with a sample supposed to contain pyochelin, thereby allowing formation of a complex between the muteins and pyochelin, and separating the complex from the sample.

In the use of the disclosed muteins for the detection of pyochelin as well as the separation of pyochelin, the muteins and/or pyochelin or a domain or fragment thereof may be immobilized on a suitable solid phase.

Accordingly, the presence or absence of a molecule such as pyochelin, e.g., in a sample, as well as its concentration or level may be determined.

In still another aspect, the present disclosure features a diagnostic or analytical kit comprising a pyochelin-binding mutein according to the disclosure.

In addition to their use in diagnostics, in yet another aspect, the disclosure encompasses the use of such a mutein of the disclosure or a composition comprising such mutein for the binding of pyochelin in a subject and/or inhibiting or lessening growth of *P. aeruginosa* in a subject.

In still another aspect, the present disclosure features a method of binding pyochelin in a subject, comprising administering to said subject an effective amount of one or more pyochelin-binding muteins of the disclosure or of one or more compositions comprising such a mutein.

In still another aspect, the present disclosure involves a method for inhibiting or lessening growth of *P. aeruginosa* in a subject, comprising administering to said subject an effective amount of one or more muteins with binding-affinity for pyochelin of the disclosure or of one or more compositions comprising such a mutein.

e) Compositions comprising pyoverdine-binding muteins and/or pyochelin-binding muteins and combinations of the muteins The present disclosure encompasses use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin for the binding of pyoverdine type I, II, III and/or pyochelin in a subject. Such use includes a step of administering to a subject an effective amount of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin. The present disclosure also contemplates the use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin for preventing or reducing iron-uptake by *P. aeruginosa* through pyochelin and/or pyoverdine in a subject. Similarly, the present disclosure discloses the use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin for the treatment or alleviation of *P. aeruginosa* infection and/or biofilm formation in a subject. In some further embodiments, the *P. aeruginosa* infection can be acute or chronic infections.

The first, second, third and/or fourth muteins or polypeptides thereof may be administered in combination, including concurrently, concomitantly or in series. In some embodiments, the first, second, third and/or fourth muteins or polypeptides thereof may be included in a composition that may be administered. The composition may include an effective amount of the first, second, third and/or fourth muteins or polypeptides thereof as active ingredients, in association with at least one pharmaceutically acceptable adjuvant, diluent or carrier. The first, second, third and/or fourth muteins or polypeptides thereof may also be administered independent from each other, including at individual intervals at independent points of time.

In some embodiments, the mutein specific for pyoverdine (type I, II or III) as used in the disclosure is able to bind pyoverdine (type I, II or III, respectively), e.g., with detectable affinity, i.e. with a dissociation constant of about 200 nM or lower, or about 100 nM or lower, or about 50 nM or lower, or about 25 nM or lower, or about 15 nM or lower. In some embodiments, the mutein specific for pyochelin as used in the disclosure is able to bind pyochelin, e.g., with detectable affinity, i.e. with a dissociation constant of about 200 nM or lower, or about 100 nM or lower, or about 50 nM or lower, or about 25 nM or lower, or about 15 nM or lower. In some further embodiments, a mutein of the combination according to the disclosure binds pyoverdine (type I, II or III) or pyochelin, respectively, with a dissociation constant for pyoverdine (type I, II or III, respectively) or pyochelin of about 10 nM or lower, or about 1 nM or lower, or about 0.1 nM or lower, or about 10 pM or lower. The present disclosure, thus, provides a combination of (i) a mutein of hNGAL that binds to pyoverdine type I (Pvd I s, sa, αKG+/−Fe), (ii) a mutein of hNGAL that binds to pyoverdine type II (Pvd II s, sa, αKG+/−Fe), (iii) a mutein of hNGAL that binds to pyoverdine type III (Pvd III s, sa, αKG+/−Fe) and/or (iv) a mutein of hNGAL that binds to pyochelin (Pch+/−Fe).

Further details on hNGAL muteins that bind to pyoverdine can be found in above section a) of the current disclosure.

In a particular embodiment, a mutein that is specific for pyoverdine type I is shown in any one of SEQ ID NOs: 2-18. In a particular embodiment, a mutein that is specific for pyoverdine type II is shown in any one of SEQ ID NOs: 19-37. In a particular embodiment, a mutein that is specific for pyoverdine type III is shown in any one of SEQ ID NOs: 38-53.

Further details of hNGAL muteins that bind to pyochelin have been disclosed in above section c) of the current disclosure.

In a particular embodiment, the mutein that is specific for pyochelin is shown in any one of SEQ ID NOs: 54-63.

The present disclosure also relates to a composition comprising at least one of the following: (i) a first mutein or polypeptide thereof specific for pyoverdine type I, (ii) a second mutein or polypeptide thereof specific for pyoverdine type II, (iii) a third mutein or polypeptide thereof specific for pyoverdine type III and (iv) a fourth mutein or polypeptide thereof specific for pyochelin, which composition can be used in a method of binding of pyoverdine type I, II, III and/or pyochelin.

The present disclosure relates to a combination of a first mutein or polypeptide or composition thereof, a second mutein or polypeptide or composition thereof, a third mutein or polypeptide or composition thereof, and/or a fourth mutein or polypeptide or composition thereof. One of these muteins can bind to pyoverdine (type I, II or III) as a given non-natural target, e.g., with detectable affinity. One of these muteins can bind to pyochelin as a given non-natural target, e.g., with detectable affinity. The respective mutein thus binds to pyoverdine type I, II, III or pyochelin, respectively, as a given non-natural target. The term "non-natural target" refers to a compound, which does not bind to the corresponding lipocalin (the wild-type hNGAL) under physiological conditions. For example, the first mutein or polypeptide or composition thereof can bind to one type of pyoverdine (type I, II or III) or pyochelin and the second, the third or the fourth mutein or polypeptide or composition thereof can bind to pyochelin or an another type of pyoverdine respectively, or vice versa. The combination of the first, the second, the third and/or the fourth muteins or polypeptides or compositions thereof may be provided in various forms and orientations.

In still another aspect, the present disclosure features a method of binding pyoverdine type I, II, III and/or pyochelin in a subject, comprising administering to said subject an effective amount of a composition that comprises at least one of the following: (i) a mutein or polypeptide thereof specific for pyoverdine type I, (ii) a mutein or polypeptide thereof specific for pyoverdine type II, (iii) a mutein or polypeptide thereof specific for pyoverdine type III and (iv) a mutein or polypeptide thereof specific for pyochelin. In some embodiments, such composition comprises two or more of, e.g., three or even all of (i)-(iv).

In still another aspect, the present disclosure features a method for inhibiting or lessening growth of P. aeruginosa in a subject, comprising administering to said subject an effective amount of a composition that comprises at least one of the following: (i) a mutein or polypeptide thereof specific for pyoverdine type I, (ii) a mutein or polypeptide thereof specific for pyoverdine type II, (iii) a mutein or polypeptide thereof specific for pyoverdine type III and (iv) a mutein or polypeptide thereof specific for pyochelin. In some embodiments, such composition comprises two or more of, e.g., three or even all of (i)-(iv).

The present disclosure also features the use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III, and/or (iv) a fourth mutein or polypeptide thereof specific for pyochelin, for complex formation with pyoverdine type I, II, III and/or pyochelin.

Therefore, in another aspect of the disclosure, the disclosed muteins or polypeptides can be used for the detection of pyoverdine and pyochelin. Such use may include the steps of contacting one or more said muteins or polypeptides, under suitable conditions, with a sample suspected of containing pyoverdine and/or pyochelin, thereby allowing formation of a complex between the muteins or polypeptides and pyoverdine and/or between the muteins and pyochelin, respectively, and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The muteins or polypeptides disclosed herein may also be used for the separation of pyoverdine and/or pyochelin. Such use may include the steps of contacting one or more said muteins, under suitable conditions, with a sample supposed to contain pyoverdine and/or pyochelin, thereby allowing formation of a complex between the muteins and pyoverdine and/or between the muteins and pyochelin, respectively, and separating the complex from the sample.

In the use of the disclosed muteins or polypeptides for the detection of pyoverdine and/or pyochelin as well as the separation of pyoverdine and/or pyochelin, the muteins and/or pyoverdine and pyochelin or a domain or fragment thereof may be immobilized on a suitable solid phase.

Accordingly, the presence or absence of pyoverdine and/or pyochelin, e.g., in a sample, as well as its concentration or level, may be determined.

In another aspect, the disclosure provides for a kit of parts. The kit includes, in one or more containers, separately or in a mixture, a mutein or polypeptide specific for pyoverdine type I or composition thereof, a mutein or polypeptide specific for pyoverdine type II or composition thereof, a mutein or polypeptide specific for pyoverdine type III or composition thereof, and/or a mutein or polypeptide specific for pyochelin or composition thereof. In some further embodiments, the kit comprises a first container that includes a first mutein or polypeptide specific for pyoverdine type I or composition thereof, a second container that includes a second mutein or polypeptide specific for pyoverdine type II or composition thereof, a third container that includes a third mutein or polypeptide specific for pyoverdine type III or composition thereof, and/or a fourth container that includes a fourth mutein or polypeptide specific for pyochelin or composition thereof. In some embodiments the kit further includes integrally thereto or as one or more separate documents, information pertaining to the contents or the kit and the use of the muteins or polypeptides thereof. The kit may include in some embodiments one or more compositions that are formulated for reconstitution in a diluent. Such a diluent, e.g. a sterile diluent, may also be included in the kit, for example within a container.

f) hNGAL Muteins and Variants and Fragments Thereof

The amino acid sequence of a mutein according to the disclosure has a high sequence identity to human lipocalin 2 when compared to sequence identities with another lipocalin (see also above). In this general context the amino acid sequence of a mutein of the combination according to the disclosure is at least substantially similar to the amino acid sequence of the corresponding lipocalin (the wild-type hNGAL). A respective sequence of a mutein of the combination according to the disclosure, being substantially similar to the sequence of mature hNGAL, such as at least 65%, at least 70%, at least 75%, at least 80%, at least 82%, at least 85%, at least 87%, at least 90% identity, including at least 95% identity to the sequence of mature hNGAL. In this regard, a mutein of the disclosure of course may contain, in comparison substitutions as described herein which renders the mutein capable of binding to pyoverdine type I, II, III or pyochelin, respectively. Typically, a mutein of hNGAL includes one or more mutations—relative to the native sequence of hNGAL—of amino acids in the four loops at the open end of the ligand binding site of hNGAL. As explained above, these regions are essential in determining the binding specificity of a mutein for pyoverdine type I, II, III or pyochelin. A mutein derived hNGAL or a homologue thereof, may have one, two, three, four or more mutated amino acid residues at any sequence position in the N-terminal region and/or in the three peptide loops BC, DE, and FG arranged at the end of the 6-barrel structure that is located opposite to the natural binding pocket.

A mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native hNGAL, provided that such a mutein should be capable of binding to pyoverdine or pyochelin, respectively. For example, a mutein can have a substitution at a position corresponding to a distinct position (i.e. at a corresponding position) of hNGAL. In some embodiments a mutein of the combination according to the disclosure includes at least two amino acid substitutions, including 2, 3, 4, 5, or even more, amino acid substitutions of a native amino acid by an arginine residue. Accordingly, the nucleic acid of a protein 'reference' scaffold as described herein is subject to mutagenesis with the aim of generating a mutein which is capable of binding to pyoverdine type I, II, III or pyochelin, respectively.

Also, a mutein disclosed herein can comprise a heterologous amino acid sequence at its N- or C-terminus, in particular at its C-terminus, such as a Strep-Tag®, e.g., Strep-Tag® II without affecting the biological activity (binding to its target e.g. pyoverdine or pyochelin, respectively) of the mutein.

Specifically, in order to determine whether an amino acid residue of the amino acid sequence of a mutein different from wild-type hNGAL corresponds to a certain position in the amino acid sequence of wild-type hNGAL, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, wild-type hNGAL can serve as "subject sequence" or "reference sequence", while the amino acid sequence of a mutein different from the wild-type hNGAL described herein serves as "query sequence". The terms "reference sequence" and "wild-type sequence" are used interchangeably herein.

In some embodiments a substitution (or replacement) is a conservative substitution. Nevertheless, any substitution—including non-conservative substitution or one or more from the exemplary substitutions listed below—is envisaged as long as the mutein retains its capability to bind to pyoverdine type I, II, III or pyochelin, respectively, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

a. Alanine (Ala), Glycine (Gly);
b. Aspartic acid (Asp), Glutamic acid (Glu);
c. Asparagine (Asn), Glutamine (Gln);
d. Arginine (Arg), Lysine (Lys);
e. isoleucine (Ile), Leucine (Leu), Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of hNGAL are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: asparitic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of hNGAL also may be substituted, generally with serine, to improve the oxidative stability of the molecule and prevent aberrant crosslinking. Conversely, cysteine bond (s) may be added to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of hNGAL as long as these deletions or insertion result in a stable folded/functional mutein.

Modifications of the amino acid sequence include directed mutagenesis of single amino acid positions in order to simplify sub-cloning of the mutated hNGAL gene or its parts by incorporating cleavage sites for certain restriction enzymes. In addition, these mutations can also be incorporated to further improve the affinity of a mutein for a given target such as pyoverdine or pyochelin. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective mutein.

It is also possible to mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages.

In some embodiments, if one of the above moieties is conjugated to a mutein of the disclosure, conjugation to an amino acid side chain can be advantageous. Suitable amino acid side chains may occur naturally in the amino acid sequence of hNGAL or may be introduced by mutagenesis. In case a suitable binding site is introduced via mutagenesis, one possibility is the replacement of an amino acid at the appropriate position by a cysteine residue.

With respect to a mutein of human lipocalin 2, exemplary possibilities of such a mutation to introduce a cysteine residue into the amino acid sequence of a lipocalin including human lipocalin 2 mutein to include the introduction of a cysteine (Cys) residue at least at one of the sequence positions that correspond to sequence positions 14, 21, 60, 84, 88, 116, 141, 145, 143, 146 or 158 of the wild-type sequence of human NGAL. In some embodiments where a human lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human lipocalin 2 mutein.

In another embodiment, in order to provide suitable amino acid side chains for conjugating one of the above compounds to a mutein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

For several applications of the muteins disclosed herein it may be advantageous to use them in the form of fusion proteins. In some embodiments, a mutein of the disclosure is fused at its N-terminus or its C-terminus to a protein, a protein domain or a peptide, for instance, a signal sequence and/or an affinity tag, as described herein in connection with the fusion molecules of the invention. A mutein of the disclosure may also be conjugated to a moiety that extends the serum half-life of the mutein, as described herein in connection with the fusion molecules of the invention. A mutein of the disclosure may also be conjugated/fused to a pharmaceutically active agent, as described herein in connection with the fusion molecules of the invention.

In general, all labels commonly used for antibodies (except those exclusively used with the sugar moiety in the Fc part of immunoglobulins) can also be used for conjugation to the muteins of the disclosure. The muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The muteins of the disclosure may, however, also be conjugated with therapeutically active nucleic acids such as antisense nucleic acid molecules, small interfering RNAs, micro RNAs or ribozymes. Such conjugates can be produced by methods well known in the art.

In addition, a mutein disclosed herein may be fused to a moiety to confer new characteristics to the muteins of the disclosure such as enzymatic activity or binding affinity for other molecules. Examples of suitable fusion partners are alkaline phosphatase, horseradish peroxidase, glutathione-S-transferase, the albumin-binding domain of protein G, protein A, antibody fragments, oligomerization domains and toxins.

In particular, it may be possible to fuse a mutein disclosed herein with a separate enzyme active site such that both "components" of the resulting fusion protein together act on a given therapeutic target. The binding domain of the mutein attaches to the disease-causing target, allowing the enzyme domain to abolish the biological function of the target.

In one embodiment of the disclosure, the method includes subjecting the nucleic acid molecule to mutagenesis at nucleotide triplets coding for at least one, or even more, of the sequence positions corresponding to the sequence positions 28, 34, 36, 39-42, 44-47, 49, 52, 54-55, 65, 68, 70, 72-75, 77, 79-81, 87, 96, 100, 103, 106, 108, 123, 125, 127, 132, 134, 141 and 145 of the linear polypeptide sequence of human NGAL (SEQ ID NO: 1).

The disclosure also includes nucleic acid molecules encoding the muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

The term "fragment" as used herein in connection with the muteins of the disclosure relates to proteins or peptides derived from full-length mature human lipocalin 2 or muteins thereof that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature human lipocalin 2 or mutein thereof and are usually detectable in an immunoassay of the mature human lipocalin 2. In general, the term "fragment", as used herein with respect to the corresponding protein ligand of a mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature human lipocalin 2 can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild-type protein. Such an insertion or deletion may be introduced independently from each other in any of the peptide segments that can be subjected to mutagenesis in the disclosure.

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100 percent.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any mutein of the disclosure).

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, for example using the wild-type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a mutein different from the wild-type human lipocalin 2 corresponds to a certain position in the amino acid sequence of the wild-type human lipocalin 2, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, the wild-type human lipocalin 2 can serve as "subject sequence" or "reference sequence", while the amino acid sequence of a mutein different from the wild-type human lipocalin 2 described herein serves as "query sequence". The terms "reference sequence" and "wild-type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By a "native sequence" human lipocalin 2 is meant human lipocalin 2 that has the same amino acid sequence as the corresponding polypeptide derived from nature. Thus, a native sequence human lipocalin 2 can have the amino acid sequence of the respective naturally-occurring human lipocalin 2. Such native sequence polypeptide can be isolated from nature or can be produced by recombinant or synthetic means. The term "native sequence" polypeptide specifically encompasses naturally-occurring truncated or secreted forms of the human lipocalin 2, naturally-occurring variant forms such as alternatively spliced forms and naturally-occurring allelic variants of human lipocalin 2. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) human lipocalin 2. Similarly, the position of a given nucleotide in accordance with the present disclosure which may be substituted may vary due to deletions or additional nucleotides elsewhere in a mutein or wild-type human lipocalin 2 5'-untranslated region (UTR) including the promoter and/or any other regulatory sequences or gene (including exons and introns).

Thus, for a corresponding position in accordance with the disclosure, it is to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a mutein based on a reference scaffold in accordance with the disclosure, it is to be understood that the positions of nucleotides/amino acids are structurally corresponding to the positions elsewhere in a mutein or wild-type human lipocalin 2, even if they may differ in the indicated number.

C. Nucleic Acid Molecules

The present invention also relates to nucleic acid molecules (DNA and RNA) that include nucleotide sequences encoding the fusion molecules of the invention. Since the degeneracy of the genetic code permits substitutions of certain codons by other codons specifying the same amino acid, the invention is not limited to a specific nucleic acid molecule encoding a fusion molecule as described herein but encompasses all nucleic acid molecules that include nucleotide sequences encoding a functional fusion molecule.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding the transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e.

DNA elements directing the initiation of transcription, as well as DNA elements which, when transcribed into RNA, will signal the initiation of translation. Such promoter regions normally include 5 non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, such as a promoter sequence. In some embodiments, a nucleic acid molecule of the invention includes a promoter sequence and a transcriptional termination sequence. Suitable prokaryotic promoters are, for example, the tet promoter, the lacUV5 promoter or the T7 promoter. Examples of promoters useful for expression in eukaryotic cells are the 5V40 promoter or the CMV promoter.

In one embodiment, the nucleic acid molecule is comprised in a vector. The term "vector", as used herein, includes any vectors known to the skilled person, including plasmid vectors, cosmid vectors, phage vectors, such as lambda phage, phagemids or phasmids, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments. Large numbers of suitable expression and cloning vectors are known in the art, and are commercially available.

In one embodiment, the nucleic acid molecule is included in a phasmid (also known as phagemid). A phasmid vector denotes a vector encoding the intergenic region of a temperent phage, such as M13 or f1, or a functional part thereof fused to the cDNA of interest. After superinfection of the bacterial host cells with such an phasmid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) Annu. Rev. Biophys. Biomol. Struct. 26, 401-424, or Rodi, D. J., and Makowski, L. (1999) Curr. Opin. Biotechnol. 10, 87-93).

The DNA molecule encoding a fusion molecule as described herein, and in particular a vector containing the coding sequence of such a fusion molecule can be transformed or transfected into a host cell capable of expressing the gene. Transformation or transfection can be performed using standard techniques. Thus, the invention is also directed to a host cell containing a nucleic acid molecule as disclosed herein.

In one embodiment, the term "cell" or "host cell" relates to an intact cell, i.e. a cell with an intact membrane that has not released its normal intracellular components such as enzymes, organelles, or genetic material. In one embodiment, an intact cell is a viable cell, i.e. a living cell capable of carrying out its normal metabolic functions. In one embodiment, said term relates according to the invention to any cell which can be transfected or transformed with an exogenous nucleic acid. In one embodiment, the cell when transfected or transformed with an exogenous nucleic acid and transferred to a recipient can express the nucleic acid in the recipient. The term "cell" includes prokaryotic cells, such as bacterial cells, and eukaryotic cells, such as yeast cells, fungal cells or mammalian cells. Suitable bacterial cells include cells from Gram-negative bacterial strains, such as strains of *Escherichia coli, Proteus*, and *Pseudomonas*, and Gram-positive bacterial strains, such as strains of *Bacillus subtilis, Streptomyces, Staphylococcus*, and *Lactococcus*. Suitable fungal cells include cells from the species of *Trichoderma, Neurospora*, and *Aspergillus*. Suitable yeast cells include cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanol/ca*), and *Hansenula*. Suitable mammalian cells include primary mammalian cells or immortalized mammalian cell lines, such as CHO cells, BHK cells, HeLa cells, COS cells, 293 HEK and the like. However, amphibian cells, insect cells (e.g., SF9 or High5), plant cells, and any other cells used in the art for the expression of heterologous proteins can be used as well.

The invention also relates to a method for the production of a fusion molecule as described herein, wherein the fusion molecule is produced starting from the nucleic acid coding for the fusion molecule by means of genetic engineering methods. The method can be carried out in vivo, the fusion molecule can, for example, be produced in a bacterial or eukaryotic host organism/cell and then isolated from this host organism/cell or its culture. It is also possible to produce a protein in vitro, for example by use of an in vitro translation system.

When producing the fusion molecule in vivo a nucleic acid encoding such fusion molecule is introduced into a suitable bacterial or eukaryotic host organism/cell by means of recombinant DNA technology (as already outlined above). For this purpose, the host cell is first transformed with a cloning vector that includes a nucleic acid molecule encoding a fusion molecule as described herein using established standard methods. The host cell is then cultured under conditions, which allow expression of the heterologous DNA and thus the synthesis of the corresponding polypeptide. Subsequently, the polypeptide is recovered either from the cell or from the culture medium.

In some embodiments, the naturally occurring disulfide bond between Cys 76 and Cys 175 may be removed in hNGAL muteins used in the fusion molecules. Accordingly, such muteins can be produced in a cell compartment having a reducing redox milieu, for example, in the cytoplasm of Gram-negative bacteria.

In case a fusion molecule of the invention includes intramolecular disulfide bonds, the nascent polypeptide may be directed to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a fusion molecule of the invention in the cytosol of a host cell, particularly *E. coli*. In this case, the fusion molecule can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) J. Mol. Biol. 315, 1-8.).

However, the fusion molecule as described herein may not necessarily be generated or produced only by use of genetic engineering. Rather, such fusion molecule can also be obtained by chemical synthesis such as Merrifield solid phase polypeptide synthesis or by in vitro transcription and translation. Methods for the solid phase and/or solution phase synthesis of proteins are well known in the art (see e.g. Bruckdorfer, T. et al. (2004) Curr. Pharm. Biotechnol. 5, 29-43), and so are methods for in vitro transcription/translation. It is also possible that promising mutations are identified using molecular modeling and then to synthesize the wanted (designed) polypeptide in vitro and investigate the binding activity for pyoverdine type I, II, III and/or pyochelin. Methods for the solid phase and/or solution phase synthesis of proteins are well known in the art (see e.g. Bruckdorfer, T. et al. (2004) Curr. Pharm. Biotechnol. 5, 29-43).

The skilled worker will appreciate methods useful to prepare fusion molecules contemplated by the present invention but whose protein or nucleic acid sequences are not explicitly disclosed herein. As an overview, such modifications of the amino acid sequence include, e.g., directed mutagenesis of single amino acid positions in order to simplify sub-cloning of an hNGAL mutein gene or its parts by incorporating cleavage sites for certain restriction enzymes. In addition, these mutations can also be incorporated to further improve the affinity of a mutein for its target (e.g. pyoverdine or pyochelin, respectively). Furthermore, mutations can be introduced to modulate certain characteristics of the muteins and fusion molecules, such as to improve folding stability, serum stability, protein resistance or water solubility or to reduce aggregation tendency, if necessary. For example, naturally occurring cysteine residues may be mutated to other amino acids to prevent disulphide bridge formation.

The current disclosure also relates to a nucleic acid molecule comprising a nucleotide sequence encoding a mutein disclosed herein. In this regard, the present disclosure provides nucleotide sequences encoding some muteins of the disclosure as shown in SEQ ID NOs: 65-126. Since the degeneracy of the genetic code permits substitutions of certain codons by other codons specifying the same amino acid, the disclosure is not limited to a specific nucleic acid molecule encoding a mutein as described herein but encompasses all nucleic acid molecules that include nucleotide sequences encoding a functional mutein. The disclosure further encompasses a host cell containing said nucleic acid molecule. All aspects and embodiments relating to nucleic acid molecules and (host) cells disclosed in connection with the fusion molecules of the present invention are also applicable to single muteins and their combinations. The same applies to methods of their production.

D. Compositions and Kits

In a further aspect, the present invention relates to a pharmaceutical composition comprising a fusion molecule as defined herein, a nucleic acid molecule as defined herein, or a cell as defined herein.

In some embodiments, the pharmaceutical compositions of the invention are sterile and/or contain an effective amount of the fusion molecules, nucleic acid molecules or cells described herein to generate the desired reaction or the desired effect.

The term "effective amount", as used throughout the description, refers to an amount that is sufficient to effect beneficial or desired results, wherein an effective amount can be administered in one or more administrations. In the case of treatment of a particular disease or of a particular condition, the beneficial or desired result particularly relates to inhibition of the course of the disease. This comprises slowing down the progress of the disease and, in particular, interrupting or reversing the progress of the disease. The beneficial or desired result in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

Pharmaceutical compositions are usually provided in a uniform dosage form and may be prepared in a manner known per se. A pharmaceutical composition may, e.g., be in the form of a solution or suspension.

A pharmaceutical composition may further comprise one or more carriers and/or excipients, all of which are, in particular embodiments, pharmaceutically acceptable. The term "pharmaceutically acceptable", as used herein, refers to the non-toxicity of a material which, in particular embodiments, does not interact with the action of the active agent of the pharmaceutical composition.

The term "carrier" refers to an organic or inorganic component, of a natural or synthetic nature, in which the active component is combined in order to facilitate, enhance or enable application.

According to the invention, the term "carrier" also includes one or more compatible solid or liquid fillers, diluents or encapsulating substances, which are suitable for administration to a subject.

Pharmaceutical compositions suitable for parenteral administration usually comprise a sterile aqueous or non-aqueous preparation of the active compound, which, in a particular embodiment, is isotonic to the blood of the recipient. Examples of compatible carriers/solvents/diluents for parenteral administration are, e.g., sterile water, Ringer solution, Ringer lactate, isotonic sodium chloride solution, polyalkylene glycols, hydrogenated naphthalenes and, in particular, biocompatible lactide polymers, lactide/glycolide copolymers or polyoxyethylene/polyoxy-propylene copolymers. In addition, usually sterile, fixed oils are used as solution or suspension medium.

The term "excipient", as used herein, is intended to include all substances which may be present in a pharmaceutical composition and which are not active ingredients, such as salts, binders, lubricants, thickeners, surface active agents, preservatives, emulsifiers, buffer substances, flavouring agents, or colorants.

Salts, which are not pharmaceutically acceptable, may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable preservatives for use in a pharmaceutical composition include benzalkonium chloride, chlorobutanol, paraben and thimerosal.

Suitable buffer substances for use in a pharmaceutical composition include acetic acid in a salt, citric acid in a salt, boric acid in a salt and phosphoric acid in a salt.

The pharmaceutical composition may also comprise one or more pharmaceutically acceptable adjuvants.

In one embodiment, the pharmaceutical composition is formulated for systemic administration, in particular parenteral (e.g., intravenous, subcutaneous) administration. In another embodiment, the pharmaceutical composition is formulated for inhalation.

In one embodiment, the pharmaceutical composition further comprises an additional pharmaceutically active agent.

In one embodiment, the additional pharmaceutically active agent is selected from the group consisting of an antibiotic, a cytostatic agent, a toxin, an enzyme, a metal or metal compound/complex, a chelating agent, a radionuclide, a small organic molecule, a therapeutically active peptide, a therapeutically active nucleic acid molecule, a hapten and an antibody. Suitable antibiotics include Tobramycin, Azithromycin, Aztreonam, Colistin and carbapenems.

Suitable metals or metal compounds/complexes are gallium, gallium compounds and gallium-based complexes.

The term "therapeutically active peptide" refers, e.g., to peptides acting as agonists/antagonists of a cell surface receptor or peptides competing for a protein binding site on a given cellular target.

The term "therapeutically active nucleic acid molecule" refers, e.g., to antisense nucleic acid molecules, small interfering RNAs, micro RNAs or ribozymes.

Particular additional pharmaceutically active agents, with which the fusion molecules of the present invention can be combined, include Dornase alfa, corticosteroids, leukotriene modifiers, N-acetylcysteine, inhaled glutathione, anticholinergics, ibuprofen and β2-adrenergic receptor agonists.

In yet another aspect, the present invention relates to a kit comprising a fusion molecule as defined herein, a nucleic acid molecule as defined herein, a cell as defined herein, or a pharmaceutical composition as defined herein. The kit may be a diagnostic or analytical kit.

As used herein, the term "kit of parts (in short: kit)" refers to an article of manufacture comprising one or more containers and, optionally, a data carrier. Said one or more containers may be filled with one or more of the means or reagents disclosed herein. Additional containers may be included in the kit that contain, e.g., diluents, buffers and further reagents. Said data carrier may be a non-electronic data carrier, e.g., a graphical data carrier such as an information leaflet, an information sheet, a bar code or an access code, or an electronic data carrier such as a compact disk (CD), a digital versatile disk (DVD), a microchip or another semiconductor-based electronic data carrier. The access code may allow the access to a database, e.g., an internet database, a centralized, or a decentralized database. Said data carrier may comprise instructions for the use of the fusion molecule, nucleic acid molecule, cell and/or pharmaceutical composition of the present invention.

All aspects and embodiments relating to compositions and kits disclosed in connection with the fusion molecules of the present invention are also applicable to single muteins and their combinations.

E. Diagnostic and Therapeutic Applications

Pyoverdines are the main siderophores of pseudomonads such as *P. aeruginosa*. In vitro experiments indicated a potential role of the *P. aeruginosa* pyoverdine in iron release from ferritransferrin, but the ability of pyoverdine to compete for iron in vivo has only recently been demonstrated (Meyer et al., 1996, Infection and Immunity, 64, p. 518-523). It was observed using a burned-mouse model that the absence of pyoverdine production in mutants raised from a virulent parental strain correlated with a loss of virulence of these mutants and that virulence was restored when the homologous pyoverdine originating from the wild-type strain was supplemented. Furthermore, supplementation with a heterologous pyoverdine did not restore the virulence of the latter mutants. Thus, a precise knowledge of the pyoverdine-mediated iron uptake system used by a given *P. aeruginosa* isolate during infection appears a prerequisite for developing new ways of treatment of *P. aeruginosa* infections via bacterial iron metabolism, e.g., by blocking the pyoverdine biosynthesis or the pyoverdine-mediated iron transport.

Pyochelin (Pch) is one of the two major siderophores produced and secreted by *Pseudomonas aeruginosa* to assimilate iron. It chelates iron in the extracellular medium and transports it into the cell via a specific outer membrane transporter, FptA. Pch strongly chelates divalent metals such as Zn(II) (pZn=11.8 at p[H] 7.4) and Cu(II) (pCu=14.9 at p[H] 7.4) and forms predominantly 1:2 ($M^{2+}$/Pch) complexes. Siderophores are not only devoted to iron(III) shuttling but most likely display other specific biological roles in the subtle metals homeostasis in microorganisms.

Therefore, numerous possible applications for the pyoverdine/pyochelin-binding fusion molecules of the invention exist in medicine.

In one aspect, the present invention relates to a fusion molecule as defined herein, a nucleic acid molecule as defined herein, a cell as defined herein, or a pharmaceutical composition as defined herein for use as a medicament.

The term "medicament", as used herein, refers to a substance/composition used in therapy, i.e., in the treatment of a disease.

The term "treatment of a disease", as used herein, includes curing, shortening the duration, ameliorating, preventing, slowing down or inhibiting progression or worsening, or preventing or delaying the onset of a disease or the symptoms thereof.

According to the invention, the term "disease" refers to any pathological state, in particular a disease or disorder associated with or caused by *P. aeruginosa* biofilm infection in a subject.

In another aspect, the present invention relates to a fusion molecule as defined herein, a nucleic acid molecule as defined herein, a cell as defined herein, or a pharmaceutical composition as defined herein for use in the prevention or treatment of *P. aeruginosa* biofilm infection in a subject.

The term "subject", as used throughout the description, means according to the invention a subject for treatment or diagnosis, in particular a diseased subject (also referred to as "patient") or a subject expected/assumed/at risk to be diseased. A "subject" is a vertebrate, particularly a mammal. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys etc., to name only a few illustrative examples. In a particular embodiment, the mammal is a human.

In yet another aspect, the present invention relates to a fusion molecule as defined herein, a nucleic acid molecule as defined herein, a cell as defined herein, or a pharmaceutical composition as defined herein for use in the prevention or treatment of a disease or disorder associated with or caused by *P. aeruginosa* biofilm infection in a subject.

In yet another aspect, the present invention relates to a method of preventing or treating *P. aeruginosa* biofilm infection in a subject, comprising administering an effective amount of a fusion molecule as defined herein, a nucleic acid molecule as defined herein, a cell as defined herein, or a pharmaceutical composition as defined herein to the subject.

In yet another aspect, the present invention relates to a method of preventing or treating a disease or disorder associated with or caused by *P. aeruginosa* biofilm infection in a subject, comprising administering an effective amount of a fusion molecule as defined herein, a nucleic acid molecule as defined herein, a cell as defined herein, or a pharmaceutical composition as defined herein to the subject.

In one embodiment, the *P. aeruginosa* biofilm infection is acute infection.

In one embodiment, the *P. aeruginosa* biofilm infection is chronic infection.

In one embodiment, the disease or disorder associated with or caused by *P. aeruginosa* biofilm infection is selected from the group consisting of cystic fibrosis, hospital acquired pneumonia, ventilator-associated pneumonia, urinary tract infection, eye infection, ear infection and burn wound infection.

In yet another aspect, the present invention relates to a fusion molecule as defined herein, a nucleic acid molecule as defined herein, a cell as defined herein, or a pharmaceutical composition as defined herein for use in binding of pyoverdine (type I, II and/or III) and/or pyochelin in a subject.

In still another aspect, the present invention features a method of binding pyoverdine (type I, II and/or III) and/or pyochelin in a subject, comprising administering to said subject an effective amount of a fusion molecule as defined herein, a nucleic acid molecule as defined herein, a cell as defined herein, or a pharmaceutical composition as defined herein.

In still another aspect, the present invention features a method for inhibiting or lessening growth of *P. aeruginosa* in a subject, comprising administering to said subject an effective amount of a fusion molecule as defined herein, a nucleic acid molecule as defined herein, a cell as defined herein, or a pharmaceutical composition as defined herein.

In yet a further aspect, the present invention relates to the use of a fusion molecule as defined herein, a nucleic acid molecule as defined herein, a cell as defined herein, or a pharmaceutical composition as defined herein in the manufacture of a medicament for (i) the prevention or treatment of *P. aeruginosa* biofilm infection in a subject, (ii) the prevention or treatment of a disease or disorder associated with or caused by *P. aeruginosa* biofilm infection in a subject, or (iii) inhibiting or lessening growth of *P. aeruginosa* in a subject.

The agents and compositions described herein may be administered via any conventional route, such as by topical or systemic (i.e., enteral or parenteral) administration. Parenteral administration includes injection or infusion, e.g., intravenously, intraarterially, subcutaneously, intradermally or intramuscularly. Topical administration includes inhalation as well as eye and ear drops. In particular embodiments, the fusion molecules of the invention are administered by inhalation (fusion molecules) or systemically, e.g., subcutaneously (Fc-fusion molecule constructs).

The present invention further relates to the use of a fusion molecule disclosed herein for detecting pyoverdine (type I, II and/or III) and/or pyochelin in a sample as well as a respective method of diagnosis.

The term "detect", "detection", "detectable" or "detecting" as used herein is understood both on a quantitative and a qualitative level, as well as a combination thereof. It thus includes quantitative, semi-quantitative and qualitative measurements of a molecule of interest.

Such use may include the steps of contacting one or more fusion molecules, under suitable conditions, with a sample suspected of containing pyoverdine and/or pyochelin, thereby allowing formation of a complex between the fusion molecule and pyoverdine (type I, II and/or III) and/or pyochelin, and detecting the complex by a suitable signal. The signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The fusion molecules disclosed herein may also be used for the separation of pyoverdine and/or pyochelin. Such use may include the steps of contacting such fusion molecule, under suitable conditions, with a sample supposed to contain pyoverdine and/or pyochelin, thereby allowing formation of a complex between the fusion molecule and pyoverdine and/or between the fusion molecule and pyochelin, respectively, and separating the complex from the sample.

In the use of the disclosed fusion molecules for the detection of pyoverdine and/or pyochelin as well as the separation of pyoverdine and/or pyochelin, the fusion molecules and/or pyoverdine and/or pyochelin or a domain or fragment thereof may be immobilized on a suitable solid phase.

Accordingly, the presence or absence of pyoverdine and/or pyochelin, e.g., in a sample, as well as its concentration or level may be determined.

A "sample" is defined as a biological sample taken from any subject. Biological samples include, but are not limited to, blood, serum, urine, feces, semen, or tissue.

The fusion molecules disclosed herein can be used in many fields similar to antibodies or fragments thereof. For example, the fusion molecules can be used for labeling with an enzyme, an antibody, a radioactive substance or any other group having biochemical activity or defined binding characteristics. By doing so, their respective targets can be detected or brought in contact with them. In addition, fusion molecules of the invention can serve to detect chemical structures by means of established analytical methods (e.g., ELISA or Western Blot) or by microscopy or immunosensorics. In this regard, the detection signal can either be generated directly by use of a suitable fusion molecule conjugate or indirectly by immunochemical detection of the bound fusion molecule via an antibody.

All aspects and embodiments relating to diagnostic and therapeutic applications disclosed in connection with the fusion molecules of the present invention are also applicable to single muteins and their combinations.

Additional objects, advantages, and features of this invention will become apparent to those skilled in the art upon examination of the following Examples and the attached Figures thereof, which are not intended to be limiting. Thus, it should be understood that although the present invention is specifically disclosed by exemplary embodiments and optional features, modifications and variations of the disclosures embodied herein may be resorted to by those skilled in the art, and that such modifications and variations are considered to be within the scope of this invention. In particular, all aspects and embodiments disclosed in connection with the fusion molecules of the invention are also applicable to single muteins disclosed herein as well as to their combinations, and vice versa.

F. Specific embodiments relating to hNGAL muteins and polypeptides comprising them, e.g., for use in the fusion molecules of the present invention.

1. A polypeptide having binding specificity for pyoverdine type I, II, III or pyochelin, wherein the polypeptide comprises an hNGAL mutein that binds pyoverdine type I, II, III or pyochelin, e.g., with detectable affinity.

2. The polypeptide of embodiment 1, wherein the hNGAL mutein comprises a mutated amino acid residue at one or more positions corresponding to positions 28, 34, 36, 39-42, 44-47, 49, 52, 54, 55, 65, 68, 70, 72-75, 77, 79-81, 87, 96, 100, 103, 106, 108, 123, 125, 127, 132, 134,141 and 145 of the linear polypeptide sequence of the mature hNGAL (SEQ ID NO: 1).

3. The polypeptide of embodiment 1, wherein said mutein is capable of binding pyoverdine type I complexed with iron with a $K_D$ of about 20 nM or lower, for example, when measured by Biacore T200 instrument in an assay essentially described in Example 6.

4. The polypeptide of embodiment 1, wherein said hNGAL mutein is capable of binding Pvd type I succinyl, Pvd type I succinamide and Pvd type I α-ketoglutaryl with and without complexed iron, with an affinity measured by an $IC_{50}$ value of about 200 nM or lower, for example, when measured in an ELISA assay essentially described in Example 5.

5. The polypeptide of embodiment 3, wherein the hNGAL mutein is capable of inhibiting iron uptake mediated by pyoverdine type I with an IC$_{50}$ value of about 150 nM or lower in a competition ELISA format essentially described in Example 7.

6. The polypeptide of embodiment 3, wherein the hNGAL mutein is capable of inhibiting bacterial growth of Pvd I strain in an assay essentially described in Example 8.

7. The polypeptide according to any of the preceding embodiments 3 to 6, wherein the hNGAL mutein comprises a mutated amino acid residue at one or more positions corresponding to positions 28, 36, 39-41, 46, 49, 52, 54, 55, 59, 65, 68, 70, 72-75, 77, 79-81, 87, 96, 100, 103, 106, 125, 127, 132, 134 and 136 of the linear polypeptide sequence of the mature hNGAL (SEQ ID NO: 1).

8. The polypeptide of any one of embodiments 3-7, wherein the amino acid sequence of the hNGAL mutein comprises at least one of the following mutated amino acid residues in comparison with the linear polypeptide sequence of the mature hNGAL: Leu 36→Asn, Thr, Val, Trp or Phe; Ala 40→Gly, Asn, Thr or Phe; Ile 41→Arg, Ala, Thr, Phe or Trp; Gln 49→Ile, Leu, Val, Ala or Pro; Tyr 52→Met, Trp or Pro; Ser 68→Asp, Val or Glu; Leu 70→Gln, Trp, Asp or Thr; Arg 72→Trp, Ala, Ser, Leu, Pro or Glu; Lys 73→Asp, Leu, Ala, Glu or Asn; Asp 77→Arg, Leu, Tyr, Ser, Gln, Thr, Ile or Asn; Trp 79→Gln, Asp, Ser, Arg, Met or Glu; Arg 81→Gln, Gly, Ile, Glu, His or Asp; Asn 96→His, Ile, Gly, Tyr or Asp; Tyr 100→Lys, Glu, Asn, Ser, Phe or Tyr; Leu 103→Lys, Pro, Gln, His, Asp, Tyr, Glu, Trp or Asn; Tyr 106→His, Gln or Phe; Lys 125→Arg, Ser, Trp, Tyr, Val or Gly; Ser 127→Trp, Asn, Ala, Thr, Tyr, His, Ile, Val or Asp; Tyr 132→Trp, Asn, Gly or Lys; and Lys 134→Asn, His, Trp, Gly, Gln or Asp.

9. The polypeptide of any one of embodiments 3-8, wherein the amino acid sequence of the hNGAL mutein comprises the following substitution in comparison with the linear polypeptide sequence of the mature hNGAL: Gln 28→His; Lys 46→Glu; Thr 54→Val or Ala; Ile 55→Val; Lys 59→Arg; Asn 65→Asp or Gln; Ile 80→Thr; Cys 87→Ser or Asn; and Thr 136→Ala.

10. The polypeptide according to any of the preceding embodiments 3-8, wherein the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 39-41, 46, 49, 52, 54-55, 59, 65, 68, 70, 72-75, 77, 79-81, 87, 96, 100, 103, 106, 125, 127, 132, 134 and 136 of the linear polypeptide sequence of the mature human NGAL (SEQ ID NO: 1).

11. The polypeptide according to any of the preceding embodiments 3-10, wherein the hNGAL mutein comprises one of the following sets of amino acid substitutions in comparison with the linear polypeptide sequence of the mature hNGAL:

(a) Gln 28→His; Leu 36→Asn; Ala 40→Gly; Ile 41→Trp; Gln 49→Ile; Tyr 52→Met; Ser 68→Val; Leu 70→Gln; Arg 72→Trp; Lys 73→Asp; Asp 77→Leu; Trp 79→Gln; Arg 81→Gln; Cys 87→Ser; Asn 96→His; Tyr 100→Lys; Leu 103→His; Tyr 106→His; Lys 125→Arg; Ser 127→Trp; Tyr 132→Trp; Lys 134→Asp;

(b) Gln 28→His; Leu 36→Thr; Ala 40→Gly; Ile 41→Phe; Gln 49→Leu; Tyr 52→Trp; Leu 70→Trp; Arg 72→Ala; Lys 73→Leu; Asp 77→Tyr; Trp 79→Asp; Arg 81→Gly; Cys 87→Ser; Asn 96→Ile; Tyr 100→Glu; Leu 103→His; Tyr 106→Gln; Lys 125→Trp; Ser 127→Asn; Tyr 132→Asn; Lys 134→Gln;

(c) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Arg 81→Ile; Cys 87→Ser; Asn 96→Gly; Tyr 100→Asn; Leu 103→Lys; Tyr 106→His; Lys 125→Tyr; Ser 127→Ala; Tyr 132→Gly; Lys 134 Asn;

(d) Gln 28→His; Leu 36→Phe; Ala 40→Asn; Ile 41→Arg; Gln 49→Pro; Tyr 52→Met; Ser 68→Asp; Leu 70→Thr; Arg 72→Glu; Lys 73→Ala; Asp 77→Arg; Trp 79→Arg; Arg 81→Ile; Cys 87→Ser; Asn 96→Tyr; Tyr 100→Lys; Leu 103→Pro; Tyr 106→Phe; Lys 125→Ser; Ser 127→Thr; Tyr 132→Trp; Lys 134→Gly;

(e) Gln 28→His; Ala 40→Gly; Ile 41→Trp; Gln 49→Val; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Phe; Leu 103→Trp; Tyr 106→Gln; Lys 125→Gly; Ser 127→Tyr; Tyr 132→Trp; Lys 134→His;

(f) Gln 28→His; Leu 36→Val; Ala 40→Phe; Ile 41→Phe; Gln 49→Ala; Tyr 52→Pro; Ser 68→Glu; Leu 70→Trp; Arg 72→Leu; Lys 73→Asn; Asp 77→Gln; Trp 79→Glu; Arg 81→His; Cys 87→Ser; Asn 96→Tyr; Leu 103→Tyr; Tyr 106→His; Lys 125→Val; Ser 127→His; Tyr 132→Lys; Lys 134→Trp;

(g) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Ile 80→Thr; Arg 81→Ile; Cys 87→Ser; Asn 96→Gly; Tyr 100→Ser; Leu 103 Gln; Tyr 106→His; Lys 125→Tyr; Ser 127→Ile; Tyr 132→Gly; Lys 134→Asn;

(h) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Asp; Asp 77→Ser; Trp 79→Ser; Arg 81→Ile; Cys 87→Ser; Asn 96→Gly; Tyr 100→Asn; Leu 103→Asp; Tyr 106→His; Lys 125→Tyr; Ser 127→Val; Tyr 132→Gly; Lys 134 Asn;

(i) Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Thr; Trp 79→Ser; Arg 81→Ile; Cys 87→Ser; Asn 96→Asp; Tyr 100→Asn; Leu 103→Glu; Tyr 106→His; Lys 125→Tyr; Ser 127 Asp; Tyr 132→Gly; Lys 134 Asn;

(j) Gln 28→His; Leu 36→Trp; Ala 40 Thr; Ile 41→Thr; Gln 49→Pro; Tyr 52→Pro; Ser 68→Asp; Leu 70→Gln; Arg 72→Ser; Lys 73→Asp; Asp 77→Val; Trp 79→Ser; Arg 81→Ile; Cys 87→Ser; Asn 96→Gly; Tyr 100→Asn; Leu 103→Asn; Tyr 106→His; Lys 125→Tyr; Ser 127→Val; Tyr 132→Gly; Lys 134 Asn;

(k) Gln 28→His; Ala 40→Gly; Ile 41→Trp; Gln 49→Leu; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Ser; Leu 103→Trp; Tyr 106→Gln; Lys 125→Gly; Ser 127→Tyr; Tyr 132→Trp; Lys 134→His;

(l) Gln 28→His; Leu 36→Trp; Ala 40 Thr; Ile 41→Thr; Gln 49→Pro; Tyr 52→Pro; Thr 54→Val; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn;

(m) Gln 28→His; Ala 40→Gly; Ile 41→Trp; Lys 46→Glu; Gln 49→Leu; Tyr 52→Met; Thr 54→Ala; Ile 55→Val; Lys 59→Arg; Ser 68→Val; Leu 70→Asp; Arg 72→Glu; Lys 73→Leu; Lys 74→Glu; Lys

75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His;

(n) Leu 36→Trp; Asn 39→Asp; Ala 40 Thr; Ile 41→Thr; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn; Thr 136→Ala;

(o) Leu 36→Trp; Ala 40 Thr; Ile 41→Ala; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134 Asn; Thr 136→Ala;

(p) Gln 28→His; Ala 40→Gly; Ile 41 Trp; Lys 46→Glu; Gln 49→Leu; Tyr 52→Met; Thr 54→Ala; Ile 55→Val; Lys 59→Arg; Asn 65→Asp; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His; or (q) Gln 28→His; Ala 40→Gly; Ile 41→Trp; Lys 46→Glu; Gln 49→Leu; Tyr 52→Met; Thr 54→Ala; Ile 55→Val; Lys 59→Arg; Asn 65→Gln; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His.

12. The polypeptide according to any one of embodiments 3-11, wherein the hNGAL mutein comprises an amino acid sequence selected from the group consisting of SEQ ID NOs: 2-18 or a Pvd-type-1-binding fragment or variant thereof.

13. The polypeptide of embodiment 1, wherein said hNGAL mutein is capable of binding pyoverdine type II complexed with iron with a $K_D$ of about 20 nM or lower, for example, when measured by Biacore T200 instrument in an assay essentially described in Example 6.

14. The polypeptide of embodiment 1, wherein said hNGAL mutein is capable of binding Pvd type II succinyl, Pvd type II succinamide and Pvd type II α-ketoglutaryl with and without complexed iron, with an affinity measured by an $IC_{50}$ value of about 200 nM or lower, for example, when measured in an ELISA assay essentially described in Example 5.

15. The polypeptide of embodiment 13, wherein the hNGAL mutein is capable of inhibiting iron uptake mediated by pyoverdine type II with an $IC_{50}$ value of about 150 nM or lower in a competition ELISA format essentially described in Example 7.

16. The polypeptide of embodiment 13, wherein the hNGAL mutein is capable of inhibiting bacterial growth of Pvd II strain in an assay essentially described in Example 8.

17. The polypeptide of embodiment 13, wherein said hNGAL mutein is capable of inhibiting growth of *P. aeruginosa* stains expressing pyoverdine type II in an assay essentially described in Example 9.

18. The polypeptide according to any of the preceding embodiments 13 to 17, wherein the hNGAL mutein comprises a mutated amino acid residue at one or more positions corresponding to positions 28, 36, 40-41, 49, 52, 54, 65, 68, 70, 72-75, 77, 79, 81, 87, 96, 100, 103, 106, 125, 127, 132 and 134 of the linear polypeptide sequence of the mature hNGAL (SEQ ID NO: 1).

19. The polypeptide of any one of embodiments 13-18, wherein the amino acid sequence of the hNGAL mutein comprises at least one of the following mutated amino acid residues in comparison with the linear polypeptide sequence of the mature hNGAL: Leu 36→Asn, Ile or Val; Ala 40→Glu, Gly, Asn, Thr or His; Ile 41→Arg, Val or Thr; Gln 49→Gly, Ala or Pro; Tyr 52→Asn, Gly, Trp or Pro; Ser 68→Asp, Arg or Glu; Leu 70→Arg or Trp; Arg 72→His, Ile, Ala, Ser or Gly; Lys 73→Asn, Met, Pro, Phe, Gln or Arg; Asp 77→His, Ile, Met, Lys, Gly or Asn; Trp 79→Ser, Tyr, Ala, Asp, Phe or Trp; Arg 81→Glu, Ser, Tyr or Asp; Asn 96→Met, Ile, Arg, Asp, Lys, Asn or Ala; Tyr 100→Lys, Glu, Asn, Ser, Phe or Tyr; Leu 103→Thr, Ile, Gln, Gly, Met, His, Trp or Val; Tyr 106→Met, Gln, Ala, Ile, Asn, Gly, Met or Phe; Lys 125→Ala, Ile or Asn; Ser 127→Lys, Arg, Ser, Met, Asp or Asn; Tyr 132→Met, Phe, Asn, Ala, Ile, Gly or Val; and Lys 134→Trp or Tyr.

20. The polypeptide of any one of embodiments 13-19, wherein the amino acid sequence of the hNGAL mutein comprises the following substitution in comparison with the linear polypeptide sequence of the mature hNGAL: Gln 28→His; Thr 54→Ala; Asn 65→Asp or Gln and Cys 87→Ser.

21. The polypeptide according to any of the preceding embodiments 13-20, wherein the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 40-41, 49, 52, 54, 65, 68, 70, 72-75, 77, 79, 81, 87, 96, 100, 103, 106, 125, 127, 132 and 134 of the linear polypeptide sequence of the mature human NGAL (SEQ ID NO: 1).

22. The polypeptide according to any of the preceding embodiments 13-21, wherein the hNGAL mutein comprises one of the following sets of amino acid substitutions in comparison with the linear polypeptide sequence of the natural wildtype hNGAL:

(a) Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Tyr 100→Asn; Leu 103→Gln; Tyr 106→Met; Ser 127→Lys; Tyr 132→Gly; Lys 134→Trp;

(b) Gln 28→His; Ala 40→Thr; Ile 41→Ile; Gln 49→Gly; Tyr 52→Asn; Ser 68→Asp; Leu 70→Arg; Arg 72→Ile; Lys 73→Met; Asp 77→His; Trp 79→Tyr; Arg 81→Glu; Cys 87→Ser; Asn 96→Ile; Tyr 100→Asn; Leu 103→Thr; Tyr 106→Gln; Lys 125→Ile; Ser 127→Arg; Tyr 132→Met; Lys 134→Trp;

(c) Gln 28→His; Leu 36→Ile; Ala 40→Thr; Ile 41→Val; Gln 49→Gly; Tyr 52→Pro; Ser 68→Glu; Leu 70→Arg; Arg 72→Ala; Lys 73→Pro; Asp 77→Ile; Trp 79→Ser; Arg 81→Ser; Cys 87→Ser; Asn 96→Met; Tyr 100→Ser; Leu 103→Gly; Tyr 106→Ala; Lys 125→Lys; Tyr 132→Val; Lys 134→Trp;

(d) Gln 28→His; Ala 40→Asn; Gln 49→Ala; Tyr 52→Pro; Ser 68→Glu; Leu 70→Arg; Arg 72→Ser; Lys 73→Gln; Asp 77→Met; Trp 79→Ala; Arg 81→Tyr; Cys 87→Ser; Asn 96→Arg; Tyr 100→Pro;

Leu 103→Thr; Tyr 106→Ile; Lys 125→Lys; Ser 127→Met; Tyr 132→Phe; Lys 134→Trp;

(e) Gln 28→His; Ala 40→His; Gln 49→Ala; Tyr 52→Pro; Ser 68→Glu; Leu 70→Asp; Arg 72→Gly; Lys 73→Arg; Asp 77→His; Trp 79→Trp; Arg 81→Glu; Cys 87→Ser; Asn 96→Arg; Tyr 100→Asp; Leu 103→Met; Tyr 106→Phe; Lys 125→Ala; Ser 127→Asp; Tyr 132→Asn; Lys 134→Trp;

(f) Gln 28→His; Leu 36→Asn; Ala 40→Gly; Ile 41→Arg; Gln 49→Pro; Tyr 52→Trp; Ser 68→Arg; Leu 70→Trp; Arg 72→Asn; Lys 73→Gln; Asp 77→Lys; Trp 79→Asp; Arg 81→Glu; Cys 87→Ser; Asn 96→Asp; Tyr 100→Thr; Leu 103→Trp; Tyr 106→Asn; Lys 125→Asn; Ser 127→Met; Tyr 132→Ile; Lys 134→Tyr;

(g) Gln 28→His; Leu 36→Val; Ala 40 Thr; Ile 41→Thr; Gln 49→Gly; Tyr 52→Gly; Ser 68→Glu; Leu 70→Arg; Arg 72→Gly; Lys 73→Arg; Asp 77→Gly; Trp 79→Trp; Arg 81→Glu; Cys 87→Ser; Asn 96→Ala; Tyr 100→Trp; Leu 103→Ile; Tyr 106→Gly; Lys 125→Lys; Ser 127 Asn; Tyr 132→Val; Lys 134→Trp;

(h) Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

(i) Gln 28→His; Leu 36→Val; Ala 40→Thr; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Leu 103→Gln; Tyr 106→Met; Ser 127→Lys; Tyr 132→Val; Lys 134 Trp;

(j) Gln 28→His; Leu 36→Val; Ala 40→Thr; Ile 41→Val; Gln 49→Gly; Tyr 52→Pro; Ser 68→Glu; Leu 70→Arg; Arg 72→His; Asp 77→Asn; Trp 79→Phe; Arg 81→Glu; Cys 87→Ser; Asn 96→Lys; Tyr 100→His; Leu 103→Gln; Tyr 106→Met; Ser 127→Lys; Tyr 132→Ala; Lys 134→Trp;

(k) Gln 28→His; Leu 36→Val; Ala 40→Gly; Ile 41→Val; Gln 49→Gly; Tyr 52→Pro; Ser 68→Glu; Leu 70→Arg; Arg 72→His; Lys 73→Asn; Asp 77→Asn; Trp 79→Trp; Arg 81→Glu; Cys 87→Ser; Tyr 100→Asn; Leu 103→His; Tyr 106→Met; Ser 127→Lys; Tyr 132→Gly; Lys 134 Trp;

(l) Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Phe; Asp 77→His; Trp 79→Tyr; Arg 81→Asp; Cys 87→Ser; Leu 103→Met; Tyr 106→Gln; Lys 125→Ile; Ser 127→Arg; Tyr 132→Ile; Lys 134→Trp;

(m) Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

(n) Gln 28→His; Leu 36→Val; Ala 40→Glu; Ile 41→Val; Gln 49→Gly; Tyr 52→Pro; Asn 65→Asp; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

(o) Gln 28→His; Leu 36→Val; Ala 40→Glu; Ile 41→Val; Gln 49→Gly; Tyr 52→Pro; Asn 65→Gln; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

(p) Gln 28→His; Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

(q) Gln 28→His; Leu 36→Val; Ala 40→Thr; Ile 41→Ile; Gln 49→Gly; Tyr 52→Asn; Thr 54→Ala; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

(r) Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127 Arg; Tyr 132→Ile; Lys 134→Trp; or (s) Leu 36→Val; Ala 40→Thr; Ile 41→Ile; Gln 49→Gly; Tyr 52→Asn; Thr 54→Ala; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127 Arg; Tyr 132→Ile; Lys 134→Trp.

23. The polypeptide according to any one of embodiments 13 to 22, wherein the hNGAL mutein comprises an amino acid sequence selected from the group consisting of SEQ ID NOs: 19-37 or a Pvd-type-II-binding fragment or variant thereof.

24. The polypeptide of embodiment 1, wherein said mutein is capable of binding pyoverdine type III complexed with iron with a $K_D$ of about 20 nM or lower, for example, when measured by Biacore T200 instrument in an assay essentially described in Example 6.

25. The polypeptide of embodiment 1, wherein said hNGAL mutein is capable of binding Pvd type III succinyl, Pvd type III succinamide and Pvd type III α-ketoglutaryl with and without complexed iron, with an affinity measured by an $IC_{50}$ value of about 200 nM or lower, for example, when measured in an assay essentially described in Example 5.

26. The polypeptide of embodiment 24, wherein the hNGAL mutein is capable of inhibiting iron uptake mediated by pyoverdine type III with an $IC_{50}$ value of about 150 nM or lower in a competition ELISA format essentially described in Example 7.

27. The polypeptide of embodiment 24, wherein the hNGAL mutein is capable of inhibiting bacterial growth of Pvd III strain in an assay essentially described in Example 8.

28. The polypeptide according to any of the preceding embodiments 24 to 27, wherein the hNGAL mutein comprises a mutated amino acid residue at one or more positions corresponding to positions 28, 36, 40-42, 45-47, 49, 52, 65, 68, 70, 72-73, 77, 79, 81, 87, 96, 100, 103, 105-106, 125, 127, 132, 134 and 145 of the linear polypeptide sequence of the mature hNGAL (SEQ ID NO: 1).

29. The polypeptide of any one of embodiments 24-28, wherein the amino acid sequence of the hNGAL mutein comprises at least one of the following mutated amino acid residues in comparison with the linear polypeptide sequence of the mature hNGAL: Leu 36→Phe or Glu; Ala 40→Trp, Leu or Arg; Ile 41→Met, Arg, Ala, Leu or Trp; Gln 49→His, Ile, Arg, Lys, Met or Pro; Tyr 52→Asn, Tyr, Arg, Ser or Met; Ser 68→Asp, Asn, Glu or Gln; Leu 70→Lys, Asn or Arg; Arg 72→Leu, Arg, Gln or Tyr; Lys 73→His, Leu, Ala, Pro, Gln or Tyr; Asp 77→Ala, Ile, Lys, Gln or Arg; Trp 79→Ser or Asp; Arg 81→His, Ala, Ser or Val; Asn 96→Met, Ile, Arg, Gly, Leu or Val; Tyr 100→Ala, Ile, Asn, Pro or Asp; Leu 103→Gln, Gly, Phe or Pro; Tyr 106 Glu; Lys 125→Trp or Thr; Ser 127→Val, His, Ile, Phe or Ala; Tyr 132→Phe; and Lys 134 Trp, Gln or Glu.

30. The polypeptide of any one of embodiments 24-29, wherein the amino acid sequence of the hNGAL mutein comprises the following substitution in comparison with the linear polypeptide sequence of the mature hNGAL: Gln 28→His; Leu 42→Arg; Asp 45→Gly; Lys 46→Arg; Asp 47→Asn; Asn 65→Asp; Cys 87→Ser; Ser 105→Pro and Thr 145→Pro.

31. The polypeptide according to any of the preceding embodiments 24-30, wherein the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 40-42, 45-47, 49, 52, 65, 68, 70, 72-73, 77, 79, 81, 87, 96, 100, 103, 105-106, 125, 127, 132, 134 and 145 of the linear polypeptide sequence of the mature human NGAL (SEQ ID NO: 1).

32. The polypeptide according to any of the preceding embodiments 24-31, wherein the hNGAL mutein comprises one of the following sets of amino acid substitutions in comparison with the linear polypeptide sequence of the mature hNGAL:

(a) Gln 28→His; Leu 36→Phe; Ala 40→Trp; Ile 41→Met; Gln 49→His; Tyr 52→Asn; Ser 68→Glu; Leu 70→Lys; Arg 72→Gln; Lys 73→Ala; Asp 77→Ile; Trp 79→Ser; Arg 81→His; Cys 87→Ser; Asn 96→Ile; Tyr 100→Asn; Leu 103→Gly; Tyr 106→Glu; Lys 125→Trp; Ser 127→His; Tyr 132→Phe; Lys 134→Gln;

(b) Gln 28→His; Leu 36→Phe; Ala 40→Arg; Ile 41→Trp; Gln 49→Ile; Tyr 52→Tyr; Ser 68→Gln; Leu 70→Asn; Arg 72→Trp; Lys 73→Leu; Asp 77→Ala; Trp 79→Ser; Arg 81→Ser; Cys 87→Ser; Asn 96→Arg; Tyr 100→Ile; Leu 103→Pro; Tyr 106→Glu; Lys 125→Thr; Ser 127→Ile; Tyr 132→Phe; Lys 134→Glu;

(c) Gln 28→His; Leu 36→Phe; Ala 40→Leu; Ile 41 Leu; Gln 49→Arg; Tyr 52→Arg; Ser 68→Asp; Leu 70→Arg; Arg 72→Leu; Lys 73→Tyr; Asp 77→Ile; Trp 79→Ser; Arg 81→Ala; Cys 87→Ser; Asn 96→Gly; Tyr 100→Ala; Leu 103→Phe; Tyr 106→Glu; Lys 125→Trp; Ser 127→Ala; Lys 134→Glu;

(d) Gln 28→His; Leu 36→Phe; Ala 40→Trp; Ile 41→Arg; Gln 49→Pro; Tyr 52→Ser; Ser 68→Asn; Leu 70→Arg; Arg 72→Trp; Lys 73→Pro; Asp 77→Arg; Trp 79→Ser; Arg 81→Ser; Cys 87→Ser; Asn 96→Met; Tyr 100→Pro; Leu 103→Gly; Tyr 106→Glu; Lys 125→Trp; Ser 127→Phe; Tyr 132→Phe; Lys 134→Glu;

(e) Gln 28→His; Leu 36→Glu; Ala 40→Leu; Ile 41→Ala; Gln 49→Lys; Tyr 52→Met; Ser 68→Glu; Leu 70→Arg; Lys 73→His; Asp 77→Gln; Trp 79→Asp; Arg 81→Ala; Cys 87→Ser; Asn 96→Leu; Tyr 100→Asp; Leu 103→Gln; Tyr 106→Glu; Ser 127→Val; Tyr 132 Phe; Lys 134 Trp;

(f) Gln 28→His; Leu 36→Glu; Ala 40→Leu; Ile 41→Ala; Gln 49→Met; Tyr 52→Met; Ser 68→Glu; Leu 70→Arg; Lys 73→Gln; Asp 77→Lys; Trp 79→Asp; Arg 81→Val; Cys 87→Ser; Asn 96→Leu; Tyr 100→Asp; Leu 103→Gln; Tyr 106→Glu; Ser 127→Val; Tyr 132→Phe; Lys 134→Trp;

(g) Gln 28→His; Leu 36→Glu; Ala 40→Leu; Ile 41→Thr; Gln 49→Met; Tyr 52→Met; Ser 68→Glu; Leu 70→Arg; Lys 73→Arg; Asp 77→Lys; Trp 79→Asp; Arg 81→Val; Cys 87→Ser; Asn 96→Val; Tyr 100→Asp; Leu 103→Gln; Tyr 106→Glu; Ser 127→Val; Tyr 132→Phe; Lys 134→Trp;

(h) Gln 28→His; Leu 36→Glu; Ala 40→Leu; Ile 41→Ala; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Tyr 106→Glu; Ser 127 Val; Tyr 132→Phe; Lys 134→Trp;

(i) Gln 28→His; Leu 36→Glu; Ala 40→Leu; Ile 41→Ala; Gln 49→Lys; Tyr 52→Met; Ser 68→Glu; Leu 70→Arg; Lys 73→Tyr; Asp 77→Gln; Trp 79→Asp; Arg 81→Val; Cys 87→Ser; Asn 96→—(e.g., deletion of the four amino acids Gly 95, Asn 96, Ile 97 and Lys 98); Tyr 100→Glu; Leu 103→Gln; Tyr 106→Glu; Ser 127→Val; Tyr 132 Phe; Lys 134 Trp;

(j) Gln 28→His; Leu 36→Glu; Ala 40→Leu; Ile 41→Ala; Leu 42→Arg; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127 Val; Tyr 132→Phe; Lys 134→Trp;

(k) Gln 28→His; Leu 36→Glu; Ala 40→Leu; Ile 41→Ala; Asp 47→Asn; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

(l) Gln 28→His; Leu 36→Glu; Ala 40→Leu; Ile 41→Ala; Asp 45→Gly; Lys 46→Arg; Gln 49→Met; Tyr 52→Met; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

(m) Gln 28→His; Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

(n) Gln 28→His; Leu 36→Glu; Ala 40→Leu; Ile 41→Ala; Asp 47→Asn; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

(o) Gln 28→His; Leu 36→Glu; Ala 40→Leu; Ile 41→Ala; Asp 45→Gly; Lys 46→Arg; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; or (p) Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Val; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp.

33. The polypeptide according to any one of embodiments 24 to 32, comprising an amino acid sequence selected from the group consisting of SEQ ID NOs: 38-53 or a Pvd-type-III-binding fragment or variant thereof.

34. The polypeptide of embodiment 1, wherein said hNGAL mutein is capable of binding pyochelin complexed with iron with a $K_D$ of about 20 nM or lower, for example, when measured by Biacore T200 instrument in an assay essentially described in Example 6.

35. The polypeptide of embodiment 1, wherein said hNGAL mutein is capable of binding pyochelin with complexed iron, with an affinity measured by an $IC_{50}$ value of about 500 nM or lower, for example, when measured in an assay essentially described in Example 5.

36. The polypeptide of embodiment 1, wherein said hNGAL mutein is capable of binding pyochelin without complexed iron, with an affinity measured by an $IC_{50}$ value of about 200 nM or lower, for example, when measured in an assay essentially described in Example 5.

37. The polypeptide of embodiment 1, wherein said hNGAL mutein is capable of binding pyochelin with and without complexed iron, with an affinity measured by an $IC_{50}$ value of about 200 nM or lower, for example, when measured in an assay essentially described in Example 5.

38. The polypeptide of embodiment 34, wherein the hNGAL mutein is capable of inhibiting iron uptake mediated by pyochelin with an $IC_{50}$ value of about 150 nM or lower in a competition ELISA format essentially described in Example 7.

39. The polypeptide of embodiment 34, wherein the hNGAL mutein is capable of inhibiting bacterial growth of Pvd I knock-out (ΔpvdA) in an assay essentially described in Example 8.

40. The polypeptide according to any of the preceding embodiments 34 to 39, wherein the hNGAL mutein comprises a mutated amino acid residue at one or more positions corresponding to positions 28, 34, 36, 40-41, 44-46, 49, 52, 54, 65, 68, 70, 72-74, 77, 79-81, 87, 96, 100, 103, 106, 108, 123, 125, 127, 132, 134 and 141 of the linear polypeptide sequence of the mature hNGAL (SEQ ID NO: 1).

41. The polypeptide of any one of embodiments 34-40, wherein the amino acid sequence of the hNGAL mutein comprises at least one of the following mutated amino acid residues in comparison with the linear polypeptide sequence of the mature hNGAL: Leu 36→His, Met or Val; Ala 40→Ile, Gln, Tyr or Phe; Ile 41→Leu, His or Trp; Gln 49→His, Arg, Ser or Ala; Tyr 52→Leu, Trp or Pro; Ser 68→Asp or His; Leu 70→Arg or Trp; Arg 72→His, Ile, Ala, Ser or Gly; Lys 73→Asn, Met, Pro, Phe, Gln or Arg; Asp 77→Arg, Thr, Pro or Asp; Trp 79→Ala, Arg, Lys or Asp; Arg 81 Thr, Ile or Trp; Asn 96→Met, Asn, Pro or Ala; Tyr 100→Gly, His or Glu; Leu 103→Gly, Met, His or Gln; Tyr 106→Met, Gly, Arg or Trp; Lys 125→Trp, Phe, Gly or Leu; Ser 127→Arg, Trp, Asp or Ile; Tyr 132→Ala, Glu or Thr; and Lys 134→Leu, Val, Asn or Phe.

42. The polypeptide of any one of embodiments 34-41, wherein the amino acid sequence of the hNGAL mutein comprises the following substitution in comparison with the linear polypeptide sequence of the mature hNGAL: Gln 28→His; Val 34→Leu; Glu 44→Gly; Asp 45→Gly; Lys→Arg or Tyr; Asn 65→Asp; Ile 80→Thr; Cys 87→Ser; Leu 94→Phe; Val 108→Ala; Phe 123→Ser and Thr 141→Ala.

43. The polypeptide according to any of the preceding embodiments 34-42, wherein the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 34, 36, 40-41, 44-46, 49, 52, 54, 65, 68, 70, 72-74, 77, 79-81, 87, 96, 100, 103, 106, 108, 123, 125, 127, 132, 134 and 141 of the linear polypeptide sequence of the mature human NGAL (SEQ ID NO: 1).

44. The polypeptide according to any of the preceding embodiments 34-43, wherein the hNGAL mutein comprises one of the following sets of amino acid substitutions in comparison with the linear polypeptide sequence of the mature hNGAL:

(a) Gln 28→His; Ala 40→Ile; Ile 41→Leu; Gln 49→His; Tyr 52→Leu; Ser 68→His; Leu 70→Thr; Arg 72→Lys; Lys 73→Trp; Asp 77→Ile; Trp 79→Ser; Arg 81→His; Cys 87→Ser; Asn 96→Met; Tyr 100→Asn; Leu 103→His; Tyr 106→Met; Lys 125→Trp; Ser 127→Asp; Tyr 132→Glu; Lys 134→Leu;

(b) Gln 28→His; Leu 36→His; Ala 40→Gln; Ile 41→Trp; Gln 49→Arg; Tyr 52→Trp; Ser 68→Asp; Leu 70→Asp; Arg 72→Ala; Lys 73→Ile; Asp 77→His; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

(c) Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Arg 81→Ile; Cys 87→Ser; Asn 96→Ala; Tyr 100→Gly; Leu 103→Met; Tyr 106→Trp; Lys 125→Gly; Ser 127→Trp; Tyr 132→Thru; Lys 134→Val;

(d) Gln 28→His; Leu 36→Val; Ala 40→Tyr; Ile 41→Trp; Gln 49→Ala; Ser 68→Asp; Leu 70→Arg; Arg 72 Trp; Lys 73→Arg; Asp 77→Arg; Trp 79→Asp; Arg 81→Trp; Cys 87→Ser; Asn 96→Pro; Tyr 100→Glu; Leu 103→Gln; Tyr 106 Arg; Lys 125→Leu; Ser 127→Arg; Tyr 132→Ala; Lys 134→Asn;

(e) Gln 28→His; Val 34→Leu; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val; Thr 141→Ala;

(f) Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val;

(g) Gln 28→His; Leu 36→His; Ala 40→Gln; Ile 41→Trp; Asp 45→Gly; Lys 46→Arg; Gln 49→Arg; Tyr 52→Trp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

(h) Gln 28→His; Leu 36→His; Ala 40→Gln; Ile 41→Trp; Glu 44→Gly; Lys 46→Tyr; Gln 49→Arg; Tyr 52→Trp; Ser 68→Asp; Leu 70→Asp; Arg 72→Ala; Lys 73→Ile; Lys 74→Glu; Asp 77→His; Trp

79→Arg; Arg 81→Thr; Cys 87→Ser; Leu 94→Phe; Tyr 100→His; Leu 103→Gly; Tyr 106→Gly; Val 108→Ala; Lys 125→Phe; Ser 127→Ile; Tyr 132→Ala; Lys 134→Phe; or (l) Leu 36→His; Ala 40→Gln; Ile 41→Trp; Asp 45→Gly; Lys 46→Arg; Gln 49→Arg; Tyr 52→Trp; Asn 65→Asp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe.

45. The polypeptide according to any one of embodiments 34 to 44, comprising an amino acid sequence selected from the group consisting of SEQ ID NOs: 54-63 or a pyochelin-binding fragment or variant thereof.

46. The polypeptide according to embodiment 1, comprising an amino acid sequence selected from the group consisting of SEQ ID NOs: 2-63 or a fragment or variant thereof.

47. The polypeptide of any one of embodiments 1-46, wherein said hNGAL mutein comprises one or more non-native cysteine residues substituting one or more amino acids of a wild-type hNGAL.

48. The polypeptide of any one of embodiments 1-46, wherein said hNGAL mutein comprises at least one amino acid substitution of a native cysteine residue by another amino acid.

49. The polypeptide of embodiment 48, wherein said another amino acid is a serine residue.

50. The polypeptide of any one of embodiments 1-46, wherein the hNGAL mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxins, a metal complex, a metal, and colloidal gold.

51. The polypeptide of any one of embodiments 1-46, wherein the hNGAL mutein is fused at its N-terminus and/or its C-terminus to a fusion partner which is a protein, or a protein domain or a peptide.

52. The polypeptide of any one of embodiments 1-46, wherein the hNGAL mutein is conjugated to a compound that extends the serum half-life of the polypeptide.

53. The polypeptide of embodiment 52 wherein the compound that extends the serum half-life is selected from the group consisting of a polyalkylene glycol molecule, hydroethylstarch, a Fc part of an immunoglobulin, a CH3 domain of an immunoglobulin, a CH4 domain of an immunoglobulin, an albumin binding peptide, and an albumin binding protein.

54. The polypeptide of embodiment 53, wherein the polyalkylene glycol is polyethylene glycol (PEG) or an activated derivative thereof.

55. A nucleic acid molecule comprising a nucleotide sequence encoding the polypeptide of any one of embodiments 1-54.

56. The nucleic acid molecule of embodiment 55, wherein the nucleic acid molecule is operably linked to a regulatory sequence to allow expression of said nucleic acid molecule.

57. The nucleic acid molecule of embodiments 55 or 56, wherein the nucleic acid molecule is comprised in a vector or in a phagemid vector.

58. A host cell containing a nucleic acid molecule of any one of embodiments 55 to 57.

59. A method of producing the polypeptide according to any one of embodiments 1-54, wherein the polypeptide is produced starting from the nucleic acid coding for the polypeptide by means of genetic engineering methods.

60. The method of embodiment 59, wherein the polypeptide is produced in a bacterial or eukaryotic host organism and is isolated from this host organism or its culture.

61. A composition comprising one or more polypeptides selected from the group consisting of (i) a polypeptide specific for pyoverdine type I, (ii) a polypeptide specific for pyoverdine type II, (iii) a polypeptide specific for pyoverdine type III and (iv) a polypeptide specific for pyochelin.

62. The composition of embodiment 61, comprising two or more polypeptides selected from the group consisting of (i) a polypeptide specific for pyoverdine type I, (ii) a polypeptide specific for pyoverdine type II, (iii) a polypeptide specific for pyoverdine type III and (iv) a polypeptide specific for pyochelin.

63. The composition of embodiment 62, comprising three or four polypeptides selected from the group consisting of (i) a polypeptide specific for pyoverdine type I, (ii) a polypeptide specific for pyoverdine type II, (iii) a polypeptide specific for pyoverdine type III and (iv) a polypeptide specific for pyochelin.

64. The composition of any one of embodiments 61-63, wherein the polypeptide specific for pyoverdine type I is a polypeptide according to any one of embodiments 3-11.

65. The composition of any one of embodiments 61-63, wherein the polypeptide specific for pyoverdine type II is a polypeptide according to any one of embodiments 12-21.

66. The composition of any one of embodiments 61-63, wherein the polypeptide specific for pyoverdine type III is a polypeptide according to any one of embodiments 22-30.

67. The composition of any one of embodiments 61-63, wherein the polypeptide specific for pyochelin is a polypeptide according to any one of embodiments 31-41.

68. The composition of any one of embodiments 61-67, wherein said composition further includes at least one pharmaceutically acceptable adjuvant, diluent or carrier.

69. A method of binding pyoverdine type I, II, III and/or pyochelin in a subject comprising administering to said subject an effective amount of the composition of any one of embodiments 61-67.

70. A method for inhibiting or lessening growth of *P. aeruginosa* in a subject, comprising administering to said subject an effective amount of the composition of any one of embodiments 61-67.

71. A kit comprising in one or more containers, separately or in admixture, the composition of any one of embodiments 61-67.

72. Use of (i) a first polypeptide according to any one of embodiments 3-11, (ii) a second polypeptide according to any one of embodiments 12-21, (iii) a third polypeptide according to any one of embodiments 22-30 and/or (iv) a fourth polypeptide according to any one of embodiments 31-41, for the binding of pyoverdine type I, II, III and/or pyochelin in a subject.

73. Use of (i) a first polypeptide according to any one of embodiments 3-12, (ii) a second polypeptide according to any one of embodiments 13-23, (iii) a third polypeptide according to any one of embodiments 24-33 and/or (iv) a fourth polypeptide according to any one of embodiments 34-45, for preventing or reducing iron-uptake by *P. aeruginosa* through pyochelin and/or pyoverdine in a subject.

74. Use of (i) a first polypeptide according to any one of embodiments 3-12, (ii) a second polypeptide according to any one of embodiments 13-23, (iii) a third polypeptide according to any one of embodiments 24-33 and/or (iv) a fourth polypeptide according to any one of embodiments 34-45, for the treatment or prevention of *P. aeruginosa* biofilm infection in a subject.

75. The use of embodiment 74, wherein the *P. aeruginosa* biofilm infection is acute or chronic infection.

76. The use of embodiments 72-75, wherein said first, second, third and/or fourth polypeptides are administered in combination, including concurrently, concomitantly or in series.

77. The use of embodiments 72-75, wherein said first, second, third and/or fourth polypeptides are administered independent from each other, including at individual intervals at independent points of time.

78. A combination of (i) a polypeptide according to any one of embodiments 3-11, (ii) a polypeptide according to any one of embodiments 12-21, (iii) a polypeptide according to any one of embodiments 22-30 and/or (iv) a polypeptide according to any one of embodiments 31-41.

VII. EXAMPLES

Example 1: Purification and Biotinylation of Pseudomonas aeruginosa Siderophores

*P. aeruginosa* produces three groups of pyoverdines i.e. pyoverdine type I, pyoverdine type II & pyoverdine type III. Each group has three forms differing in the side chain which is succinyl, succinamide or α-ketoglutaryl. In addition *P. aeruginosa* produces pyochelin. All ten siderophores can complex iron as $Fe^{3+}$.

For selection and screening of muteins of interest, the siderophores may be biotinylated. Biotinylation was performed for pyoverdine I succinyl variant at the succinyl side chain, for pyoverdine II succinyl variant at the L-ornithine side chain and for pyoverdine III succinyl variant mainly at the glycine side chain. Pyochelin was biotinylated at the phenol ring.

Example 2: Selection of Muteins Specifically Binding to *P. aeruginosa* Siderophores hNGAL-based libraries, generated by random mutagenesis of mature hNGAL, were used for selection of muteins specifically binding to the different siderophores of *P. aeruginosa*. Biotinylated and iron loaded Pvd I succinyl, Pvd II succinyl, and Pvd III succinyl as well as biotinylated non-iron-loaded pyochelin were used in independent phage display and selection processes.

$2 \times 10^{12}$ phagemids from these libraries were incubated with 200 nM or 500 nM or 1 μM biotinylated target. Paramagnetic beads coated with neutravidin or streptavidin were used to capture target/phagemid complexes which were subsequently isolated with a magnet. Unbound phagemids were removed by washing the beads with PBST or PBS. Bound phagemids were first eluted with 300 μl 70 mM triethylamine for 10 min followed by immediate neutralization of the supernatant with 100 μl 1M Tris-Cl pH 6.0. After one intermediate wash cycle remaining phagemids were eluted with 100 mM glycine pH2.2 for 10 min followed by immediate neutralization with 50 μl 0.5 M Tris-base. Both elution fractions were pooled and used to infect 4 ml of *E. coli* XL1-blue culture ($OD_{550}$ 0.45-0.6) for reamplification. After incubation for 30 min under agitation bacteria were collected by centrifugation at 5000×g for 2 min, resuspended in 1 ml 2×YT medium and plated on three big LB/Amp agar plates (10 g/l bacto tryptone, 5 g/l yeast extract, 5 g/l NaCl, pH 7.5, 15 g/l agar, 100 μg/ml ampicillin). Plates were incubated overnight at 32° C. Infected cells were scraped from the agar plates using 50 ml 2×YT medium supplemented with 100 μg/ml ampicillin (2×YT/Amp). 50 ml 2×YT/Amp medium were inoculated with the appropriate volume of bacterial suspension to reach an $OD_{550}$ of 0.08. The culture was incubated at 37° C. on a shaker (160 rpm) until an $OD_{550}$ of 0.5 was reached and then infected with helperphages ($1.5 \times 10^{11}$ pfu) by incubation for 15 min with gentle agitation and for 45 min on a shaker at 37° C. Subsequently, kanamycin was added to a final concentration of 70 μg/ml to select bacteria infected by helperphages. Finally, expression of the pIII-hNGAL muteins was induced by addition of 25 ng/ml anhydrotetracyclin.

After 15 h incubation at 24° C. the supernatant of the culture was cleared by centrifugation (5000×g for 20 min). Subsequently, 20 ml supernatant were passed through a polyethersulfone membrane with a pore size of 0.22 μm. To the filtrate 5 ml of a solution containing 20% (w/v) PEG-8000 and 15% (w/v) NaCl in water was added and gently mixed. The solution was incubated for 30 min on ice before centrifugation for 20 min at 4° C. & 5000×g. The pellet containing the phagemids was dissolved in 1 ml buffer containing 200 mM boric acid, 160 mM NaCl and 1 mM EDTA. Insoluble particles were removed by centrifugation (5000×g for 5 min).

The supernatant was transferred to a fresh tube and mixed with 200 μl of a solution containing 20% (w/v) PEG-8000 and 15% (w/v) NaCl in water. The solution was incubated 30 min on ice and precipitated phagemids were subsequently collected by centrifugation (5000×g for 5 min). Phagemids were resuspended in PBS supplemented with 50 mM benzamidine and used for the next round of phagemid selection.

Four consecutive rounds of selection were performed. Different washing conditions were applied: i) eight times with 1 ml PBS/T 5 min incubation for each washing step in all 4 selection rounds, ii) the number of wash cycles increased from round 1 to 4 iii) fast washing steps were altered with 5 min incubation washing steps and the number of washings steps was increased from round to round.

Phagemid DNA was prepared from *E. coli* cells infected with the output of the fourth selection round and the hNGAL mutein cassette was isolated by digestion of the DNA with BstX1 and subsequent purification via agarose gel electrophoresis using standard methods (Sambrook et al., (1989) *Molecular cloning: a laboratory manual*). The hNGAL mutein cassette was inserted into the likewise cut vector, which allows bacterial production of the hNGAL muteins under the control of a tetracycline promoter. $CaCl_2$-competent TG1-F' cells were transformed with the ligation mixture and plated on LB/Amp plates.

For optimization of Pvd I, Pvd II, Pvd III and Pch-specific muteins, additional libraries were generated based on mutein SEQ ID NO: 4, SEQ ID NO: 6, SEQ ID NO: 19, SEQ ID NO: 20, SEQ ID NO: 42, SEQ ID NO: 55, SEQ ID NO: 56 and subsequently SEQ ID NO: 8, SEQ ID NO: 12 and SEQ ID NO: 45. Libraries were generated using either a biased randomization of selected positions or error prone polymerase chain reaction (PCR) based methods. Selection of muteins was performed as described but with increased stringency.

In order to facilitate expression in eukaryotic cells, potential N-glycosylation sites (Asn-X-Ser/Thr) were removed.

Furthermore, mutations were introduced to further optimize for stability.

Example 3: Identification of Muteins Specifically Binding to the Respective *P. aeruginosa* Siderophores Using High-Throughput ELISA Screening Individual colonies were used to inoculate 2×YT/Amp medium and grown overnight (14-18 h) to stationary phase. Subsequently, 50 μl 2×YT/Amp were inoculated from the stationary phase cultures and incubated for 3 h at 37° C. and then shifted to 22° C. until an $OD_{595}$ of 0.6-0.8 was reached. Production of muteins was induced by addition of 10 μl 2×YT/Amp supplemented with 1.2 μg/ml anhydrotetracyclin. Cultures were incubated at 22° C. until the next day. After addition of 40 μl of 5% (w/v) BSA in PBS/T and incubation for 1 h at 25° C. cultures were ready for use in screening assays.

Specific binding of the isolated muteins to the respective siderophore targets was tested by coating a 1:1 mixture of neutravidin and streptavidin (5 μg/ml in PBS) overnight at 4° C. on microtiterplates. After blocking the plate 1 h with 2% BSA in PBST the respective biotinylated siderophore target used for selection was captured on the coated microtiterplates at a concentration of 1.5-2.5 µg/ml in PBS/T. Plates coated in the same manner with biotinylated-aldosterone were used as negative control target in the screening. Subsequently, 20 µl of BSA-blocked cultures were added to the coated microtiter plate containing either captured target or aldosterone and incubated for 1 h at 25° C. Bound muteins were detected after 1 h incubation with anti-17 antibody conjugated with horseradish peroxidase (Merck KgaA, Darmstadt) or anti-Strep-Tag® antibody conjugated with horseradish peroxidase (IBA, Boettingen). For quantification, 20 µl of QuantaBlu fluorogenic peroxidase substrate was added and the fluorescence determined at an excitation wavelength of 320 nm and an emission wavelength of 430 nm. Muteins specifically binding to the respective siderophore targets were then sequenced.

To select for muteins with increased affinity and stability screening was performed with i) reduced antigen concentration and/or ii) competition with unbiotinylated target and/or iii) incubation of the screening supernatant at 65° C. or 70° C. before addition to the target plate and/or iv) using reverse screening formats were the muteins were captured via the Strep-Tag® on microtiter plates coated with anti-Strep-Tag® antibody and different concentrations of biotinylated target was added and detected via extravidin-HRP (Sigma Aldrich, St. Louis, Mo.).

Example 4: Expression of Muteins

Unique muteins were expressed with C-terminal sequence SAWSHPQFEK (SEQ ID NO: 127; including the SA linker and the Strep-Tag® II, WSHPQFEK (SEQ ID NO: 128) in *E. coli* in 2YT-Amp media to purify the muteins after expression using Streptactin affinity chromatography and preparative size exclusion chromatography were applicable.

Example 5: Affinity of Muteins to Soluble *P. aeruginosa* Siderophores Determined in an ELISA Based Setting Solution binding of muteins was assayed by a "Solution binding ELISA", the principle of which was as follows: a constant concentration of the tested mutein was incubated with variable concentrations of ligands (Pvd I s, sa, αKG+/−Fe/Pvd II s, sa, αKG+/−Fe/Pvd III s, sa, αKG+/−Fe/Pch+/−Fe) for 1 h. After this pre-incubation in solution, an aliquot of the mutein/ligand mixture was transferred to an ELISA plate with biotinylated Pvd I s (+Fe), Pvd II s (+Fe), Pvd III s (+Fe) or Pch immobilized via Neutravidin to measure the remaining concentration of free muteins. The concentration of free (non ligand-bound) muteins was determined via a quantitative ELISA setup.

In detail, a 384-well plate suitable for fluorescence measurements (Greiner FLUOTRAC™ 600, black flat bottom, high-binding) was coated with 20 µl of Neutravidin at a concentration of 5 µg/ml in PBS overnight at 4 C. After washing, the Neutravidin-coated wells were blocked with 100 µl blocking buffer containing 0.1% Tween 20 and 2% BSA (PBS-T/BSA) for 1 h at room temperature. After washing again, 20 µl biotinylated pyoverdine or pyochelin in blocking buffer at a concentration of 1 µg/mL were added for 1 h at room temperature and excess reagent was removed.

A fixed concentration of muteins was incubated in solution with varying concentrations of ligand (Pvd I s, sa, αKG+/−Fe/Pvd II s, sa, αKG+/−Fe/Pvd III s, sa, αKG+/−Fe/Pch+/−Fe), using a suitable starting concentration which was serially diluted at a 1:3 ratio down to the picomolar range in PBS-T/BSA. After 1 h incubation at room temperature, 20 µl of the reaction mixture was transferred to the 384-well plate upon which biotinylated pyoverdine or pyochelin was immobilized to capture unbound (free) muteins for 20 min at RT. To allow for transformation of ELISA readout results into absolute free mutein concentrations, a standard curve containing varying concentrations of muteins was prepared in PBS-T/BSA and incubated for 20 min on the same ELISA plate as well.

The residual supernatants were discarded and 20 µl HRP-labeled anti-hNGAL antibody was added at a predetermined optimal concentration in PBS-T/BSA and incubated for 1 h at RT. The anti-hNGAL antibody had been obtained by immunization of rabbits with a mixture of muteins, and was subsequently coupled to HRP using a kit (EZ-link Plus Activated Peroxidase, Thermo Scientific) according to the manufacturer's instructions, to obtain the antibody-HRP conjugate. After washing, 20 µl fluorogenic HRP substrate (QuantaBlu, Thermo) was added to each well, and the reaction was allowed to proceed for 15 to 60 minutes. The fluorescence intensity of every well on the plate was read using a fluorescence microplate reader (Tecan or Molecular Devices). To evaluate the data, free mutein concentration, $c(mutein)_{free}$, was calculated based on the standard curve results, and plotted versus ligand concentration, c(Ligand). To obtain the ligand concentration at which formation the ligand/mutein complex was blocked by 50% ($IC_{50}$), the curves were fitted by nonlinear regression with a single-sites binding model according to $c(mutein)_{free}=c(mutein)_{tot}/(1+c(Ligand)/IC_{50}))$, with the total tracer concentration $c(mutein)_{tot}$ and the $IC_{50}$ value as free parameters. Curve fitting was performed using GraphPad Prism 4 software.

The resulting $IC_{50}$ values are summarized in Tables 1A-D. Muteins selected against biotinylated and iron loaded Pvd I succinyl, Pvd II succinyl and Pvd III succinyl, respectively bound to all subtypes of the respective Pvd group i.e. muteins selected against biotinylated and iron loaded Pvd I succinyl bound with similar affinity to Pvd I succinyl, -succinamide, -α-ketoglutaryl with or without complexed iron ion, muteins selected against biotinylated and iron loaded Pvd II succinyl bound with similar affinity to Pvd II succinyl, -succinamide, -α-ketoglutaryl with or without complexed iron ion and muteins selected against biotinylated and iron loaded Pvd III succinyl bound with similar affinity to Pvd III succinyl, -succinamide, -α-ketoglutaryl with or without complexed iron ion. Most of the selected muteins bound with comparable affinity to all subtypes of the respective group with or without complexed iron ion.

The selection against biotinylated non-iron-loaded pyochelin resulted in lipocalin muteins binding preferably to non iron-loaded pyochelin, such as lipocalin muteins SEQ ID NO: 56 and 57 binding with two- to three digit nM affinity to iron-loaded Pch and with weak affinity or not at all to non-iron loaded Pch, and in lipocalin muteins such as SEQ ID NO: 55 binding preferably to iron-loaded pyochelin.

Affinity optimization of SEQ ID NO: 56 resulted in lipocalin muteins binding with improved affinity to non-iron loaded Pch and still with no or weak affinity to iron loaded Pch, whereas affinity optimization of SEQ ID NO: 55 resulted in lipocalin muteins binding with more than 75 fold improved affinity to non-iron loaded Pch but also with single digit nM affinity to iron loaded Pch.

Thus, with lipocalin mutein selection and optimization it was accomplished that only four different muteins are sufficient to bind all 10 subtypes of *P. aeruginosa* siderophores with and without complexed iron ion (Pvd I s, sa, αKG+/−Fe; Pvd II s, sa, αKG+/−Fe; Pvd III s, sa, αKG+/−Fe; Pch+/−Fe).

TABLE 1A

Binding of muteins to *P. aeruginosa* siderophore pyoverdine I succinyl, -succinamide, -α-ketoglutaryl +/− $Fe^{3+}$ in solution.

| | Solution binding ELISA IC50: nM | | | | | |
|---|---|---|---|---|---|---|
| | Pvd I s (+Fe) | Pvd I sa (+Fe) | Pvd I aKG (+Fe) | Pvd I s (−Fe) | Pvd I sa (−Fe) | Pvd I aKG (−Fe) |
| SEQ ID NO: 2 | 24 | 19 | 13 | 26 | 19 | 13 |
| SEQ ID NO: 4 | 97 | 43 | 91 | 57 | 28 | 50 |
| SEQ ID NO: 5 | 97 | 49 | 73 | 57 | 32 | 42 |
| SEQ ID NO: 6 | 44 | 30 | 37 | 48 | 31 | 36 |
| SEQ ID NO: 7 | 173 | 126 | 59 | 290 | 129 | 53 |
| SEQ ID NO: 8 | 2.38 | 1.33 | 2.15 | 2.3 | 0.98 | 1.8 |
| SEQ ID NO: 9 | 3.3 | 1.37 | 2.4 | 3.7 | 1.6 | 2.9 |
| SEQ ID NO: 10 | 3.4 | 1.1 | 2.87 | 3.8 | 0.92 | 2.9 |
| SEQ ID NO: 11 | 2.97 | 1.9 | 2.57 | 4 | 2 | 3.1 |
| SEQ ID NO: 12 | 6.8 | 4.7 | 6.4 | 6.9 | 4.8 | 5.6 |
| SEQ ID NO: 13 | 0.5 | 0.27 | 0.37 | 0.36 | 0.2 | 0.24 |
| SEQ ID NO: 14 | 2.4 | 1.7 | 3.1 | 2.4 | 1.1 | 2.2 |
| SEQ ID NO: 15 | 1.1 | 0.59 | 1.2 | 0.86 | 0.42 | 0.69 |
| SEQ ID NO: 16 | 1.3 | 0.84 | 1.6 | 1 | 0.63 | 0.83 |
| SEQ ID NO: 18 | 5.3 | 2.2 | 3.9 | 2.8 | 1.8 | 2.5 |

TABLE 1B

Binding of muteins to soluble *P. aeruginosa* siderophore pyoverdine II succinyl, -succinamide, -α-ketoglutaryl +/− $Fe^{3+}$ in solution.

| | Solution binding ELISA IC50: nM | | | | | |
|---|---|---|---|---|---|---|
| | Pvd II s (+Fe) | Pvd II sa (+Fe) | Pvd II aKG (+Fe) | Pvd II s (−Fe) | Pvd II sa (−Fe) | Pvd II aKG (−Fe) |
| SEQ ID NO: 19 | 30 | 36 | 21 | 23 | 42 | 34 |
| SEQ ID NO: 20 | 48 | 40 | 85 | 63 | 40 | 89 |
| SEQ ID NO: 26 | 0.34 | 0.39 | 1.3 | 0.45 | 0.45 | 0.75 |
| SEQ ID NO: 27 | 0.78 | 1.53 | 1.97 | 1.02 | 1.12 | 1.4 |
| SEQ ID NO: 28 | 0.91 | 1.75 | 2.25 | 1.14 | 1.5 | 1.65 |
| SEQ ID NO: 29 | 0.68 | 1.5 | 1.9 | 0.95 | 1.2 | 1.6 |
| SEQ ID NO: 30 | 0.29 | 0.53 | 3 | 0.4 | 0.3 | 2.85 |
| SEQ ID NO: 31 | 0.29 | 0.29 | 1.1 | 0.38 | 0.35 | 0.64 |
| SEQ ID NO: 32 | 0.27 | 0.32 | 1.25 | 0.42 | 0.37 | 0.72 |
| SEQ ID NO: 33 | 0.28 | 0.32 | 1.3 | 0.4 | 0.32 | 0.7 |
| SEQ ID NO: 34 | 0.29 | 0.32 | 1.6 | 0.27 | 0.32 | 1.2 |
| SEQ ID NO: 35 | 0.33 | 0.39 | 0.76 | 0.34 | 0.42 | 0.99 |
| SEQ ID NO: 36 | 0.33 | 0.39 | 0.76 | 0.34 | 0.42 | 0.99 |
| SEQ ID NO: 37 | 0.19 | 0.28 | 2.1 | 0.2 | 0.3 | 1.4 |

TABLE 1C

Binding of muteins to *P. aeruginosa* siderophore pyoverdine III succinyl, -succinamide, -α-ketoglutaryl +/− $Fe^{3+}$ in solution.

| | Solution binding ELISA IC50: nM | | | | | |
|---|---|---|---|---|---|---|
| | Pvd III s (+Fe) | Pvd III sa (+Fe) | Pvd III aKG (+Fe) | Pvd III s (−Fe) | Pvd III sa (−Fe) | Pvd III aKG (−Fe) |
| SEQ ID NO: 39 | 146 | 147 | 23 | 95 | 94 | 23 |
| SEQ ID NO: 42 | 35 | 15 | 78 | 25 | 7.2 | 69 |
| SEQ ID NO: 43 | 0.31 | 0.25 | 1.4 | 0.6 | 0.46 | 1.90 |
| SEQ ID NO: 44 | 0.35 | 0.26 | 0.93 | 0.35 | 0.21 | 1.10 |
| SEQ ID NO: 45 | 0.75 | 0.43 | 1.50 | 0.41 | 0.46 | 1.70 |
| SEQ ID NO: 46 | 0.69 | 0.30 | 1.02 | 0.44 | 0.30 | 1.20 |
| SEQ ID NO: 47 | 0.37 | 0.30 | 0.82 | 0.17 | 0.28 | 0.58 |
| SEQ ID NO: 48 | 0.28 | 0.22 | 0.95 | 0.29 | 0.24 | 0.64 |
| SEQ ID NO: 49 | 0.32 | 0.27 | 0.79 | 0.21 | 0.27 | 0.62 |
| SEQ ID NO: 50 | 0.29 | 0.35 | 0.95 | 0.29 | 0.37 | 0.82 |
| SEQ ID NO: 51 | 0.37 | 0.37 | 0.97 | 0.35 | 0.34 | 1.1 |
| SEQ ID NO: 52 | 0.32 | 0.31 | 1 | 0.31 | 0.31 | 1 |
| SEQ ID NO: 53 | 0.21 | 0.25 | 0.54 | 0.19 | 0.63 | 0.33 |

TABLE 1D

Binding of muteins to *P. aeruginosa* siderophore pyochelin+/− $Fe^{3+}$ in solution.

| | Solution binding ELISA IC50:nM | |
|---|---|---|
| | pch (+Fe) | pch (−Fe) |
| SEQ ID NO: 55 | 361 | N/A |
| SEQ ID NO: 56 | N/A | 51 |
| SEQ ID NO: 57 | N/A | 147 |
| SEQ ID NO: 58 | N/A | 10 |
| SEQ ID NO: 59 | N/A | 11 |
| SEQ ID NO: 60 | 8.6 | 45 |
| SEQ ID NO: 61 | 5.1 | 42 |
| SEQ ID NO: 62 | 4.7 | 26 |
| SEQ ID NO: 63 | 5.6 | 26 |

For high throughput affinity ranking, the same assay was used however with less different concentrations of ligand.

Example 6: Affinity of Muteins Binding to *P. aeruginosa* Siderophores Determined in Biacore In a Surface Plasmon Resonance (SPR) based assay a Biacore 1200 instrument (GE Healthcare) was used to measure the binding affinity of muteins to pyoverdine I succinyl, -succinamide, -α-ketoglutaryl with complexed iron ion or to pyoverdine II succinyl, -succinamide, -α-ketoglutaryl with complexed iron ion or to pyoverdine III succinyl, -succinamide, -α-ketoglutaryl with complexed iron ion. Muteins selected for binding to pyoverdines and negative control (SEQ ID NO: 64) were biotinylated for 2 h at room temperature applying an appropriate excess of EZ-Link NHS-PEG4-Biotin (Thermo, Cat#21329) followed by separation of non-reacted Biotin using a Zeba Spin Desalting Plate (Thermo, Cat#21329) according to the manufactures instructions.

In the SPR affinity assay, biotinylated muteins and negative control were captured on a sensor chip CAP using the Biotin CAPture Kit (GE Healthcare): Sensor Chip CAP is pre-immobilized with an ssDNA oligo. Undiluted Biotin CAPture Reagent (streptavidin conjugated with the complementary ss-DNA oligo) was applied at a flow rate of 2 µl/min for 300 s. Subsequently, 1 µg/ml to 100 µg/mL of biotinylated muteins or negative control were applied for 300 s at a flow rate of 5 µl/min. The reference channel was loaded with Biotin CAPture Reagent only.

To determine the binding affinity, four to five dilutions of the respective Pvd representatives (Pvd I, II, III, including succinyl, succinamide, -α-ketoglutaryl +Fe) at a concentration in the range of 5-2000 nM were prepared in HBS-EP+ buffer (GE Healthcare) and applied to the prepared chip surface. Applying a flow rate of 30 µl/min, a single cycle or multi cycle kinetics approach was used with a sample contact time of 120-180 s and a dissociation time of 900-2400 s. Absence of binding to the negative control SEQ ID NO: 64 was confirmed using a high concentration (e.g. 1200 nM) of the respective Pvd. After ligand immobilization, for analysis using single cycle kinetics all 4-5 concentrations of Pvd were applied consecutively in ascending order before the dissociation was monitored. For analysis using multi cycle kinetics 4 dilutions of Pvd were applied, each followed a dissociation phase. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Data were evaluated with Biacore T200 Evaluation software (V 1.0). Double referencing was used. A 1:1 Binding model was used to fit the raw data.

The resulting kinetic constants for a selection of lipocalin muteins are summarized in Tables 2A-C. Lipocalin muteins could be generated for each Pvd group binding in the subnM to low single digit nM range to all suptypes of the respective Pvd group. The natural ligand of wild-type hNGAL Fe-enterobactin, however, is not bound by the Pvd specific lipocalin muteins.

TABLE 2A

Kinetic constants of Pvd I specific lipocalin muteins to Pvd I succinyl, -succinamide, and -α-ketoglutaryl complexed with $Fe^{3+}$.

| | Pvd I s (+Fe) | | | Pvd I sa (+Fe) | | | Pvd I k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 8 | 5.37E+04 | 1.79E−04 | 3.33 | 1.11E+05 | 1.20E−04 | 1.08 | 4.74E+04 | 2.35E−04 | 4.95 | no bdg. |
| SEQ ID NO: 9 | 3.31E+04 | 3.30E−04 | 9.97 | 8.02E+04 | 2.57E−04 | 3.20 | 3.80E+04 | 5.32E−04 | 14.03 | no bdg. |
| SEQ ID NO: 10 | 3.47E+04 | 4.78E−04 | 13.78 | 8.63E+04 | 3.04E−04 | 3.52 | 5.02E+04 | 6.31E−04 | 12.57 | no bdg. |
| SEQ ID NO: 11 | 2.84E+04 | 4.04E−04 | 14.22 | 6.76E+04 | 2.97E−04 | 4.40 | 3.48E+04 | 5.86E−04 | 16.84 | no bdg. |
| SEQ ID NO: 13 | 1.17E+05 | 6.15E−05 | 0.53 | 1.65E+05 | 4.24E−05 | 0.26 | 9.51E+04 | 8.37E−05 | 0.88 | no bdg. |
| SEQ ID NO: 16 | 3.56E+04 | 1.88E−04 | 5.28 | 5.43E+04 | 1.56E−04 | 2.87 | 3.14E+04 | 2.54E−04 | 8.10 | no bdg. |

TABLE 2B

Kinetic constants of Pvd II specific lipocalin muteins to Pvd II succinyl, -succinamide, and -α-ketoglutaryl complexed with $Fe^{3+}$.

| | Pvd II s (+Fe) | | | Pvd II sa (+Fe) | | | Pvd II k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 32 | 1.15E+06 | 1.09E−03 | 0.94 | 1.37E+06 | 9.55E−04 | 0.7 | 1.09E+05 | 3.74E−04 | 3.44 | no bdg. |
| SEQ ID NO: 33 | 1.23E+06 | 1.25E−03 | 1.02 | 1.41E+06 | 1.04E−03 | 0.74 | 9.93E+04 | 4.16E−04 | 4.19 | no bdg. |

TABLE 2B-continued

Kinetic constants of Pvd II specific lipocalin muteins to Pvd II
succinyl, -succinamide, and -α-ketoglutaryl complexed with $Fe^{3+}$.

| | Pvd II s (+Fe) | | | Pvd II sa (+Fe) | | | Pvd II k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 35 | 1.31E+05 | 4.59E−05 | 0.35 | 2.48E+05 | 4.58E−05 | 0.18 | 4.35E+04 | 1.49E−04 | 3.42 | no bdg. |
| SEQ ID NO: 36 | 1.10E+05 | 4.30E−05 | 0.39 | 1.38E+05 | 3.67E−05 | 0.27 | 2.86E+04 | 5.62E−05 | 1.97 | no bdg. |

TABLE 2C

Kinetic constants of Pvd III specific lipocalin muteins to Pvd III
succinyl, -succinamide, and -α-ketoglutaryl complexed with $Fe^{3+}$.

| | Pvd III s (+Fe) | | | Pvd III sa (+Fe) | | | Pvd III k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 43 | 7.05E+04 | 1.58E−04 | 2.24 | 3.52E+04 | 1.07E−04 | 3.04 | 5.73E+04 | 3.03E−04 | 5.29 | n.d. |
| SEQ ID NO: 44 | 5.62E+04 | 1.42E−04 | 2.53 | 3.03E+04 | 8.90E−05 | 2.94 | 4.82E+04 | 2.71E−04 | 5.64 | n.d. |
| SEQ ID NO: 45 | 5.90E+04 | 1.59E−04 | 2.70 | 3.27E+04 | 9.91E−05 | 3.03 | 4.73E+04 | 3.30E−04 | 6.99 | n.d. |
| SEQ ID NO: 46 | 8.32E+04 | 1.66E−04 | 2.00 | 4.36E+04 | 6.90E−05 | 1.58 | 7.67E+04 | 2.41E−04 | 3.15 | n.d. |
| SEQ ID NO: 47 | 7.89E+04 | 7.91E−05 | 1.00 | 1.28E+05 | 2.52E−05 | 0.20 | 2.92E+04 | 2.62E−04 | 8.97 | n.d. |
| SEQ ID NO: 48 | 6.70E+04 | 1.06E−04 | 1.58 | 1.48E+05 | 9.51E−05 | 0.64 | 2.72E+04 | 1.58E−04 | 5.81 | n.d. |
| SEQ ID NO: 49 | 6.88E+04 | 1.05E−04 | 1.52 | 1.34E+05 | 1.12E−04 | 0.84 | 2.81E+04 | 4.29E−05 | 1.53 | n.d. |
| SEQ ID NO: 53 | 5.10E+04 | 4.19E−05 | 0.82 | 6.73E+04 | 3.90E−05 | 0.58 | 3.88E+04 | 1.40E−04 | 3.60 | no bdg. |

In addition, absence of binding to various siderophores not belonging to the respective pyoverdine subgroup (I, II, III) and to MMP-9 was confirmed using the assay described above by applying high concentrations (≥1 µM) of the following analytes to the immobilized mutein: Fe-enterobactin, desferoxamine, pyochelin, pyoverdines from the respective other subgroups, MMP-9 proform and activated MMP-9. An overview of this analysis is provided in Table 3.

For determination of kinetic constants and resulting $K_D$ for the interaction of mutein SEQ ID NO: 62 with Pch +Fe the mutein or the negative control SEQ ID NO: 64 was immobilized to the surface of a CMS chip using standard amine chemistry: The surface of the chip was activated using EDC and NHS. Subsequently, 5 µg/mL of mutein or the negative control solution in 10 mM acetate pH 4.0 was applied at a flow rate of 10 µl/min until a high immobilization level of approximately 2000 RU was achieved. Residual activated groups were quenched with ethanolamine. The reference channels were treated with EDC/NHS following ethanolamine (blank immobilization).

To determine the affinity, five dilutions of pyochelin (+Fe) were prepared in HBS-P+ buffer and applied to the prepared chip surface. The binding assay was carried out with a contact time of 180 s, dissociation times of 1200-1800 s and applying a flow rate of 30 µl/min. Measurements were performed at 25° C. Regeneration of the immobilized mutein surface was achieved by three consecutive injections of 10 mM Gly-HCl pH 1.5 (120 s) followed by an extra wash with running buffer and a stabilization period. Data were evaluated with Biacore T200 Evaluation software (V 1.0). Double referencing was used. The 1:1 Binding model was used to fit the raw data.

The resulting kinetic constant for SEQ ID NO: 62 is shown in Table 2D.

Using the same assay, absence of binding to siderophores different from pyochelin and to MMP-9 was confirmed by applying high concentrations (≥1 µM) of the following analytes to the immobilized mutein SEQ ID NO: 62: Fe-enterobactin, desferoxamine, pyoverdine, MMP-9 proform and activated MMP-9. An overview of the results is shown in Table 3.

TABLE 2D

Kinetic constants of pyochelin specific lipocalin mutein
SEQ ID NO: 62 to pyochelin complexed with $Fe^{3+}$.

| | pch (+Fe) | | |
|---|---|---|---|
| SEQ ID | $k_{on}$ [1/MS] | $k_{off}$ [1/s] | $K_D$ [nM] |
| SEQ ID NO: 62 | 2.25E+06 | 6.43E−04 | 0.29 |

TABLE 3

Specificity of lipocalin muteins binding to Pvd I, Pvd II, Pvd III or pyochelin.

| | Pvd I s (+Fe) | Pvd II s (+Fe) | Pvd III s (+Fe) | Pch (+Fe) | Enterobactin (+Fe) | Desferoxamin | proform MMP-9 | activated MMP-9 |
|---|---|---|---|---|---|---|---|---|
| SEQ ID NO: 16 | + | − | − | − | − | − | − | − |

TABLE 3-continued

Specificity of lipocalin muteins binding to Pvd I, Pvd II, Pvd III or pyochelin.

| | Pvd I s (+Fe) | Pvd II s (+Fe) | Pvd III s (+Fe) | Pch (+Fe) | Entero-bactin (+Fe) | Desfer-oxamin | proform MMP-9 | activated MMP-9 |
|---|---|---|---|---|---|---|---|---|
| SEQ ID NO: 36 | – | + | – | – | – | – | – | – |
| SEQ ID NO: 53 | – | – | + | – | – | – | – | – |
| SEQ ID NO: 62 | – | – | – | + | – | – | – | – |
| SEQ ID NO: 64 | – | – | – | – | + | – | – | – |

Example 7: Functional Testing of Muteins Binding to P. aeruginosa Siderophores; Inhibition of Iron Uptake To determine the functional iron uptake inhibition in living bacteria, a dose range concentration of the lipocalin muteins binding to P. aeruginosa siderophore are incubated for 1 hour with 100 nM radioactive iron loaded siderophore in a Tris.HCl 50 mM pH 8.0 buffer before being incubated for 30 minutes with bacteria at a final concentration of OD=1 at 595 nm in a 96 well plate. Subsequently bacteria are filtered with a cell harvester through a 96 well plate GF/B filter preincubated with a Poly Ethylene Imine solution at 5% and washed 3 times with Tris buffer. After filtering and drying, 30 µl of scintillant cocktail are added in each filter well before counting. To iron load pyoverdine, siderophore is incubated for 15 minutes with $^{55}$Fe—Cl$_3$ in Tris buffer with a 4 to 1 ratio of pyoverdine and iron in a 200 µM final solution. For loading pyochelin with radioactive iron, a 40 µl solution of $^{55}$FeCl$_3$ at 0.25 mM in HCl 0.5 N is added to a methanol solution of pyochelin at 1 mM. After a 15 minutes incubation time, 940 µl Tris HCl 50 mM pH 8.0 is added to obtain a 20 µM $^{55}$Fe-Pch solution with a 2 to 1 ratio between pyochelin and iron. The bacteria are prepared as follow: 10 ml of an overnight culture in Mueller Hinton Medium inoculated with an isolated clone is centrifuged and the washed pellet is resuspended in 25 ml of succinate medium and incubated under shaking for 2 hours. In parallel, 20 ml of Mueller Hinton Medium are inoculated with 5 ml of the overnight culture and incubated under shaking for 2 hours to be used as background iron uptake level. The 25 ml bacteria cultures are then centrifuged and washed with the corresponding medium before the pellet is resuspended in Tris.HCL 50 mM pH8.0 buffer and the OD at 595 nm measured to have a final concentration in the assay of OD=1.

Percentage of incorporation is calculated for each concentration point and the inhibition is calculated with in-house software. For this calculation, the maximum level of iron uptake is based on the value obtained in Minimum Succinate Medium without any lipocalin mutein, and the background value is obtained in the rich Mueller Hinton Medium where the siderophore receptor is not expressed.

TABLE 4

Lipocalin muteins block iron uptake of P. aeruginosa as exemplarily shown for lipocalin muteins SEQ ID NO: 16, 37, 53 and 62.

| SEQ ID | Iron uptake IC50: nM | | |
|---|---|---|---|
| SEQ ID NO: 16 | Pvd I s 121 | Pvd I sa 123 | Pvd I aKG 183 |

TABLE 4-continued

Lipocalin muteins block iron uptake of P. aeruginosa as exemplarily shown for lipocalin muteins SEQ ID NO: 16, 37, 53 and 62.

| SEQ ID | Iron uptake IC50: nM | | |
|---|---|---|---|
| SEQ ID NO: 37 | Pvd II s 118 | Pvd II sa 107 | Pvd II aKG 51 |
| SEQ ID NO: 53 | Pvd III s 74 | Pvd III sa 32 | Pvd III aKG 8 |
| SEQ ID NO: 62 | | | Pch 54 |

Example 8: Functional Testing of Muteins Binding to P. aeruginosa Siderophores; Growth Inhibition Bacterial growth inhibition is determined by incubating the muteins binding to P. aeruginosa siderophores in the Chelex treated Succinate Medium complemented with a Trace Element Solution and 0.1 mg/ml BSA with a MS bacterial culture diluted at a final OD of 0.05 at 595 nm in a black 96 well plate with transparent bottom. The plate is incubated over night at 37° C. with an every 20 minutes shaking and OD reading at 595 nm in an IEMS Reader MF from Thermo Labsystem. Growth inhibition is exemplarily shown for a Pvd I strain and Pvd I specific mutein SEQ ID NO: 16 in FIG. 4A, for a Pvd II strain and Pvd II specific mutein SEQ ID NO: 19, and SEQ ID NO: 36 in FIG. 4B, for a Pvd III strain and Pvd III specific mutein SEQ ID NO: 53 in FIG. 4C and for a Pvd I knock-out (ΔpvdA) strain relying on pyochelin for iron uptake to grow and pyochelin specific mutein SEQ ID NO: 62 in FIG. 4D. Control is bacterial growth without lipocalin mutein.

Example 9: Stability Assessment of Muteins

To determine melting temperatures as a general indicator for overall stability, siderophore-specific muteins (SEQ ID NOs: 13-18; 26, 31-36; 47-53; 58-62) at a protein concentration of 1 mg/ml in PBS (Gibco) were scanned (25-100° C.) at 1° C./min using a capillary nanoDSC instrument (CSC 6300, TA Instruments). The melting temperature (Tm) was calculated from the displayed thermogram using the integrated Nano Analyze software.

The resulting melting temperatures as well as the onset of melting for the lipcalin muteins (SEQ ID NOs: 13-18; 26, 31-36; 47-53; 58-62) are listed in Tables 5A-D below. For all Pvd groups as well as for pch lipcalin muteins with Tms in the range of 70° C., best lipocalin mutein for each Pvd type and pch ranging from 68 to 74° C., could be selected indicating good stability of the molecules.

TABLE 5A

Tm and onset of melting as determined by nanoDSC of Pvd I specific lipocalin muteins.

| | nanoDSC | |
|---|---|---|
| SEQ ID | Tm ° C. | onset |
| SEQ ID NO: 13 | 59 | 51 |
| SEQ ID NO: 14 | 61 | 51 |
| SEQ ID NO: 15 | 68 | 59 |
| SEQ ID NO: 16 | 69 | 60 |
| SEQ ID NO: 17 | 61 | 53 |
| SEQ ID NO: 18 | 61 | 54 |

TABLE 5B

Tm and onset of melting as determined by nanoDSC of Pvd II specific lipocalin muteins.

| | nanoDSC | |
|---|---|---|
| SEQ ID | Tm ° C. | onset |
| SEQ ID NO: 26 | 65 | 58 |
| SEQ ID NO: 31 | 67 | 60 |
| SEQ ID NO: 32 | 64 | 56 |
| SEQ ID NO: 33 | 67 | 61 |
| SEQ ID NO: 34 | 67 | 56 |
| SEQ ID NO: 35 | 71 | 63 |
| SEQ ID NO: 36 | 70 | 61 |

TABLE 5C

Tm and onset of melting as determined by nanoDSC of Pvd III specific lipocalin muteins.

| | nanoDSC | |
|---|---|---|
| SEQ ID | Tm ° C. | onset |
| SEQ ID NO: 47 | 62 | 53 |
| SEQ ID NO: 48 | 64 | 55 |
| SEQ ID NO: 49 | 59 | 50 |
| SEQ ID NO: 50 | 61 | 52 |
| SEQ ID NO: 51 | 62 | 53 |
| SEQ ID NO: 52 | 59 | 49 |
| SEQ ID NO: 53 | 68 | 59 |

TABLE 5D

Tm and onset of melting as determined by nanoDSC of pch specific lipocalin muteins.

| | nanoDSC | |
|---|---|---|
| SEQ ID | Tm ° C. | onset |
| SEQ ID NO: 58 | 63 | 51 |
| SEQ ID NO: 59 | 60 | 54 |
| SEQ ID NO: 60 | 68 | 56 |
| SEQ ID NO: 61 | 69 | 63 |
| SEQ ID NO: 62 | 74 | 63 |

To assess storage and freeze/thaw stability muteins at a conc. of 1 mg/ml in PBS were incubated for 1 week at 37° C. or underwent three freeze/thaw cycles. Active mutein was measured in a quantitative ELISA setting. Monomeric protein was measured in an analytical size exclusion chromatography. Exemplary data for SEQ ID NO: 16, 36, 53, 62 are shown in Table 6.

For assaying protein activity the following ELISA was applied: A 384-well plate suitable for fluorescence measurements (Greiner FLUOTRAC™ 600, black flat bottom, high-binding) was coated with 20 μL of Neutravidin (Thermo Scientific) at a concentration of 5 μg/ml in PBS overnight at 4° C. After washing, the Neutravidin-coated wells were blocked with 100 μl blocking buffer (2% w/v BSA in PBS containing 0.1% v/v Tween-20) for 1 h. After washing again, 20 μl of biotinylated and iron loaded pyoverdine I succinyl, pyoverdine II succinyl, pyoverdine III succinyl or biotinylated pyochelin at a concentration of 1 μg/ml in blocking buffer were added. The plate was washed and 20 μl of appropriately diluted protein standard, unstressed reference sample or stressed sample was transferred to the ELISA plate and incubated. To quantitate plate-bound protein, the ELISA plate was washed, residual supernatants were discarded and 20 μl HRP-labeled anti-hNGAL antibody was added at a predetermined optimal concentration in blocking buffer and incubated. After washing, 20 μl fluorogenic HRP substrate (QuantaBlu, Pierce) was added to each well, and the reaction was allowed to proceed for 20-30 minutes. The fluorescence intensity of every well on the plate was read using a fluorescence microplate reader (Tecan).

Unless otherwise stated all incubation steps were performed at for 1 h at room temperature and after each incubation step the plate was washed with 100 μl PBS-T buffer (PBS, 0.05% Tween 20) for five times using a Biotek EL×405 select CW washer.

For the ELISA described above, a calibration curve including 11 dilutions typically ranging from 0.008-500 ng/mL was prepared and three different, independent dilutions within the linear range of the calibration curve were prepared for each sample. Blocking buffer optionally supplemented with 1% human or murine plasma was used for the dilutions.

The calibration curve was fit using a 4 Parameter Logistic (4PL) nonlinear regression model and used to calculate active protein concentrations for the tested samples. The determined active protein concentrations were referenced against an unstressed sample stored at the same concentration and in the same matrix.

Analytical size exclusion chromatography was performed on an Agilent HPLC system with two Superdex 75 5/150 GL columns (GE Healthcare) in a row using PBS (Gibco) as an eluent at a flow rate of 0.3 mL/min.

To assess storage stability in plasma muteins at a conc. of 0.5 mg/ml were incubated for 1 week at 37° C. in human, mouse and rat plasma. Active mutein was measured in a quantitative ELISA setting as described.

All tested lipocalin muteins proved to be stable under all tested conditions.

evaluated with a one-way analysis of variance followed by Dunnett's test (ZAR J. H., Biostatistical Analysis, Prentice Hall International Editions, 4th edition, 1999.; C. W. Dunnett, "A multiple comparison procedure for comparing several treatments with a control", J. Amer. Statist. Assoc., 50: 1096-1121 (1955)).

In a *P. aeruginosa*-induced lung infection model in mice, SEQ ID NO: 19 was administered 1 hour before and at time

TABLE 6

Stability after 3 freeze/thaw cycles (F/T); 1 week storage in PBS at 37° C. and 1 week storage in human (hu), mouse (mu) or rat plasma assessed by recovery of activity in qELISA and monomer content in analytical SEC: stable in qELISA = 100 +/− 15%; stable in aSEC = 100 +/− 5% (recovery of monomer peak area compared to non-stressed reference sample); for all samples including references a monomer content of 100 area percent has been detected.

| Mutein | sidero-phore | 3xF/T, −20° C. 1 mg/ml | | 1 week PBS, 37° C., 1 mg/ml | | 1 week hu plasma, 37° C. | 1 week mu plasma, 37° C. | 1 week rat plasma, 37° C. |
|---|---|---|---|---|---|---|---|---|
| | | % recovery of activity in qELISA | % monomer in aSEC | % recovery of activity in qELISA | % monomer in aSEC | % recovery of activity in qELISA | | |
| SEQ ID NO: 16 | Pvd I | 102 | 98 | 86 | 98 | 86 | 100 | 100 |
| SEQ ID NO: 36 | Pvd II | 99 | 101 | 104 | 98 | 93 | 91 | 110 |
| SEQ ID NO: 53 | Pvd III | 98 | 99 | 107 | 102 | 92 | 83 | 101 |
| SEQ ID NO: 62 | pch | 107 | 100 | 95 | 104 | 97 | 102 | 95 |

Example 10: In Vivo Potency of Lipocalin Muteins in Mouse Model

The prophylactic effect of SEQ ID NO: 19 following intravenous (i.v.) administration in a *P. aeruginosa*-induced pulmonary infection in mice was studied.

SEQ ID NO: 19 was administered 1 hour before infection and at time of infection. Lung bacteria load was evaluated 24 h after infection.

The strain used in this study was *P. aeruginosa* (ATCC27853). Starting from *P. aeruginosa* stored at −80° C. in PBS/15% Glycerol, an overnight culture was conducted at 37° C. under shaking in Mueller-Hinton broth, and followed by additional subculture (100 µl overnight culture+100 ml of MHB) until end of logarithmic phase of growth. The culture was washed twice and resuspended in phosphate-buffer saline before to be frozen at $1\times10^9$ CFU/ml. For each experiment a fresh vial was thawed and inoculum verified by viable counts.

7 to 8 weeks-old Male Swiss mice (5 animals/group) purchased from Janvier laboratories, (Route des chenes secs, 53940 Le Genest Saint Ile, France), were allowed at least 5 days acclimatization prior to use. Animals were maintained at temperature of 22±2° C. with relative humidity of 40-70% and 12-15 air fresh changes/hour. Light cycle 12/12 hours: light 7 a.m. to 7 p.m. (normal cycle). Temperature and relative humidity derivations are recorded continuously. Animals were housing 5 per cages and they allowed access to water and standard diet (AO4 C standard diet (SAFE)) ad libitum. All experiments were performed with approval of the ethics committee of Sanofi R&D (CEPAL).

Lung infection was induced by intranasal challenge of male Swiss mice with $1\times10^7$ CFU/mouse of *P. aeruginosa* in 50 µl NaCl 0.9%.

SEQ ID NO: 19 at concentrations of 200, 400, 1000 or 2000 µg/mouse was administered 1 h before infection and at time of infection, with i.v. bolus.

Twenty four hours after infection, animals were euthanized and bacterial count from lung homogenates were determined and expressed in log 10 CFU/ml as mean±SEM.

Statistical analysis was performed using SAS v9.2. The Excel software 2003 was used for figure presentations. Comparisons on SEQ ID NO: 19 doses versus vehicle were of bacteria challenge and SEQ ID NO: 19 prevented the development of infection in mice in a dose-dependent manner. A significant prevention effect was observed for SEQ ID NO: 19 starting at 200 µg/mouse, with a maximal effect at 2000 µg/mouse.

Example 11: Crystallisation

To determine the three dimensional structure of SEQ ID NO: 31 protein in complex with Pvd-Fe the following procedure was applied.

The protein sequence depicted in FIG. 6 was cloned in the pET-24a plasmid and expressed as N-terminally tagged 6His-TEV protease recognition site construct.

The plasmid was used to transform BL21(DE3) Star *E. coli* cells and the resulted clones were inoculated in Overnight Express Instant TB Medium (Novagen) and the cells were harvested after 47 hours of incubation at 18° C. with 200 RPM agitation at final OD600 4.7. The cell pellet was resuspended in buffer containing 500 mM NaCl, 10 mM Imidazole, 1 mM $MgCl_2$, 1 mM TCEP, 5% glycerol and 20 mM Tris pH 7.4 and lysed by standard ultra-sonication procedure. The resulted extract was cleared by low speed centrifugation and supernatant was filtered through 22 nm membrane before loading to Ni NTA (Qiagen) 5 ml column pre-equilibrated with 100 mM NaCl, 10 mM Imidazole, 100 mM HEPES pH 8 buffer. The protein was eluted by linear gradient of imidazole 10 mM to 300 mM and further dialyzed overnight to 100 mM NaCl, 10 mM Imidazole, 100 mM HEPES pH 8 buffer. The protein was concentrated to 20 mg/ml and loaded to Gel filtration Superdex 75 column (GE). The resulted protein was dialyzed to 100 mM NaCl, 10 mM HEPES pH 8 buffer overnight in the presence of TEV protease (1/50 ratio) to remove 6His N-terminal tag following by negative Ni NTA purification step as described above to separate the cleaved protein. Final protein was concentrated to 12 mg/ml in 100 mM NaCl, 50 mM HEPES pH 7.5 aliquoted, snap frozen in liquid nitrogen and stored at −80° C. for further use.

For crystallization the protein was incubated with 10× times higher molar concentration of Pvd-Fe overnight and plated for crystallization screening carried out in SBS format plates where 100 nL protein drops were mixed with 100 nL of crystallization screening solution in vapor diffusion sitting drops format experiments at 20° C. and 4° C. A number of crystallization hits were detected and crystallization conditions were further optimized in order to obtain well diffracting x-ray quality crystals.

The crystals diffraction quality was assessed using synchrotron x-ray source and the best diffracting crystals were obtained under 20% PEG3350 and 0.2 M LiSO$_4$ conditions at 20° C. The best crystals were cryoprotected by increasing PEG3350 concentration to 35% than snap frozen in liquid nitrogen and 1.8 Å data set was collected at 100 K temperature.

X-ray data were processed by MOSFLM and the protein structure was determined by molecular replacement method using pdb 1LKE as a search model and the structural model was further refined to Rfree=0.233–R=0.200 quality in P41212 with 2 ternary protein complexes per asymmetric unit.

The protein structure presents classical lipocalin scaffold with Pvd-Fe bound to both mutein proteins present in the asymmetric unit, FIG. 7. The amino acid residues involved in the Pvd-Fe binding analysed and presented on FIG. 8. The oxygens of the Pvd directly binding Fe are identified and presented on FIG. 9.

Example 12: Generation of Fusion Molecule Constructs

Four single lipocalin muteins were genetically fused to form a fusion molecule by gene synthesis (see FIG. 10A). The lipocalin muteins were separated from each other by linkers like (G4S)$_2$, potential N-glycosylation sites (N-X-SM were removed, and the resulting constructs were subsequently subcloned into the episomal expression vector pXL, an analogue of the pTT vector described by Durocher et al. (2002), Nucl. Acids Res. 30(2). The fusion molecule of SEQ ID NO: 134 was generated by genetic fusion of the lipocalin muteins of SEQ ID NOs: 36, 16, 53 and 62. The fusion molecule of SEQ ID NO: 135 was generated by genetic fusion of the lipocalin muteins of SEQ ID NOs: 34, 17, 50 and 63.

So-called Fc-fusion molecule constructs were generated by fusion of four single lipocalin muteins separated by a (G4S)$_2$ linker to the Fc-domain of human IgG4 (SEQ ID NO: 140). SEQ ID NO: 136 was generated by genetic fusion of the lipocalin muteins of SEQ ID NOs: 36, 16, 53 and 62 separated by (G4S)$_2$ linkers to the N-terminus of human IgG4 Fc-domain (SEQ ID NO: 140). SEQ ID NO: 137 was generated by genetic fusion of the lipocalin muteins of SEQ ID NOs: 34, 17, 50 and 63 separated by (G4S)$_2$ linkers to the N-terminus of human IgG4 Fc-domain (SEQ ID NO: 140). SEQ ID NO: 138 was generated by genetic fusion of the lipocalin muteins of SEQ ID NOs: 34, 17, 50 and 63 separated by (G4S)$_2$ linkers to the C-terminus of human IgG4 Fc-domain (SEQ ID NO: 140). SEQ ID NO: 139 was generated by genetic fusion of the lipocalin muteins of SEQ ID NOs: 34 and 17 separated by a (G4S)$_2$ linker to the N-terminus of human IgG4 Fc-domain (SEQ ID NO: 140) and the lipocalin muteins of SEQ ID NOs: 50 and 63 separated by (G4S)$_2$ linker to the C-terminus of human IgG4 Fc-domain (SEQ ID NO: 140). The overall structures of these Fc-fusion molecule constructs are shown in FIGS. 10B, 10C and 10D.

Further exemplary fusion molecule constructs are those of SEQ ID NOs: 143 to 186. It is noted that the internal references used for the muteins and fusion molecule constructs in the sequence listing do not necessarily reflect the mutations or all the mutations in comparison to the reference sequence, i.e., the sequence of wild-type hNGAL (e.g., SEQ ID NO: 1). The actual mutations can be readily determined by comparing the mutein/fusion molecule sequences with the reference sequence.

Example 13: Expression of Fusion Molecule Constructs and Quality Control

The expression plasmids for transfection were propagated in *E. coli* and prepared using the Endo Free Mega Kit from Qiagen. Fusion molecules were produced by transient transfection of HEK293 cells growing in FreeStyle F17 expression medium from Life Technologies. Cells were cultivated at 37° C. in a Kuehner ISF1-X incubator shaker at 110 rpm with 8% CO$_2$. Cells were removed six to seven days after transfection by centrifugation for 20 min at 4500 g. Supernatants were filtered via a 0.2 µm membrane to remove remaining particles.

His-tagged proteins were purified by affinity chromatography on HisTrap columns from GE Healthcare. To avoid unspecific binding, 20 mM imidazol was added before the capture step. The proteins were washed with MES buffer (50 mM MES, 1 M NaCl, pH 6.5) and Tris buffer (50 mM Tris, 50 mM NaCl pH 8) and eluted with a gradient up to 500 mM imidamidazol in Tris buffer.

Fc variants were purified by affinity chromatography on HiTrap Protein A columns from GE Healthcare. The Proteins were washed with PBS buffer (Life Technologies) followed by elution with 100 mM Citrate buffer pH 3 and neutralized with Tris buffer pH 9. Polishing step of His-tagged proteins and Fc variants consisted of size exclusion chromatography (SEC) using Superdex 200 (GE Healthcare) with PBS (Life Technologies). After concentration by ultrafiltration, the fusion molecules were sterile filtered (0.2 µm), aliquoted and stored at −80° C.

Further quality control was done by analytical SEC, SDS-PAGE (see FIG. 11) and mass spectrometry. Analytical SEC was performed using a BioSECcurity HPLC (PSS) equipped either with a TSKgel3000SWXL (7.8×300 mm, Tosoh) with guard column (7.8×50 mm, Tosoh) or with a MabPac SEC-1 column (4×300 mm, Thermo) and MabPac SEC-1 guard column (4×50 mm, Thermo Fisher). The analysis was run at 1 ml/min (for TSKgel column) or 0.25 ml/min (for MabPac column) using 250 mM NaCl, 100 mM Na-phosphate pH 6.7 with detection at 280 nm and 260 nm. 5 µg of protein (at 1 mg/ml in D-PBS) were applied onto the column. For estimation of the molecular size the column was calibrated using gel filtration standard mixtures (Gel filtration kit MWGF-1000, SIGMA Aldrich and Protein-Kit, PSS). Data evaluation was performed using WinGPC software v5.11 (PSS). Results for one fusion molecule and one Fc-fusion molecule construct are shown in Table 7 below.

TABLE 7

Analysis of fusion molecule constructs by analytical SEC (TSKgel3000SWXL column).

| Protein | Aggregate by SEC | MW by SEC |
|---|---|---|
| SEQ ID NO: 134 | <1% | 125 kDa |
| SEQ ID NO: 136 | 1% | 457 kDa |

Accurate mass analyses were performed using a 6540 UHD Accurate Mass Q-TOF LC-MS system (Agilent) equipped with a dual ESI ion source. Measurements were done in positive ion mode with extended mass range (2

GHz). Samples were diluted to a concentration of 0.5 mg/ml in D-PBS. For measurement of reduced samples, 10 mM of TCEP was added. Deglycosylation under native conditions was done with samples at 0.5 mg/ml in D-PBS after addition of 250 units of PNGaseF (NEB) to 12.5 µg of protein and incubation at 37 CC for 18 hrs. 2 µg of protein was applied onto a Poroshell 300SB-C8 column (0.5×75 mm, 5 µm, Agilent) with guard column (Narrow bore Poroshell 300SB-C8, 2.1×12.5 mm, 5 µm, Agilent) run at 40° C. Eluent A was LC water with 0.1% formic acid; Eluent B was 90% acetonitrile with 0.1% formic acid. Separation was achieved with a linear gradient from 5% B to 100% B in 7 mins and a flow rate of 180 µl/min. Data processing and analysis was done using MassHunter Qualitative Analysis software version B.06. Results for one fusion molecule and one Fc-fusion molecule construct are shown in Table 8 below.

TABLE 8

Accurate mass analysis of fusion molecule constructs by ESI-MS.

| Protein | Exact mass, reduced | Accurate mass, reduced | Delta mass | Mass error |
|---|---|---|---|---|
| SEQ ID NO: 134 | 85234.2 Da (PyroE) | 85232.0 Da (PyroE) | 2.2 Da | 25 ppm |
| SEQ ID NO: 136 | 109473.1 Da (PyroE, deglycosylated) | 109483.7 Da (PyroE, deglycosylated) | −10.5 Da | −96 ppm |

Example 14: Expression of Single Lipocalin Muteins

The expression plasmids for transfection were propagated in E. coli and prepared using the Endo Free Mega Kit from Qiagen. Lipocalin muteins were produced by transient transfection of HEK293 cells growing in FreeStyle F17 expression medium from Life Technologies. Cells were cultivated at 37° C. in a Kuehner ISF1-X incubator shaker at 110 rpm with 8% $CO_2$. Cells were removed six to seven days after transfection by centrifugation for 20 min at 4500 g. Supernatants were filtered via a 0.2 µm membrane to remove remaining particles. His-tagged proteins were purified by affinity chromatography on HisTrap columns from GE Healthcare. To avoid unspecific binding, 20 mM imidazol was added before capture step. The proteins were washed with MES buffer (50 mM MES, 1 M NaCl, pH 6.5) and Tris buffer (50 mM Tris, 50 mM NaCl pH 8) and eluted with a gradient up to 500 mM imidazol in Tris buffer. Polishing step consisted of size exclusion chromatography (SEC) using Superdex 75 (GE Healthcare) with PBS (Life Technologies). After concentration by ultrafiltration, the proteins were sterile filtered (0.2 µm), aliquoted and stored at −80° C. Protein concentration was determined by measurement of absorbance at 280 nm. Further quality control was done by analytical SEC, SDS-PAGE and mass spectrometry.

Example 15: Stability Assessment of Fusion Molecules

To determine melting temperatures as a general indicator for overall stability, the siderophore-specific fusion molecule of SEQ ID NO: 134 and the single lipocalin muteins (SEQ ID NOs: 16, 36, 53 and 62) were used at a protein concentration of 1 mg/ml in PBS (Gibco) and scanned in a temperature range from 25-100° C. with an increment of 1° C./min using a capillary nanoDSC instrument (CSC 6300, TA Instruments). The melting temperatures (Tm) were calculated from the displayed thermogram using the integrated Nano Analyze software. The resulting melting temperatures as well as the onset of melting are listed in Table 9 below.

TABLE 9

Tm and onset of melting as determined by nanoDSC for single lipocalin muteins and a fusion molecule specific for P. aeruginosa siderophores.

|  |  |  | Tm: ° C. | onset of melting: ° C. |
|---|---|---|---|---|
| Fusion molecule |  | SEQ ID NO: 134 | 64/66 | 57 |
| Single lipocalin muteins | Pvd I | SEQ ID NO: 16 | 70 | 61 |
|  | Pvd II | SEQ ID NO: 36 | 71 | 66 |
|  | Pvd III | SEQ ID NO: 53 | 69 | 63 |
|  | Pch | SEQ ID NO: 62 | 76 | 67 |

The onset of melting is between 61-67° C. for the single lipocalin muteins (SEQ ID NOs: 16, 36, 53 and 62) and 57° C. for the fusion molecule (SEQ ID NO: 134). The melting temperature is between 66-76° C. for the single lipocalin muteins (SEQ ID NOs: 16, 36, 53 and 62) and 64/66° C. for the fusion molecule (SEQ ID NO: 134). Onset of melting and the melting temperature, although slightly lower for the fusion molecule compared to the single lipocalin muteins, is comparable between the fusion molecule and the single lipocalin muteins and indicates good stability for the proteins.

To assess storage and freeze/thaw stability, the fusion molecule of SEQ ID NO: 134 or the Fc-fusion molecule of SEQ ID NO: 136 at a concentration of 1 mg/ml in PBS were incubated for 1 week at 37° C. or 42° C. or underwent three freeze/thaw cycles. Active fusion molecule concentration was measured in a quantitative ECL-assay setting. Three different simultaneous binding formats as described in Example 8 were employed to examine the ability to bind to each pyoverdine (I, II and III) and pyochelin simultaneously. Peak area of monomeric protein was measured in an analytical size exclusion chromatography.

For the quantitative ECL-Assay as described in Example 9, a calibration curve including 11 dilutions typically ranging from 0.1-5000 ng/mL was prepared and three different, independent dilutions within the linear range of the calibration curve were prepared for each sample. Blocking buffer optionally supplemented with 1% human plasma was used for the dilutions. The calibration curve was fit using a 4 Parameter Logistic (4PL) nonlinear regression model and used to calculate active protein concentrations for the tested samples. The determined active protein concentrations were referenced against an unstressed sample stored at the same concentration and in the same matrix.

Analytical size exclusion chromatography was performed on an Agilent HPLC system with two Superdex 75 5/150 GL columns (GE Healthcare) in a row using PBS (Gibco) as an eluent at a flow rate of 0.3 mL/min. Monomer peak areas of the stressed samples and unstressed references were calculated using a WinGPC Unichrom GPC/SEC software (PSS: Polymer Standards Service-USA Inc.). Recovery of monomer peak area was calculated as recovery=monomer peak area sample/monomer peak area reference. To assess storage stability in plasma, a fusion molecule and an Fc-fusion molecule at a conc. of 0.5 mg/ml were incubated for 1 week at 37° C. in human plasma. Concentration of active fusion molecule was measured in a quantitative ECL-Assay setting as described above.

Data for the constructs of SEQ ID NO: 134 and SEQ ID NO: 136 are shown in Table 10 below. The fusion molecule and the Fc-fusion molecule constructs exhibited high stability under all tested conditions.

blocking buffer at a concentration of 1 µg/mL were added for 1 h at room temperature and excess reagent was removed. A fixed concentration of mutein or fusion molecule construct was incubated in solution with varying concentrations of ligand (Pvd I s, sa, αKG+/−Fe/Pvd II s, sa, αKG+/−Fe/Pvd III s, sa, αKG+/−Fe/Pch+/−Fe), using a suitable starting concentration which was serially diluted at a 1:3 ratio down to the picomolar range in PBS-T/BSA. After 1 h incubation at room temperature, 20 µl of the reaction mixture was transferred to the 384-well plate upon which biotinylated pyoverdine or pyochelin was immobilized to capture unbound (free) mutein or fusion molecule construct for 20 min at RT. To allow for transformation of ELISA readout

TABLE 10

Stability after 3 freeze/thaw cycles (F/T); 1 week storage in PBS at 37° C. or 42° C. and 1 week storage in human (hu) plasma assessed by recovery of activity in qELISA and monomer content in analytical SEC: fully stable in qELISA = 100 +/− 15%; fully stable in aSEC = 100 +/− 5% (recovery of monomer peak area compared to non-stressed reference sample);

| | 3x F/T −20° C., 1 mg/ml | | | | | 1 week at 37° C. PBS 1 mg/ml | | | | |
|---|---|---|---|---|---|---|---|---|---|---|
| | % recovery of activity in qELISA | | | | | % recovery of activity in qELISA | | | | |
| | capture PvdI | capture Pvd II | capture Pvd III | Φ | aSEC % monomer | capture PvdI | capture Pvd II | capture Pvd III | Φ | aSEC % monomer |
| | Detection via pch-sulfotag | | | | | Detection via pch-sulfotag | | | | |
| SEQ ID NO: 134 | 94% | 96% | 94% | 95% | 96% | 111% | 100% | 104% | 105% | 97% |
| SEQ ID NO: 136 | 94% | 95% | 95% | 95% | 99% | 99% | 103% | 106% | 103% | 100% |

| | 1 week at 42° C. PBS 1 mg/ml | | | | | 1 week hu plasma 37° C. 0.5 mg/ml | | | | |
|---|---|---|---|---|---|---|---|---|---|---|
| | % recovery of activity in qELISA | | | | | % recovery of activity in qELISA | | | | |
| | capture PvdI | capture Pvd II | capture Pvd III | Φ | aSEC % monomer | capture PvdI | capture Pvd II | capture Pvd III | Φ | |
| | Detection via pch-sulfotag | | | | | Detection via pch-sulfotag | | | | |
| SEQ ID NO: 134 | 87% | 88% | 92% | 89% | 103% | 91% | 92% | 104% | 96% | |
| SEQ ID NO: 136 | 92% | 97% | 110% | 100% | 100% | 78% | 79% | 83% | 80% | |

Φ: Average recovery in qELISA for capture of Pvd I, II, III.

Example 16: Affinity of Fusion Molecules for *P. aeruginosa* Siderophores Determined in an ELISA Based Setting Solution binding of individual muteins, fusion molecules or Fc-fusion molecules was assayed by a "Solution binding ELISA", the principle of which was as follows: a constant concentration of the tested individual mutein or fusion molecule construct was incubated with variable concentrations of ligands (Pvd I s, sa, αKG+/−Fe/Pvd II s, sa, αKG+/−Fe/Pvd III s, sa, αKG+/−Fe/Pch+/−Fe) for 1 h. After this pre-incubation in solution, an aliquot of the mutein/ligand mixture was transferred to an ELISA plate with biotinylated Pvd I s (+Fe), Pvd II s (+Fe), Pvd III s (+Fe) or Pch immobilized via Neutravidin to measure the remaining concentration of free mutein or fusion molecule construct. The concentration of free (non ligand-bound) mutein or fusion molecule construct was determined via a quantitative ELISA setup.

In detail, a 384-well plate suitable for fluorescence measurements (Greiner FLUOTRAC™ 600, black flat bottom, high-binding) was coated with 20 µl of Neutravidin at a concentration of 5 µg/ml in PBS overnight at 4° C. After washing, the Neutravidin-coated wells were blocked with 100 µl blocking buffer containing 0.1% Tween 20 and 2% BSA (PBS-T/BSA) for 1 h at room temperature. After washing again, 20 µl biotinylated pyoverdine or pyochelin in results into absolute free mutein/fusion molecule construct concentrations, a standard curve containing varying concentrations of mutein/fusion molecule construct was prepared in PBS-T/BSA and incubated for 20 min on the same ELISA plate as well.

The residual supernatants were discarded and 20 µl HRP-labeled anti-hNGAL antibody was added at a predetermined optimal concentration in PBS-T/BSA and incubated for 1 h at RT. The anti-hNGAL antibody had been obtained by immunization of rabbits with a mixture of muteins, and was subsequently coupled to HRP using a kit (EZ-link Plus Activated Peroxidase, Thermo Scientific) according to the manufacturer's instructions, to obtain the antibody-HRP conjugate. After washing, 20 µl fluorogenic HRP substrate (QuantaBlu, Thermo) was added to each well, and the reaction was allowed to proceed for 15 to 60 minutes. The fluorescence intensity of every well on the plate was read using a fluorescence microplate reader (Tecan or Molecular Devices). To evaluate the data, free mutein or fusion molecule construct concentration, c(mutein/fusion molecule)$_{free}$, was calculated based on the standard curve results, and plotted versus ligand concentration, c(Ligand). IC$_{50}$ values were fitted by nonlinear regression with a single-sites binding model. Curve fitting was performed using GraphPad Prism 4 software.

The resulting IC$_{50}$ values are summarized in Table 11. The fusion molecule and Fc-fusion molecule bound all the respective siderophores with virtually the same affinity as the individual muteins.

TABLE 11

Binding of fusion molecule, Fc-fusion molecule proteins with lipocalin muteins fused to the N-terminus of the Fc domain and single lipocalin muteins to target in solution. A tracer concentration of 0.1 nM lipocalin mutein or fusion molecule (0.2 nM for SEQ ID NO: 16) was used - therefore, the assay sensitivity was not limited. Pvdx: Pvd I, Pvd II, Pvd III.

| | | | Binding to target in solution; $IC_{50}$: nm | | | | | | | |
|---|---|---|---|---|---|---|---|---|---|---|
| Format | Target group | | Pvd x s (+Fe) | Pvd x sa (+Fe) | Pvd x aKG (+Fe) | Pvd x s (−Fe) | Pvd x sa (−Fe) | Pvd x aKG (−Fe) | pch +Fe | pch −Fe |
| Fusion molecule | Pvd I | SEQ ID NO: 134 | 1.9 | 0.8 | 1.6 | 1.4 | 0.92 | 1.0 | | |
| | Pvd II | | 0.3 | 0.4 | 0.88 | 0.47 | 0.45 | 0.81 | | |
| | Pvd III | | 0.2 | 0.31 | 0.58 | 0.18 | 0.27 | 0.7 | | |
| | pch | | | | | | | | 8.4 | 47 |
| Fc-fusion molecule | Pvd I | SEQ ID NO: 136 | 2 | | | not tested | | | | |
| | Pvd II | | 0.4 | | | | | | | |
| | Pvd III | | 0.4 | | | | | | | |
| | pch | | | | | | | | 1.7 | 7.9 |
| Single Lipocalin muteins | Pvd I | SEQ ID NO: 16 | 1.9 | | | not tested | | | | |
| | Pvd II | SEQ ID NO: 36 | 0.55 | | | | | | | |
| | Pvd III | SEQ ID NO: 53 | 0.28 | | | | | | | |
| | pch | SEQ ID NO: 62 | | | | | | | 7.4 | 41 |

The fusion molecule and Fc-fusion molecule constructs bind to Pvd targets with $IC_{50}$ values in the subnM to 2 nM range, to iron loaded Pch with an $IC_{50}$<10 nM and to iron free Pch with an $IC_{50}$<50 nM comparable with the $IC_{50}$ values of the respective single lipocalin muteins as exemplarily shown for Pvdx s (+Fe) and pyochelin (+/−Fe), proving that the binding potency of the individual lipocalin muteins is fully kept in the fusion molecule formats.

Example 17: Comparison of Binding Potency of Different Fusion Molecule Formats Determined in an ELISA Based Setting Binding of the Fc-fusion molecule constructs of SEQ ID NOs: 137, 138 and 139 (see Example 1 and FIGS. 10B, 10C and 10D) in comparison to the contained individual lipocalin muteins (SEQ ID NOs: 34, 17, 50 and 63) to the respective siderophore groups (Pvd Is (+Fe), Pvd IIs (+Fe), Pvd IIIs (+Fe) and Pch) in solution was tested in a solution binding assay comparable to that described in Example 5.

As shown in Table 12 and FIG. 12, the resulting $IC_{50}$ values are comparable for the individual lipocalin muteins and the different Fc-fusion molecule formats.

TABLE 12

Binding of Fc-fusion molecule proteins and single lipocalin muteins to respective targets in solution. A tracer concentration of 0.1 nM or 0.2 nM Fc-fusion molecule or lipocalin mutein was used - therefore, the assay sensitivity was not limited. The iron loaded succinyl variant of Pvd I, Pvd II and Pvd III was used as representative of the respective pyoverdine group.

| | Affinity to soluble single target IC50: nM | | | |
|---|---|---|---|---|
| | Pvd I s (+Fe) | Pvd II s (+Fe) | Pvd III s (+Fe) | Pch (+Fe) |
| SEQ ID NO: 137 | 7.3 | 0.7 | 0.33 | 9.8 |
| SEQ ID NO: 138 | 5.4 | 0.5 | 0.46 | 9.5 |
| SEQ ID NO: 139 | 6 | 0.57 | 0.31 | 7.8 |
| SEQ ID NO: 34, 17, 50, 63 | 4.6 | 0.47 | 0.31 | 5.6 |

Example 18: Affinity of Fusion Molecule Binding to *P. aeruginosa* Siderophores Determined in a Biacore Assay In a surface plasmon resonance (SPR) based assay, a Biacore 1200 instrument (GE Healthcare) was used to measure the binding affinity of individual muteins or fusion molecules to pyoverdine siderophores (to pyoverdine I succinyl, -succinamide, -α-ketoglutaryl with complexed iron ion or to pyoverdine II succinyl, -succinamide, -α-ketoglutaryl with complexed iron ion or to pyoverdine III succinyl, -succinamide, -α-ketoglutaryl with complexed iron ion). To this end, muteins selected for binding to pyoverdines (SEQ ID NOs: 16, 36, 53), a fusion molecule (SEQ ID NO: 134) and a negative control (SEQ ID NO: 64) were biotinylated for 2 h at room temperature applying an appropriate excess of EZ-Link NHS-PEG4-Biotin (Thermo, Cat#21329) followed by separation of non-reacted biotin using a Zeba Spin Desalting Plate (Thermo, Cat#21329) according to the manufacturer's instructions.

In the SPR affinity assay, biotinylated muteins and negative control were captured on a sensor chip CAP using the Biotin CAPture Kit (GE Healthcare), wherein the Sensor Chip CAP is pre-immobilized with an ssDNA oligo. Undiluted Biotin CAPture Reagent (streptavidin conjugated with the complementary ss-DNA oligo) was applied at a flow rate of 2 μl/min for 300 s. Subsequently, 20 μg/ml to 100 μg/mL of biotinylated muteins or fusion molecule negative control were applied for 300 s at a flow rate of 5 μl/min. The reference channel was loaded with Biotin CAPture Reagent only. To determine the binding affinity, four dilutions of the respective Pvd were prepared in HBS-EP+ buffer (GE Healthcare) and applied to the chip surface. Applying a flow rate of 30 μl/min, a single cycle kinetics approach was used with a sample contact time of 180 s and a dissociation time of 1800-2400 s. Absence of binding to the negative control of SEQ ID NO: 64 was confirmed using a high concentration of 1200 nM of the respective Pvd. After ligand immobilization, the four concentrations of Pvd were applied consecutively in ascending order before the dissociation was monitored. All measurements were performed at 25° C. Regeneration of the Sensor Chip surface was achieved with an injection of 6 M Gua-HCl with 0.25 M NaOH followed by an extra wash with running buffer and a stabilization period of 120 s. Data were evaluated with Biacore 1200 Evaluation software (V 1.0). Double referencing was preformed. A 1:1 binding model was used to fit the raw data. In addition, absence of binding to various siderophores not produced by *P. aeruginosa* and to MMP-9 was confirmed using the assay described above by applying high concentrations 1 µM) of the following analytes to the immobilized fusion molecule: Fe-enterobactin, desferoxamine, MMP-9 proform and activated MMP-9.

Biacore Analysis for Determination of Lipocalin Mutein Affinity to Pyochelin

For determination of kinetic constants and resulting $K_D$ for the interaction of mutein SEQ ID NO: 62 with pch +Fe, the mutein or the negative control (SEQ ID NO: 64) was immobilized to the surface of a CM5 chip using standard amine chemistry: The surface of the chip was activated using EDC and NHS. Subsequently, 5 µg/mL of mutein or the negative control solution in 10 mM acetate pH 4.0 was applied at a flow rate of 10 µl/min until a high immobilization level of approximately 2000 RU was achieved. Residual activated groups were quenched with ethanolamine. The reference channels were treated with EDC/NHS following ethanolamine (blank immobilization). To determine the affinity, four to five dilutions of pyochelin (+/−Fe), were prepared in HBS-P+ buffer and applied to the prepared chip surface. The binding assay was carried out with a contact time of 180 s, dissociation times of 1500-1 800 s and applying a flow rate of 30 µl/min. Measurements were performed at 25° C. Regeneration of the immobilized mutein surface was achieved by three consecutive injections of 10 mM Gly-HCl pH 1.5 (120 s) followed by an extra wash with running buffer and a stabilization period. Data were evaluated with Biacore T200 Evaluation software (V 1.0). Double referencing was used. The 1:1 Binding model was used to fit the raw data. Using the same assay, absence of binding to siderophores different from pyochelin and to MMP-9 was confirmed by applying high concentrations (≥1 µM) of the following analytes to the immobilized mutein of SEQ ID NO: 62: Fe-enterobactin, desferoxamine, pyoverdine, MMP-9 proform and activated MMP-9.

Biacore Analysis for Detection of Fusion Molecule Binding to Pyochelin.

Specific binding of pyochelin to the captured fusion molecule of SEQ ID NO: 134 was clearly demonstrated in an SPR-based assay using a Series S Sensor Chip NTA and NTA Reagent Kit (both GE Healthcare). His-tagged fusion molecule (SEQ ID NO: 134) and His-tagged lipocalin muteins (SEQ ID NO: 16 binding Pvd II and SEQ ID NO: 53 binding Pvd II, both used as negative controls) were captured via $Ni^{2+}$ loaded NTA. Pyochelin was used as analyte. While binding of pyochelin (+/−Fe) was clearly detectable and sensorgrams were fairly comparable to pyochelin-binding to covalently immobilized mutein SEQ ID NO: 62, kinetic constants could not be determined due to the instability of the prepared surface (dissociation of captured fusion molecule from the Nickel-NTA chip).

Results from the different Biacore analyses for the fusion molecule and the corresponding single lipocalin muteins are summarized in below Table 13.

TABLE 13

Kinetic constants assessed in a Biacore assay to respective targets and specificity testing. Pvd x: Pvd I, Pvd II, Pvd III.

| | Target group | | Pvd x s +Fe | Pvd x sa +Fe | Pvd x aKG +Fe | Pvd x s −Fe | Pvd x sa −Fe | Pvd x aKG −Fe | pch +Fe | pch −Fe | Fe-Entero-bactin | Defer-oxamin | proform MMP9 | activated MMP9 |
|---|---|---|---|---|---|---|---|---|---|---|---|---|---|---|
| Fusion molecule | Pvd I | SEQ ID NO: 134 | 3.24 | 1.06 | 4.72 | 5.73 | 4.01 | 4.73 | | | | | no bdg | |
| | Pvd II | | 0.21 | 0.23 | 1.19 | 1.51 | 1.79 | 3.27 | | | | | | |
| | Pvd III | | 0.53 | 0.27 | 1.04 | 3.07 | 1.65 | 18.71 | | | | | | |
| | pch | | | | | | | | bdg detectable but high drift | | | | | |
| Single Lipocalin muteins | Pvd I | SEQ ID NO: 16 | 5.28 | | | | | | | | | | | |
| | Pvd II | SEQ ID NO: 36 | 0.24 | | | | | | | | | | | |
| | Pvd III | SEQ ID NO: 53 | 0.62 | | | | | | | | | | | |
| | pch | SEQ ID NO: 62 | | | | | | | 0.29 | 39.55 | | | | |

Affinities measured in a Biacore assay for the fusion molecule and lipocalin muteins against Pvd I s +Fe, Pvd II s +Fe and Pvd III s +Fe are comparable. Affinities measured in Biacore for the fusion molecule of SEQ ID NO: 134 against all Pvd subtypes are in the subnanomolar to single digit nanomolar range and also comparable with the $IC_{50}$ values determined in the solution binding ELISA described in Example 5. Furthermore, binding affinities are similar to pyoverdine targets with and without bound iron. Binding of the fusion molecule of SEQ ID NO: 134 to pyochelin was detectable in a Biacore assay capturing the His-tagged fusion molecule of SEQ ID NO: 134 via Ni-NTA, but due to the high drift, no accurate $K_D$ could be determined. Challenges to set up an SPR assay to detect the binding to a small organic target such as pyochelin were not unexpected. Specificity assessment confirmed that the fusion molecule of SEQ ID NO: 134 and the single lipocalin muteins of SEQ ID NOs: 16, 36, 53 and 62 bind specifically to their targets but not to other siderophores, i.e. Fe-enterobactin and desferoxamin or to MMP-9 protein. The lipocalin muteins of SEQ ID NOs: 1 and 64 used as positive control for Fe-enterobactin, showed binding to the natural ligand Fe-enterobactin and MMP-9 specific antibodies used as positive control for MMP-9, showed binding to MMP-9. SEQ ID NO: 64 did not show binding to pyoverdines or pyochelin (data not shown).

Example 19: Simultaneous Binding of Fusion Molecules to Pyoverdine and Pyochelin Simultaneous binding of a fusion molecule (SEQ ID NO: 134) to two representative targets of the respective four respective target groups at a time (pyoverdine I succinyl (+Fe) and pyochelin, pyoverdine II succinyl (+Fe) and pyochelin or pyoverdine III succinyl (+Fe) and pyochelin) was shown in an electrochemiluminescence (ECL) assay performed on a Meso Scale discovery (MSD) platform. Briefly, the respective biotinylated pyoverdine was captured on an MSD plate via Neutravidin and variable concentrations of fusion molecule were added. Bound fusion molecule was detected with Sulfo-tag labeled pyochelin.

Unless otherwise specified, all incubation steps were performed for 1 h at room temperature with shaking at 300 rpm, and the plate was washed after each incubation step with 80 μL PBST buffer (PBS pH 7.4, 0.05% Tween 20) for five times using a Biotek EL×405 select CW washer. The assay buffer was PBST/BSA (PBS pH 7.4, 0.1% Tween 20, 2% BSA). A 384-well MSD plate (L25XA, Meso Scale Discovery) was coated with 20 μL of Neutravidin at a concentration of 5 μg/mL in PBS overnight at 4° C. After washing, the coated wells were blocked with 60 μL blocking buffer (PBST/BSA), and biotinylated pyoverdine at a concentration of 0.2 μg/mL was added and incubated after a further washing step. Concentration of fusion molecule was adjusted to 5 μg/mL, and then the solution was serially diluted at a 1:3 ratio in PBS-T/BSA. A volume of 20 μL of the dilution was transferred to the 384-well plate and allowed to bind for 1 h. After the incubation, the residual supernatants were discarded, and 20 μL of Sulfo-tag labeled pyochelin at 0.1 μg/mL in PBS-T/BSA was added and incubated for 1 h. After washing, 35 μL of 2× concentrated MSD Read Buffer T with surfactant (R92TC, Meso Scale Discovery) was added, and the plate was measured on a Sector Imager 2400 reader (MSD) within 15 minutes. ECL signals were plotted against fusion molecule concentration and fitted using a single site binding model in Prism Graphpad 5. The resulting $EC_{50}$ values are not representative for binding affinities.

Simultaneous binding of the fusion molecule to each of the representatives of the respective pyoverdine type (Pvd I s (+Fe), Pvd II s (+Fe) and Pvd III s (+Fe)) and pyochelin could be detected. The resulting binding curves are shown in FIG. 13.

Example 20: Functional Testing of Fusion Molecules Binding to P. aeruginosa Siderophores Inhibition of Iron Uptake To determine the functional iron uptake inhibition in living bacteria, a dose range concentration of the fusion molecule of SEQ ID NO: 134 was incubated for 1 hour with 100 nM radioactive iron loaded siderophore in a Tris-HCl 50 mM pH 8.0 buffer before being incubated for 30 minutes with bacteria at a final concentration of OD=1 at 595 nm in a 96-well plate. Subsequently, bacteria were filtered with a cell harvester through a 96-well plate GF/B filter preincubated with a poly ethylene imine solution at 5% and washed 3 times with a 5% BSA solution. After filtering and drying, 30 μl of scintillant cocktail were added in each filter well before counting. To iron load pyoverdine, siderophore was incubated for 15 minutes with $^{55}$Fe—$Cl_3$ in Tris buffer with a 4 to 1 ratio of pyoverdine and iron in a 200 μM final solution. For loading pyochelin with radioactive iron, a 40 μl solution of $^{55}FeCl_3$ at 0.25 mM in HCl 0.5 N was added to a methanol solution of pyochelin at 1 mM. After a 15 minute incubation, 940 μl Tris HCl 50 mM pH 8.0 was added to obtain a 20 μM $^{55}$Fe-Pch solution with a 2 to 1 ratio between pyochelin and iron. The bacteria were prepared as follow: 10 ml of an overnight culture in Mueller Hinton Medium inoculated with an isolated clone was centrifuged, and the washed pellet was resuspended in 25 ml of succcinate medium and incubated under shaking for 2 hours. In parallel, 20 ml of Mueller Hinton Medium were inoculated with 5 ml of the overnight culture and incubated under shaking for 2 hours to be used as background iron uptake level. The 25 ml bacteria cultures were then centrifuged and washed with the corresponding medium before the pellet was resuspended in Tris-HCl 50 mM pH 8.0 buffer and the OD at 595 nm measured to have a final concentration in the assay of OD=1. Percentage of incorporation was calculated for each concentration point, and the inhibition was calculated with in-house software. For this calculation, the maximum level of iron uptake was based on the value obtained in minimum succinate medium without any fusion molecule, and the background value was obtained in the rich Mueller Hinton Medium where the siderophore receptor is not expressed.

The fusion molecule effectively blocked iron uptake in living cells (see Table 14 and Table 15). It showed comparable inhibition of iron uptake as the single lipocalin muteins and $IC_{50}$ values were in the 100-200 nM range (Table 14). Single lipocalin muteins can only block iron uptake of the P. aeruginosa strain expressing the respective pyoverdine group, i.e., SEQ ID NO: 16 can only block iron uptake in P. aeruginosa strains expressing pyoverdines of group 1, SEQ ID NO: 36 can only block iron uptake in P. aeruginosa strains expressing pyoverdines of group 11 and SEQ ID NO: 53 can only block iron uptake in P. aeruginosa strains expressing pyoverdines of group III. SEQ ID NO: 62 can only block iron uptake in P. aeruginosa strains mediated by pyochelin. The fusion molecule protein, however, can block iron uptake in all P. aeruginosa strains, i.e., SEQ ID NO: 134 can block iron uptake in Pvd 1, 11 and III expressing strains as well as iron uptake mediated by pyochelin.

TABLE 14

Fusion molecule and single lipocalin muteins block iron uptake of P. aeruginosa strains in the same $IC_{50}$ range.

| | | Iron uptake assay; IC50: nM | | | |
|---|---|---|---|---|---|
| | P. aeruginosa strain | Pvd I strain ATCC15692 Pvd I s | Pvd II strain ATCC27853 Pvd II s | Pvd III strain ATCC33360 Pvd III s | Pch-dependent strain ATCC15692 ΔpvdA Pch |
| Fusion molecule | SEQ ID NO: 134 | 108 | 116 | 153 | 177 |
| Single lipocalin muteins | SEQ ID NO: 16 | 123 | | | |
| | SEQ ID NO: 36 | | 109 | | |
| | SEQ ID NO: 53 | | | 134 | |
| | SEQ ID NO: 62 | | | | 221 |

TABLE 15

Fusion molecule blocks iron uptake in living bacterial cells.
Iron uptake inhibition IC50 nM

| | Pvd I | | | Pvd II | | | Pvd III | | | |
|---|---|---|---|---|---|---|---|---|---|---|
| | succinyl | succinamide | α-ketoglutaryl | succinyl | succinamide | α-ketoglutaryl | succinyl | succinamide | α-ketoglutaryl | Pch |
| Fusion molecule | 104 | 99 | 181 | 117 | 107 | 51.4 | 116 | 68 | 11 | 165 |

Example 21: Functional Testing of Fusion Molecules Binding to *P. aeruginosa* Siderophores Growth Inhibition Bacterial growth inhibition was determined by incubating the fusion molecule of SEQ ID NO: 134 binding to *P. aeruginosa* siderophores in Chelex-treated succinate medium complemented with a trace element solution and 0.1 mg/ml BSA with a MS bacterial culture diluted at a final OD of 0.05 at 595 nm in a black 96-well plate with transparent bottom. The plate was incubated over night at 37° C. with an every 20 minutes shaking and OD reading at 595 nm in an IEMS Reader MF from Thermo Labsystem.

In FIGS. 14A to 14D, growth inhibition is exemplarily shown for the different pyoverdine type *P. aeruginosa* strains (Pvd I strain, Pvd II strain and Pvd III strain) and for a strain deleted for the pvdA gene to demonstrate the inhibition of pyochelin-mediated iron uptake. The control was bacterial growth in the absence of lipocalin muteins.

The fusion molecule was capable of inhibiting growth of every single *P. aeruginosa* strain tested.

Example 22: In Vivo Potency of Fusion Molecules

*P. aeruginosa*, PA01, was recovered from long-term storage at −80° C. by sub-culturing onto fresh blood agar plates and incubating at 37° C. overnight. The inoculum was prepared by picking 5-10 distinct colonies from the culture plates followed by suspension in 10 mL of Muller-Hinton broth. The culture was incubated for 18 hours on an orbital shaker at 300 rpm and 37° C. The culture was washed twice in PBS, then the pellet was resuspended in PBS and adjusted to an optical density of 0.669 at 600 nm (approximately $1.2 \times 10^9$ CFU/mL). This was further diluted to give an inoculum concentration of $6 \times 10^7$ CFU/mL. 1 mL of this inoculum was added to 30 mL of bacteriological agar, used to prepare the agarose beads (Cash H. A. et al., 1979). The final concentration of PA01 in the agarose beads was $2 \times 10^6$ CFU/mL ($1 \times 10^5$ CFU per 50 µL inoculum). The inoculum was tested for infectivity in 3 rats prior to the main study and achieved a tissue burden of $5 \times 10^6$ CFU/gram of lung tissue at 48 hours post infection similar to previous models.

Sprague Dawley rats used in this study were supplied by Charles River Laboratories UK. Rats were 200-225 g at the time of delivery and were specific pathogen free. Following arrival, rats were allowed at least 7 days acclimatization before the study was started. Rats were 250-300 g at the start of the study. Rats were group housed in sterile individually ventilated cages exposing the animals at all times to HEPA filtered sterile air. Rats had free access to food and water (sterile) and had sterile aspen chip bedding (changed every 3-4 days or as appropriate). The room temperature was 22° C.±1° C., with a relative humidity of 50-60% and maximum background noise of 56 dB. Rats were exposed to 12 hour light/dark cycles with dawn/dusk phases. All animal studies were performed under UK Home Office Licensure and with local ethical committee clearance. All studies were performed by technicians who have completed parts 1, 2 and 3 of the UK Home Office Personal License course and hold current personal licenses.

Deeply anaesthetised rats were infected intratracheally with 50 µL of PA01 embedded beads at $1 \times 10^5$ CFU/rat. Uninfected control rats were inoculated with sterile bead slurry. Treatment was initiated 3 days post infection, and animals were dosed on Days 3, 4, 5, 6, 7 and 8 post infection. Fusion molecule (SEQ ID NO: 134; RA10680550) was administered intravenously (IV) twice a day (bis die, BD) with a 5 hour interval between the two doses. Tobramycin was administered IV BD with a 12 hour interval. Animals were euthanized at Days 3, 5, 7, 9 and 15 post infection. On days 3, 5 and 7, animals were euthanized 4 hours post the first dose of treatment. From Day 9 animals were euthanized at the time the first dose of treatment had been given. Following euthanasia, bronchoalveolar lavages (BAL) were collected and the lung removed, for bacterial colony forming units (CFU) and white cells counting and cytokine/inflammatory markers analysis.

Fusion molecule monotherapy showed significant efficacy compared to the respective vehicle group and in most cases cleared the tissue burden by Day 7 post infection (FIG. 15).

Tobramycin at 20 mg/kg/dose cleared the infection starting from day 5 post-infection. Combination therapy with a fusion molecule and Tobramycin induced accelerated clearance of lung burden, indicating no antagonist effect of the fusion molecule on Tobamycin activity (FIG. 15).

Fusion molecule monotherapy showed anti-inflammatory properties, reducing both total white cell counts and absolute numbers of monocytes and neutrophils (FIG. 16). Fusion molecule monotherapy was significantly more effective than vehicle or Tobramycin monotherapy, suggesting that the fusion molecule is more anti-inflammatory than Tobramycin. Similar results were seen in the combination group, but the fusion molecule monotherapy data suggests that it is the fusion molecule not Tobramycin driving the anti-inflammatory effects caused by combination therapy.

Example 23: In Vivo Efficacy of Fusion Molecules in a Mouse Model of Lung Colonization with *P. aeruginosa* on Quorum Sensing Transcript Reduction

*P. aeruginosa*, PA01, was grown at 37° C. in a rotating, shaking water bath in a tryptic soy broth (Biomerieux Laboratories, Lyon, France) for 8 h. The inoculum was calibrated at $1 \times 10^9$ colony-forming units (cfu)/ml by spectroscopy and pathogen was then entrapped in agar beads.

Male C57BL/6 mice (8 wks of age) purchased from Charles River Laboratories (Domaine des oncins, L'Arbresle, France) were maintained in a protected unit. All experiments were performed with the approval of the Lille Institutional Animal Care and Use Committee. Mice were anesthetized with sevoflurane inhalation (Abbott, UK) and placed in dorsal recumbency. Transtracheal insertion of a 24-G animal feeding needle was used to instillate 60 µl of a the agarose beads preparation ($2 \times 10^9$ cfu/mouse)

Treatment was initiated either 1 h (early phase of colonization) or 48 h (late phase of colonization) post infection and animals were dosed intraperitoneally (ip) twice a day at 5 h intervals for 2 days.

At 48 h (for early phase) or 96 h (for late phase) post-infection, mice were euthanized and lung collected for RNA extraction. Following retrotranscription, gene expression of ExoA, Alginate and RhL was conducted by qPCR analysis.

The fusion molecule (SEQ ID NO: 134; RA10680550) prevents the ability of bacteria to resist to host immune response, blocking virulence factor expression. Fusion molecule treatment induced a significant reduction of the three main genes of the quorum sensing during the early phase of colonization (FIG. 17A). This effect is maintained for rhII even in an established colonization (FIG. 17B). These data demonstrated the potency of fusion molecules to prevent the ability of bacteria to resist to host immune response, blocking virulence factor expression.

Example 24: Effect of Linker Molecule Lengths on the Binding Capacity of Fusion Molecules Different linker molecule lengths and linker molecule compositions were tested for fusion molecule design. More particularly, linker lengths ranging from the $(G4S)_2$ peptide linker (10 amino acids) down to a single glycine as linker were tested and found to have no or only minor influence on binding of single targets (FIG. 18). It can be assumed that peptide linkers of more than 10 amino acids in length will also have no negative influence on the binding capacity of the fusion molecules.

Example 25: Strains, Compounds, Media and Growth Condition

*P. aeruginosa* strains ATCC15692/PA01 (pyoverdine I siderotype), ATCC27853 (pyoverdine II siderotype and ATCC33360 (pyoverdine III siderotype) were obtained from the American Type Culture Collection and maintained as instructed. The compounds tested were the Fc-fusion molecule of SEQ ID NO: 136 (also referred to as SAR439349 or RA10680578) or a non-binding control Fc-fusion molecule (RA11043715). Unless specified otherwise, bacteria were grown in Chelex®-treated succinate medium (C-MS) prepared as follows: succinate medium was prepared with $K_2HPO_4$: 6 g/L, $KH_2PO_4$: 3 g/l, $(NH_4)_2SO_4$: 1 g/L, $MgSO_4 \cdot 7H_2O$: 0.2 g/L, and Sodium Succinate: 4 g/L; then Chelex®-100 (Biorad) was added at 50 g/L for 5 h at room temperature before filtration using 0.22 µM membranes.

For each experiment, single colonies of various strains of *P. aeruginosa* picked from a Tryptic Soy Agar plate were grown overnight in cell culture tubes with shaking at 37° C. in C-MS. The overnight cultures were centrifuged to eliminate pyoverdine present in the growth medium. Bacterial pellets were then resuspended and diluted in fresh C-MS medium at a density of $5 \cdot 10^5$ cfu/mL and grown in duplicates or triplicates in 96-wells plates with shaking in a 37° C. incubator. Values of cfu/mL were approximated from the optical density at 600 nm (OD600 nm) using the following formula: 0.125 OD600 nm unit=$1.5 \times 10^8$ cfu/mL.

Example 26: Kinetics of Pyoverdine Production in the Presence of Fc-Fusion Molecules Bacteria prepared as described in Example 25 were grown alone (untreated control) or in the presence of various doses of an Fc-fusion molecule (SEQ ID NO: 136) or a control Fc-fusion molecule in a total volume of 200 µL in duplicates in 96-well plates for 24 hours. At various times, pyoverdine fluorescence in the cultures was measured as described before (Wilderman et al., 2001, Infect Immun., 69(9), p. 5385-94) directly in the plate using a microplate reader (Enspire, Perkin Elmer Instruments) with an excitation wavelength of 405 nm and an emission wavelength of 460 nm. Simultaneously, bacterial biomass was evaluated by measuring OD600 nm, which was converted to cfu/mL. Experiments were reproduced at least 5 times with each of the ATCC15692, ATCC27853 and ATCC33360 strains of *P. aeruginosa*.

To present the raw data, the means and s.e.m. of cfu/ml and fluorescence arbitrary unit values for a representative experiment are given for untreated control and treatment with the two compounds (with a dose-response) in FIGS. 19A and 19B, respectively, for ATCC27853; FIGS. 190 and 19D, respectively, for ATCC15692 and FIGS. 19E and 19F, respectively, for ATCC33360. To account for an impact of the compound on biomass, which could explain the differences in pyoverdine levels, the average amount of fluorescence of pyoverdine at each time point was divided by the corresponding average OD600 nm. These relative amounts were then normalized to the relative amount of pyoverdine fluorescence of the untreated control. The normalized relative amounts are shown in FIGS. 20A, 20B, 20C for ATCC27853, ATCC15692 and ATCC33360, respectively. Experiments were performed twice in triplicates and means and s.e.m. are represented. One way ANOVA and Dunnett's post-tests against untreated control were performed to ascertain the impact of treatment with an Fc-fusion molecule (* $p<0.05$,  p→0.01, * $p<0.001$). In addition, the points were fitted to a standard dose-response curve and yielded $IC_{50}$ values of 0.04 mg/mL, 0.11 mg/mL and 0.8 mg/mL for ATCC27853, ATCC15692 and ATCC33360, respectively.

The specificity of the fluorescence signal to pyoverdine was ascertained by measuring the fluorescence of cultures of strain ATCC27853, and that of a pvdA/pchD double mutant strain of ATCC27853 grown as described in Example 25. As mean values of fluorescence obtained in this experiment show in FIG. 21, the mutant strain unable to synthesize these siderophores does not exhibit any fluorescence signal. To normalize the fluorescence signal, purified pyoverdine II obtained from the supernatant of wild-type ATCC27853 was used to spike the cultures prior to fluorescence signal acquisition and a calibration curve was obtained, as shown in FIG. 22 by the mean values of fluorescence obtained in this experiment. In addition, in order to ascertain that the drop in fluorescence signal in the presence of an Fc-fusion molecule was not due to fluorescence quenching upon pyoverdine binding by the compound, an Fc-fusion molecule was added extemporaneously to a culture supernatant containing pyoverdine (obtained with a filtered 24 hours-culture of ATCC27853) and fluorescence was read immediately and after 24 h. As shown in FIG. 23 with the mean values of fluorescence observed in this experiment, no fluorescence quenching was observed.

Taken together these experiments show that the fluorescence measured is specifically due to pyoverdine presence and that the drop in fluorescence observed upon treatment with an Fc-fusion molecule is due to the compound preventing the production of pyoverdine by exponentially growing bacteria in an iron starved medium. Moreover, this phenomenon is robust and seen in representative strains of all three siderotypes.

Example 27: Kinetics of Growth in the Presence of Fc-Fusion Molecules

Bacteria prepared as described in Example 25 were grown alone (untreated control) or in the presence of 0.1 or 1 mg/mL of an Fc-fusion molecule (SEQ ID NO: 136) or a non-binding control Fc-fusion molecule in a total volume of 200 µL in duplicates in 96-well plates for 24 hours. Every 30 min., OD600 nm was measured directly in the plate and converted to cfu/mL. Experiments were reproduced 5 times with various P. aeruginosa strains and representative experiments exemplifying the impact of 1 mg/mL treatment on ATCC15692 and ATCC33360 are shown as means and s.e.m. of cfu/mL in FIGS. 24A and 24B, respectively. The growth rate of the exponential phases of the growth curves were calculated and are represented as $\Delta cfu \cdot mL^{-1} \cdot \Delta h^{-1}$ in Table 16.

TABLE 16

Growth rate of the exponential phases of the growth curves for Fc-fusion molecule-treated bacteria.

| Fc-fusion molecule | Slope ($\Delta cfu \cdot mL^{-1} \cdot \Delta h^{-1}$) | Fc-fusion molecule control | Slope ($\Delta cfu \cdot mL^{-1} \cdot \Delta h^{-1}$) |
|---|---|---|---|
| ATCC15692 0 | 0.619 | | |
| 0.1 mg/mL | 0.181 | 0.1 mg/mL | 0.508 |
| 1 mg/mL | 0.098 | 1 mg/mL | 0.487 |
| ATCC33360 0 | 0.572 | | |
| 0.1 mg/mL | 0.387 | 0.1 mg/mL | 0.419 |
| 1 mg/mL | 0.111 | 1 mg/mL | 0.356 |

Overall, these results show that the Fc-fusion molecule is specifically slowing the exponential growth of bacteria in an iron starved medium and that this phenomenon is seen in representative strains of all three siderotypes.

The impact of another fusion molecule (RA10680550; SEQ ID NO: 134) at 10 µM on bacterial growth in C-MS medium was also tested against 5 recent VAP clinical isolates of P. aeruginosa, and in all 5 cases a reduction in the slope of exponential growth was observed.

Example 28: Impact of Fc-Fusion Molecules on pchD Promoter Activity

Pyochelin biosynthesis gene expression has been shown to be positively regulated by iron-bound pyochelin acting at a transcriptional level via the PchR regulator (Heinrichs et al., 1996, J Bacteriol., 178(9), p. 2586-92). In order to test the impact of Fc-fusion molecules on pyochelin biosynthesis gene expression, the synthetic luxCDABE operon was cloned under the control of the pchD promoter and the PpchD::lux fusion was inserted in the chromosome of ATCC33360.

To measure the pchD promoter activity, ATCC33360 bearing the PpchD::lux fusion were grown alone (untreated control) or in the presence of 0.1 or 1 mg/mL of an Fc-fusion molecule (SEQ ID NO: 136) or a non-binding control Fc-fusion molecule and in the presence of various amounts of FeCl$_3$ in a total volume of 200 µL in duplicates in 96-well plates for 24 hours, with shaking in a 37° C. incubator. After 24 h of growth, luminescence was measured directly in the plate using a microplate reader (Enspire, Perkin Elmer Instruments).

The impact of iron concentration on Ppchd transcriptional activity was evaluated in 3 independent experiments performed in triplicates, and a representative experiment is shown in FIG. 25 as means and s.e.m. of the observed luminescence. As expected, pchD promoter expression was induced in the C-MS medium without addition of iron and repressed by iron addition. This validates the functionality of the reporter fusion.

The impact of Fc-fusion molecule treatment on Ppchd transcriptional activity in the presence of various amounts of supplementary iron was evaluated in a single experiment performed in triplicates, and the results are shown in FIG. 26 as means and s.e.m. of the observed luminescence. It shows that the activity of this promoter activity was abolished in the presence of an Fc-fusion molecule regardless of the amount of supplemented iron, whereas the control Fc-fusion molecule had no effect.

The impact of a range of doses of the Fc-fusion molecule or the control Fc-fusion molecule on PpchD transcriptional activity was tested with no iron being supplemented in 3 experiments performed with triplicates. In each experiment, the amount of luciferase activity was normalized to the untreated control. The means and s.e.m. of the observed luminescence obtained in these 3 experiments are shown in FIG. 27. The points were fitted to a standard dose-response curve and yielded an IC$_{50}$ value of 0.03 mg/mL (95% CI: 0.02-0.05) for the Fc-fusion molecule and was undefined for the isotypic control Fc-fusion molecule.

Overall, these results show that the Fc-fusion molecule is specifically preventing the signal normally transduced by iron-bound pyochelin in an iron-starved medium. This should result in reduced amounts of this siderophore, as was observed with pyoverdine. Conversely, since a similar positive regulation of pyoverdine synthesis by pyoverdine itself has been shown (Lamont et al., 2000, Proc Natl Acad Sci USA, 99(10), p. 7072-7), it is tempting to speculate that the impact of the Fc-fusion molecule on pyoverdine production seen above is due to the blocking of pyoverdine-mediated signalling. Siderophore-mediated signalling is also known to impact the synthesis of virulence factors (Lamont et al., 2000, Proc Natl Acad Sci USA, 99(10), p. 7072-7), and thus it is expected that the Fc-fusion molecule will affect virulence.

The invention is not to be limited in scope by the specific embodiments and examples described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes. Other embodiments are within the following claims.

What is claimed is:

1. A fusion molecule having binding specificity for pyoverdine type I, II and III and pyochelin, comprising (a) a first polypeptide comprising a first human neutrophil gelatinase-associated lipocalin (hNGAL) mutein that binds pyoverdine type 1; (b) a second polypeptide comprising a second hNGAL mutein that binds pyoverdine type II; (c) a third polypeptide comprising a third hNGAL mutein that binds pyoverdine type III; and (d) a fourth polypeptide comprising a fourth hNGAL mutein that binds pyochelin; wherein the first, second, third and fourth polypeptides are covalently linked, wherein the first hNGAL mutein comprises 10 or more mutations at positions 28, 36, 39-41, 46, 49, 52, 54, 55, 59, 65, 68, 70, 72-75, 77, 79-81, 87, 96, 100, 103, 106, 125, 127, 132, 134, and 136 of SEQ ID NO: 1; the second hNGAL mutein comprises 10 or more mutations at positions 36, 40, 49, 52, 54, 65, 68, 70, 72, 73, 77, 79, 81, 87, 103, 106, 125, 127, 132, and 134 of SEQ ID NO: 1; the third hNGAL mutein comprises 10 or more mutations at positions 36, 40, 41, 42, 49, 52, 65, 68, 70, 73, 77, 79, 81, 87, 96, 100, 103, 105, 106, 127, and 134 of SEQ ID NO: 1; and the fourth hNGAL mutein comprises 10 or more mutations at positions 36, 40, 41, 45, 46, 49, 52, 65, 68, 70, 72, 73, 77, 79, 81, 87, 100, 103, 106, 125, 127, 132, and 134 of the linear polypeptide sequence of the mature hNGAL (SEQ ID NO: 1).

2. The fusion molecule of claim 1, wherein the first, second, third, and fourth hNGAL mutein binds pyoverdine type I, pyoverdine type II, pyoverdine type III and pyochelin, respectively, each with a dissociation constant $K_D$ of 200 nM or lower.

3. The fusion molecule of claim 1, wherein the first, second, third and fourth polypeptides are covalently linked via linker molecules.

4. The fusion molecule of claim 3, wherein the linker molecules are peptide linkers.

5. The fusion molecule of claim 1, further comprising a multimerization domain allowing multimerization of the fusion molecule.

6. The fusion molecule of claim 5, wherein the multimerization domain is a dimerization domain allowing the dimerization of the fusion molecule.

7. The fusion molecule of claim 6, wherein the dimerization domain is selected from the group consisting of an Fc domain, an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an uteroglobin dimerization domain and variants or fragments of any one of the foregoing.

8. The fusion molecule of claim 7, wherein the Fc domain is a human IgG4-Fc domain.

9. The fusion molecule of claim 1, having a general formula selected from the group consisting of $$N'\text{-}X_1\text{-}L_1\text{-}X_2\text{-}L_2\text{-}X_3\text{-}L_3\text{-}X_4\text{-}C' \quad\quad (I),$$

$$N'\text{-}X_1\text{-}L_1\text{-}X_2\text{-}L_2\text{-}X_3\text{-}L_3\text{-}X_4\text{-}L_4\text{-}MD\text{-}C' \quad\quad (II),$$

$$N'\text{-}MD\text{-}L_1\text{-}X_1L_2\text{-}X_2\text{-}L_3\text{-}X_3\text{-}L_4\text{-}X_4\text{-}C' \quad\quad (III),$$

$$N'\text{-}X_1\text{-}L_1\text{-}X_2\text{-}L_2\text{-}MD\text{-}L_3\text{-}X_3\text{-}L_4\text{-}X_4\text{-}C' \quad\quad (IV),$$

$$N'\text{-}X_1\text{-}L_1\text{-}MD\text{-}L_2\text{-}X_2\text{-}L_3\text{-}X_3\text{-}L_4\text{-}X_4\text{-}C' \quad\quad (V), \text{ and}$$

$$N'\text{-}X_1\text{-}L_1\text{-}X_2\text{-}L_2\text{-}X_3\text{-}L_3\text{-}MD\text{-}L_4\text{-}X_4\text{-}C' \quad\quad (VI)$$

wherein
$X_1$, $X_2$, $X_3$ and $X_4$ are, at each occurrence, selected from the group consisting of the first, second, third and fourth polypeptides, with the proviso that the fusion molecule comprises each of the first, second, third and fourth polypeptides;

MD comprises a multimerization domain; and $L_1$, $L_2$, $L_3$ and $L_4$ are, at each occurrence, independently selected from a covalent bond and a linker molecule.

10. The fusion molecule of claim 1, being present as a multimeric complex.

11. The fusion molecule of claim 1, wherein the fusion molecule has one or more of the following properties:
   (i) it further comprises at least one label or tag allowing the detection and/or isolation of the fusion molecule;
   (ii) it further comprises one or more modifications increasing the stability of the fusion molecule and/or extending the serum half-life of the fusion molecule;
   (iii) it inhibits or reduces iron uptake by *P. aeruginosa* through pyochelin and/or pyoverdine;
   (iv) it inhibits or reduces virulence factor expression by *P. aeruginosa*;
   (v) it inhibits or reduces pyochelin- and/or pyoverdine-mediated signalling;
   (vi) it inhibits or reduces *P. aeruginosa* bacterial growth; and
   (vii) it is associated with or conjugated/fused to a pharmaceutically active agent.

12. The fusion molecule of claim 11, wherein the pharmaceutically active agent is selected from the group consisting of an antibiotic, a cytostatic agent, a toxin, a metal or metal compound/complex, a chelating agent, a hapten and an antibody.

13. A pharmaceutical composition comprising the fusion molecule of claim 1.

14. A kit comprising a fusion molecule of claim 1.

15. A fusion molecule having binding specificity for pyoverdine type I, II and III and pyochelin, comprising
   (a) a first polypeptide comprising a first hNGAL mutein that binds pyoverdine type I consisting of SEQ ID NO: 16;
   (b) a second polypeptide comprising a second hNGAL mutein that binds pyoverdine type II consisting of SEQ ID NO: 36;
   (c) a third polypeptide comprising a third hNGAL mutein that binds pyoverdine type III consisting of SEQ ID NO: 53; and
   (d) a fourth polypeptide comprising a fourth hNGAL mutein that binds pyochelin consisting of SEQ ID NO: 62;
   wherein the first, second, third and fourth polypeptides are covalently linked.

* * * * *